US012799185B2

(12) United States Patent
Bourgine et al.

(10) Patent No.: US 12,799,185 B2
(45) Date of Patent: Nov. 17, 2026

(54) ANTI-HBV ANTIBODIES AND METHODS OF USE

(71) Applicants: Hoffmann-La Roche Inc., Little Falls, NJ (US); Institut Pasteur, Paris (FR)

(72) Inventors: Maryline Bourgine, Paris (FR); Maxime Beretta, Paris (FR); Hugo Mouquet, Paris (FR); Verena Hehle, Utrecht (NL); Stanislas Pol, Paris (FR); Hélène Strick-Marchand, Paris (FR); Malika Ait-Goughoulte, Basel (CH); Nadège Pelletier, Basel (CH); Jens Fischer, Penzberg (DE); Guy Georges, Penzberg (DE); Tilman Schlothauer, Penzberg (DE); Erwin Van Puijenbroek, Schlieren (CH); Wouter Driessen, Basel (CH)

(73) Assignees: Hoffmann-La Roche Inc., Little Falls, NJ (US); Institut Pasteur, Paris (FR)

( * ) Notice: Subject to any disclaimer, the term of this patent is extended or adjusted under 35 U.S.C. 154(b) by 208 days.

(21) Appl. No.: 18/008,093

(22) PCT Filed: Jun. 8, 2021

(86) PCT No.: PCT/EP2021/065260
§ 371 (c)(1),
(2) Date: Dec. 2, 2022

(87) PCT Pub. No.: WO2021/249990
PCT Pub. Date: Dec. 16, 2021

(65) Prior Publication Data
US 2023/0340081 A1 Oct. 26, 2023

(30) Foreign Application Priority Data
Jun. 8, 2020 (EP) .................................... 20305612

(51) Int. Cl.

| | |
|---|---|
| ***C07K 16/082*** | (2026.01) |
| ***A61K 39/00*** | (2006.01) |
| ***A61K 39/42*** | (2006.01) |
| ***A61K 45/06*** | (2006.01) |
| ***A61P 31/20*** | (2006.01) |

(52) U.S. Cl.
CPC ............ *C07K 16/082* (2013.01); *A61K 39/42* (2013.01); *A61K 45/06* (2013.01); *A61P 31/20* (2018.01); *A61K 2039/505* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 9,512,201 | B2 | 12/2016 | Van Den Nieuwenhof et al. | |
| 10,689,434 | B2 * | 6/2020 | Luo | C07K 16/082 |
| 11,382,969 | B2 * | 7/2022 | Georges | C12N 7/00 |
| 11,390,664 | B2 * | 7/2022 | Corti | A61P 31/14 |
| 12,404,318 | B2 * | 9/2025 | Bakardjiev | A61K 45/06 |
| 12,410,239 | B2 * | 9/2025 | Luo | A61P 1/16 |
| 12,509,504 | B2 * | 12/2025 | Li | C07K 16/118 |

FOREIGN PATENT DOCUMENTS

| | | | |
|---|---|---|---|
| JP | 2008-519860 | A | 6/2008 |
| JP | 2016-504015 | A | 2/2016 |
| JP | 2018-535650 | A | 12/2018 |
| RU | 2165772 | C1 | 4/2001 |
| RU | 2217153 | C1 | 11/2003 |
| RU | 2367960 | C2 | 9/2009 |
| WO | 199739029 | A2 | 10/1997 |
| WO | 2006/053301 | A2 | 5/2006 |
| WO | 2014048910 | A1 | 4/2014 |
| WO | 2017/059878 | A1 | 4/2017 |

OTHER PUBLICATIONS

Andrews, S.F. et al. (2015). "Immune History Profoundly Affects Broadly Protective B Cell Responses to Influenza," Science Translational Medicine 7(316):316ra192, 26 pages.
Bauer, T. et al. (2011). "Immune Control of Hepatitis B Virus," Digestive Diseases 29:423-433.
Bertoletti, A. et al. (2016). Adaptive Immunity in HBV Infection, J. Hepatology 64:S71-S83.
Bruel, T. et al. (2016). "Elimination of HIV-1-Infected Cells by Broadly Neutralizing Antibodies," Nat. Commun. 7:10844, 12 pages.
Burton, A.R. et al. (2018). "Circulating and Intrahepatic Antiviral B Cells Are Defective in Hepatitis B," J. Clin. Invest. 128(10):4588-4603.
Chotiyaputta, W. et al., (2009, e-pub. Jul. 7, 2009). "Hepatitis B Virus Variants," Nature Reviews Gastroenterology & Hepatology 6:453-462.
Chu, C.-M et al. (2016). "Chapter 11: Natural History of Hepatitis B Virus Infection," in Hepatitis B Virus in Human Diseases pp. 217-247.
Corti, D. et al., (2018, e-pub. May 5, 2018). "Viral Envelope-Specific Antibodies in Chronic Hepatitis B Virus Infection," Current Opinion in Virology 30:48-57.
Cougot, D. et al. (2012). Inhibition of PP1 Phosphatase Activity by HBx: A Mechanism for the Activation of Hepatitis B Virus Transcription. Science Signaling 5(205):ra1, 12 pages.
Dilillo D.J. et al., (2014, e-pub Jan. 12, 2014). "Broadly Neutralizing Hemaglutinin Stalk-Specific Antibodies Require FcγR Interactions for Protection Against Influenza Virus in vivo," Nat. Med.. 20(2):143-151.

(Continued)

*Primary Examiner* — Marianne P Allen
(74) *Attorney, Agent, or Firm* — MORRISON & FOERSTER LLP

(57) ABSTRACT

The invention provides anti-S-HBs antibodies and methods of using the same.

25 Claims, 42 Drawing Sheets

Specification includes a Sequence Listing.

(56) References Cited

OTHER PUBLICATIONS

Dion, S. et al. (2013). "Adeno-Associated Virus-Mediated Gene Transfer Leads to Persistent Hepatitis B Virus Replication in Mice Expressing HLA-A2 and HLA-DR1 Molecules," J. Virol. 87(10):5554-5563.
Dondelinger, M. et al. (2018). "Understanding the Significance and Implications of Antibody Numbering and Antigen-Binding Surface/Residue Definition," Frontiers in Immunology 9(2278):1-15.
Dusséaux, M. et al. (2017). Viral Load Affects the Immune Response to HBV in Mice With Humanized Immune System and Liver, Gastroenterology 153:1647-1661.
Eren, R. et al. (2000). "Preclinical Evaluation of Two Human Anti-Hepatitis B Virus (HBV) Monoclonal Antibodies in the HBV-Trimera Mouse Model and in HBV Chronic Carrier Chimpanzees," Hepatology 32:588-596.
Fanning, G.C. et al. (2019). "Therapeutic Strategies for Hepatitis B Virus Infection: Towards a Cure," Nature Reviews Drug Discovery 18:827-844.
Friguet, B. et al. (1985). "Measurements of the True Affinity Constant in Solution of Antigen-Antibody Complexes by Enzyme-Linked Immunosorbent Assay," J. Immunol. Methods 77(2):305-319.
Galun, E. et al. (2002). "Clinical Evaluation (Phase I) of a Combination of Two Human Monoclonal Antibodies to HBV: Safety and Antiviral Properties," Hepatology 35:673-679.
Gao, Y. et al. (2017). "Antibody-Mediated Immunotherapy Against Chronic Hepatitis B Virus Infection," Human Vaccines & Immunotherapeutics 13(8):1768-1773.
Gehring, A.J. et al. (2019). "Targeting Innate and Adaptive Immune Responses to Cure Chronic HBV Infection," Gastroenterology 156(2):325-337.
Hantz, O. et al. (2009). "Persistence of the hepatitis B Virus Covalently Closed Circular DNA in HepaRG Human Hepatocyte-Like Cells," J. Gen. Virol. 90:127-135.
Hayer, J. et al. (2012, e-pub. Nov. 3, 2012). "HBVdb: A Knowledge Database for Hepatitis B Virus," Nucleic Acids Research 41:D566-D570.
Hehle, V. et al. (2020). "Potent Human Broadly Neutralizing Antibodies to Hepatitis B Virus from Natural Controllers," J. Exp. Med. 217(10):1-17, 23 pages.
Huang, C.H., et al. (2012, e-pub. May 23, 2012). "Influence of Mutations in hepatitis B Virus Surface Protein on Viral Antigenicity and Phenotype in Occult HBV Strains From Blood Donors," J. Hepatol. 57:720-729.
International Preliminary Report on Patentability, issued Dec. 13, 2022, for PCT Application No. PCT/EP2021/065260, filed Jun. 8, 2021, 20 pages.
International Search Report and Written Opinion, mailed Jan. 12, 2022, , for PCT Application No. PCT/EP2021/065260, filed Jun. 8, 2021, 29 pages.
Kato, H. et al. (2016). "Chapter 3: Hepatitis B Virus Genotypes," Molecular and Translational Medicine, pp. 63-78.
Kucinskaite-Kodze, I. et al. (2016, e-pub. Nov. 2, 2015). "New Broadly Reactive Neutralizing Antibodies Against Hepatitis B Virus Surface Antigen," Virus Research 211:209-221.
Kusumoto, S. et al. (2019). "Risk of HBV Reactivation in Patients with B-Cell Lymphomas Receiving Obinutuzumab or Rituximab Immunochemotherapy," Blood 133(2):137-146.
Küttner, G. et al. (1999). "Characterization of Neutralizing Anti-Pre-S1 and Anti-Pre-S2 (HBV) Monoclonal Antibodies and Their Fragments," Molecular Immunology 36:669-683.
Lee, H.W. et al. (2019). "Efficacy of Lenvervimab, A Recombinant Human Immunoglobulin in Treatment of Chronic Hepatitis B Virus Infection," Clinical Gastroenterology and Hepatology 18(13):3043-3045.
Lever, A.M.L. et al. (1990). "Monoclonal Antibody to HBsAg for Chronic Hepatitis B Virus Infection with Hypogammaglobulinaemia," Lancet 335:1529, 1 page.
Li, D. et al. (2017). "A Potent Human Neutralizing Antibody Fc-Dependently Reduces Established HBV Infections," eLife 6:e26738, 30 pages.
Lorin, V. et al. (2015, e-pub. Apr. 22, 2015). "Efficient Generation of Human IgA Monoclonal Antibodies," J. Immunol. Methods 422:102-110.
Maini, M.K. et al. (2019). "Restoring, Releasing or Replacing Adaptive Immunity in Chronic Hepatitis B," Nature Reviews Gastroenterology & Hepatology 16:662-675.
Mcmahon, B.J. (2009). "The Natural History of Chronic Hepatitis B Virus Infection," Hepatology 49:S45-S55.
Meffre, E. et al. (2004). "Surrogate Light Chain Expressing Human Peripheral B Cells Produce Self-reactive Antibodies," J. Exp. Med. 199(1):145-150.
Michel, M.-L. et al. (1984). "Synthesis in Animal Cells of Hepatitis B Surface Antigen Particles Carrying a Receptor for Polymerized Human Serum Albumina," Proc. Natl. Acad. Sci. USA 81:7708-7712.
Mouquet, H. et al. (2006). "A Truncated Alternative Spliced Isoform of Human Desmoglein 1 Contains a Specific T Cell Epitope Binding to the Pemphigus Foliaceus-Associated HLA Class II DRβ1*0102 Molecule," J. Immunol. 177:6517-6526.
Mouquet, H. et al. (2012, e-pub. Oct. 30, 2012). "Complex-Type N-Glycan Recognition by Potent Broadly Neutralizing HIV Antibodies," Proc. Natl. Acad. Sci. USA 109:E3268-E3277.
Pelegrin, M. et al. (2015). "Antiviral Monoclonal Antibodies: Can They Be More Than Simple Neutralizing Agents?" Trends in Microbiology 23(10):653-665.
Perrillo, R.P. et al. (2015). "American Gastroenterological Association Institute Technical Review on Prevention and Treatment of Hepatitis B Virus Reactivation During Immunosuppressive Drug Therapy," Gastroenterology 148 (1):221-244 e3.
Planchais, C. et al. (2019). "HIV-1 Envelope Recognition by Polyreactive and Cross-Reactive Intestinal B Cells," Cell Reports 27:572-585.
Prigent, J. et al. (2016). "Scarcity of Autoreactive Human Blood IgA+ Memory B Cells," Eur. J. Immunol. 46:2340-2351.
Prigent, J. et al. (2018). "Conformational Plasticity in Broadly Neutralizing HIV-1 Antibodies Triggers Polyreactivity," Cell Reports 23:2568-2581.
Rehermann, B. et al. (2005). "Immunology of Hepatitis B Virus and Hepatitis C Virus Infection," Nature Review, Immunology 5:215-229.
Reichmann, L. et al. (1988). "Reshaping Human Antibodies for Therapy," Nature 332:323-327.
Salimzadeh, L. et al. (2018). "PD-1 Blockade Partially Recovers Dysfunctional Virus-Specific B Cells in Chronic Hepatitis B Infection," J. Clin. Invest. 128(10):4573-4587.
Salisse, J. et al. (2009). "A Function Essential to Viral Entry Underlies the Hepatitis B Virus "a" Determinant," J. Virol. 83(18):9321-9328.
Samuel, D. et al. (1993). "Liver Transplantation in European Patients with the Hepatitis B Surface Antigen," New Engl. J. Med. 329(25):1842-1847.
Sela-Culang, I. et al. (2013). "The Structural Basis of Antibody-Antigen Recognition," Frontiers in Immunology 4(302):1-13.
Shouval, D. et al. (1982). "Immunotherapy in Nude Mice of Human Hepatoma Using Monoclonal Antibodies Against Hepatitis B Virus," Nature 298:567-569.
Shouval, D. et al. (1982). "Selecting Binding and Complement-Mediated Lysis of Human Hepatoma Cells (PLC/PRF/5) in Culture by Monoclonal Antibodies to Hepatitis B Surface Antigen," Proc. Natl. Acad. Sci. U.S.A. 79:650-654.
Strick-Marchand, H. et al. (2015). "A Novel Mouse Model for Stable Engraftment of a Human Immune System and Human Hepatocytes," PLoS One 10(3):e0119820_14pgs.
Sureau, C. (2010). "Chapter 25—The Use of Hepatocytes to Investigate HDV Infection: The HDV/HepaRG Model," in Methods in Molecular Biology 640:463-473.
Sureau, C. et al. (2016). "The Hepatitis Delta Virus: Replication and Pathogenesis," J. Hepatol. 64:S102-S116.

(56) References Cited

OTHER PUBLICATIONS

Tateno, C. et al. (2015). "Generation of Novel Chimeric Mice with Humanized Livers by Using Hemizygous cDNA-uPA/SCID Mice," PLoS One 10(11):e0142145, 20 pages.
Tiller, T. et al. (2008). "Efficient Generation of Monoclonal Antibodies from Single Human B Cells by Single Cell RT-PCR and Expression Vector Cloning," J. Immunol. Methods 329:112-124.
Tiller, T. et al. (2007). "Autoreactivity in Human IgG+ Memory B Cells," Immunity 26:205-213.
Tu, T. et al. (2018, e-pub. May 15, 2018). "Virus Entry and its Inhibition to Prevent and Treat Hepatitis B and Hepatitis D Virus Infections," Current Opinion in Virology 30:68-79.
Van Nunen, A.B. et al. (2001). "Efficacy and Safety of an Intravenous Monoclonal Anti-HBs in Chronic Hepatitis B Patients," Liver 21:207-212.
Verrier, E.R. et al. (2016). "A Targeted Functional RNA Interference Screen Uncovers Glypican 5 as an Entry Factor for Hepatitis B and D Viruses," Hepatology 63:35-48.
Wardemann H. et al. (2007). "B-Cell Self-Tolerance in Humans," Adv. Immunol. 95:83-110.
Wardemann, H. et al. (2003). "Predominant Autoantibody Production by Early Human B Cell Precursors," Science 301:1374-1377.
West, D.J. et al. (1996). "Vaccine Induced Immunologic Memory for Hepatitis B Surface Antigen: Implications for Policy on Booster Vaccination," Vaccine 14(11):1019-1027.
Xu, X. et al. (2015). "Reversal of B-Cell Hyperactivation and Functional Impairment is Associated with HBsAg Seroconversion in Chronic Hepatitis B Patients," Cellular & Molecular Immunology 12:309-316.
Zhang, T.Y. et al. (2016, e-pub. Sep. 30, 2015). Prolonged Suppression of HBV in Mice by a Novel Antibody That Targets a Unique Epitope on Hepatitis B Surface Antigen, Gut 65:658-671.
Zhu, D. et al. (2016). "Clearing Persistent Extracellular Antigen of Hepatitis B Virus: An Immunomodulatory Strategy To Reverse Tolerance for an Effective Therapeutic Vaccination," J. Immunol 196(7):3079-3087, 19 pages.

* cited by examiner

| | Age | Gender | anti-HBs titers* | Vaccines |
|---|---|---|---|---|
| **Bv1** | 22 | F | 564 | HBVax-5 |
| **Bv2** | 49 | F | 500 | Genhevac B |
| **Bv3** | 64 | F | 602 | Genhevac B |
| **Bv4** | 38 | M | 684 | Genhevac B |
| **Bv5** | 28 | M | >500 | Genhevac B |
| **Bv6** | 28 | F | 473 | Engerix B |

F, female; M, male. *Given as IU/ml.

| | Age | Gender | Seroconvertion in chronic phase | HBV load | HBsAg | HBeAg | anti-HBc | anti-HBs titers* | anti-HDV |
|---|---|---|---|---|---|---|---|---|---|
| **Bc1** | 46 | F | yes | - | - | - | + | >1000 | - |
| **Bc2** | 44 | M | yes | - | - | - | + | >1000 | - |
| **Bc3** | 45 | M | yes | - | - | - | + | 74 | - |
| **Bc4** | 65 | F | yes | - | - | - | + | >1000 | - |
| **Bc5** | 60 | M | yes | - | - | - | + | >1000 | - |
| **Bc6** | 70 | F | yes | - | - | - | + | 52 | - |
| **Bc7** | 66 | M | yes | - | - | - | + | 947 | - |
| **Bc8** | 69 | F | yes | - | - | - | + | 109 | - |

FIG. 6

| mAb # | $V_H$ | $D_H$ | $J_H$ | Subtype | $CDR_H3$ | Length | (+) | (-) | GRAVY | SHM # | SHM % | κ/λ | $V_L$ | $J_L$ | $CDR_L3$ | Length | SHM # | SHM % | Clon. # | Neut | SEQ ID NOs |
|---|---|---|---|---|---|---|---|---|---|---|---|---|---|---|---|---|---|---|---|---|---|
| Bv1.116 | 1-18 | 5-5/-18 | 6 | γ1 | DRDIQLPFGDFYYGMDV | 17 | 1 | 4 | -0.41 | 11 | 3.7 | κ | 4-1 | 1 | QQYYSSPRT | 9 | 5 | 1.8 | 1 | >50 | 287 & 313 |
| Bv1.186 | 3-11 | 6-19 | 1 | γ2 | ATHYKTGWYDENFQH | 15 | 3 | 2 | -1.67 | 19 | 6.5 | λ | 2-14 | 3/2 | SSFRSAPISTV | 11 | 15 | 5.6 | 3 | >50 | 288 & 314 |
| Bv3.205 | 3-21 | 3-10 | 4 | γ3 | ATYTRFGETLGYLDF | 15 | 1 | 2 | -0.13 | 36 | 12.2 | κ | 3-11 | 3 | QHRSNWPP | 8 | 15 | 5.7 | 4 | >50 | 289 & 315 |
| Bv3.219 | 3-30 | 1-26 | 4 | γ1 | VKAEGATTHFFDH | 13 | 3 | 2 | -0.44 | 17 | 5.8 | κ | 4-1 | 2 | QQYYTTPFT | 9 | 7 | 2.5 | 2 | 1.647 | 290 & 316 |
| Bv4.104 | 3-33 | 3-22 | 4 | γ1 | EDYYDSNAFDY | 11 | 0 | 4 | -1.60 | 13 | 4.4 | λ | 2-23 | 3 | CSYAGSSTWL | 10 | 12 | 4.4 | 1 | 1.21E-06 | 57 & 60 |
| Bv4.105 | 3-49 | 3-3 | 4 | γ3 | EGGHSGFWSGFNKIPTFDY | 19 | 2 | 2 | -0.65 | 14 | 9.2 | κ | 1(D)-39 | 3 | QQSYTSPWVT | 10 | 18 | 6.8 | 1 | 2.95E-06 | 237 & 240 |
| Bv4.106 | 1-46 | 3-10/2-21 | 3 | γ1 | ERSIRDLAFDI | 11 | 2 | 3 | -0.26 | 18 | 6.1 | κ | 1-5 | 2 | QQYNSLYT | 8 | 8 | 3.0 | 3 | 1.58E-03 | 291 & 317 |
| Bv4.108 | 3-23 | 6-19/3-16 | 4 | γ2 | GWGGDFGY | 8 | 0 | 1 | -0.56 | 25 | 8.5 | κ | 3-30 | 4 | LQSSHWPLT | 9 | 11 | 3.9 | 4 | >50 | 292 & 318 |
| Bv4.115 | 1-46 | 3-22 | 4 | γ1 | DAGDDTSGPFDS | 12 | 0 | 4 | -1.18 | 34 | 8.2 | κ | 1-5 | 2 | QQYNTFS | 7 | 10 | 3.6 | 1 | 3.87E-06 | 129 & 132 |
| Bv4.164 | 1-2 | 3-22 | 4 | γ1 | LYYDSSDERNYFDY | 14 | 1 | 4 | -1.59 | 4 | 1.4 | κ | 4-1 | 4 | QQYYGSRLS | 9 | 8 | 2.8 | 1 | >50 | 293 & 319 |
| Bv4.169 | 1-18 | 2-2/-21 | 4 | γ2 | DQGTASCYTGH | 11 | 1 | 1 | -0.36 | 14 | 4.8 | κ | 3-15 | 5 | QQYNNWPIT | 9 | 11 | 4.2 | 1 | >50 | 294 & 320 |
| Bv4.189 | 4-34 | 3-10 | 6 | γ3 | IVPGIWRWFYGMDV | 15 | 1 | 1 | 0.87 | 31 | 10.7 | κ | 1-9 | 4 | QQVKSYPLT | 9 | 19 | 7.2 | 1 | >50 | 295 & 321 |
| Bv5.156 | 3-53 | 3-10 | 4 | γ3 | GGTYYSASGSPK | 12 | 1 | 0 | -0.86 | 17 | 5.8 | κ | 1-5 | 2 | QQYNSFPYT | 9 | 12 | 4.5 | 1 | >50 | 296 & 322 |
| Bv6.117 | 1-69 | 3-10 | 4 | γ1 | YSLVRGVTVDY | 11 | 1 | 1 | 0.85 | 16 | 5.4 | λ | 4-60 | 3 | ETWDSNTQV | 9 | 8 | 2.9 | 1 | >50 | 297 & 323 |
| Bv6.172 | 5-10 | 3-8/3-22 | 6 | γ1 | LSTTYPLNYYGMDV | 14 | 0 | 1 | -0.10 | 23 | 7.8 | λ | 1-40 | 3 | QSYDTSLSGWV | 11 | 15 | 5.6 | 1 | 3.06E-06 | 111 & 114 |
| Bv6.232 | 3-33 | 3-10 | 6 | γ3 | PRGRSARGYYHHYGMDV | 17 | 5 | 1 | -1.35 | 10 | 3.4 | λ | 1-40 | 1 | QSYDSSLSGSYV | 12 | 3 | 1.1 | 2 | >50 | 298 & 324 |
| Bv6.250 | 4-30 | 3-3 | 5 | γ1 | GGFTIFGVIIPWFDP | 15 | 0 | 1 | 1.11 | 9 | 3.0 | κ | 3-11 | 2 | QQRSNWPPMYT | 11 | 2 | 0.8 | 2 | >50 | 299 & 325 |
| Bc1.119 | 4-4 | 3-10/6-25 | 4 | γ1 | LGSSVHFYFDS | 11 | 1 | 1 | 0.25 | 32 | 10.9 | λ | 1-44 | 1 | AAWDDSLFAYA | 11 | 13 | 4.9 | 1 | 4.92E+01 | 300 & 326 |
| Bc1.128 | 3-30 | 3-22 | 1 | γ1 | DSNGFGVLS | 9 | 0 | 1 | 0.16 | 19 | 6.5 | κ | 1-17 | 1 | LQHNSFPWT | 9 | 11 | 4.2 | 8 | 5.44E-04 | 183 & 186 |
| Bc1.130 | 4-4 | 6-13 | 4 | γ1 | VRSIPSASYLDF | 12 | 1 | 1 | 0.32 | 16 | 5.4 | λ | 1-47 | 3 | AAWDDRLSGRV | 11 | 11 | 4.1 | 1 | 6.34E-04 | 301 & 327 |
| Bc1.150 | 1-18 | 4-17 | 3 | γ1 | DRNRVTTRHLHHAFDV | 16 | 6 | 2 | -1.14 | 20 | 6.8 | κ | 3-20 | 1 | QQYGSSPWT | 9 | 7 | 2.6 | 1 | 5.42E+01 | 302 & 328 |
| Bc1.156 | 3-30 | 3-10 | 5 | γ1 | ANLPLWFGELDS | 12 | 0 | 2 | 0.15 | 31 | 10.7 | κ | 3-20 | 5 | QQYGSSLVIT | 10 | 16 | 6.0 | 5 | 4.33E-03 | 303 & 329 |
| Bc1.180 | 1-69 | 2-21 | 3 | γ1 | EGDGLDM | 7 | 0 | 3 | -0.80 | 35 | 11.9 | κ | 3-20 | 2 | QQFGSLPYT | 9 | 13 | 4.9 | 2 | 5.00E-08 | 21 & 24 |
| Bc1.187 | 3-33 | 2-2 | 4 | γ1 | DGLYASAPNDV | 11 | 0 | 2 | -0.37 | 27 | 9.2 | κ | 1(D)-33 | 4 | QQTYTLPPN | 9 | 28 | 10.6 | 2 | 5.00E-08 | 3 & 6 |
| Bc1.216 | 3-7 | 6-13/3-22 | 4 | γ2 | GPSGSSGYWALDN | 13 | 0 | 1 | -0.68 | 14 | 4.8 | κ | 4-1 | 2 | QQYYTTTYT | 9 | 7 | 2.5 | 2 | >50 | 304 & 330 |
| Bc1.221 | 3-33 | 6-13/6-25 | 4 | γ1 | DSNGYGLDS | 9 | 0 | 2 | -1.16 | 29 | 10.0 | κ | 1-17 | 1 | LQHNSFPWT | 9 | 6 | 2.3 | 1 | 5.38E+01 | 305 & 186 |
| Bc1.229 | 3-33 | 4-17 | 4 | γ1 | EGLTSVTMLDS | 11 | 0 | 2 | 0.30 | 15 | 5.1 | κ | 1(D)-33 | 3 | QQSYSTPLFT | 10 | 12 | 4.5 | 8 | 2.53E-05 | 147 & 150 |
| Bc1.263 | 1-69 | 5-5/-18 | 4 | γ1 | DRGGKPLYSYGYGLDY | 16 | 2 | 2 | -1.06 | 9 | 3.1 | κ | 3-11 | 1 | QQRSTT | 6 | 5 | 1.9 | 8 | 3.96E-06 | 219 & 222 |
| Bc2.150 | 3-15 | 2-2 | 5 | γ2 | AFLLSSSWPTDNWFHP | 16 | 1 | 1 | -0.21 | 14 | 4.7 | λ | 2-11 | 3/2 | SSYAGSYTFVV | 11 | 15 | 5.6 | 1 | >50 | 306 & 331 |
| Bc2.298 | 1-2 | 3-10 | 3 | γ1 | SQDNLWFGAFGGGSFDI | 17 | 0 | 2 | 0.02 | 21 | 7.1 | κ | 1-9 | 3 | QQKRT | 5 | 1 | 0.4 | 1 | 6.65E-01 | 307 & 332 |
| Bc3.106 | 3-23 | 1-1 | 6 | γ3 | DPGHTSNWRDNYQYYGMDV | 19 | 2 | 3 | -1.81 | 9 | 3.1 | κ | 1-17 | 1 | LQHNSYPRT | 9 | 0 | 0.0 | 1 | 1.39E-07 | 39 & 42 |
| Bc3.136 | 3-48 | 2-2 | 3 | γ2 | DLAMPRWFFNL | 11 | 1 | 1 | 0.26 | 15 | 5.1 | κ | 3-20 | 4 | QQYGSSPLA | 9 | 13 | 4.9 | 2 | 1.96E+00 | 308 & 333 |
| Bc4.159 | 1-2 | 3-22 | 6 | γ1 | VVRAVTNYYYYYYYMDV | 17 | 1 | 1 | -0.05 | 27 | 9.2 | κ | 3-20 | 4 | HQYGYSSGS | 9 | 14 | 5.2 | 2 | 2.03E-01 | 309 & 334 |
| Bc4.178 | 1-69 | 7-27 | 4 | γ1 | GHWGQFDS | 8 | 1 | 1 | -1.24 | 44 | 15.0 | κ | 3D-15 | 4 | QYYNNWPLG | 9 | 26 | 9.8 | 1 | 1.94E-03 | 310 & 335 |
| Bc4.194 | 3-11 | 3-3 | 4 | γ3 | SPEAPRLLRFLQWLYFDY | 18 | 2 | 2 | -0.24 | 39 | 13.4 | κ | 1(D)-39 | 5 | QQSYSFPIT | 9 | 36 | 13.6 | 13 | 1.47E-02 | 311 & 336 |
| Bc4.196 | 3-30 | 3-3 | 5 | γ1 | DQAATFWSAYFRNWFDP | 17 | 1 | 2 | -0.64 | 12 | 4.1 | κ | 3-15 | 1 | QQYNNWPPSWT | 11 | 3 | 1.1 | 2 | 1.04E+01 | 312 & 337 |
| Bc4.204 | 3-33 | 2-2 | 6 | γ3 | GGAEESTNWRFLWVPRYYYYMDV | 23 | 2 | 3 | -0.66 | 28 | 9.5 | λ | 2-11 | 3/2 | CSYAGSFNLV | 10 | 21 | 7.8 | 4 | 2.29E-04 | 201 & 204 |

FIG. 7A

| mAb # | $V_H$ | $D_H$ | $J_H$ | Subtype | $CDR_H3$ | Length | (+) | (-) | GRAVY | SHM # | SHM % | κ/λ | $V_L$ | $J_L$ | $CDR_L3$ | Length | SHM # | SHM % | Clon. # | Neut | SEQ ID NOs |
|---|---|---|---|---|---|---|---|---|---|---|---|---|---|---|---|---|---|---|---|---|---|
| Bc4.235 | 4-31 | 6-19 | 4 | γ2 | VKWLVTTYYFDS | 12 | 1 | 1 | 0.16 | 19 | 6.4 | λ | 2-11 | 3/2 | CSYAGPYNLGL | 11 | 17 | 6.3 | 3 | 6.90E-03 | 370 & 403 |
| Bc4.236 | 1-18 | 5-24 | 6 | γ3 | ESRSRLQLWLRTYYNYYMGV | 20 | 3 | 1 | -0.77 | 49 | 16.7 | κ | 1-27 | 4 | QQYHSAPALS | 10 | 23 | 8.7 | 9 | 7.43E-04 | 371 & 404 |
| Bc5.108 | 3-15 | 3-3 | 4 | γ3 | DGGRGFFEWTYEY | 13 | 1 | 3 | -1.14 | 21 | 7.0 | λ | 1-51 | 3/2 | GTWDNSLRGVV | 11 | 21 | 7.9 | 1 | 1.70E+01 | 372 & 405 |
| Bc5.115 | 3-33 | 3-16 | 6 | γ1 | DFGVWGNYYNYYGMDV | 16 | 0 | 3 | -0.61 | 9 | 3.1 | κ | 4-1 | 3 | QQYYGAPLT | 9 | 7 | 2.6 | 5 | >50 | 373 & 406 |
| Bc5.183 | 3-33 | 2-8 | 6 | γ1 | DHAQTWWNHYYHYYGMDV | 18 | 3 | 2 | -1.32 | 14 | 4.8 | λ | 7-43 | 3 | LLYYGGSWV | 9 | 14 | 5.2 | 1 | 5.96E+00 | 374 & 407 |
| Bc6.125 | 1-69 | 3-9 | 4 | γ1 | ASQPGNNVVLRYSDWLLRPLDY | 22 | 2 | 2 | -0.45 | 23 | 7.8 | κ | 1(D)-33 | 4 | QQYAILPLT | 9 | 17 | 6.4 | 6 | 2.8E+01 | 375 & 408 |
| Bc6.132 | 3-43D | 3-16 | 4 | γ1 | DMGGSFRLMDY | 11 | 1 | 2 | -0.36 | 11 | 3.7 | κ | 1-16 | 4 | QQYSSYPLT | 9 | 3 | 1.1 | 1 | >50 | 376 & 409 |
| Bc6.149 | 4-59 | 3-3 | 5 | γ1 | DKGTLWSGYQNWIDP | 15 | 1 | 2 | -1.11 | 19 | 6.5 | κ | 1(D)-39 | 4 | QQSHSFPLT | 9 | 16 | 6.1 | 1 | 3.2E-02 | 377 & 410 |
| Bc6.162 | 1-69 | 3-10 | 5 | γ1 | GYYGSGSYFASGNNWFDP | 18 | 0 | 1 | -0.75 | 11 | 3.7 | λ | 2-11 | 1 | CSYAGSFTYV | 10 | 2 | 0.7 | 2 | >50 | 378 & 411 |
| Bc6.176 | 4-59 | 2-8 | 5 | γ2 | YTDCTTTSCFSNWFDP | 16 | 0 | 2 | -0.51 | 18 | 6.2 | λ | 2-11 | 3/2 | CSYAGSDTFVV | 11 | 13 | 4.8 | 2 | 1.7E+01 | 379 & 412 |
| Bc6.182 | 4-39 | 3-22 | 6 | γ1 | DRRYYDSGGYPSGGMDV | 17 | 2 | 3 | -1.30 | 21 | 7.1 | κ | 3-15 | 2 | QQYNNWPRT | 9 | 7 | 2.7 | 26 | >50 | 380 & 413 |
| Bc6.208 | 5-10 | 1-14/-20/-7 | 4 | γ1 | RGYNTGWGQDY | 11 | 1 | 1 | -1.85 | 17 | 5.8 | λ | 1-44 | 3 | VAWDDSLNVV | 10 | 11 | 4.1 | 2 | 3.0E-01 | 381 & 414 |
| Bc6.235 | 1-69 | 3-10 | 4 | γ1 | TLVAGFDN | 8 | 0 | 1 | 0.56 | 19 | 6.5 | κ | 4-1 | 2 | QQFYSSPQT | 9 | 16 | 5.7 | 2 | 6.4E+00 | 382 & 415 |
| Bc6.259 | 3-30 | 5-12 | 6 | γ2 | DRVDKVTTSHDAYYGLDV | 18 | 3 | 4 | -0.70 | 16 | 5.5 | κ | 1-9 | 1 | QQVNFYPPWP | 10 | 11 | 4.2 | 2 | >50 | 383 & 416 |
| Bc6.286 | 4-59 | 5-19/-13/-25 | 4 | γ1 | GLYSFYDD | 8 | 0 | 2 | -0.53 | 24 | 8.2 | λ | 1-51 | 3 | GTWDSSLSEPWV | 12 | 6 | 2.2 | 6 | >50 | 384 & 417 |
| Bc6.295 | 7-4 | 3-9 | 6 | γ1 | EGLPYFDSSTYYYNGLDV | 18 | 0 | 3 | -0.52 | 21 | 7.2 | λ | 1-44 | 3/2 | AAWDDSLNGRNVV | 13 | 9 | 3.4 | 1 | >50 | 385 & 418 |
| Bc6.316 | 1-69 | 3-9 | 4 | γ1 | SKAPDSTYVLRYIDWYLPPDF | 21 | 2 | 3 | -0.47 | 39 | 13.3 | κ | 4-1 | 1 | QQYSTTPQT | 9 | 17 | 5.7 | 2 | 2.8E+01 | 386 & 419 |
| Bc6.356 | 4-39 | 2-2 | 4 | γ1 | VGYCSSTSCHGPIFDY | 16 | 1 | 1 | 0.11 | 0 | 0.0 | λ | 1-47 | 3 | AAWDDSLSGWV | 11 | 3 | 1.1 | 3 | >50 | 387 & 420 |
| Bc7.123 | 3-7 | 2-2/-15 | 4 | γ2 | YCSYNCPGPLDY | 12 | 0 | 1 | -0.54 | 14 | 4.8 | κ | 3-15 | 1 | QQYNQWPRT | 9 | 7 | 2.7 | 1 | >50 | 388 & 421 |
| Bc7.169 | 1-69 | 3-9 | 4 | γ3 | GLTSADY | 7 | 0 | 1 | -0.16 | 0 | 0.0 | κ | 1-5 | 1 | QQYNSYSTWT | 10 | 0 | 0.0 | 2 | 6.9E-01 | 389 & 422 |
| Bc7.215 | 3-7 | 3-3 | 4 | γ3 | DHRSRFLEWLLYHYFDY | 17 | 4 | 3 | -0.85 | 22 | 7.5 | κ | 3-15 | 4 | QQYNHWPLT | 9 | 19 | 7.2 | 6 | >50 | 390 & 423 |
| Bc7.226 | 3-23 | 3-10/-3 | 4 | γ2 | DVFAWSFDY | 9 | 0 | 2 | 0.18 | 37 | 12.6 | κ | 3-11 | 4 | QQGYSWPLS | 9 | 17 | 6.4 | 6 | 5.29E-01 | 391 & 424 |
| Bc7.253 | 1-8 | 3-10 | 4 | γ1 | GRGGSGSYSPFDY | 13 | 1 | 1 | -1.03 | 3 | 1.0 | κ | 4-1 | 3 | QQYYRTPFT | 9 | 5 | 1.7 | 2 | 4.6E+01 | 392 & 425 |
| Bc7.296 | 1-18 | 3-3 | 6 | γ4 | GSGSFWSGIGYYYYYSMNV | 19 | 0 | 0 | -0.12 | 24 | 8.2 | κ | 4-1 | 2 | QQYYSTLYT | 9 | 13 | 4.6 | 17 | 1.2E+01 | 393 & 426 |
| Bc7.323 | 4-39 | 3-9 | 3 | γ3 | GAPRYFDWLFRDAFDI | 16 | 2 | 3 | -0.21 | 9 | 3.0 | λ | 7-43 | 3/2 | LLYYGGAQLV | 10 | 8 | 3.0 | 1 | >50 | 394 & 427 |
| Bc8.104 | 1-69 | 6-13 | 3 | γ3 | QGSSTWFATLYAFPI | 15 | 0 | 0 | 0.45 | 16 | 5.4 | κ | 3-20 | 1 | HQYGSSPPT | 9 | 11 | 4.1 | 1 | 2.61E-06 | 93 & 96 |
| Bc8.109 | 3-30 | 2-8 | 4 | γ1 | LYCTGGTCYA | 10 | 0 | 0 | 0.58 | 16 | 5.5 | κ | 2(D)-28 | 2 | MQTLQMYT | 8 | 6 | 2.2 | 2 | 4.64E-03 | 395 & 428 |
| Bc8.111 | 3-23 | 6-6/-13 | 4 | γ1 | DPYMVAAVARTVDY | 14 | 1 | 2 | 0.25 | 12 | 4.1 | λ | 6-57 | 3 | QSYESSNWV | 9 | 12 | 3.0 | 1 | 2.51E-06 | 396 & 78 |
| Bc8.113 | 3-30 | 6-19 | 4 | γ1 | KATLAGTDGGYFDY | 14 | 1 | 3 | -0.43 | 26 | 8.9 | λ | 3-21 | 3/2 | QVWDSDSDHVV | 11 | 19 | 7.3 | 7 | 3.04E-02 | 397 & 429 |
| Bc8.138 | 3-21 | 4-11/-4 | 4 | γ1 | GIEGYNYSRYFDF | 13 | 1 | 2 | -0.80 | 21 | 7.1 | λ | 2-14 | 3 | SSYTLTSDRKTTTLV | 15 | 14 | 5.2 | 1 | >50 | 398 & 430 |
| Bc8.148 | 3-20 | 2-2 | 5 | γ1 | DLDSSTYWGNWFDP | 14 | 0 | 3 | -1.06 | 17 | 5.8 | κ | 2(D)-28 | 5 | MQALQTPIT | 9 | 7 | 2.5 | 2 | 3.76E+00 | 399 & 431 |
| Bc8.159 | 4-4 | 3-10/-22 | 4 | γ1 | GRLGITRDRYYFDS | 14 | 3 | 2 | -1.02 | 16 | 5.4 | κ | 1(D)-33 | 2 | QQYYNLPHT | 9 | 11 | 4.2 | 3 | 5.28E-05 | 165 & 168 |
| Bc8.176 | 4-4 | 1-7 | 4 | γ1 | NRLGTTRDRYYFDY | 14 | 3 | 2 | -1.65 | 18 | 6.1 | κ | 1(D)-33 | 1 | QQYHSLPLT | 9 | 11 | 4.2 | 1 | 2.03E+00 | 400 & 432 |
| Bc8.186 | 3-33 | 5-5/-18 | 4 | γ1 | EGHTAMATLDY | 11 | 1 | 2 | -0.36 | 8 | 2.7 | κ | 1(D)-39 | 4 | QQSYSMPKLT | 10 | 20 | 6.4 | 2 | 3.75E-01 | 401 & 433 |
| Bc8.260 | 4-34 | 5-12 | 1 | γ1 | TGPPFSKWLHMAGEKYFHF | 19 | 4 | 1 | -0.50 | 13 | 4.5 | κ | 4-1 | 2 | QQYYSTPYT | 9 | 12 | 4.3 | 2 | >50 | 402 & 286 |

(-) and (+) indicate the numbers of negatively and positively charged amminoacids in the IgH complementary determining region (CDR3), respectively.
SHM indicate the total number and frequency of somatic hypermutations in the VH and VL Ig genes. *Given as μg/ml.

FIG. 7B

ANTI-HBV ANTIBODIES AND METHODS OF USE

CROSS REFERENCE TO RELATED APPLICATIONS

This application is a national stage application under 35 U.S.C. § 371 of International Application No. PCT/EP2021/065260, filed internationally on Jun. 8, 2021, which claims priority benefit of European Patent Application No. 20305612.2, filed on Jun. 8, 2020, the disclosures of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 008318008_ST25 June 2026.TXT, date recorded: Jun. 4, 2026, size: 292, 142 bytes).

TECHNICAL FIELD

The present invention relates to antibodies against the hepatitis B virus (HBV) and methods of using the same.

BACKGROUND

Chronic hepatitis B virus (HBV) infection is a major healthcare problem affecting more than 250 million people worldwide despite the availability of effective vaccines (WHO, 2017). The infection accounts for approximately 1 million deaths per year due to HBV-associated cirrhosis, liver failure, and hepatocellular carcinoma (WHO, 2017). HBV is a DNA virus belonging to the Hepadnaviridae family, which is produced as infectious virions or Dane particles, but also as non-infectious subviral particles (Seeger et al., 2013). Virions and subviral particles display at their surface three forms of HBV envelope glycoproteins or HBV surface antigens (HBsAg): the L-HBs (large), the M-HBs (middle) and the S-HBs (small). Defective particles outnumbering infectious HBV virions are therefore acting as immune decoys (Seeger et al., 2013). Current therapies for treating chronic HBV rarely achieve functional cure as defined by HBsAg loss and anti-HBs antibody seroconversion. Yet, HBV infection can be successfully controlled by natural immune responses in more than 90% of the patients infected as adults, and in the ~1% of chronically infected patients who spontaneously clear the infection called HBV seroconverters or natural controllers (Bauer et al., 2011; Chu and Liaw, 2016; McMahon, 2009; Rehermann and Nascimbeni, 2005). Robust and multispecific HBV-specific $CD4^+$ and $CD8^+$ T cell responses are key immune effectors in controlling the infection (Bauer et al., 2011). However, B cells and the antibodies are also instrumental for the long-term clearance and protection from viral rebound after functional cure (Bertoletti and Ferrari, 2016; Corti et al., 2018; Rehermann and Nascimbeni, 2005). For instance, despite that $HBsAg^-$/anti-$HBs^+$ antibody seroconversion in patients is correlated with an undetectable level of HBV DNA (McMahon, 2009), functionally cured individuals undergoing B cell depletion therapy to treat Non-Hodgkin Lymphoma have a higher risk of HBV reactivation, which can quickly lead to severe liver dysfunction (Kusumoto et al., 2019; Perrillo et al., 2015). Hence, key immune components to control and eventually eliminate HBV infection likely include a broad and robust antigen-specific T cell response, as well as the development of neutralizing anti-HBs antibodies mediating HBsAg clearance and lifelong protective immunity (Bertoletti and Ferrari, 2016; Corti et al., 2018).

Neutralizing antibodies produced in response to HBV infection target all 3 HBsAg forms. They recognize either the S-HBs antigenic loop and interfere with the pre-attachment to heparane sulfate proteoglycans (HS) on hepatocytes, or the preS1 domain of the L-HBs and block the binding to the host cellular receptor, the sodium taurocholate co-transporting polypeptide (NTCP) (Corti et al., 2018). IgG antibodies against the "a determinant" part of the S-HBs loop induced by HBV vaccination (based on recombinant S-HBs immunogens), or administrated to individuals at risk of exposure by polyclonal HBV immunoglobulin infusions confer protection against HBV infection (Samuel et al., 1993; West and Calandra, 1996). Several neutralizing anti-preS and anti-S-HBs antibodies have been isolated from immunized mice and from few human immune donors (Corti et al., 2018). S-HBs neutralizing antibodies may contribute to the viral clearance and long-term suppression in HBV seroconverters as they do for protecting vaccinees from infection. However, no studies have been performed on the memory B-cell response to HBV in functionally cured HBV-infected individuals by cloning and charactering human HBsAg-specific antibodies.

SUMMARY

The invention provides anti-S-HBs antibodies and methods of using the same.

BRIEF DESCRIPTION OF THE FIGURES

(FIG. 1A) Average S-HBsAg-reactivity of serum IgGs from HBV vaccinees (HBVv, n=6, bottom curve) and controllers (HBVc, n=8, top curve). Shaded regions indicate value ranges. Representative flow-cytometry plots showing S-HBs-binding $IgG^+$ memory B cells in HBV vaccinees and controllers (Bv4 and Bc3 are shown). nS-HBsAg and rS-HBsAg are human-derived native and recombinant S-HBs antigens, respectively.

(FIG. 1B) S-HBsAg-ELISA reactivities of S-HBsAg-captured $IgG^+$ memory B-cell antibodies (left) and percentage of S-HBs-specific monoclonal antibodies (% S-$HBsAg^+$) isolated from HBVv and HBVc (right). % S-$HBsAg^+$ according to S-HBs antibody titers in HBVc (<150 and >900 IU/ml) are indicated. capt-rHBAgs, rHBAgs capture ELISA.

(FIG. 1C) Bubble plot showing the level of clonal expansions according to percentages of somatic mutations in the IgH and IgL chain variable domains of S-HBs-specific IgG antibodies. The size of the expansions for each donor is indicated in the bar graph below.

(FIG. 1D) Volcano plot analysis comparing the immunoglobulin (Ig) gene repertoire of S-HBsAg-specific B cells from HBV immune donors and IgG memory B cells from healthy individuals (Top). Dots above the dashed line indicate statistically significant differences between both Ig gene repertoires. Comparison of the $V_H(D_H)J_H$ rearrangement frequencies are shown (Bottom). pV, p-value; FC, fold changes.

(FIG. 1E) Distribution of conformational-dependent vs non-conformational antibodies among S-HBs memory IgGs.

Total number of tested antibodies is indicated in the center of the pie chart. Infrared immunoblot shows anti-S-HBs IgG memory B-cell antibodies reactive against denatured S-HBs protein (top right). ELISA binding curves of peptide-reactive S-HBs antibodies are shown (bottom right, mean of quadruplicates±SD).

FIG. 2A-2F. Neutralizing activity of human S-HBs memory antibodies.

(FIG. 2A) Neutralizing activity of S-HBs IgG antibodies against in vitro infection of HepaRG cells by genotype D HBV. Fifty percent inhibitory concentration ($IC_{50}$) values for each antibody (n=72) (Top left), and distribution of neutralizing vs non-active antibodies (Bottom left) are shown.

(FIG. 2B) Neutralization capacity according to bound S-HBs antigens (Top right) and percentage of somatic hypermutations (% SHM) (Bottom right) are indicated.

(FIG. 2C) In vitro neutralizing activity of selected S-HBs IgG antibodies against HDV using HDV RNA quantification in HepaRG cells by northern blotting. ge, genome equivalents.

(FIG. 2D) In vivo neutralization activity of human S-HBs antibodies in AAV-HBV-transduced mice. Circulating blood S-HBs levels were monitored in AAV-HBV-transduced mice treated once i.v. with 0.5 mg of anti-S-HBs antibodies PIBv4.104 (n=9), Bc1.187 (n=9), Bc1.263 (n=6), Bc4.204 (n=4) or mGO53 isotype control (n=5). Thick lines represent the average values.

(FIG. 2E) Logic changes of S-HBs titers at nadir (day post-injection 2, dpi2) upon antibody administration of 0.25 mg (white) and 0.5 mg (black) per mouse are shown. Means are indicated with lines.

(FIG. 2F) Circulating blood S-HBs and HBV DNA levels were monitored in AAV-HBV-transduced mice (n=6) injected once i.v. with 1 mg of the anti-S-HBs antibody Bc1.187. Average $\log_{10}$ changes overtime of S-HBs and HBV DNA levels are shown on the right.

FIG. 3A-3E. Cross-reactivity of human HBV neutralizing antibodies.

Figure 14:
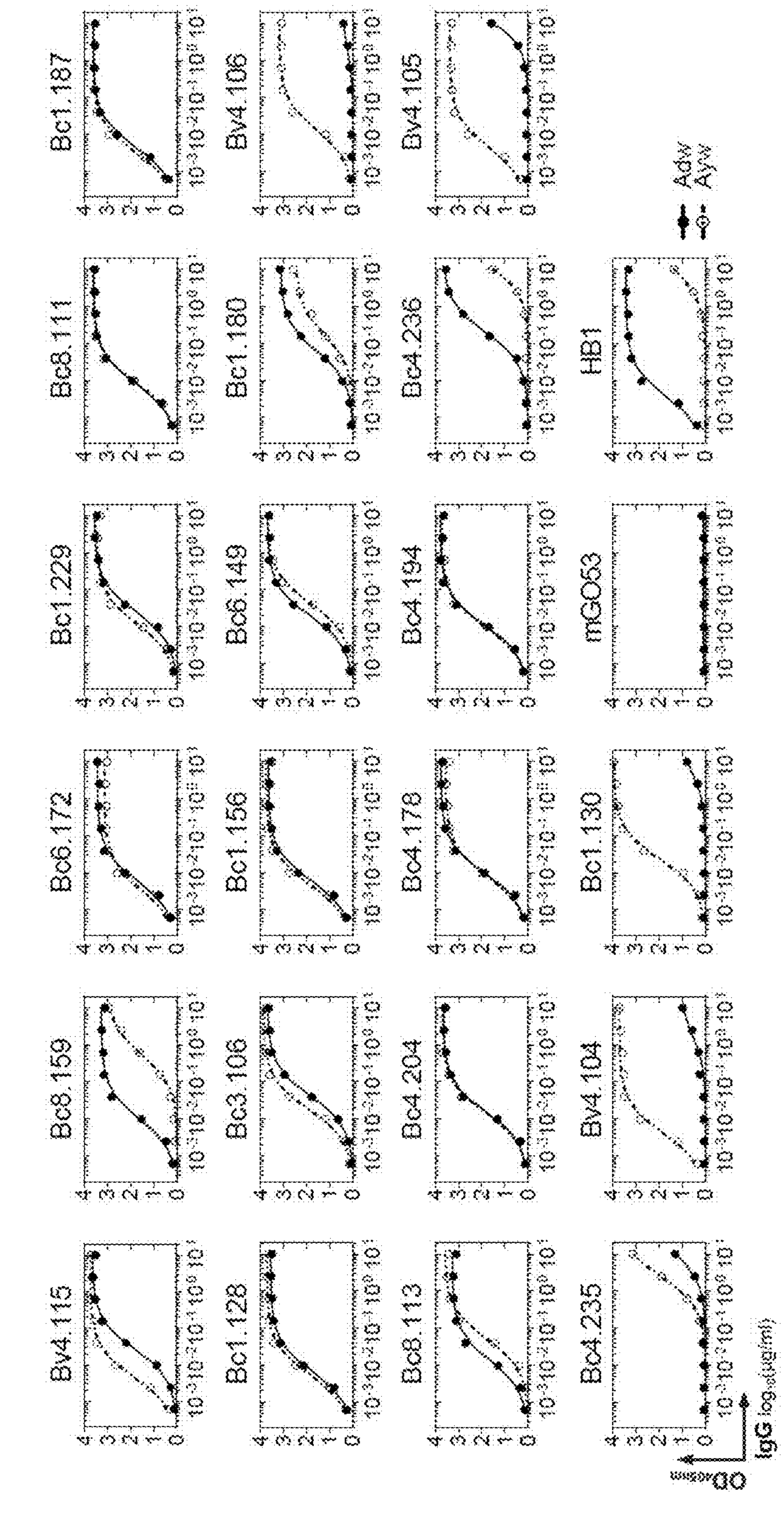

(FIG. 3A) Heat map comparing the ELISA reactivity of HBV neutralizing antibodies against Adw and Ayw genotype D S-HBs proteins (measured as AUC values from FIG. 14). Representative ELISA graphs on the right show the reactivity of selected antibodies against recombinant HBV vaccines Engerix-B (Ayw) and GenHevac (Adw). Error bars indicate the SD of assay duplicates.

(FIG. 3B) Heat map comparing the reactivity of HBV neutralizing antibodies against S-HBs antigens from genotypes depicted in the phylogenic tree (Top left), as % of bound S-HBS-expressing cells determined by flow cytometry. Data represent one of two independent experiments. HB1 and mGO53 are positive and negative controls, respectively. Cytograms in the bottom left shows a representative reactivity profile of HB1 antibody. ELISA graphs on the right show the reactivity of selected antibodies against recombinant S-HBs antigens from all genotypes but G. Error bars indicate the SD of assay duplicates.

(FIG. 3C) Same as in (FIG. 3B) but for S-HBs mutant proteins depicted on the diagram in the top left.

(FIG. 3D) Graph comparing the neutralizing activity of Bc1.187 against infection of primary human hepatocytes by HBV viruses from A to D genotypes. Error bars indicate the SEM of assay triplicates.

(FIG. 3E) Graphs show neutralization curves of HBV viruses from genotype A, C and D by PIBv4.104 and Bc1.187 as determined by the HepaRG neutralization assay. Error bars indicate the SEM of assay triplicates.

FIG. 4A-4E. Binding features of human HBV neutralizing antibodies.

(FIG. 4A) Heat map shows the ELISA binding of selected HBV neutralizing antibodies to recombinant HBsAg mutant proteins. Color value is proportional to the reactivity level.

(FIG. 4B) Heatmap showing competition for S-HBs binding of the HBV neutralizing antibodies. Lighter colors indicate stronger inhibition; black indicates no competition.

(FIG. 4C) Graphs comparing binding to S-HBs of the selected HBV neutralizing antibodies and their germline counterparts as measured by flow cytometry (top) and ELISA (bottom).

(FIG. 4D) Neutralizing activity of the germline versions of Bc1.187, Bc4.204 and PIBv4.104 against genotype D HBV viruses as determined by the HepaRG neutralization assay. Error bars indicate the SD of assay triplicates.

(FIG. 4E) Reactivity profile of selected S-HBs human antibodies on human protein microarrays. Each spot correspond to the z-scores given on a single protein by the reference (Ref: mGO53, y axis) and test antibody (x axis). Labels indicate immunoreactive proteins (z>5).

Figure 5A:
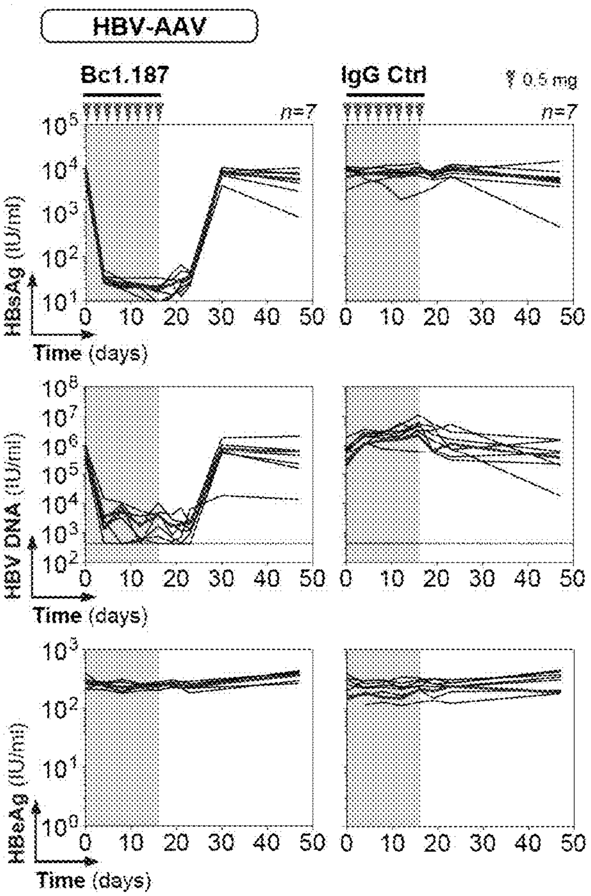
Figure 5B:
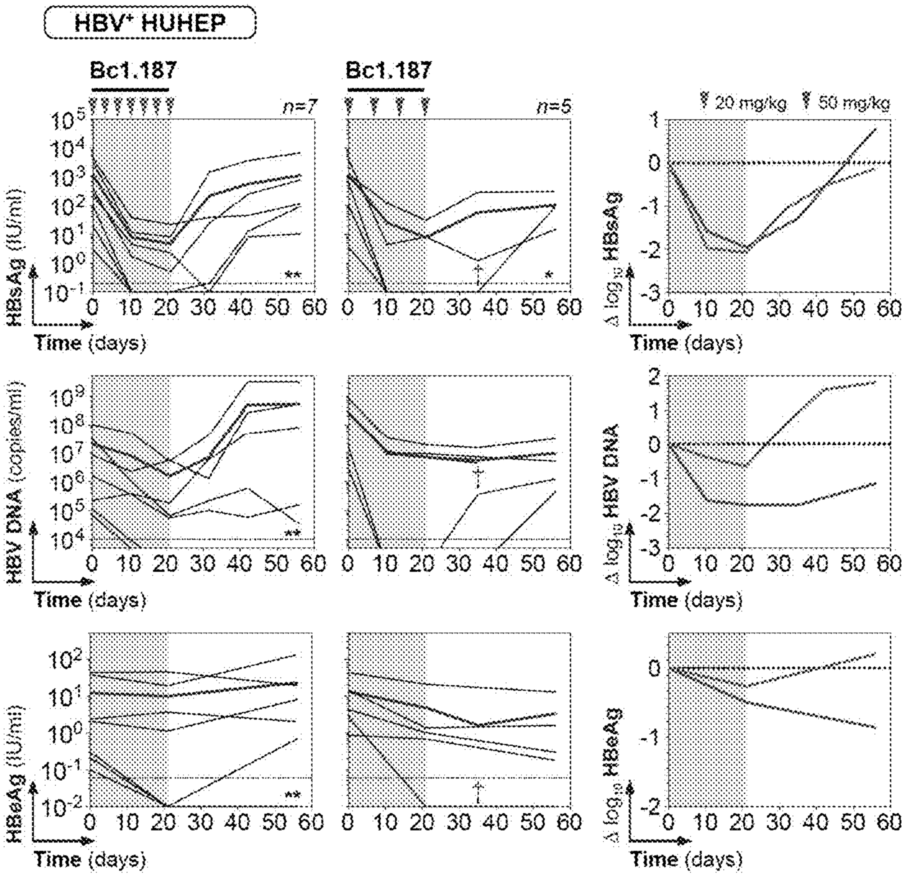

FIG. 5A-5B. In vivo therapy with potent HBV cross-neutralizing antibody Bc1.187.

(FIG. 5A) Evolution of HBV infection overtime in AAV-HBV-transduced mice (n=7 per group) treated every 2 days for 16 days with 0.5 mg i.v. of anti-S-HBs Bc1.187 or isotype control mGO53 chimeric antibody. Circulating blood HBsAg, HBeAg and HBV DNA levels are shown. Thick lines indicate the averages.

(FIG. 5B) Evolution of HBV infection overtime in HUHEP mice receiving weekly i.p. injections of human anti-S-HBs antibody Bc1.187 (20 mg/kg~0.4 mg, n=7, straight lines; 50 mg/kg~1 mg, n=5, dotted lines) for 3 weeks. Circulating blood HBsAg, HBeAg and HBV DNA levels (left) and $\Delta \log_{10}$ values compared to baseline (right) are shown. Thick lines indicate the averages.

FIG. 6. Table showing clinical and immunovirological characteristics of the HBV immune donors.

FIG. 7A (SEQ ID NOs: 287-290, 57, 237, 291-292, 129, 293-297, 111, 298-300, 183, 301-303, 21, 3, 304-305, 147, 219, 306-307, 39, 308-312, 201, 313-316, 60, 240, 317-318, 132, 319-323, 114, 324-326, 186, 327-329, 24, 6, 330, 186, 150, 222, 331-332, 42, 333-337 and 204)) and FIG. 7B. (SEQ ID NOs: 370-394, 93, 395-399, 165, 400-427, 96, 428, 78, 429-431, 168, 432-433 and 286) Table showing Immunoglobulin gene repertoire and neutralizing activity of human anti-S-HBs antibodies.

Figure 8A:
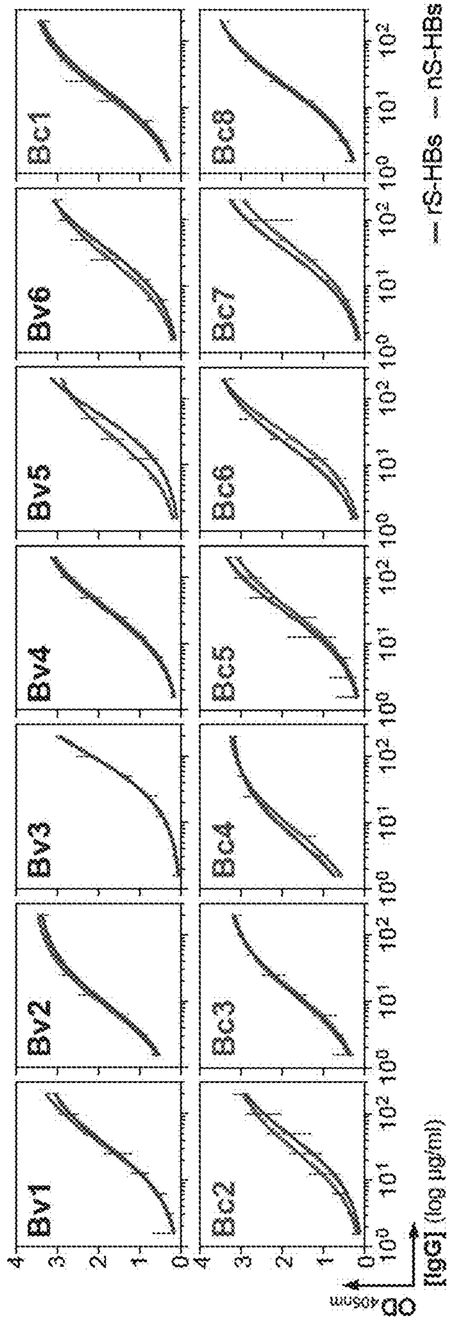
Figure 8B:
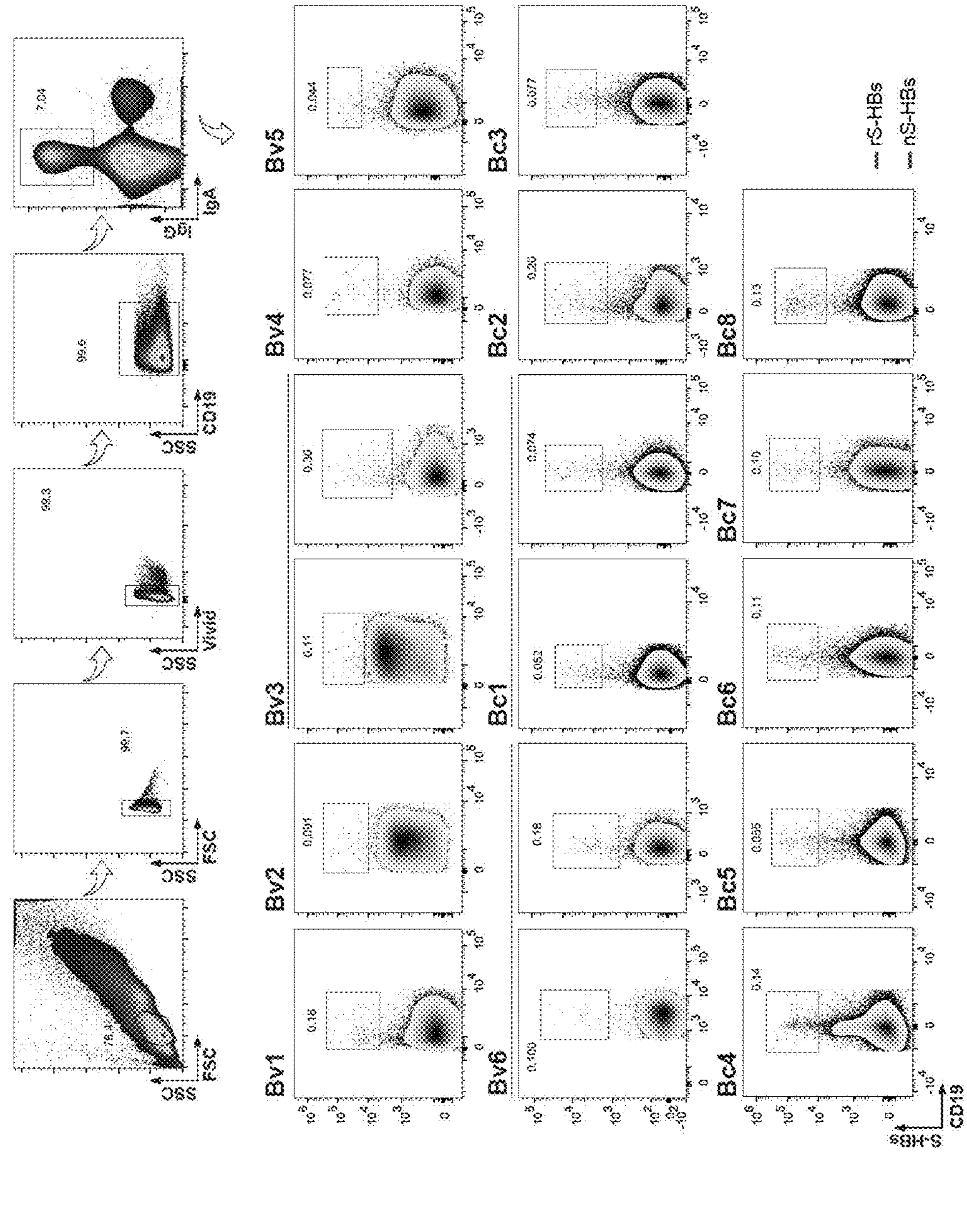

FIG. 8A-8B. Binding of purified serum IgGs and blood IgG+ memory B cells to S-HBs antigens.

(FIG. 8A) Representative ELISA graphs showing the reactivity of purified serum IgG antibodies from HBV vaccinees (HBVv) and controllers (HBVc) against recombinant (rS-HBs) and human-derived native (nS-HBs) S-HBs particles. Error bars indicate the SEM of duplicate values. (FIG. 8B) Flow cytometric cytograms showing the gating strategy used to single-cell sort IgG+ memory B cells binding to fluorescently labeled rS-HBs and nS-HBs proteins used as baits. The S-HBS-reactive IgG+ memory B-cell population is shown for all donors.

Figure 9A:
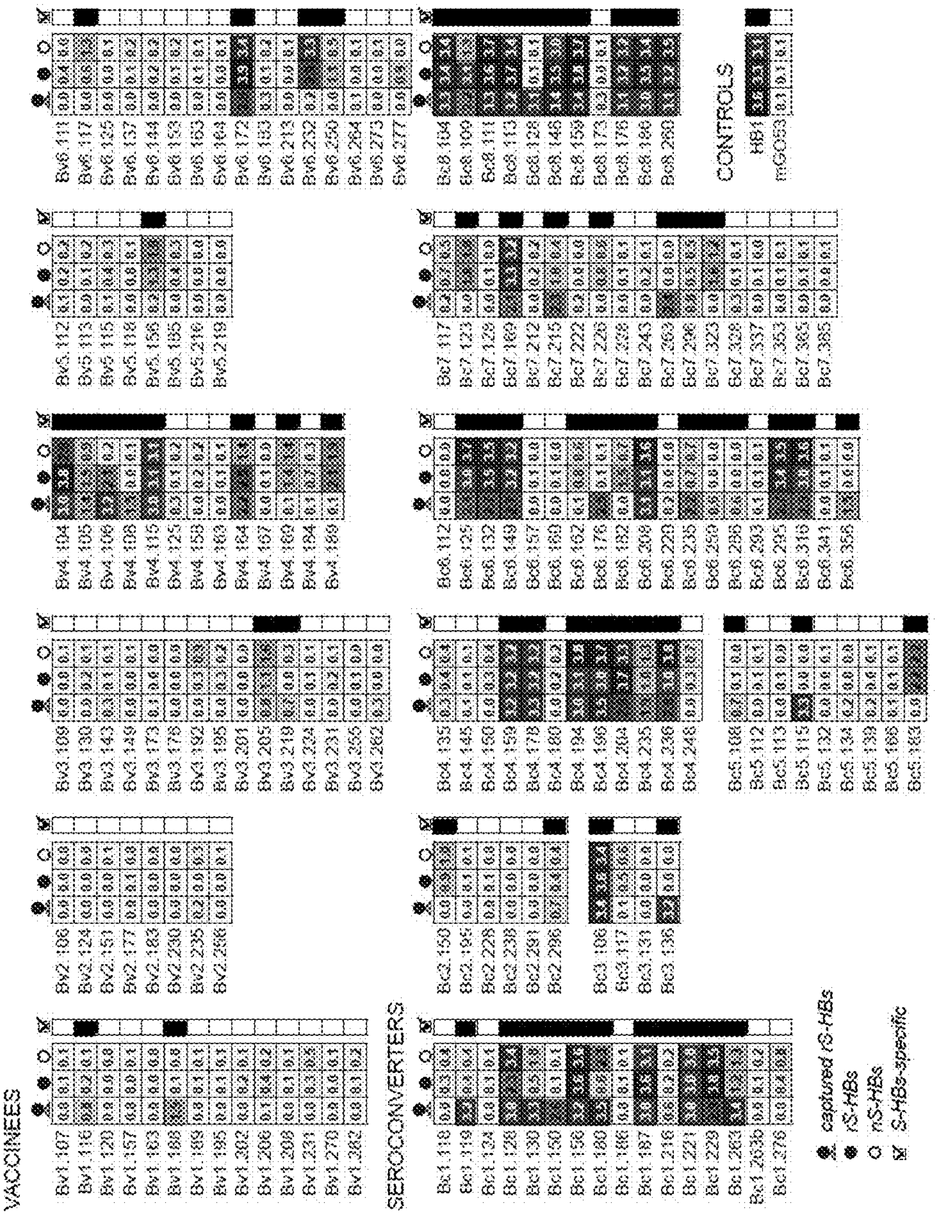
Figure 9B:
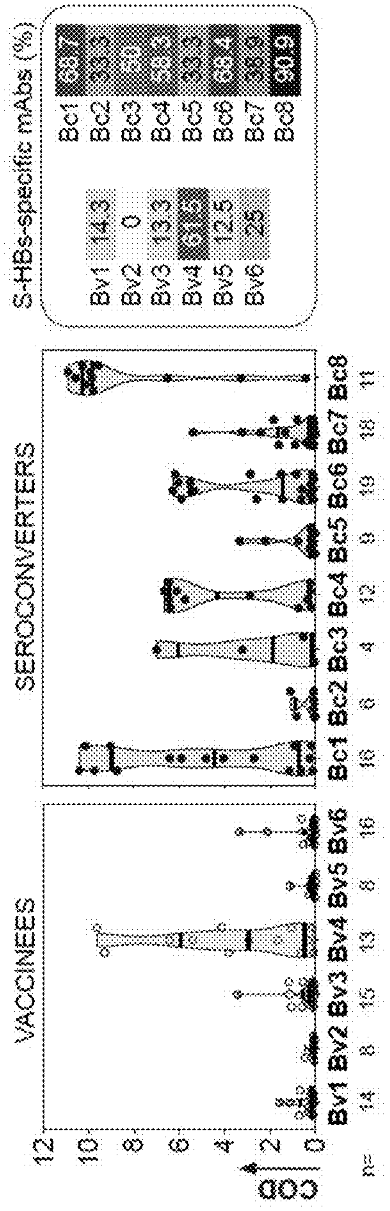

FIG. 9A-9B. S-HBs reactivity of S-HBs-captured IgG+ memory B-cell antibodies.

(FIG. 9A) Heatmap showing the ELISA reactivity against nS-HBs and rS-HBs (immobilized and captured) of S-HBs-binding memory antibodies cloned from HBV vaccinees and seroconverters. Mean of triplicate optical density values are shown. (FIG. 9B) Violin plots showing the cumulative ELISA optical density (COD) values for the bindings shown in (A). The proportion of S-HBs-specific antibodies cloned from S-HBs-captured IgG+ memory B cells is shown per donor (Right).

FIG. 10A-10H. Immunoglobulin gene repertoire of S-HBs-specific IgG+ memory B-cells.

(FIG. 10A) Pie charts comparing the distribution of VH/JH gene usage of blood S-HBs-specific IgG+ memory B cells and IgG+ memory B cells from healthy individuals (IgG.mB) (Prigent et al., 2016). The number of antibody sequences analyzed is indicated in the center of each pie chart.

(FIG. 10B) Bar graph comparing the distribution of single immunoglobulin VH genes expressed by S-HBs-specific and control IgG+ memory B cells. (FIG. 10C) (SEQ ID NOs: 338-339, 218, 340-342, 92, 343-344, 20 and 345) Amino acid alignment of the CDRH2 region (defined by Kabat) of VH1-69-expressing S-HBs antibodies. Residues in grey indicate substitutions compared to the germline VH gene (on the top). (FIG. 10D) Same as (B) but for IgG subtypes (Left) and κ- vs λ-Ig chain usage (Right). (FIG. 10E) Same as (B) but for the CDRH3 lengths and positive charge numbers. The average of CDRH3 lengths is indicated below each histogram. (FIG. 10F) Same as (A) but for Vκ/Jκ and Vλ/Jλ gene usages. (FIG. 10G) Violin plots comparing the number of mutations in VH, Vκ and Vλ genes in S-HBs-specific and control IgG+ memory B cells. The average number of mutations (mut.) is indicated below each dot plot. Numbers of mutations were compared across groups of antibodies using unpaired student t-test with Welch's correction. (FIG. 10H) Graphs showing the Bayesian estimation of antigen-driven selection based on anti-S-HBs IgH and IgL sequences. Groups were compared (in A, B, D, E, and F) using 2× 2 and 2× 5 Fisher's Exact tests.

Figure 11A:
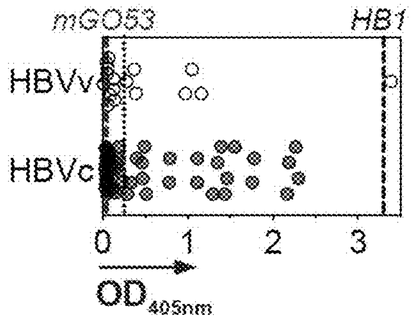
Figure 11B:
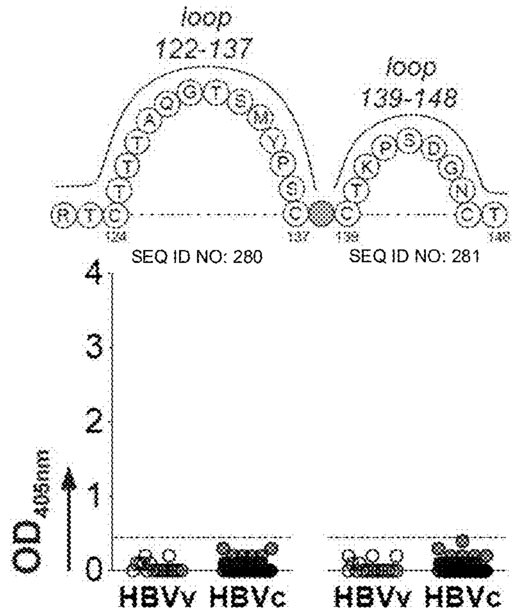
Figure 11C:
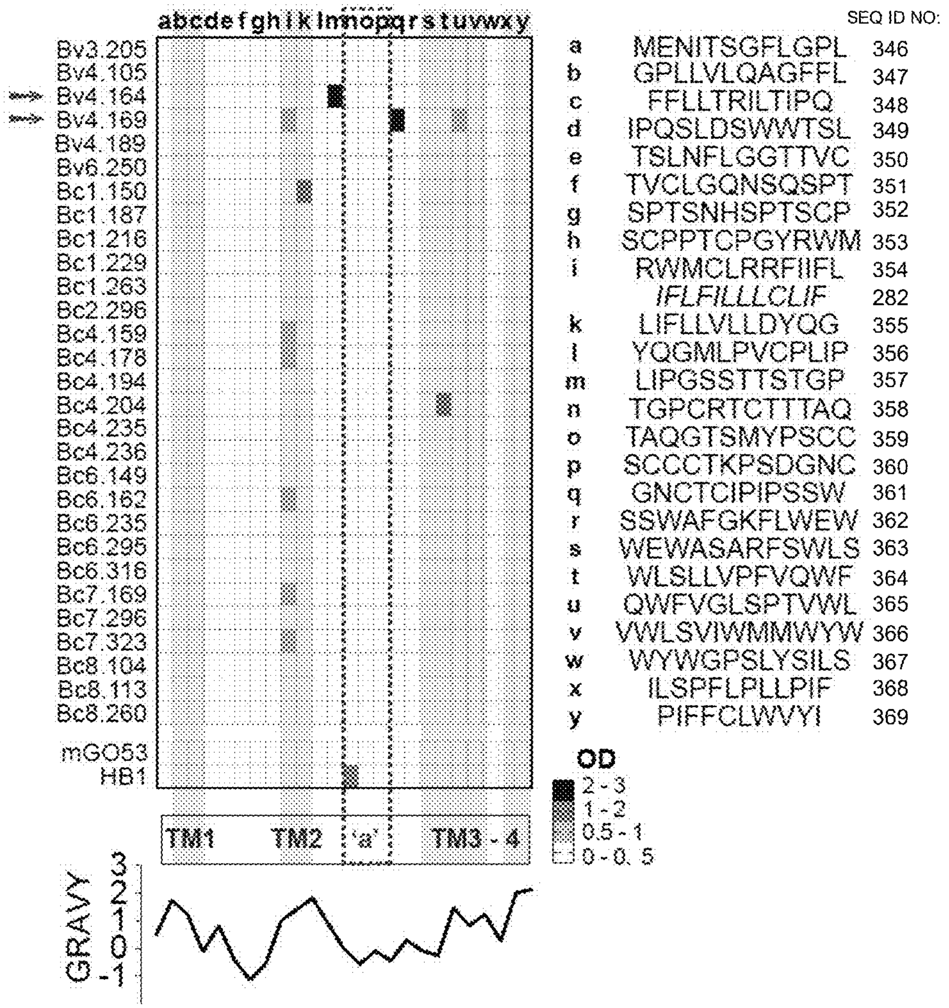

FIG. 11A-11C. Reactivity of human anti-S-HBs antibodies against denatured S-HBsAg and S-HBsAg peptides.

(FIG. 11A) ELISA reactivity of anti-S-HBs antibodies against transmembrane domains-deleted S-HBsAg protein (ΔTM-rS-HBsAg). HB1 and mGO53 are positive and negative control, respectively. The dotted line indicates the cut-off $OD_{405nm}$ for positive reactivity. (FIG. 11B) Same as (FIG. 11A) but for cyclic peptides corresponding to putative S-HBsAg loops 122-137 (SEQ ID NO: 280) and 139-148 (SEQ ID NO: 281). (FIG. 11C) (SEQ ID NOs: 346-354, 282 and 355-369) Heat mapped reactivity of anti-S-HBs antibodies against S-HBsAg overlapping linear peptides. Amino acid sequences (Right) and values of grand average of hydropathy (GRAVY) (Below) of S-HBsAg peptides are indicated.

Figure 12A:
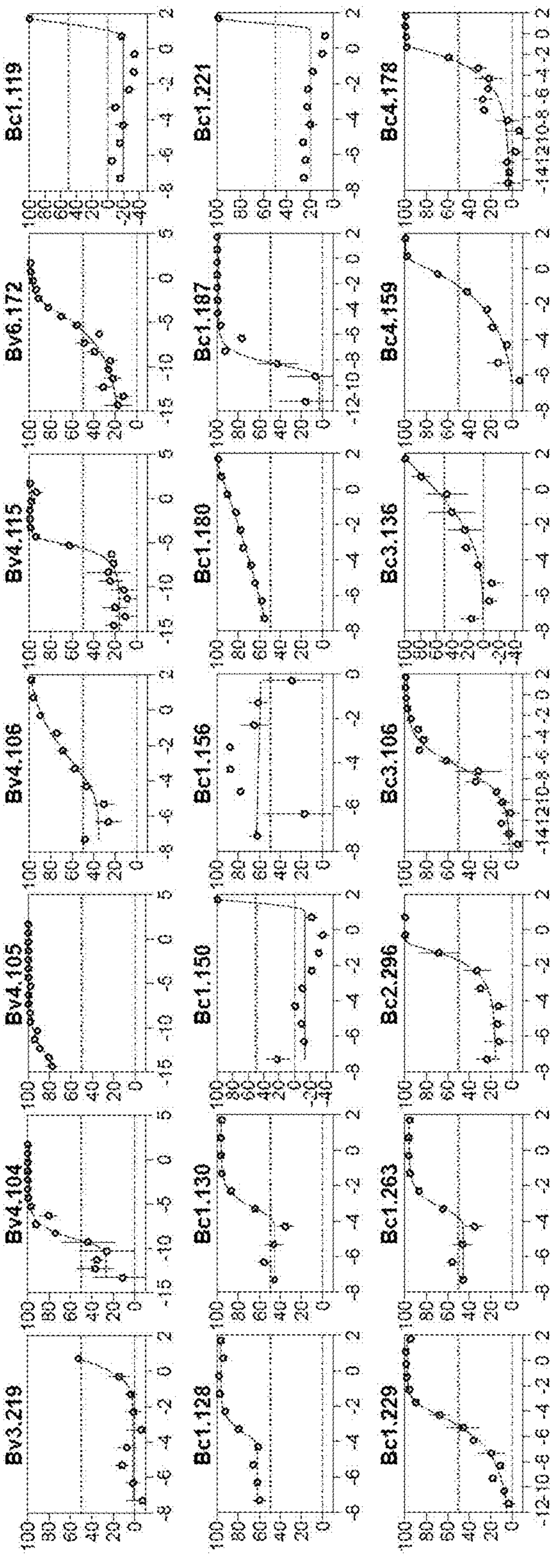
Figure 12B:
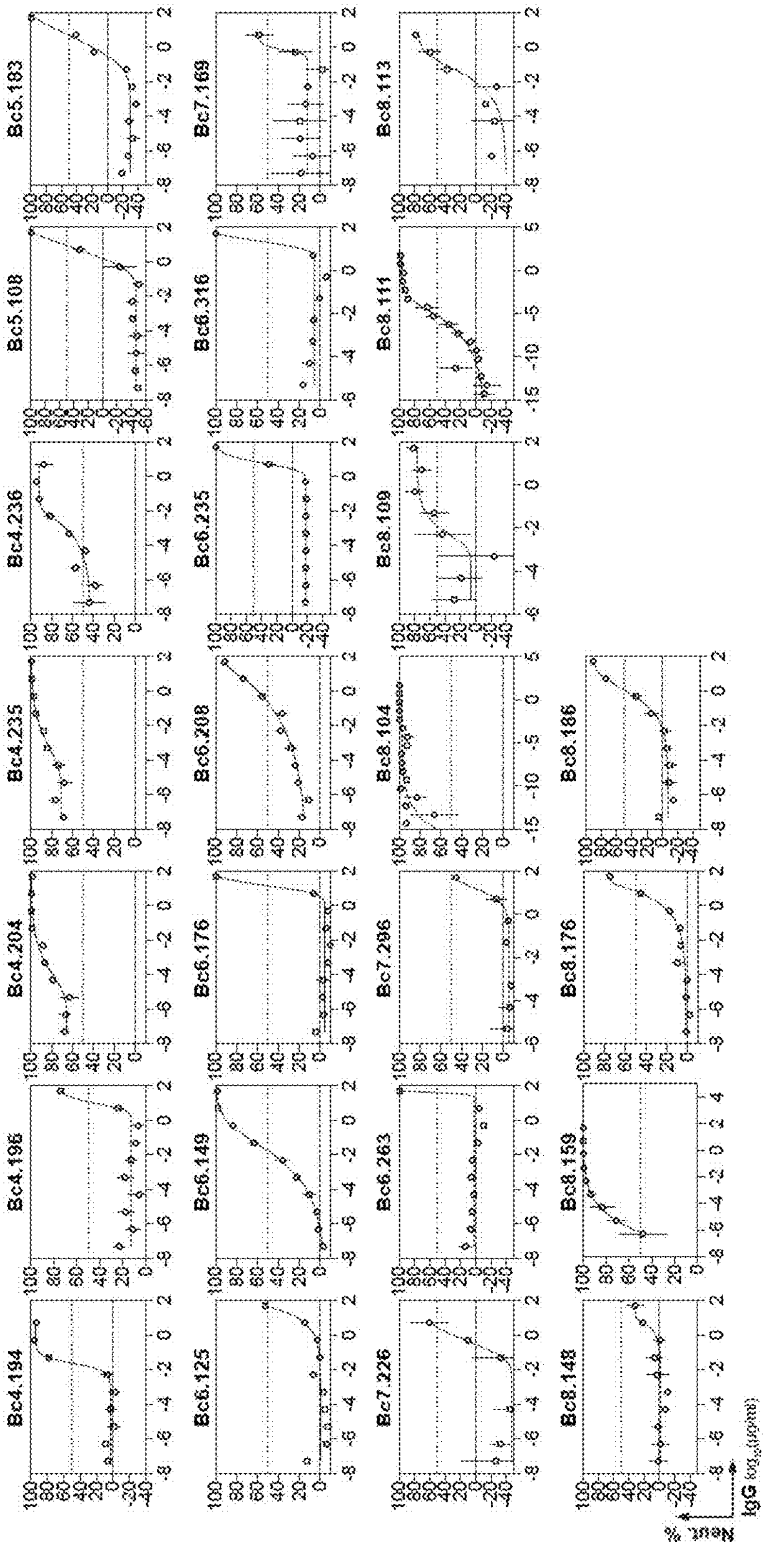

FIG. 12A-12B. In vitro HBV neutralization by human S-HBs antibodies.

Graphs show neutralization curves of genotype D HBV viruses by selected human S-HBs antibodies as measured in the in vitro HepaRG assay. The dotted horizontal line indicated 50% neutralization, from which the IC50 value can be derived from the antibody concentration on the x-axis.

Figure 13A:
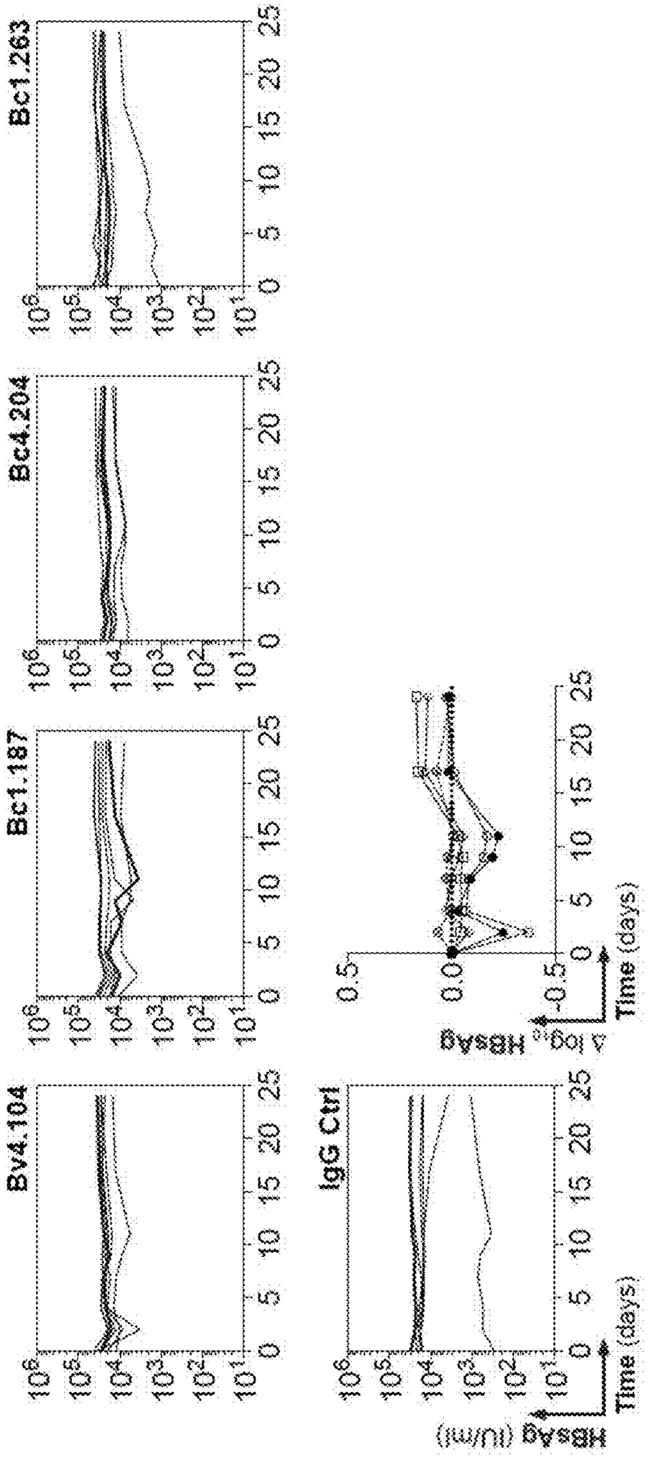
Figure 13B:
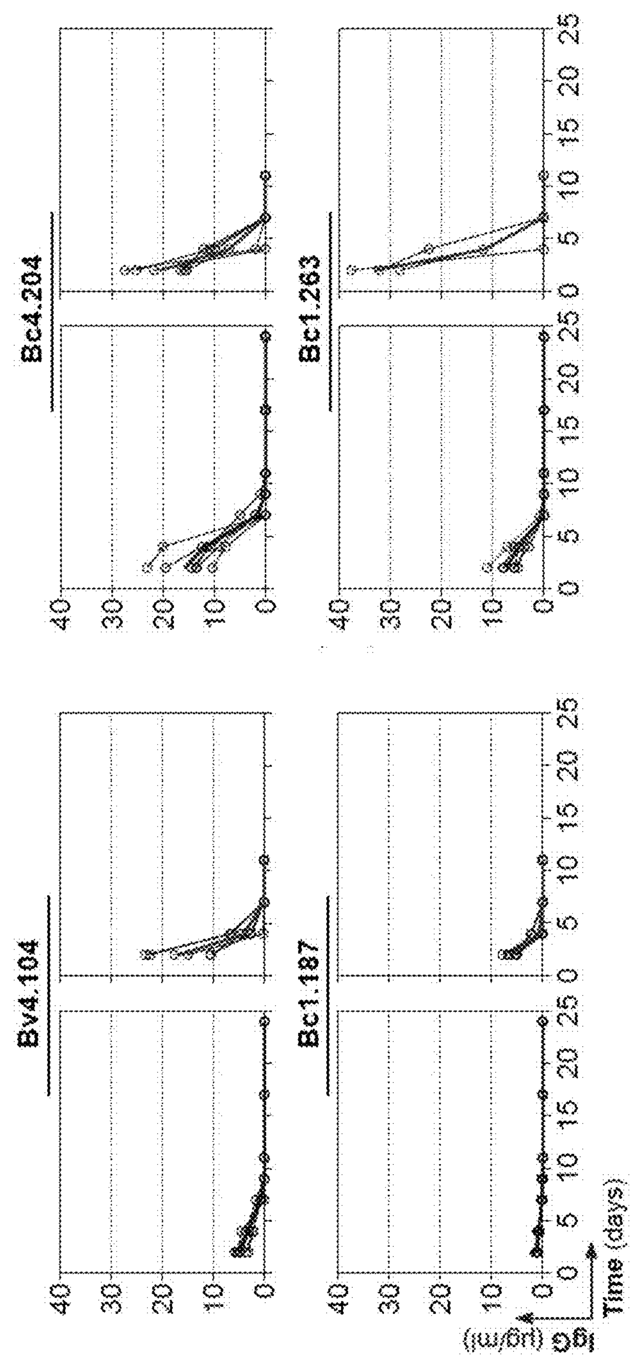

FIG. 13A-13B. Passive administration of human S-HBs antibodies in HBV-AAV mice.

(FIG. 13A) In vivo neutralization activity of human S-HBs antibodies in AAV-HBV-transduced mice. Circulating blood HBsAg levels were monitored in AAV-HBV-transduced mice treated once i.v. with 0.25 mg of anti-S-HBs antibodies Bv4.104 (n=6), Bc1.187 (n=6), Bc1.263 (n=6), Bc4.204 (n=6) or mGO53 isotype control (n=5). Thick lines indicate means. Log 10 changes overtime of HBsAg titers (Δ log 10 S-HBs) upon antibody administration of 0.25 mg i.v. per mouse are shown. (FIG. 13B) Graphs showing the evolution of human IgG titers overtime in mice treated once with 0.25 mg (left) and 0.5 mg (right) of S-HBs antibodies. Thick lines indicate means.

FIG. 14. Binding of HBV neutralizing antibodies to recombinant serotype-specific S-HBs proteins.

Representative ELISA graph showing the binding of selected HBV neutralizing antibodies to purified recombinant Adw (Straight lines) and Ayw (Dotted lines) S-HBs proteins. HB1 and mGO53 are positive and negative control, respectively. Mean values±SEM of assay duplicates from one of two independent experiments are shown.

Figure 15A:
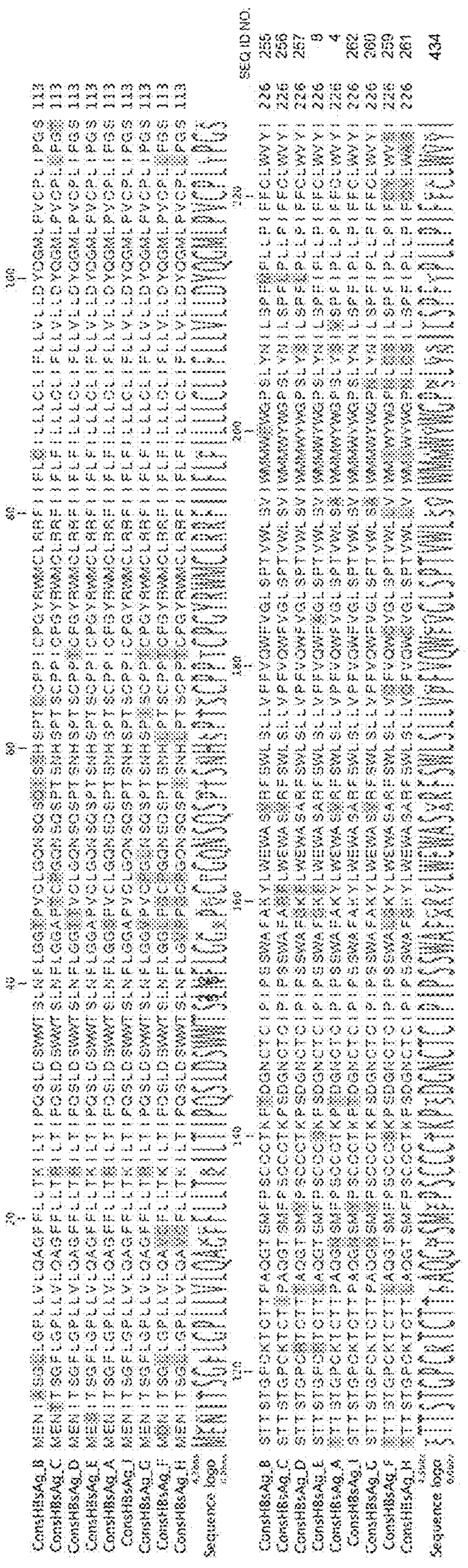
Figure 15B:
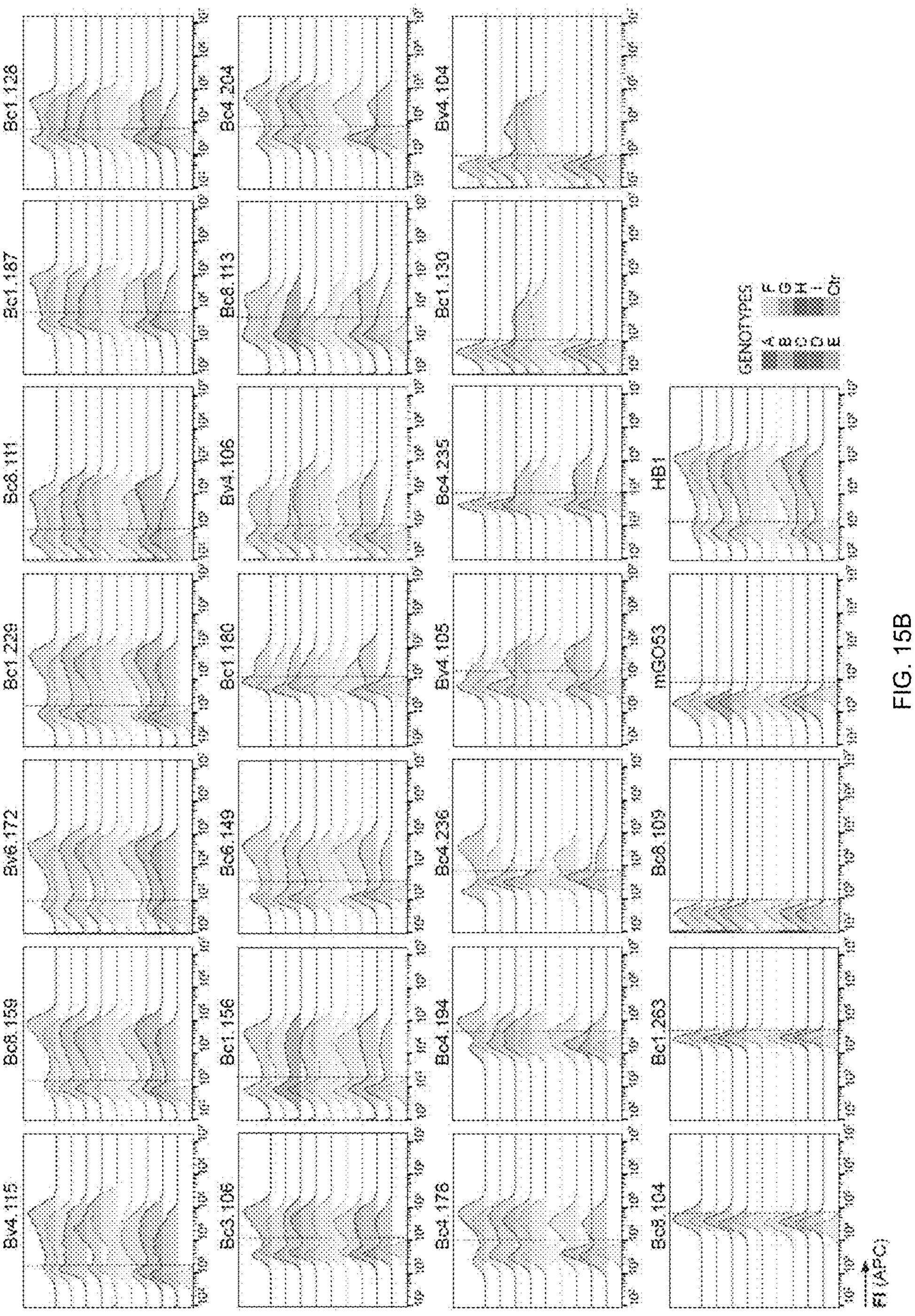

FIG. 15A-15B. Cross-reactivity of HBV neutralizing antibodies against genotype-specific S-HBs proteins.

(FIG. 15A) (SEQ ID NOs: 255-258, 254, 262, 260, 259 and 261) Amino acid alignment of the consensus S-HBs protein sequences from different HBV genotypes used in (B). Residue variations are highlighted in grey. (FIG. 15B) Cytograms comparing the reactivity profiles of selected HBV neutralizing antibodies against genotype-specific S-HBs antigens. Data represent one of two independent experiments. HB1 and mGO53 are positive and negative control, respectively. Ctr, non-transfected cell control (first from the bottom); FI, fluorescence intensity.

Figure 16:
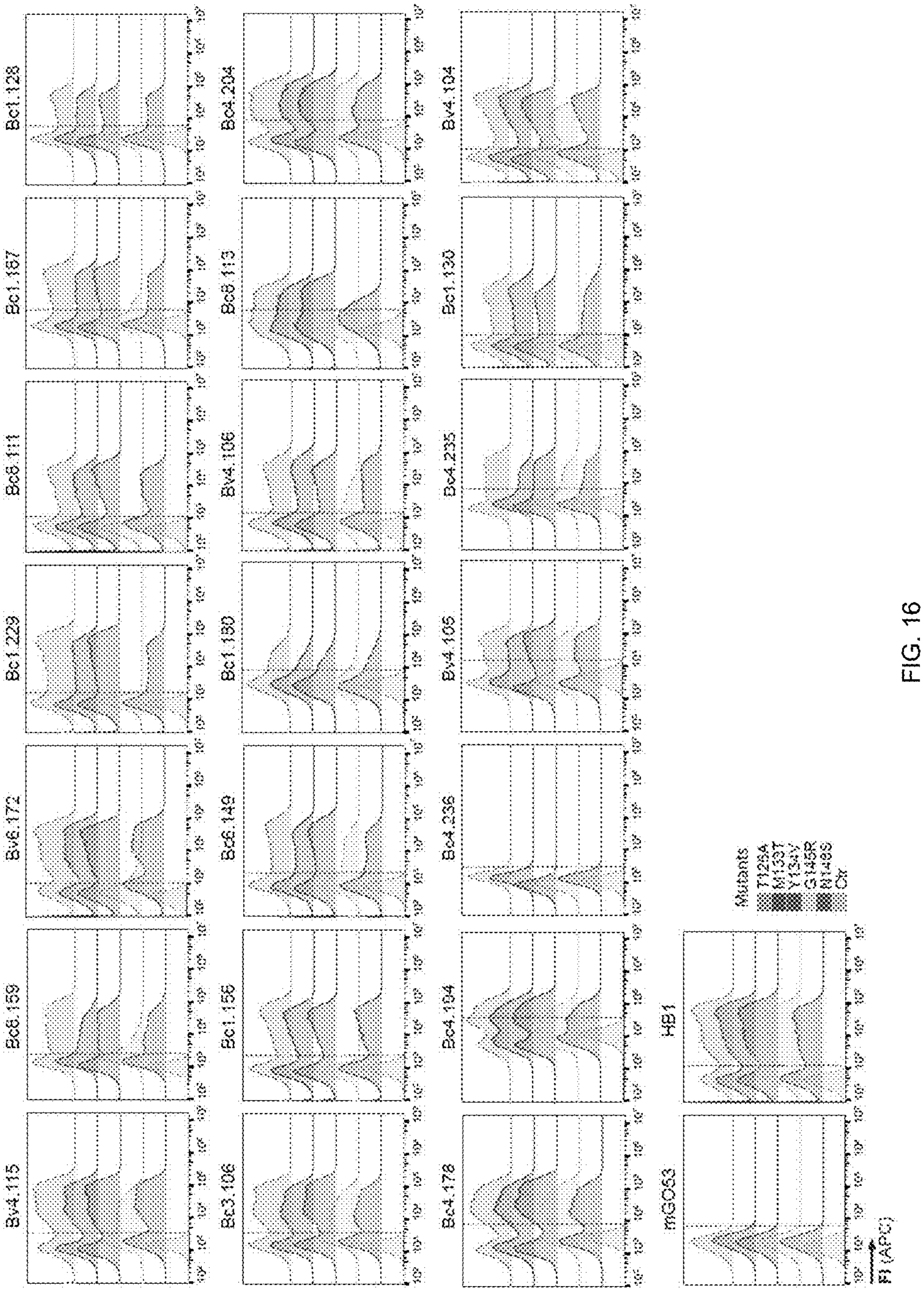

FIG. 16. Reactivity of HBV neutralizing antibodies against S-HBs mutant proteins.

Cytograms comparing the reactivity of selected HBV neutralizing antibodies against genotype D S-HBs mutant proteins displaying naturally occurring escape mutations (T126A, M133T, Y134V or G145R), or a mutation in the S-HBs N-glycosylation site (N126S). Data represent one of two independent experiments. HB1 and mGO53 are positive and negative control, respectively. Ctr, non-transfected cell control (first from the bottom); FI, fluorescence intensity.

Figure 17A:
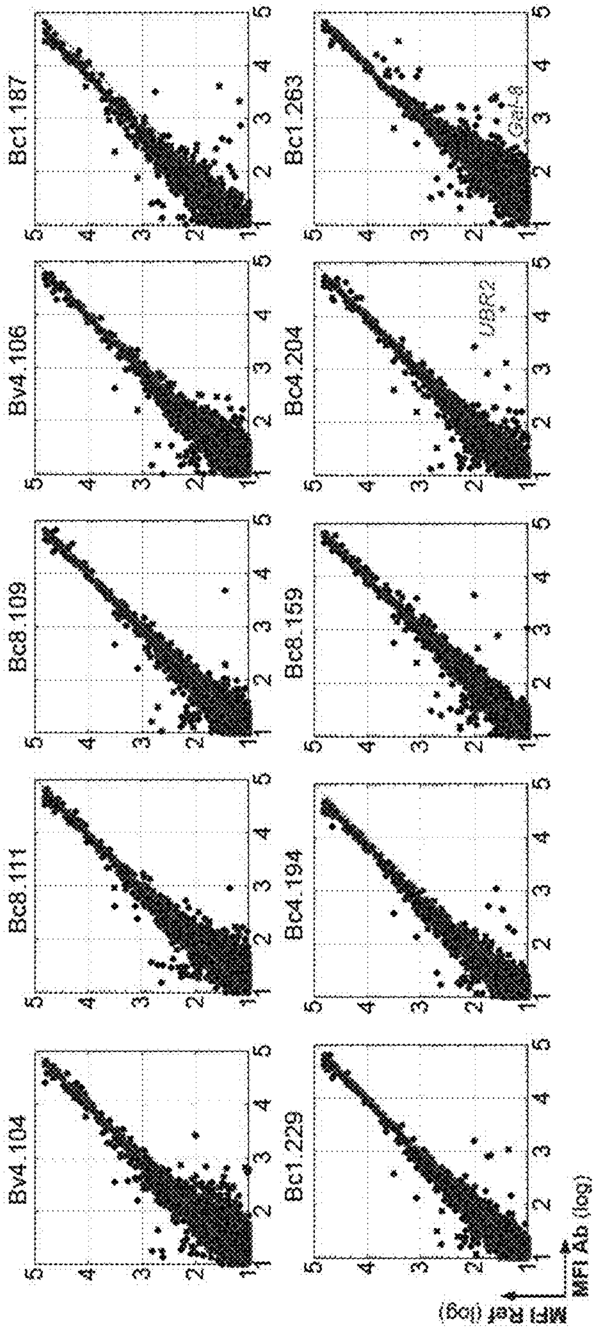
Figure 17B:
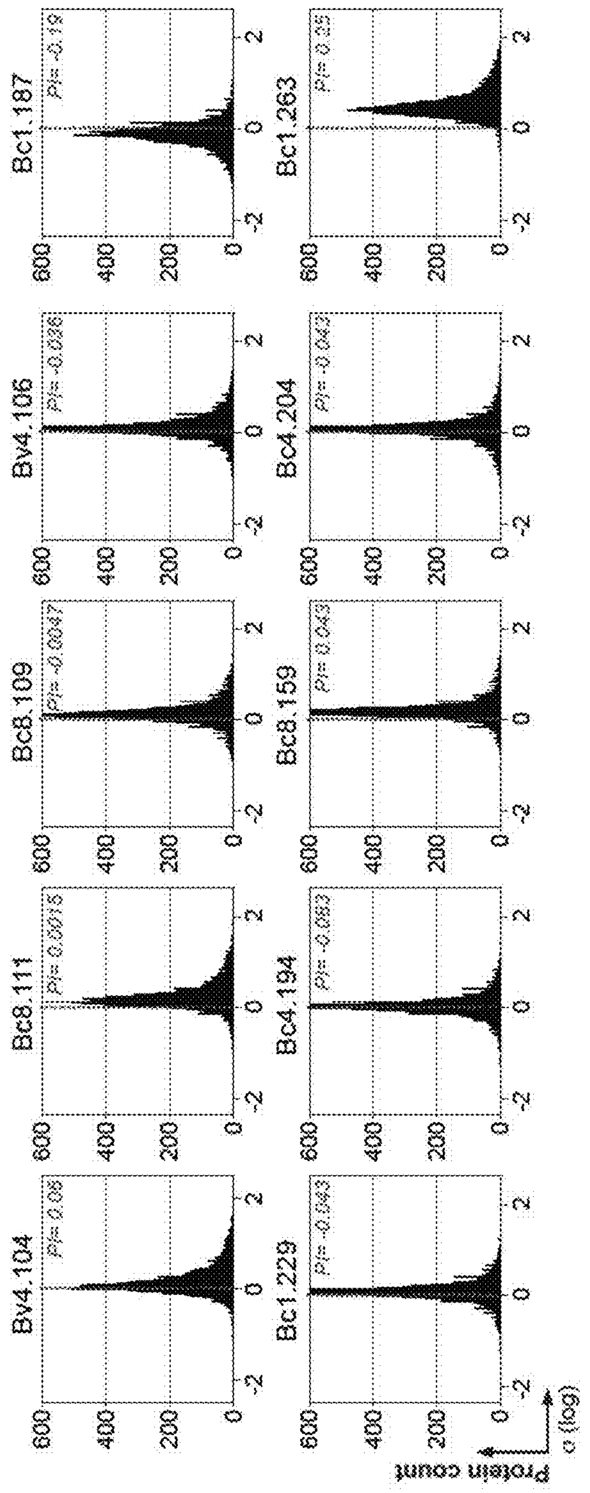
Figure 17C:
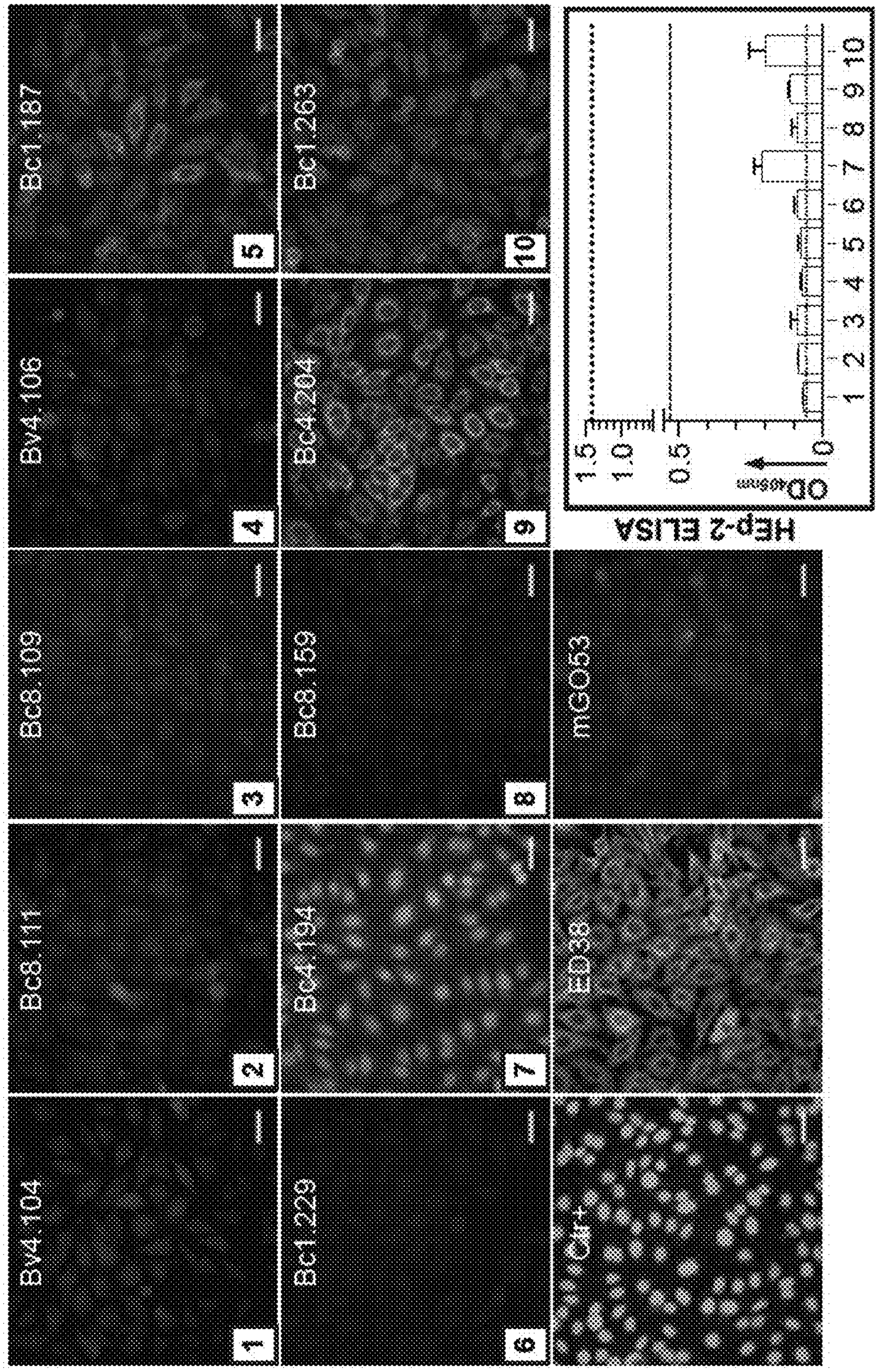

FIG. 17A-17C. Poly- and self-reactivity of potent HBV neutralizing antibodies. (FIG. 17A) Reactivity profiles of selected human S-HBs antibodies (n=8) human protein microarrays. For each protein spot, the mean fluorescence intensity (MFI) given by the reference (Ref: mGO53) and test are depicted on the y and x axis, respectively. Each dot represents the average of duplicate array proteins. The diagonal lines indicate equal binding for reference and test antibodies. Labelled dots indicate immunoreactive proteins with a z-score >5. (FIG. 17B) Frequency histograms showing the log 10 protein displacement (σ) of the MFI signals for S-HBs antibodies compared to non-reactive antibody mGO53. The polyreactivity index (PI) corresponds to the Gaussian mean of all array protein displacements. (FIG. 17C) Binding of selected S-HBs antibodies to HEp2-expressing self antigens was assayed by IFA and ELISA. Ctr+, positive control of the kit. mGO53 and ED38 are negative and positive control antibodies, respectively. The scale bars represent 40 μM. Bar graph in the bottom right shows the HEp-2 reactivity as measured by ELISA. Means±SD of values from two independent experiments performed in duplicate are shown.

FIG. 18A-18E. Passive administration of neutralization antibodies in chronically HBV-infected mice.

(FIG. 18A) Circulating blood HBsAg levels overtime in AAV-HBV-transduced mice (n=7) treated every 3-4 days for 17 days with 0.5 mg i.p. of human anti-S-HBs antibody Bc1.187 or mGO53 isotype control. Averaged Δ log 10 HBsAg values are shown (Right). Shaded area indicates the antibody therapy period. (FIG. 18B) Murine anti-human IgG antibody levels in the treated mice shown in (A) as measured by ELISA. (FIG. 18C) IgG concentrations of passively-administrated chimeric Bc1.187 antibody (0.5 mg i.v.) in B6 mice (n=4). Half-life in days (t1/2) of muBc1.187 antibody is indicated in the upper-right corner. (FIG. 18D) Δ log 10 S-HBs levels overtime in C57BL/6J mice receiving weekly i.v. injections (0.5 mg) of chimeric anti-S-HBs antibody Bc1.187 and mGO53 isotype control. Thick lines indicate the averages. (FIG. 18E) Δlog 10 HBsAg and HBV DNA levels overtime in AAV-HBV-transduced mice (n=7) treated every 2 days for 16 days with 0.5 mg i.v. of chimeric anti-S-HBs antibody Bc1.187 or mGO53 isotype control. Thick lines indicate the averages. Shaded area indicates the antibody therapy period.

Figure 19A:
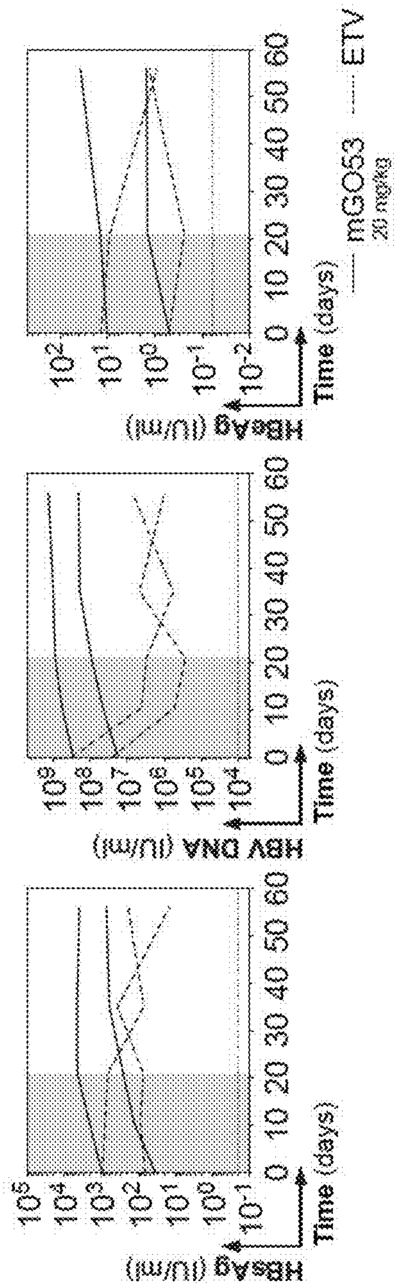
Figure 19B:
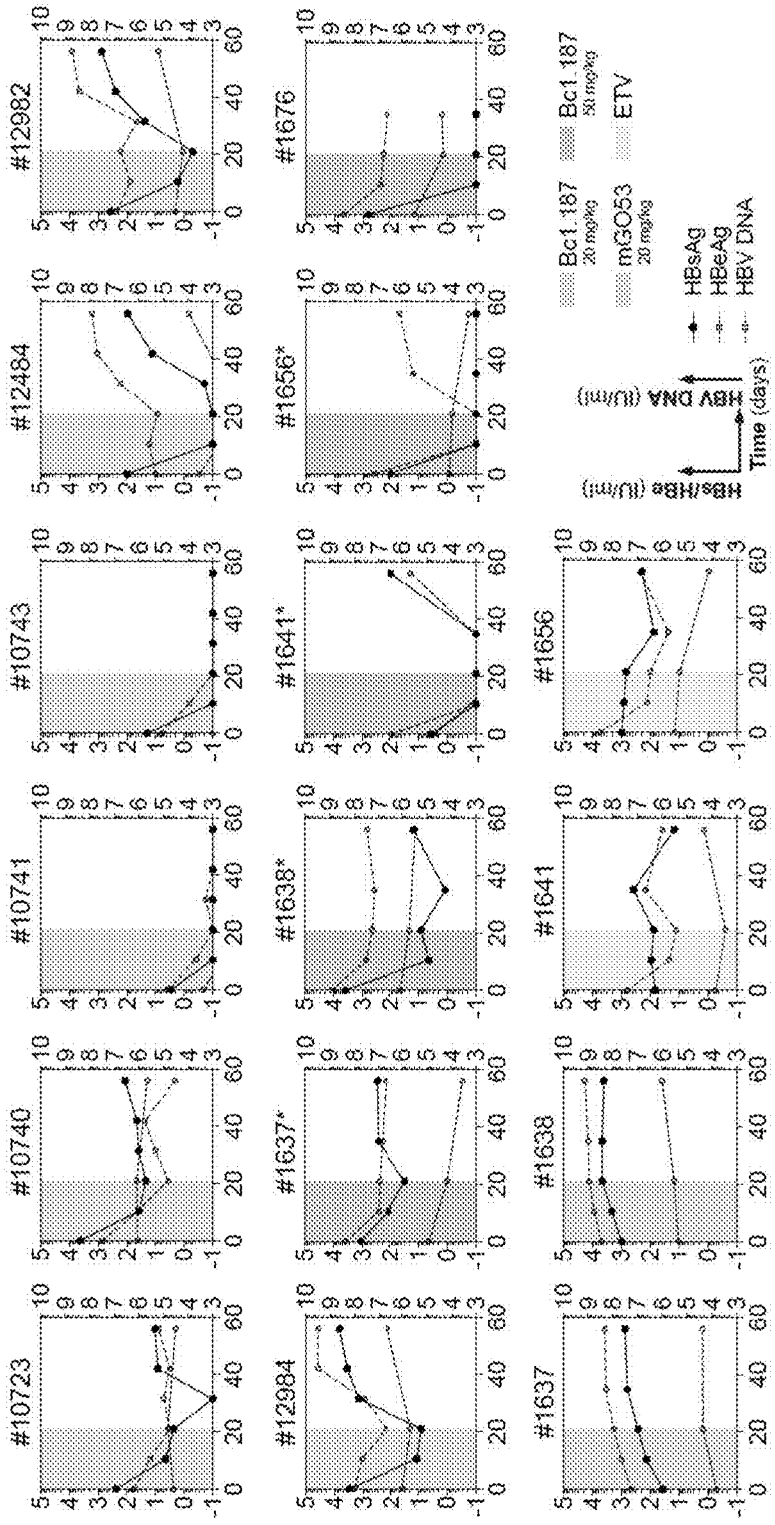
Figure 19C:
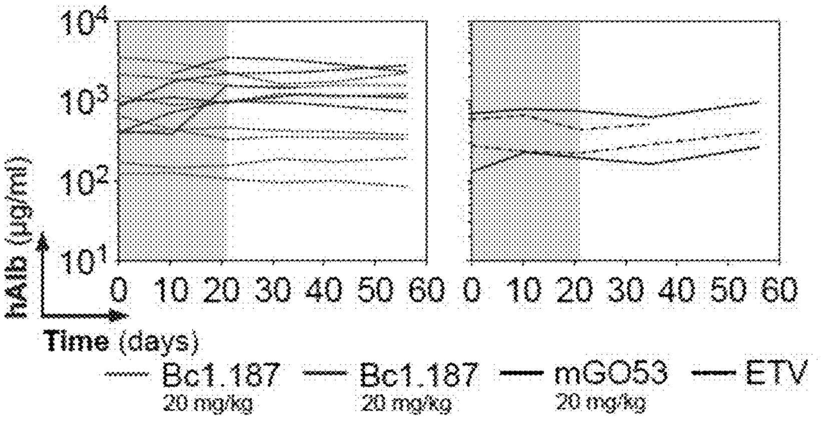

FIG. 19A-19C. Bc1.187 antibody treatment of HBV-infected HUHEP mice.

(FIG. 19A) Blood HBsAg, HBeAg and HBV DNA levels overtime for each individual HUHEP mouse infected with genotype D HBV, and treated with anti-HBs Bc1.187 for 3 weeks with either 20 mg/kg or 50 mg/kg human antibody i.p. (FIG. 19B) Evolution of HBV infection overtime in HUHEP mice receiving a treatment with the non-HBV isotype control mGO53 (20 mg/kg i.p.) or Entecavir (ETV) every 3-4 days for 3 weeks. Blood levels of HBsAg, HBeAg and HBV DNA are shown. (FIG. 19C) Graphs showing the levels of human serum albumin overtime in infected HUHEP mice and treated i.p. with 20 mg/kg (straight lines) and 50 mg/kg (dotted lines) of Bc1.187 for 17 days (shaded area).

DETAILED DESCRIPTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some aspects, the number of amino acid changes are 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary methods for measuring binding affinity are described in the following.

An "affinity matured" antibody refers to an antibody with one or more alterations in one or more complementary determining regions (CDRs), compared to a parent antibody which does not possess such alterations, such alterations resulting in an improvement in the affinity of the antibody for antigen.

The terms "anti-S-HBs-antibody" and "an antibody that binds to S-HBs" refer to an antibody that is capable of binding S-HBs with sufficient affinity such that the antibody is useful as a diagnostic and/or therapeutic agent in targeting S-HBs. In one aspect, the extent of binding of an anti-S-HBs antibody to an unrelated, non-S-HBs protein is less than about 10% of the binding of the antibody to S-HBs as measured, e.g., by surface plasmon resonance (SPR) or using ELISA or flow cytometry as disclosed herein. In certain aspects, an antibody that binds to S-HBs has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). An antibody is said to "specifically bind" to S-HBs when the antibody has a $K_D$ of 1 μM or less, and/or or if the extent of binding of an anti-S-HBs antibody to an unrelated, non-S-HBs protein is less than about 10% of the binding of the antibody to S-HBs as above, e.g., as measured by surface plasmon resonance (SPR) or by a flow cytometry or ELISA assay as described herein. In certain aspects, an anti-S-HBs antibody binds to an epitope of S-HBs that is conserved among S-HBs from different HBV genotypes.

The term "antibody" herein is used in the broadest sense and encompasses various antibody structures, including but not limited to monoclonal antibodies, polyclonal antibodies, multispecific antibodies (e.g., bispecific antibodies), other antibody formats (e.g., comprising a VH domain, a VL domain and optionally an Fc domain, in a format different to a regular IgG) and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, Nature Biotechnology 23:1126-1136 (2005).

The term "epitope" denotes the site on an antigen, either proteinaceous or nonproteinaceous, to which an anti-S-HBs antibody binds. Epitopes can be formed both from contiguous amino acid stretches (linear epitope) or comprise non-contiguous amino acids (conformational epitope), e.g., coming in spatial proximity due to the folding of the antigen, i.e. by the tertiary folding of a proteinaceous antigen. Linear epitopes are typically still bound by an anti S-HBs antibody after exposure of the proteinaceous antigen to denaturing agents, whereas conformational epitopes are typically destroyed upon treatment with denaturing agents. An epitope comprises at least 3, at least 4, at least 5, at least 6, at least 7, or 8-10 amino acids in a unique spatial conformation.

Screening for antibodies binding to a particular epitope (i.e., those binding to the same epitope) can be done using methods routine in the art such as, e.g., without limitation, alanine scanning, peptide blots (see Meth. Mol. Biol. 248 (2004) 443-463), peptide cleavage analysis, epitope excision, epitope extraction, chemical modification of antigens (see Prot. Sci. 9 (2000) 487-496), and cross-blocking (see "Antibodies", Harlow and Lane (Cold Spring Harbor Press, Cold Spring Harb., NY).

Antigen Structure-based Antibody Profiling (ASAP), also known as Modification-Assisted Profiling (MAP), allows to bin a multitude of monoclonal antibodies specifically binding to S-HBs based on the binding profile of each of the antibodies from the multitude to chemically or enzymatically modified antigen surfaces (see, e.g., US 2004/0101920). The antibodies in each bin bind to the same epitope which may be a unique epitope either distinctly different from or partially overlapping with epitope represented by another bin.

Also competitive binding can be used to easily determine whether an antibody binds to the same epitope of S-HBs as, or competes for binding with, a reference anti-S-HBs antibody. For example, an "antibody that binds to the same epitope" as a reference anti-S-HBs antibody refers to an antibody that blocks binding of the reference anti-S-HBs antibody to its antigen in a competition assay by 50% or more, and conversely, the reference antibody blocks binding of the antibody to its antigen in a competition assay by 50% or more. Also for example, to determine if an antibody binds to the same epitope as a reference anti-S-HBs antibody, the reference antibody is allowed to bind to S-HBs under saturating conditions. After removal of the excess of the reference anti-S-HBs antibody, the ability of an anti-S-HBs antibody in question to bind to S-HBs is assessed. If the anti-S-HBs antibody is able to bind to S-HBs after saturation binding of the reference anti-S-HBs antibody, it can be concluded that the anti-S-HBs antibody in question binds to a different epitope than the reference anti-S-HBs antibody. But, if the anti-S-HBs antibody in question is not able to bind to S-HBs after saturation binding of the reference anti-S-HBs antibody, then the anti-S-HBs antibody in question may bind to the same epitope as the epitope bound by the reference anti-S-HBs antibody. To confirm whether the antibody in question binds to the same epitope or is just hampered from binding by steric reasons routine experimentation can be used (e.g., peptide mutation and binding analyses using ELISA, RIA, surface plasmon resonance, flow cytometry or any other quantitative or qualitative antibody-binding assay available in the art). This assay should be carried out in two set-ups, i.e. with both of the antibodies being the saturating antibody. If, in both set-ups, only the first (saturating) antibody is capable of binding to S-HBs, then it can be concluded that the anti-S-HBs antibody in question and the reference anti-S-HBs antibody compete for binding to S-HBs.

In some aspects, two antibodies are deemed to bind to the same or an overlapping epitope if a 1-, 5-, 10-, 20- or 100-fold excess of one antibody inhibits binding of the other by at least 50%, at least 75%, at least 90% or even 99% or more as measured in a competitive binding assay (see, e.g., Junghans et al., Cancer Res. 50 (1990) 1495-1502).

In some aspects, two antibodies are deemed to bind to the same epitope if essentially all amino acid mutations in the antigen that reduce or eliminate binding of one antibody also reduce or eliminate binding of the other. Two antibodies are deemed to have "overlapping epitopes" if only a subset of the amino acid mutations that reduce or eliminate binding of one antibody reduce or eliminate binding of the other.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. In certain aspects, the antibody is of the $IgG_1$ isotype. In certain aspects, the antibody is of the $IgG_1$ isotype with the P329G, L234A and L235A mutation to reduce Fc-region effector function. In other aspects, the antibody is of the $IgG_2$ isotype. In certain aspects, the antibody is of the $IgG_4$ isotype with the S228P mutation in the hinge region to improve stability of $IgG_4$ antibody. The heavy chain constant domains that correspond to the different classes of immunoglobulins are called α, δ, ε, γ, and μ, respectively. The light chain of an antibody may be assigned to one of two types, called kappa (κ) and lambda (λ), based on the amino acid sequence of its constant domain.

The terms "constant region derived from human origin" or "human constant region" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., et al., Sequences of Proteins of Immunological Interest, 5th ed., Public Health Service, National Institutes of Health, Bethesda, MD (1991) (see also e.g. Johnson, G., and Wu, T. T., Nucleic Acids Res. 28 (2000) 214-218; Kabat, E. A., et al., Proc. Natl. Acad. Sci. USA 72 (1975) 2785-2788). Unless otherwise specified herein, numbering of amino acid residues in the constant region is according to the EU numbering system, also called the EU index of Kabat, as described in Kabat, E. A. et al., Sequences of Proteins of Immunological Interest, 5th ed., Public Health Service, National Institutes of Health, Bethesda, MD (1991), NIH Publication 91-3242.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of an agent, e.g., a pharmaceutical composition, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, EU numbering system). Therefore, the C-terminal lysine (Lys447), or the C-terminal glycine (Gly446) and lysine (Lys447), of the Fc region may or may not be present. Amino acid sequences of heavy chains including an Fc region are denoted herein with the C-terminal glycine-lysine dipeptide if not indicated otherwise. In one aspect, a heavy chain including an Fc region as specified herein, comprised in an antibody according to the invention, lacks the C-terminal glycine-lysine dipeptide (G446 and K447, EU numbering system). In one aspect, a heavy chain including an Fc region as specified herein, comprised in an antibody according to the invention, lacks the C-terminal lysine residue (K447, numbering according to EU index). Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

"Framework" or "FR" refers to variable domain residues other than complementary determining regions (CDRs). The FR of a variable domain generally consists of four FR domains: FR1, FR2, FR3, and FR4. Accordingly, the CDR and FR sequences generally appear in the following sequence in VH (or VL): FR1-CDR-H1 (CDR-L1)-FR2-CDR-H2 (CDR-L2)-FR3-CDR-H3 (CDR-L3)-FR4.

The terms "full length antibody", "intact antibody", and "whole antibody" are used herein interchangeably to refer to an antibody having a structure substantially similar to a native antibody structure or having heavy chains that contain an Fc region as defined herein.

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one aspect, for the VL, the subgroup is subgroup kappa I as in Kabat et al., supra. In one aspect, for the VH, the subgroup is subgroup III as in Kabat et al., supra.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence and which determine antigen binding specificity, for example "complementarity determining regions" ("CDRs").

Generally, antibodies comprise six CDRs: three in the VH (CDR-H1, CDR-H2, CDR-H3), and three in the VL (CDR-L1, CDR-L2, CDR-L3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262:732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, the individual or subject is a human.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., *J. Chromatogr. B* 848:79-87 (2007). Any of the antibodies described herein may be isolated antibodies.

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al, Nature Medicine 2017, published online 12 Jun. 2017, doi: 10.1038/nm.4356 or EP 2 101 823 B1).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-S-HBs antibody" refers to one or more nucleic acid molecules encoding anti-S-HBs antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical composition.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable domain (VH), also called a variable heavy domain or a heavy chain variable region, followed by three constant heavy domains (CH1, CH2, and CH3). Similarly, from N- to C-terminus, each light chain has a variable domain (VL), also called a variable light domain or a light chain variable region, followed by a constant light (CL) domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, percent amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from www.fasta.bioch.virginia.edu/fasta_www2/fasta_down.shtml or www.ebi.ac.uk/Tools/sss/fasta. Alternatively, a public server accessible at fasta.bioch-.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the pharmaceutical composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

The terms "S-HBs" or "S-HBsAg" as used interchangeably herein (referring to small hepatitis B surface antigen) encompass "full-length", unprocessed S-HBs as well as any form of S-HBs that results from processing in the cell. The term also encompasses naturally occurring variants of S-HBs, e.g., splice variants or allelic variants. The amino acid sequence of an exemplary S-HBs is shown in SEQ ID NO: 253. Antibodies of the present invention may bind at least to S-HBs of SEQ ID NO: 253 e.g., with affinity or binding activity as discussed herein. Optionally, antibodies of the present invention may additionally or alternatively bind to one or more proteins comprising or consisting of consensus sequences selected from SEQ ID NO: 254-262, e.g., to a protein of SEQ ID NO: 257.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some aspects, antibodies of the invention are used to delay development of a disease or to slow the progression of a disease.

Hepatitis B may be either chronic or acute, and the antibodies of the present invention may be used to treat either condition. Acute hepatitis generally refers to an infection within the first six months after exposure to the virus. Chronic hepatitis generally refers to an infection which is ongoing after six months. In some embodiments, treatment of hepatitis may refer to a reduction of HBV virus, an elimination of HBV virus, the reduction of symptoms due to HBV infection, the prevention or reduction of the progression of hepatitis to liver disease such as cirrhosis, liver fibrosis, liver failure and/or liver cancer, a reduction in detectable HBV surface antigen (HBsAg) in serum, and/or HBV surface antigen (HBsAg) seroconversion, i.e., an absence of detectable HBsAg in serum. Detection of HBsAg may be by any of the screening assays well established in the art, such as Elecsys HBsAg II (Roche Diagnostics), Auszyme Monoclonal [overnight incubation] version B, IMx HBsAg (Abbott) or Monolisa S-HBsAg ULTRA (Bio-Rad, France) ELISA.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three complementary determining regions (CDRs). (See, e.g., Kindt et al. *Kuby Immunology, 6th* ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., *Nature* 352:624-628 (1991).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the invention is based, in part, on the identification by the inventors of antibodies from individuals that can naturally clear chronic hepatitis B virus (HBV) infection and acquire protection from re-infection ("controllers") and from individuals vaccinated against HBV ("vaccinees"). The inventors have determined that such antibodies may have advantageous properties, such as high affinity or binding activity to the S-HBs antigen, potent neutralizing activity and/or cross-genotypic reactivity. In certain aspects, antibodies that bind to S-HBs are provided. Antibodies of the invention are useful, e.g., for the diagnosis or treatment of hepatitis B.

A. Exemplary Anti-S-HBs Antibodies

In one aspect, the invention provides antibodies that bind to S-HBs. In one aspect, provided are isolated antibodies that bind to S-HBs. In one aspect, the invention provides antibodies that specifically bind to S-HBs. In certain aspects, an anti-S-HBs antibody has one or more of the following properties:

- binds to S-HBs (e.g., of SEQ ID NO: 253); and/or
- binds to one or more S-HBs proteins having SEQ ID NO: 254 to 262, (e.g., at least SEQ ID NO: 257), optionally to two or more of said proteins (e.g., at least SEQ ID NO: 257 and 258), optionally to three, four, five, six, seven, eight or more of said proteins, optionally to all of said proteins; and/or
- binds to S-HBs of subtype adw and/or ayw, e.g., of genotype D, preferably both adw and ayw subtypes;
- avoids significant cross-reactivity against self-antigens such as galectin-3/-8 and E3 ubiquitin-protein ligase UBR2; and/or
- has a neutralizing activity (e.g., as measured in vitro or in vivo) against HBV genotype D;
- has a neutralizing activity (e.g., as measured in vitro or in vivo) against each of HBV genotypes A to D; and/or
- can suppress virus viremia in vivo.

For example, in some embodiments, the antibody may have a neutralizing IC50 value against HBV genome D of ≤1 ng/ml, measured in vitro.

In other exemplary embodiments, an antibody may have the following properties:

- is cross reactive with each of the proteins of SEQ ID NO: 254 to 262; and
- has neutralizing activity (e.g., as measured in vitro or in vivo) against HBV genotype D.

Said exemplary antibodies may preferably also avoid significant cross-reactivity against self-antigens such as galectin-3/-8 and E3 ubiquitin-protein ligase UBR2.

The antibodies may bind to S-HBs and/or to one or more S-HBs proteins having SEQ ID NO: 254 to 262 with a $K_D$ as discussed herein, e.g., ≤1 μM, ≤100 nM, ≤10 nM, ≤1 nM, ≤0.1 nM, ≤0.01 nM, or ≤0.001 nM. In some embodiments, the antibody may bind to S-HBs and/or one or more S-HBs proteins having SEQ ID NO: 254 to 262 with a $K_D$ value which is no more than 50, 10, 9, 8, 7, 6, 5, 4, 3, or 2 fold higher than the $K_D$ of a reference antibody against the same antigen, or which is less than or equal to the $K_D$ of said reference antibody, wherein the reference antibody is selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105.

Alternatively, the antibodies may show binding activity against S-HBs and/or to one or more S-HBs proteins having SEQ ID NO: 254 to 262 which is at least 25%, 50%, 60%, 70%, 75%, 80%, 85%, 90%, 95% or 100% of the binding activity of a reference antibody to the same antigen, wherein the reference antibody is selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105 (when assessed in the same assay, e.g., an ELISA assay or a flow cytometry assay). In some embodiments, it may be preferred that the activity is at least 50% of the activity of the reference antibody. Optionally the reference antibody may be Bc1.187, i.e., the antibody may show at least 25%, 50%, 60%, 70%, 75%, 80%, 85%, 90%, 95% or 100% of the binding activity of Bc1.187 to the reference antigen, when assessed in the same assay.

In other aspects, the antibodies may bind to S-HBs/or to one or more S-HBs proteins having SEQ ID NO: 254 to 262 with an EC50 that is no more than 50, 10, 9, 8, 7, 6, 5, 4, 3, or 2 fold higher than, or is less than or equal to, the EC50 of a reference antibody, wherein the EC50 is measured by ELISA or by flow cytometry, and wherein the reference antibody is selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105.

"Avoids significant cross reactivity with" means that the antibody does not show significant binding to the reference protein, e.g., has a $K_D$ greater than 1 μM, or has no detectable binding e.g., in an assay described herein.

In some embodiments antibodies according to the invention which are neutralizing against a HBV genotype, e.g., genotype D, may for instance have an IC50 value for viral infectivity in vitro of ≤50 ng/ml, or ≤10 ng/ml. It may be preferred that the antibody has an IC50 of ≤1 ng/ml, ≤500 pg/ml or in some embodiments ≤100 pg/ml, ≤50 pg/ml, or ≤10 pg/ml. In some embodiments, a neutralizing antibody may have an IC50 value of ≤1 pg/ml, optionally ≤0.1 pg/ml. Optionally the IC50 value may be greater than 0.01 μg/ml or 0.005 pg/ml. In another embodiment, an antibody which is neutralizing against a particular HBV genotype, e.g., genotype D, may have an IC50 value which is no more than 50, 10, 9, 8, 7, 6, 5, 4, 3, or 2 fold higher than, or is less than or equal to, the IC50 value of a reference antibody against the same genotype, wherein the reference antibody is selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105 (when assessed in the same assay).

In another embodiment, an antibody which is neutralizing against a particular HBV genotype may have or retain at least 50%, 60%, 70%, 75%, 80%, 85%, 90%, 95% or 100% of the in vivo neutralizing activity or viremia suppressing activity of a reference antibody to the same genotype, e.g., a reference antibody selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105 when assessed using the same assay (e.g., an assay as described herein).

In some embodiments, an antibody may be cross reactive with each of the proteins of SEQ ID NO: 254 to 262 (having binding activity to each e.g., as described above) and have an IC50 for in vitro neutralization of HBV-genotype D of ≤100 pg/ml. Optionally, the $IC_{50}$ value may be ≤50 pg/ml or ≤10 pg/ml. In some embodiments, the IC50 value may be ≤1 pg/ml, optionally ≤0.1 pg/ml.

Various embodiments of particular antibodies according to the present invention are set out in sections A-N below.

A

In one aspect, the invention provides an antibody comprising a VH domain comprising at least one, at least two, or all three VH CDR sequences selected from (a) CDR-H1 comprising the amino acid sequence of SEQ ID NO:1; (b) CDR-H2 comprising the amino acid sequence of SEQ ID NO: 2; and (c) CDR-H3 comprising the amino acid sequence of SEQ ID NO:3. In another aspect, the antibody comprises a VH domain comprising the following CDRs (a) CDR-H1 comprising the amino acid sequence of SEQ ID NO:1; (b) CDR-H2 comprising the amino acid sequence of SEQ ID NO:2; and (c) CDR-H3 comprising the amino acid sequence of SEQ ID NO: 3; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 7 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO: 8, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:9, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:10 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 16. In one aspect, an anti-S-HBs antibody comprises a heavy chain variable domain (VH) sequence having at least 95%, sequence identity to the amino acid sequence of SEQ ID NO:16. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 16. In certain aspects, substitutions, insertions, or deletions occur in regions outside the CDRs (i.e., in the FRs). Optionally, the anti-S-HBs antibody comprises the VH sequence in SEQ ID NO: 16, including post-translational modifications of that sequence. In a particular aspect, the VH comprises one, two or three CDRs selected from: (a) CDR-H1, comprising the amino acid sequence of SEQ ID NO:1, (b) CDR-H2, comprising the amino acid sequence of SEQ ID NO:2, and (c) CDR-H3, comprising the amino acid sequence of SEQ ID NO: 3.

In another aspect, an anti-S-HBs antibody comprises one or more of the heavy chain CDR sequences of the VH of SEQ ID NO:16. In one aspect, an anti-S-HBs antibody comprises one or more (preferably all three) of the heavy chain CDR amino acid sequences of the VH domain of SEQ ID NO:16 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:16. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:4; (b) CDR-L2 comprising the amino acid sequence of SEQ ID NO: 5; and (c) CDR-L3 comprising the amino acid sequence of SEQ ID NO:6. In another aspect, the antibody comprises a VL domain comprising the following CDRs (a) CDR-L1 comprising the amino acid sequence of SEQ ID NO:4; (b) CDR-L2 comprising the amino acid sequence of SEQ ID NO:5; and (c) CDR-L3 comprising the amino acid sequence of SEQ ID NO: 6; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 11 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:12 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:13 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:14 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:15. In one aspect, an anti-S-HBs antibody comprises a light chain variable domain (VL) sequence having at least 95% sequence identity to the amino acid sequence of SEQ ID NO:15. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:15. In certain aspects, the substitutions, insertions, or deletions occur in regions outside the CDRs (i.e., in the FRs). Optionally, the anti-S-HBs antibody comprises the VL sequence in SEQ ID NO:15, including post-translational modifications of that sequence. In a particular aspect, the VL comprises one, two or three CDRs selected from: (a) CDR-L1, comprising the amino acid sequence of SEQ ID NO:4, (b) CDR-L2, comprising the amino acid sequence of SEQ ID NO:5, and (c) CDR-L3, comprising the amino acid sequence of SEQ ID NO:6.

In another embodiment, an anti-S-HBs antibody comprises one or more of the CDR sequences of the VL of SEQ ID NO:15. In one aspect, an anti-S-HBs antibody comprises one or more (preferably all three) of the light chain CDR amino acid sequences of the VL domain of SEQ ID NO: 15 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:15. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:3; and a VL domain comprising CDR-L3 of SEQ ID NO:6. Optionally the VH domain further comprises CDR-H2 of SEQ ID NO: 2.

In another exemplary embodiment, the antibody comprises:

i) a VH domain comprising the following CDRs (a) CDR-H1 comprising the amino acid sequence of SEQ ID NO:1; (b) CDR-H2 comprising the amino acid sequence of SEQ ID NO:2; and (c) CDR-H3 comprising the amino acid sequence of SEQ ID NO:3; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:4; (b) CDR-L2 comprising the amino acid sequence of SEQ ID NO:5; and (c) CDR-L3 comprising the amino acid sequence of SEQ ID NO:6; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 16; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 15.

In another exemplary embodiment, the anti-S-HBs antibody comprises (a) CDR-H1 comprising the amino acid sequence of SEQ ID NO:1; (b) CDR-H2 comprising the amino acid sequence of SEQ ID NO:2; (c) CDR-H3 comprising the amino acid sequence of SEQ ID NO:3; (d) CDR-L1 comprising the amino acid sequence of SEQ ID NO:4; (e) CDR-L2 comprising the amino acid sequence of SEQ ID NO:5; and (f) CDR-L3 comprising the amino acid sequence of SEQ ID NO:6, and a VH domain having at least 90%, 91%, 92%, 93%, 94%, 95%, 96%, 97%, 98%, 99%, or 100% sequence identity to the amino acid sequence of SEQ ID NO: 16, and a VL domain having at least 90%, 91%, 92%, 93%, 94%, 95%, 96%, 97%, 98%, 99%, or 100% sequence identity to the amino acid sequence of SEQ ID NO:15. In one aspect, the VH domain has at least 95% sequence identity to the amino acid sequence of SEQ ID NO: 16. In one aspect, the VL domain has at least 95% sequence identity to the amino acid sequence of SEQ ID NO:15. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:16 and a VL sequence of SEQ ID NO:15.

In one aspect, the antibody comprises the VH and VL sequences in SEQ ID NO:16 and SEQ ID NO: 15, respectively, including post-translational modifications of those sequences.

In a further aspect, the antibody may comprise the full length light chain of SEQ ID NO: 17 and/or the full length heavy chain of SEQ ID NO: 18 or 263.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 16 and a VL sequence of SEQ ID NO:15. In certain aspects, an antibody is provided that binds to one or more of the following residues of S-HBs of SEQ ID NO: 253: C137; and optionally C138, K141, G145, and/or C149. In some embodiments the antibody may further bind to one or more of I152, N146, C147, and/or T148; and optionally W156. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bc1.187 to S-HBs (e.g., of SEQ ID NO: 253), when assessed in the same assay, e.g., an ELISA assay or a flow cytometry assay. Additionally or alternatively, antibodies as described in this section may have or retain at least 50%, 60%, 70%, 75%, 80%, 85%, 90%, 95% or 100% of the binding activity of a reference antibody Bc1.187 to one or more of SEQ ID NO: 254-262 (e.g., to at least SEQ ID NO: 257), optionally each of the proteins of SEQ ID NO: 254 to 262, when assessed in the same assay, e.g., an ELISA assay or a flow cytometry assay.

Reference antibody Bc1.187 is an anti-S-HBs antibody comprising a VH sequence of SEQ ID NO: 16 and a VL sequence of SEQ ID NO:15. It has the full length heavy chain of SEQ ID NO: 18 or 263 and the full length light chain of SEQ ID NO: 17. SEQ ID NO: 263 comprises the IgG1 constant region expressed by vector LT615368.1, as used in the examples.

In some embodiments, the antibody described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bc1.187 to the same antigen, when assessed in the same assay.

Additionally or alternatively, the antibody as described in this section may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bc1.187 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bc1.187, as measured by ELISA or by flow cytometry. Alternatively or additionally, the antibody may bind one or more of SEQ ID NO: 254-262 (e.g., to at least SEQ ID NO: 257), optionally each of the proteins of SEQ ID NO: 254 to 262 with an EC50 that is no more than 50, 10, 9, 8, 7, 6, 5, 4, 3, or 2 fold higher than, or is less than or equal to, the EC50 of reference antibody Bc1.187, as measured by ELISA or by flow cytometry.

In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D with an IC50 value of ≤1 pg/ml, optionally ≤0.1 pg/ml.

In another embodiment, the antibody may have an IC50 value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the IC50 value of reference antibody Bc1.187 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the in vivo neutralizing activity of reference antibody Bc1.187 against HBV genotype A, B, C and/or D, optionally at least D, optionally all of A, B, C and D, when assessed using the same assay (e.g., an assay as described herein).

Optionally the antibody can suppress virus viremia in vivo, e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bc1.187 against HBV genotype A, B, C and/or D, optionally at least D, optionally all of A, B, C and D, when assessed using the same assay (e.g., an assay as described herein).

B

In one aspect, the invention provides an antibody comprising a VH domain comprising at least one, at least two, or all three VH CDR sequences selected from (a) CDR-H1 comprising the amino acid sequence of SEQ ID NO:19; (b) CDR-H2 comprising the amino acid sequence of SEQ ID NO: 20; and (c) CDR-H3 comprising the amino acid sequence of SEQ ID NO:21. In another aspect, the antibody comprises a VH domain comprising the following CDRs (a) CDR-H1 comprising the amino acid sequence of SEQ ID NO:19; (b) CDR-H2 comprising the amino acid sequence of SEQ ID NO:20; and (c) CDR-H3 comprising the amino acid sequence of SEQ ID NO: 21; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 25 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO: 26, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:27, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:28 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:34. In one aspect, an anti-S-HBs antibody comprises a heavy chain variable domain (VH) sequence having at least 95%, sequence identity to the amino acid sequence of SEQ ID NO:34. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 34. In certain aspects, substitutions, insertions, or deletions occur in regions outside the CDRs (i.e., in the FRs). Optionally, the anti-S-HBs antibody comprises the VH sequence in SEQ ID NO: 34, including post-translational modifications of that sequence. In a particular aspect, the VH comprises one, two or three CDRs selected from: (a) CDR-H1, comprising the amino acid sequence of SEQ ID NO 19, (b) CDR-H2, comprising the amino acid sequence of SEQ ID NO:20, and (c) CDR-H3, comprising the amino acid sequence of SEQ ID NO: 21.

In another aspect, an anti-S-HBs antibody comprises one or more of the heavy chain CDR sequences of the VH of SEQ ID NO:34. In one aspect, an anti-S-HBs antibody comprises one or more (preferably all three) of the heavy chain CDR amino acid sequences of the VH domain of SEQ ID NO:34 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:34. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:22; (b) CDR-L2 comprising the amino acid sequence of SEQ ID NO: 23; and (c) CDR-L3 comprising the amino acid sequence of SEQ ID NO:24. In another aspect, the antibody comprises a VL domain comprising the following CDRs (a) CDR-L1 comprising the amino acid sequence of SEQ ID NO:22; (b) CDR-L2 comprising the amino acid sequence of SEQ ID NO:23; and (c) CDR-L3 comprising the amino acid sequence of SEQ ID NO: 24; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 29 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:30 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:31 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:32 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:33. In one aspect, an anti-S-HBs antibody comprises a light chain variable domain (VL) sequence having at least 95% sequence identity to the amino acid sequence of SEQ ID NO:33. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:33. In certain aspects, the substitutions, insertions, or deletions occur in regions outside the CDRs (i.e., in the FRs). Optionally, the anti-S-HBs antibody comprises the VL sequence in SEQ ID NO:33, including post-translational modifications of that sequence. In a particular aspect, the VL comprises one, two or three CDRs selected from: (a) CDR-L1, comprising the amino acid sequence of SEQ ID NO:22, (b) CDR-L2, comprising the amino acid sequence of SEQ ID NO:23, and (c) CDR-L3, comprising the amino acid sequence of SEQ ID NO:24.

In another embodiment, an anti-S-HBs antibody comprises one or more of the CDR sequences of the VL of SEQ ID NO:33. In one aspect, an anti-S-HBs antibody comprises one or more (preferably all three) of the light chain CDR amino acid sequences of the VL domain of SEQ ID NO: 33 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:33. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:21; and a VL domain comprising CDR-L3 of SEQ ID NO: 24. Optionally the VH domain further comprises CDR-H2 of SEQ ID NO: 20.

In another exemplary embodiment, the antibody comprises:

i) a VH domain comprising the following CDRs (a) CDR-H1 comprising the amino acid sequence of SEQ ID NO:19; (b) CDR-H2 comprising the amino acid sequence of SEQ ID NO:20; and (c) CDR-H3 comprising the amino acid sequence of SEQ ID NO:21; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:22; (b) CDR-L2 comprising the amino acid sequence of SEQ ID NO:23; and (c) CDR-L3 comprising the amino acid sequence of SEQ ID NO:24; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 34; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 33.

In another exemplary embodiment, the anti-S-HBs antibody comprises (a) CDR-H1 comprising the amino acid sequence of SEQ ID NO:19; (b) CDR-H2 comprising the amino acid sequence of SEQ ID NO:20; (c) CDR-H3 comprising the amino acid sequence of SEQ ID NO:21; (d) CDR-L1 comprising the amino acid sequence of SEQ ID NO:22; (e) CDR-L2 comprising the amino acid sequence of SEQ ID NO:23; and (f) CDR-L3 comprising the amino acid sequence of SEQ ID NO:24, and a VH domain having at least 90%, 91%, 92%, 93%, 94%, 95%, 96%, 97%, 98%, 99%, or 100% sequence identity to the amino acid sequence of SEQ ID NO:34, and a VL domain having at least 90%, 91%, 92%, 93%, 94%, 95%, 96%, 97%, 98%, 99%, or 100% sequence identity to the amino acid sequence of SEQ ID NO:33. In one aspect, the VH domain has at least 95% sequence identity to the amino acid sequence of SEQ ID NO:34. In one aspect, the VL domain has at least 95% sequence identity to the amino acid sequence of SEQ ID NO:33. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:34 and a VL sequence of SEQ ID NO:33.

In one aspect, the antibody comprises the VH and VL sequences in SEQ ID NO:34 and SEQ ID NO: 33, respectively, including post-translational modifications of those sequences.

In a further aspect, the antibody may comprise the full length light chain of SEQ ID NO: 35 and/or the full length heavy chain of SEQ ID NO: 36 or 264.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 34 and a VL sequence of SEQ ID NO:33. In certain aspects, an antibody is provided that binds one or more of to the following residues of S-HBs of SEQ ID NO: 253: C138, C139 and/or C149, and optionally R169. Optionally the antibody may further bind to one or more of L109, R122, C147, T148, I152, W156, F161, and/or W165. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bc1.180 to S-HBs (e.g., of SEQ ID NO: 253), when assessed in the same assay, e.g., an ELISA assay or a flow cytometry assay.

Additionally or alternatively, antibodies as described in this section may have or retain at least 50%, 60%, 70%, 75%, 80%, 85%, 90%, 95% or 100% of the binding activity of a reference antibody Bc1.180 to one or more of SEQ ID NO: 254-262 (e.g., to at least SEQ ID NO: 257), optionally, each of the proteins of SEQ ID NO: 254 to 262, when assessed in the same assay, e.g., an ELISA assay or a flow cytometry assay.

Reference antibody Bc1.180 has a VH sequence of SEQ ID NO:34 and a VL sequence of SEQ ID NO:33. It has a full length heavy chain of SEQ ID NO: 36 or 264 and a full length light chain of SEQ ID NO: 35. SEQ ID NO: 264 comprises the IgG1 constant region expressed by vector LT615368.1, as used in the examples.

In some embodiments, the antibody as described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bc1.180 to the same antigen, when assessed in the same assay.

Additionally or alternatively, the antibody as described in this section may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bc1.180 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bc1.180, as measured by ELISA or by flow cytometry. Alternatively or additionally, the antibody may bind one or more of SEQ ID NO: 254-262 (e.g., to at least SEQ ID NO: 257), optionally each of the proteins of SEQ ID NO: 254 to 262 with an EC50 that is no more than 50, 10, 9, 8, 7, 6, 5, 4, 3, or 2 fold higher than, or is less than or equal to, the EC50 of reference antibody Bc1.180, as measured by ELISA or by flow cytometry. In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D, e.g., with an IC50 value of ≤1 pg/ml, optionally ≤0.1 pg/ml.

In another embodiment, the antibody may have an IC50 value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the IC50 value of reference antibody Bc1.180 against the same genotype, when assessed using the same assay (e.g., an assay as described herein).

In another embodiment, the antibody may have or retain at least 50%, 60%, 70%, 75%, 80%, 85%, 90%, 95% or 100% of the in vivo neutralizing activity of reference antibody Bc1.180 against HBV genotype A, B, C and/or D, optionally at least D, optionally all of A, B, C and D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bc1.180 against HBV genotype A, B, C and/or D, optionally at least D, optionally all of A, B, C and D, when assessed using the same assay (e.g., an assay as described herein).

C.

In one aspect, the invention provides an antibody comprising a VH domain comprising at least one, at least two, or all three VH CDR sequences selected from (a) CDR-H1 comprising the amino acid sequence of SEQ ID NO:37; (b) CDR-H2 comprising the amino acid sequence of SEQ ID NO: 38; and (c) CDR-H3 comprising the amino acid sequence of SEQ ID NO:39. In another aspect, the antibody comprises a VH domain comprising the following CDRs (a) CDR-H1 comprising the amino acid sequence of SEQ ID NO:37; (b) CDR-H2 comprising the amino acid sequence of SEQ ID NO:38; and (c) CDR-H3 comprising the amino acid sequence of SEQ ID NO: 39; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 43 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO: 44, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:45, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:46 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:52. In one aspect, an anti-S-HBs antibody comprises a heavy chain variable domain (VH) sequence having at least 95%, sequence identity to the amino acid sequence of SEQ ID NO:52. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 52. In certain aspects, substitutions, insertions, or deletions occur in regions outside the CDRs (i.e., in the FRs). Optionally, the anti-S-HBs antibody comprises the VH sequence in SEQ ID NO: 52, including post-translational modifications of that sequence. In a particular aspect, the VH comprises one, two or three CDRs selected from: (a) CDR-H1, comprising the amino acid sequence of SEQ ID NO 37, (b) CDR-H2, comprising the amino acid sequence of SEQ ID NO:38, and (c) CDR-H3, comprising the amino acid sequence of SEQ ID NO: 39.

In another aspect, an anti-S-HBs antibody comprises one or more of the heavy chain CDR sequences of the VH of SEQ ID NO:52. In one aspect, an anti-S-HBs antibody comprises one or more (preferably all three) of the heavy chain CDR amino acid sequences of the VH domain of SEQ ID NO:52 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:52. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:40; (b) CDR-L2 comprising the amino acid sequence of SEQ ID NO: 41; and (c) CDR-L3 comprising the amino acid sequence of SEQ ID NO:42. In another aspect, the antibody comprises a VL domain comprising the following CDRs (a) CDR-L1 comprising the amino acid sequence of SEQ ID NO:40; (b) CDR-L2 comprising the amino acid sequence of SEQ ID NO:41; and (c) CDR-L3 comprising the amino acid sequence of SEQ ID NO: 42; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 47 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:48 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:49 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:50 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:51. In one aspect, an anti-S-HBs antibody comprises a light chain variable domain (VL) sequence having at least 95% sequence identity to the amino acid sequence of SEQ ID NO:51. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:51. In certain aspects, the substitutions, insertions, or deletions occur in regions outside the CDRs (i.e., in the FRs). Optionally, the anti-S-HBs antibody comprises the VL sequence in SEQ ID NO:51, including post-translational modifications of that sequence. In a particular aspect, the VL comprises one, two or three CDRs selected from: (a) CDR-L1, comprising the amino acid sequence of SEQ ID NO:40, (b) CDR-L2, comprising the amino acid sequence of SEQ ID NO:41, and (c) CDR-L3, comprising the amino acid sequence of SEQ ID NO:42.

In another embodiment, an anti-S-HBs antibody comprises one or more of the CDR sequences of the VL of SEQ ID NO:51. In one aspect, an anti-S-HBs antibody comprises one or more (preferably all three) of the light chain CDR amino acid sequences of the VL domain of SEQ ID NO: 51 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:51. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:39; and a VL domain comprising CDR-L3 of SEQ ID NO: 42. Optionally the VH domain further comprises CDR-H2 of SEQ ID NO: 38.

In another exemplary embodiment, the antibody comprises:

i) a VH domain comprising the following CDRs (a) CDR-H1 comprising the amino acid sequence of SEQ ID NO:37; (b) CDR-H2 comprising the amino acid sequence of SEQ ID NO:38; and (c) CDR-H3 comprising the amino acid sequence of SEQ ID NO:39; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:40; (b) CDR-L2 comprising the amino acid sequence of SEQ ID NO:41; and (c) CDR-L3 comprising the amino acid sequence of SEQ ID NO:42; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 52; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 51.

In another exemplary embodiment, the anti-S-HBs antibody comprises (a) CDR-H1 comprising the amino acid sequence of SEQ ID NO:37; (b) CDR-H2 comprising the amino acid sequence of SEQ ID NO:38; (c) CDR-H3 comprising the amino acid sequence of SEQ ID NO:39; (d) CDR-L1 comprising the amino acid sequence of SEQ ID NO:40; (e) CDR-L2 comprising the amino acid sequence of SEQ ID NO:41; and (f) CDR-L3 comprising the amino acid sequence of SEQ ID NO:42, and a VH domain having at least 90%, 91%, 92%, 93%, 94%, 95%, 96%, 97%, 98%, 99%, or 100% sequence identity to the amino acid sequence of SEQ ID NO:52, and a VL domain having at least 90%, 91%, 92%, 93%, 94%, 95%, 96%, 97%, 98%, 99%, or 100% sequence identity to the amino acid sequence of SEQ ID NO:51. In one aspect, the VH domain has at least 95% sequence identity to the amino acid sequence of SEQ ID NO:52. In one aspect, the VL domain has at least 95% sequence identity to the amino acid sequence of SEQ ID NO:51. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:52 and a VL sequence of SEQ ID NO:51.

In one aspect, the antibody comprises the VH and VL sequences in SEQ ID NO:52 and SEQ ID NO: 51, respectively, including post-translational modifications of those sequences.

In a further aspect, the antibody may comprise the full length light chain of SEQ ID NO: 53 and/or the full length heavy chain of SEQ ID NO: 54 or 265.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 52 and a VL sequence of SEQ ID NO:51. In certain aspects, an antibody is provided that binds to one or more of the following residues of S-HBs of SEQ ID NO: 253: L109, C138, I152, W156, and/or R169. Optionally the antibody further binds to P111 and/or F161. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bc3.106 to S-HBs (e.g., of SEQ ID NO:253), when assessed in the same assay, e.g., an ELISA assay or a flow cytometry assay.

Additionally or alternatively, antibodies as described in this section may have or retain at least 50%, 60%, 70%, 75%, 80%, 85%, 90%, 95% or 100% of the binding activity of a reference antibody Bc3.106 to one or more of the proteins SEQ ID NO: 254-262 (e.g., to at least SEQ ID NO: 257), optionally, to each of the proteins of SEQ ID NO: 254 to 262, when assessed in the same assay, e.g., an ELISA assay or a flow cytometry assay.

Reference antibody Bc3.106 has the VH sequence of SEQ ID NO:52 and a VL sequence of SEQ ID NO:51. It has the full length heavy chain of SEQ ID NO: 54 or 265 and the full length light chain of SEQ ID NO: 53. SEQ ID NO: 265 comprises the IgG1 constant region expressed by vector LT615368.1, as used in the examples.

In some embodiments, the antibody as described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bc3.106 to the same antigen, when assessed in the same assay.

Additionally or alternatively, the antibody may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bc3.106 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bc3.106, as measured by ELISA or by flow cytometry. Alternatively or additionally, the antibody may bind one or more of SEQ ID NO: 254-262 (e.g., to at least SEQ ID NO: 257), optionally each of the proteins of SEQ ID NO: 254 to 262 with an EC50 that is no more than 50, 10, 9, 8, 7, 6, 5, 4, 3, or 2 fold higher than, or is less than or equal to, the EC50 of reference antibody Bc3.106, as measured by ELISA or by flow cytometry.

In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D, e.g., with an IC50 value of ≤10 pg/ml, optionally ≤1 pg/ml.

In another embodiment, the antibody may have an $IC_{50}$ value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the $IC_{50}$ value of reference antibody Bc3.106 against the same genotype, when assessed using the same assay (e.g., an assay as described herein).

In another embodiment, the antibody may have or retain at least 50%, 60%, 70%, 75%, 80%, 85%, 90%, 95% or 100% of the in vivo neutralizing activity of reference antibody Bc3.106 against HBV genotype A, B, C and/or D, optionally at least D, optionally all of A, B, C and D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bc3.106 against HBV genotype A, B, C and/or D, optionally at least D, optionally all of A, B, C and D, when assessed using the same assay (e.g., an assay as described herein).

D.

In one aspect, the invention provides an antibody comprising a VH domain comprising at least one, at least two, or all three VH CDR sequences selected from (a) CDR-H1 comprising the amino acid sequence of SEQ ID NO:55; (b) CDR-H2 comprising the amino acid sequence of SEQ ID NO: 56; and (c) CDR-H3 comprising the amino acid sequence of SEQ ID NO:57. In another aspect, the antibody comprises a VH domain comprising the following CDRs (a) CDR-H1 comprising the amino acid sequence of SEQ ID NO:55; (b) CDR-H2 comprising the amino acid sequence of SEQ ID NO:56; and (c) CDR-H3 comprising the amino acid sequence of SEQ ID NO: 57; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 61 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO: 62, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:63, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:64 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:70. In one aspect, an anti-S-HBs antibody comprises a heavy chain variable domain (VH) sequence having at least 95%, sequence identity to the amino acid sequence of SEQ ID NO:70. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 70. In certain aspects, substitutions, insertions, or deletions occur in regions outside the CDRs (i.e., in the FRs). Optionally, the anti-S-HBs antibody comprises the VH sequence in SEQ ID NO: 70, including post-translational modifications of that sequence. In a particular aspect, the VH comprises one, two or three CDRs selected from: (a) CDR-H1, comprising the amino acid sequence of SEQ ID NO 55, (b) CDR-H2, comprising the amino acid sequence of SEQ ID NO:56, and (c) CDR-H3, comprising the amino acid sequence of SEQ ID NO: 57.

In another aspect, an anti-S-HBs antibody comprises one or more of the heavy chain CDR sequences of the VH of SEQ ID NO:70. In one aspect, an anti-S-HBs antibody comprises one or more (preferably all three) of the heavy chain CDR amino acid sequences of the VH domain of SEQ ID NO:70 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:70. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:58; (b) CDR-L2 comprising the amino acid sequence of SEQ ID NO: 59; and (c) CDR-L3 comprising the amino acid sequence of SEQ ID NO:60. In another aspect, the antibody comprises a VL domain comprising the following CDRs (a) CDR-L1 comprising the amino acid sequence of SEQ ID NO:58; (b) CDR-L2 comprising the amino acid sequence of SEQ ID NO:59; and (c) CDR-L3 comprising the amino acid sequence of SEQ ID NO: 60; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 65 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:66 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:67 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:68 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:69. In one aspect, an anti-S-HBs antibody comprises a light chain variable domain (VL) sequence having at least 95% sequence identity to the amino acid sequence of SEQ ID NO:69. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:69. In certain aspects, the substitutions, insertions, or deletions occur in regions outside the CDRs (i.e., in the FRs). Optionally, the anti-S-HBs antibody comprises the VL sequence in SEQ ID NO:69, including post-translational modifications of that sequence. In a particular aspect, the VL comprises one, two or three CDRs selected from: (a) CDR-L1, comprising the amino acid sequence of SEQ ID NO:58, (b) CDR-L2, comprising the amino acid sequence of SEQ ID NO:59, and (c) CDR-L3, comprising the amino acid sequence of SEQ ID NO:60.

In another embodiment, an anti-S-HBs antibody comprises one or more of the CDR sequences of the VL of SEQ ID NO:69. In one aspect, an anti-S-HBs antibody comprises one or more (preferably all three) of the light chain CDR amino acid sequences of the VL domain of SEQ ID NO: 69 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:69. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:57; and a VL domain comprising CDR-L3 of SEQ ID NO: 60. Optionally the VH domain further comprises CDR-H2 of SEQ ID NO: 56.

In another exemplary embodiment, the antibody comprises:

i) a VH domain comprising the following CDRs (a) CDR-H1 comprising the amino acid sequence of SEQ ID NO:55; (b) CDR-H2 comprising the amino acid sequence of SEQ ID NO:56; and (c) CDR-H3 comprising the amino acid sequence of SEQ ID NO:57; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:58; (b) CDR-L2 comprising the amino acid sequence of SEQ ID NO:59; and (c) CDR-L3 comprising the amino acid sequence of SEQ ID NO:60; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 70; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 69.

In another exemplary embodiment, the anti-S-HBs antibody comprises (a) CDR-H1 comprising the amino acid sequence of SEQ ID NO:55; (b) CDR-H2 comprising the amino acid sequence of SEQ ID NO:56; (c) CDR-H3 comprising the amino acid sequence of SEQ ID NO:57; (d) CDR-L1 comprising the amino acid sequence of SEQ ID NO:58; (e) CDR-L2 comprising the amino acid sequence of SEQ ID NO:59; and (f) CDR-L3 comprising the amino acid sequence of SEQ ID NO:60, and a VH domain having at least 90%, 91%, 92%, 93%, 94%, 95%, 96%, 97%, 98%, 99%, or 100% sequence identity to the amino acid sequence of SEQ ID NO:70, and a VL domain having at least 90%, 91%, 92%, 93%, 94%, 95%, 96%, 97%, 98%, 99%, or 100% sequence identity to the amino acid sequence of SEQ ID NO:69. In one aspect, the VH domain has at least 95% sequence identity to the amino acid sequence of SEQ ID NO:70. In one aspect, the VL domain has at least 95% sequence identity to the amino acid sequence of SEQ ID NO:69. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:70 and a VL sequence of SEQ ID NO:69.

In one aspect, the antibody comprises the VH and VL sequences in SEQ ID NO:70 and SEQ ID NO: 69, respectively, including post-translational modifications of those sequences.

In a further aspect, the antibody may comprise the full length light chain of SEQ ID NO: 71 and/or the full length heavy chain of SEQ ID NO: 72 or 266.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 70 and a VL sequence of SEQ ID NO:69. In certain aspects, an antibody is provided that binds to one or more of the following residues of S-HBs of SEQ ID NO: 253: C121, R122, C124, C137, C139, K141, N146, C147 and/or C149. In some embodiments the antibody may also bind to one or more of I110, T118, P120, C138, P142, D144, T148 and/or I152. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bv4.104 to S-HBs (e.g., of SEQ ID NO:253), when assessed in the same assay, e.g., an ELISA assay or a flow cytometry assay.

Additionally or alternatively, antibodies as described in this section may have or retain at least 50%, 60%, 70%, 75%, 80%, 85%, 90%, 95% or 100% of the binding activity of a reference antibody Bv4.104 to one or more, or to each of the proteins of SEQ ID NO: 257 and 258, optionally at least to a protein of SEQ ID NO: 257, when assessed in the same assay, e.g., an ELISA assay or a flow cytometry assay.

Reference antibody Bv4.104 has a VH sequence of SEQ ID NO:70 and a VL sequence of SEQ ID NO:69. It has a full length heavy chain of SEQ ID NO: 72 or 266 and a full length light chain of SEQ ID NO: 71. SEQ ID NO: 266 comprises the IgG1 constant region expressed by vector LT615368.1, as used in the examples.

In some embodiments, the antibody as described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bv4.104 to the same antigen, when assessed in the same assay.

Additionally or alternatively, the antibody may bind to one or more, or to each of the proteins of SEQ ID NO: 257 and 258, optionally at least to a protein of SEQ ID NO: 257, with a $K_D$ value which is no more than 50, 10, 9, 8, 7, 6, 5, 4, 3, or 2 fold higher than, or is less than or equal to, the $K_D$ value of reference antibody Bv4.104 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bv4.104, as measured by ELISA or by flow cytometry. Alternatively or additionally, the antibody may bind one or more, or to each of the proteins of SEQ ID NO: 257 and 258, optionally at least to a protein of SEQ ID NO: 257, with an EC50 that is no more than 50, 10, 9, 8, 7, 6, 5, 4, 3, or 2 fold higher than, or is less than or equal to, the EC50 of reference antibody Bv4.104, as measured by ELISA or by flow cytometry.

In some embodiments antibodies as described in this section may have or retain in vitro neutralizing activity against HBV genotype D, e.g., with an IC50 value of ≤100 pg/ml, optionally ≤10 pg/ml.

In another embodiment, the antibody may have an $IC_{50}$ value for neutralization of HBV genotype D which is no more than 50, 10, 9, 8, 7, 6, 5, 4, 3, or 2 fold higher than, or is less than or equal to, the $IC_{50}$ value of reference antibody Bv4.104 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the in vivo neutralizing activity of reference antibody Bv4.104 against HBV genotype D, when assessed using the same assay (e.g., an assay as described herein).

Optionally the antibody can suppress virus viremia in vivo e.g., in an individual infected with HBV genotype D. Optionally, the antibody may have or retain at least 50%, 60%, 70%, 75%, 80%, 85%, 90%, 95% or 100% of the in vivo viremia suppressing activity of reference antibody Bv4.104 against HBV genotype D, when assessed using the same assay (e.g., an assay as described herein).

E.

In one aspect, the invention provides an antibody comprising a VH domain comprising at least one, at least two, or all three VH CDR sequences selected from (a) CDR-H1 comprising the amino acid sequence of SEQ ID NO:73; (b) CDR-H2 comprising the amino acid sequence of SEQ ID NO: 74; and (c) CDR-H3 comprising the amino acid sequence of SEQ ID NO:75. In another aspect, the antibody comprises a VH domain comprising the following CDRs (a) CDR-H1 comprising the amino acid sequence of SEQ ID NO:73; (b) CDR-H2 comprising the amino acid sequence of SEQ ID NO:74; and (c) CDR-H3 comprising the amino acid sequence of SEQ ID NO: 75; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 79 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO: 80, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:81, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:82 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:88. In one aspect, an anti-S-HBs antibody comprises a heavy chain variable domain (VH) sequence having at least 95%, sequence identity to the amino acid sequence of SEQ ID NO:88. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 88. In certain aspects, substitutions, insertions, or deletions occur in regions outside the CDRs (i.e., in the FRs). Optionally, the anti-S-HBs antibody comprises the VH sequence in SEQ ID NO: 88, including post-translational modifications of that sequence. In a particular aspect, the VH comprises one, two or three CDRs selected from: (a) CDR-H1, comprising the amino acid sequence of SEQ ID NO 73, (b) CDR-H2, comprising the amino acid sequence of SEQ ID NO:74, and (c) CDR-H3, comprising the amino acid sequence of SEQ ID NO: 75.

In another aspect, an anti-S-HBs antibody comprises one or more of the heavy chain CDR sequences of the VH of SEQ ID NO:88. In one aspect, an anti-S-HBs antibody comprises one or more (preferably all three) of the heavy chain CDR amino acid sequences of the VH domain of SEQ ID NO:88 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:88. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:76; (b) CDR-L2 comprising the amino acid sequence of SEQ ID NO: 77; and (c) CDR-L3 comprising the amino acid sequence of SEQ ID NO:78. In another aspect, the antibody comprises a VL domain comprising the following CDRs (a) CDR-L1 comprising the amino acid sequence of SEQ ID NO:76; (b) CDR-L2 comprising the amino acid sequence of SEQ ID NO:77; and (c) CDR-L3 comprising the amino acid sequence of SEQ ID NO: 78; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 83 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:84 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:85 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:86 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:87. In one aspect, an anti-S-HBs antibody comprises a light chain variable domain (VL) sequence having at least 95% sequence identity to the amino acid sequence of SEQ ID NO:87. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:87. In certain aspects, the substitutions, insertions, or deletions occur in regions outside the CDRs (i.e., in the FRs). Optionally, the anti-S-HBs antibody comprises the VL sequence in SEQ ID NO:87, including post-translational modifications of that sequence. In a particular aspect, the VL comprises one, two or three CDRs selected from: (a) CDR-L1, comprising the amino acid sequence of SEQ ID NO:76, (b) CDR-L2, comprising the amino acid sequence of SEQ ID NO:77, and (c) CDR-L3, comprising the amino acid sequence of SEQ ID NO:78.

In another embodiment, an anti-S-HBs antibody comprises one or more of the CDR sequences of the VL of SEQ ID NO:87. In one aspect, an anti-S-HBs antibody comprises one or more (preferably all three) of the light chain CDR amino acid sequences of the VL domain of SEQ ID NO: 87 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:87. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:75; and a VL domain comprising CDR-L3 of SEQ ID NO: 78. Optionally the VH domain further comprises CDR-H2 of SEQ ID NO: 74.

In another exemplary embodiment, the antibody comprises:

i) a VH domain comprising the following CDRs (a) CDR-H1 comprising the amino acid sequence of SEQ ID NO:73; (b) CDR-H2 comprising the amino acid sequence of SEQ ID NO:74; and (c) CDR-H3 comprising the amino acid sequence of SEQ ID NO:75; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:76; (b) CDR-L2 comprising the amino acid sequence of SEQ ID NO:77; and (c) CDR-L3 comprising the amino acid sequence of SEQ ID NO:78; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 88; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 87.

In another exemplary embodiment, the anti-S-HBs antibody comprises (a) CDR-H1 comprising the amino acid sequence of SEQ ID NO:73; (b) CDR-H2 comprising the amino acid sequence of SEQ ID NO:74; (c) CDR-H3 comprising the amino acid sequence of SEQ ID NO:75; (d) CDR-L1 comprising the amino acid sequence of SEQ ID NO:76; (e) CDR-L2 comprising the amino acid sequence of SEQ ID NO:77; and (f) CDR-L3 comprising the amino acid sequence of SEQ ID NO:78, and a VH domain having at least 90%, 91%, 92%, 93%, 94%, 95%, 96%, 97%, 98%, 99%, or 100% sequence identity to the amino acid sequence of SEQ ID NO:88, and a VL domain having at least 90%, 91%, 92%, 93%, 94%, 95%, 96%, 97%, 98%, 99%, or 100% sequence identity to the amino acid sequence of SEQ ID NO:87. In one aspect, the VH domain has at least 95% sequence identity to the amino acid sequence of SEQ ID NO:88. In one aspect, the VL domain has at least 95% sequence identity to the amino acid sequence of SEQ ID NO:87. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:88 and a VL sequence of SEQ ID NO:87.

In one aspect, the antibody comprises the VH and VL sequences in SEQ ID NO:88 and SEQ ID NO: 87, respectively, including post-translational modifications of those sequences.

In a further aspect, the antibody may comprise the full length light chain of SEQ ID NO: 89 and/or the full length heavy chain of SEQ ID NO: 90 or 267.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 88 and a VL sequence of SEQ ID NO:87. In certain aspects, an antibody is provided that binds to one or more of the following residues of S-HBs of SEQ ID NO: 253: C121, and/or one or more of I110, P120, C124, C137, C139, C147, T148 and/or C149. Optionally the antibody may further bind to one or more of C138, K141, P142, D144, G145, P150, I152, and/or W156. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bc8.111 to S-HBs (e.g., of SEQ ID NO:253), when assessed in the same assay, e.g., an ELISA assay or a flow cytometry assay.

Additionally or alternatively, antibodies as described in this section may have or retain at least 50%, 60%, 70%, 75%, 80%, 85%, 90%, 95% or 100% of the binding activity of reference antibody Bc8.111 to one or more of the proteins of SEQ ID NO: 254-262 (e.g., to at least SEQ ID NO: 257), optionally to each of the proteins of SEQ ID NO: 254 to 262, when assessed in the same assay e.g., an ELISA assay or a flow cytometry assay.

Reference antibody Bc8.111 has a VH sequence of SEQ ID NO:88 and a VL sequence of SEQ ID NO:87. It has a full length heavy chain of SEQ ID NO: 90 or 267 and a full length light chain of SEQ ID NO: 89. SEQ ID NO: 267 comprises the IgG1 constant region expressed by vector LT615368.1, as used in the examples. In some embodiments, the antibody described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bc8.111 to the same antigen, when assessed in the same assay.

Additionally or alternatively, the antibody may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bc8.111 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bc8.111, as measured by ELISA or by flow cytometry. Alternatively or additionally, the antibody may bind one or more, or to each of the proteins of SEQ ID NO: 254-262, optionally at least to a protein of SEQ ID NO: 257, with an EC50 that is no more than 50, 10, 9, 8, 7, 6, 5, 4, 3, or 2 fold higher than, or is less than or equal to, the EC50 of reference antibody Bc8.111, as measured by ELISA or by flow cytometry.

In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D, e.g., with an $IC_{50}$ value of ≤100 pg/ml, optionally ≤10 pg/ml.

In another embodiment, the antibody may have an $IC_{50}$ value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the IC50 value of reference antibody Bc8.111 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the in vivo neutralizing activity of reference antibody Bc8.111 against HBV genotype A, B, C and/or D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bc8.111 against HBV genotype A, B, C and/or D, when assessed using the same assay (e.g., an assay as described herein).

F.

In one aspect, the invention provides an antibody comprising a VH domain comprising at least one, at least two, or all three VH CDR sequences selected from (a) CDR-H1 comprising the amino acid sequence of SEQ ID NO:91; (b) CDR-H2 comprising the amino acid sequence of SEQ ID NO: 92; and (c) CDR-H3 comprising the amino acid sequence of SEQ ID NO:93. In another aspect, the antibody comprises a VH domain comprising the following CDRs (a) CDR-H1 comprising the amino acid sequence of SEQ ID NO:91; (b) CDR-H2 comprising the amino acid sequence of SEQ ID NO:92; and (c) CDR-H3 comprising the amino acid sequence of SEQ ID NO: 93; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 97 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO: 98, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:99, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:100 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 106. In one aspect, an anti-S-HBs antibody comprises a heavy chain variable domain (VH) sequence having at least 95%, sequence identity to the amino acid sequence of SEQ ID NO:106. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 106. In certain aspects, substitutions, insertions, or deletions occur in regions outside the CDRs (i.e., in the FRs). Optionally, the anti-S-HBs antibody comprises the VH sequence in SEQ ID NO: 106, including post-translational modifications of that sequence. In a particular aspect, the VH comprises one, two or three CDRs selected from: (a) CDR-H1, comprising the amino acid sequence of SEQ ID NO 91, (b) CDR-H2, comprising the amino acid sequence of SEQ ID NO:92, and (c) CDR-H3, comprising the amino acid sequence of SEQ ID NO: 93.

In another aspect, an anti-S-HBs antibody comprises one or more of the heavy chain CDR sequences of the VH of SEQ ID NO:106. In one aspect, an anti-S-HBs antibody comprises one or more (preferably all three) of the heavy chain CDR amino acid sequences of the VH domain of SEQ ID NO: 106 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:106. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:94; (b) CDR-L2 comprising the amino acid sequence of SEQ ID NO: 95; and (c) CDR-L3 comprising the amino acid sequence of SEQ ID NO:96. In another aspect, the antibody comprises a VL domain comprising the following CDRs (a) CDR-L1 comprising the amino acid sequence of SEQ ID NO:94; (b) CDR-L2 comprising the amino acid sequence of SEQ ID NO:95; and (c) CDR-L3 comprising the amino acid sequence of SEQ ID NO:96; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 101 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:102 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:103 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:104 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 105. In one aspect, an anti-S-HBs antibody comprises a light chain variable domain (VL) sequence having at least 95% sequence identity to the amino acid sequence of SEQ ID NO: 105. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:105. In certain aspects, the substitutions, insertions, or deletions occur in regions outside the CDRs (i.e., in the FRs). Optionally, the anti-S-HBs antibody comprises the VL sequence in SEQ ID NO:105, including post-translational modifications of that sequence. In a particular aspect, the VL comprises one, two or three CDRs selected from: (a) CDR-L1, comprising the amino acid sequence of SEQ ID NO:94, (b) CDR-L2, comprising the amino acid sequence of SEQ ID NO:95, and (c) CDR-L3, comprising the amino acid sequence of SEQ ID NO:96.

In another embodiment, an anti-S-HBs antibody comprises one or more of the CDR sequences of the VL of SEQ ID NO:105. In one aspect, an anti-S-HBs antibody comprises one or more (preferably all three) of the light chain CDR amino acid sequences of the VL domain of SEQ ID NO: 105 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:105. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:93; and a VL domain comprising CDR-L3 of SEQ ID NO: 96. Optionally the VH domain further comprises CDR-H2 of SEQ ID NO: 92.

In another exemplary embodiment, the antibody comprises:

i) a VH domain comprising the following CDRs (a) CDR-H1 comprising the amino acid sequence of SEQ ID NO:91; (b) CDR-H2 comprising the amino acid sequence of SEQ ID NO:92; and (c) CDR-H3 comprising the amino acid sequence of SEQ ID NO:93; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:94; (b) CDR-L2 comprising the amino acid sequence of SEQ ID NO:95; and (c) CDR-L3 comprising the amino acid sequence of SEQ ID NO:96; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 106; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 105.

In another exemplary embodiment, the anti-S-HBs antibody comprises (a) CDR-H1 comprising the amino acid sequence of SEQ ID NO:91; (b) CDR-H2 comprising the amino acid sequence of SEQ ID NO:92; (c) CDR-H3 comprising the amino acid sequence of SEQ ID NO:93; (d) CDR-L1 comprising the amino acid sequence of SEQ ID NO:94; (e) CDR-L2 comprising the amino acid sequence of SEQ ID NO:95; and (f) CDR-L3 comprising the amino acid sequence of SEQ ID NO:96, and a VH domain having at least 90%, 91%, 92%, 93%, 94%, 95%, 96%, 97%, 98%, 99%, or 100% sequence identity to the amino acid sequence of SEQ ID NO:106, and a VL domain having at least 90%, 91%, 92%, 93%, 94%, 95%, 96%, 97%, 98%, 99%, or 100% sequence identity to the amino acid sequence of SEQ ID NO:105. In one aspect, the VH domain has at least 95% sequence identity to the amino acid sequence of SEQ ID NO:106. In one aspect, the VL domain has at least 95% sequence identity to the amino acid sequence of SEQ ID NO 105. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:106 and a VL sequence of SEQ ID NO:105.

In one aspect, the antibody comprises the VH and VL sequences in SEQ ID NO: 106 and SEQ ID NO:105, respectively, including post-translational modifications of those sequences.

In a further aspect, the antibody may comprise the full length light chain of SEQ ID NO: 107 and/or the full length heavy chain of SEQ ID NO: 108 or 268.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 106 and a VL sequence of SEQ ID NO:105. In certain aspects, an antibody is provided that binds to one or more of the following residues of S-HBs of SEQ ID NO: 253: W156 and/or R169. Optionally the antibody may additional bind to one or more of I152 and/or C138. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bc8.104 to S-HBs (e.g., of SEQ ID NO:253), when assessed in the same assay, e.g., an ELISA assay or a flow cytometry assay.

Additionally or alternatively, antibodies as described in this section may have or retain at least 50%, 60%, 70%, 75%, 80%, 85%, 90%, 95% or 100% of the binding activity of reference antibody Bc8.104 to one or more of the proteins of SEQ ID NO: 254-262 (e.g., to at least SEQ ID NO: 257), optionally each of the proteins of SEQ ID NO: 254 to 262, when assessed in the same assay, e.g., an ELISA assay or a flow cytometry assay.

Reference antibody Bc8.104 has a VH sequence of SEQ ID NO:106 and a VL sequence of SEQ ID NO:105. It has a full length heavy chain of SEQ ID NO: 108 or 268 and a full length light chain of SEQ ID NO: 107. SEQ ID NO: 268 comprises the IgG1 constant region expressed by vector LT615368.1, as used in the examples.

In some embodiments, the antibody described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bc8.104 to the same antigen, when assessed in the same assay.

Additionally or alternatively, the antibody described in this section may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bc8.104 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bc8.104, as measured by ELISA or by flow cytometry. Alternatively or additionally, the antibody may bind one or more, or to each of the proteins of SEQ ID NO: 254-262, optionally at least to a protein of SEQ ID NO: 257, with an EC50 that is no more than 50, 10, 9, 8, 7, 6, 5, 4, 3, or 2 fold higher than, or is less than or equal to, the EC50 of reference antibody Bc8.104, as measured by ELISA or by flow cytometry.

In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D, e.g., with an IC50 value of ≤100 pg/ml, optionally ≤10 pg/ml.

In another embodiment, the antibody may have an IC50 value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the IC50 value of reference antibody Bc8.104 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the neutralizing activity of reference antibody Bc8.104 against HBV genotype A, B, C and/or D, optionally at least D, optionally all of A, B, C and D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bc8.104 against HBV genotype A, B, C and/or D, optionally at least D, optionally all of A, B, C and D, when assessed using the same assay (e.g., an assay as described herein).

G.

In one aspect, the invention provides an antibody comprising a VH domain comprising at least one, at least two, or all three VH CDR sequences selected from (a) CDR-H1 comprising the amino acid sequence of SEQ ID NO:109; (b) CDR-H2 comprising the amino acid sequence of SEQ ID NO:110; and (c) CDR-H3 comprising the amino acid sequence of SEQ ID NO:111. In another aspect, the antibody comprises a VH domain comprising the following CDRs (a) CDR-H1 comprising the amino acid sequence of SEQ ID NO:109; (b) CDR-H2 comprising the amino acid sequence of SEQ ID NO:110; and (c) CDR-H3 comprising the amino acid sequence of SEQ ID NO: 111; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 115 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO:116, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:117, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:118 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:124. In one aspect, an anti-S-HBs antibody comprises a heavy chain variable domain (VH) sequence having at least 95%, sequence identity to the amino acid sequence of SEQ ID NO:124. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 124. In certain aspects, substitutions, insertions, or deletions occur in regions outside the CDRs (i.e., in the FRs). Optionally, the anti-S-HBs antibody comprises the VH sequence in SEQ ID NO: 124, including post-translational modifications of that sequence. In a particular aspect, the VH comprises one, two or three CDRs selected from: (a) CDR-H1, comprising the amino acid sequence of SEQ ID NO 109, (b) CDR-H2, comprising the amino acid sequence of SEQ ID NO: 110, and (c) CDR-H3, comprising the amino acid sequence of SEQ ID NO: 111.

In another aspect, an anti-S-HBs antibody comprises one or more of the heavy chain CDR. sequences of the VH of SEQ ID NO:124. In one aspect, an anti-S-HBs antibody comprises one or more (preferably all three) of the heavy chain CDR amino acid sequences of the VH domain of SEQ ID NO:124 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:124. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:112; (b) CDR-L2 comprising the amino acid sequence of SEQ ID NO: 113; and (c) CDR-L3 comprising the amino acid sequence of SEQ ID NO:114. In another aspect, the antibody comprises a VL domain comprising the following CDRs (a) CDR-L1 comprising the amino acid sequence of SEQ ID NO:112; (b) CDR-L2 comprising the amino acid sequence of SEQ ID NO:113; and (c) CDR-L3 comprising the amino acid sequence of SEQ ID NO: 114; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 119 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:120 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:121 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:122 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:123. In one aspect, an anti-S-HBs antibody comprises a light chain variable domain (VL) sequence having at least 95% sequence identity to the amino acid sequence of SEQ ID NO: 123. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:123. In certain aspects, the substitutions, insertions, or deletions occur in regions outside the CDRs (i.e., in the FRs). Optionally, the anti-S-HBs antibody comprises the VL sequence in SEQ ID NO:123, including post-translational modifications of that sequence. In a particular aspect, the VL comprises one, two or three CDRs selected from: (a) CDR-L1, comprising the amino acid sequence of SEQ ID NO:112, (b) CDR-L2, comprising the amino acid sequence of SEQ ID NO:113, and (c) CDR-L3, comprising the amino acid sequence of SEQ ID NO:114.

In another embodiment, an anti-S-HBs antibody comprises one or more of the CDR sequences of the VL of SEQ ID NO:123. In one aspect, an anti-S-HBs antibody comprises one or more (preferably all three) of the light chain CDR amino acid sequences of the VL domain of SEQ ID NO: 123 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:123. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:111; and a VL domain comprising CDR-L3 of SEQ ID NO: 114. Optionally the VH domain further comprises CDR-H2 of SEQ ID NO: 110.

In another exemplary embodiment, the antibody comprises:

i) a VH domain comprising the following CDRs (a) CDR-H1 comprising the amino acid sequence of SEQ ID NO:109; (b) CDR-H2 comprising the amino acid sequence of SEQ ID NO: 110; and (c) CDR-H3 comprising the amino acid sequence of SEQ ID NO:111; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:112; (b) CDR-L2 comprising the amino acid sequence of SEQ ID NO: 113; and (c) CDR-L3 comprising the amino acid sequence of SEQ ID NO:114; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 124; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 123.

In another exemplary embodiment, the anti-S-HBs antibody comprises (a) CDR-H1 comprising the amino acid sequence of SEQ ID NO:109; (b) CDR-H2 comprising the amino acid sequence of SEQ ID NO:110; (c) CDR-H3 comprising the amino acid sequence of SEQ ID NO: 111; (d) CDR-L1 comprising the amino acid sequence of SEQ ID NO:112; (e) CDR-L2 comprising the amino acid sequence of SEQ ID NO:113; and (f) CDR-L3 comprising the amino acid sequence of SEQ ID NO:114, and a VH domain having at least 90%, 91%, 92%, 93%, 94%, 95%, 96%, 97%, 98%, 99%, or 100% sequence identity to the amino acid sequence of SEQ ID NO: 124, and a VL domain having at least 90%, 91%, 92%, 93%, 94%, 95%, 96%, 97%, 98%, 99%, or 100% sequence identity to the amino acid sequence of SEQ ID NO:123. In one aspect, the VH domain has at least 95% sequence identity to the amino acid sequence of SEQ ID NO:124. In one aspect, the VL domain has at least 95% sequence identity to the amino acid sequence of SEQ ID NO 123. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO: 124 and a VL sequence of SEQ ID NO:123.

In one aspect, the antibody comprises the VH and VL sequences in SEQ ID NO: 124 and SEQ ID NO:123, respectively, including post-translational modifications of those sequences.

In a further aspect, the antibody may comprise the full length light chain of SEQ ID NO: 125 and/or the full length heavy chain of SEQ ID NO: 126 or 269.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 124 and a VL sequence of SEQ ID NO:123. In certain aspects, an antibody is provided that binds to one or more of the following residues of S-HBs of SEQ ID NO: 253: C137, C138 and/or D144. Optionally, the antibody may further bind to one or more of P142, N146, T148, C149, I152 and/or W156. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bv6.172 to S-HBs (e.g., of SEQ ID NO:253), when assessed in the same assay, e.g., an ELISA assay or a flow cytometry assay.

Additionally or alternatively, antibodies as described in this section may have or retain at least 50%, 60%, 70%, 75%, 80%, 85%, 90%, 95% or 100% of the binding activity of reference antibody Bv6.172 to one or more of the proteins of SEQ ID NO: 254-262 (e.g., to at least SEQ ID NO: 257), optionally each of the proteins of SEQ ID NO: 254 to 262, when assessed in the same assay, e.g., an ELISA assay or a flow cytometry assay.

Reference antibody Bv6.172 has a VH sequence of SEQ ID NO: 124 and a VL sequence of SEQ ID NO:123. It has a full length heavy chain of SEQ ID NO: 126 or 269 and a full length light chain of SEQ ID NO: 125. SEQ ID NO: 269 comprises the IgG1 constant region expressed by vector LT615368.1, as used in the examples.

In some embodiments, the antibody as described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bv6.172 to the same antigen, when assessed in the same assay.

Additionally or alternatively, the antibody may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bv6.172 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bv6.172, as measured by ELISA or by flow cytometry. Alternatively or additionally, the antibody may bind one or more, or to each of the proteins of SEQ ID NO: 254-262, optionally at least to a protein of SEQ ID NO: 257, with an EC50 that is no more than 50, 10, 9, 8, 7, 6, 5, 4, 3, or 2 fold higher than, or is less than or equal to, the EC50 of reference antibody Bv6.172, as measured by ELISA or by flow cytometry.

In some embodiments antibodies as described in this section may have or retain in vitro neutralizing activity against HBV genotype D, e.g., with an IC50 value of ≤100 pg/ml, optionally ≤10 pg/ml.

In another embodiment, the antibody may have an $IC_{50}$ value for neutralization of HBV genotype A, B, C and/or D which is no more than 50, 10, 9, 8, 7, 6, 5, 4, 3, or 2 fold higher than, or is less than or equal to, the $IC_{50}$ value of reference antibody Bv6.172 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the in vivo neutralizing activity of reference antibody Bv6.172 against HBV genotype A, B, C and/or D, optionally at least D, optionally all of A, B, C and D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bv6.172 against HBV genotype A, B, C and/or D, optionally at least D, optionally all of A, B, C and D, when assessed using the same assay (e.g., an assay as described herein).

H.

In one aspect, the invention provides an antibody comprising a VH domain comprising at least one, at least two, or all three VH CDR sequences selected from (a) CDR-H1 comprising the amino acid sequence of SEQ ID NO:127; (b) CDR-H2 comprising the amino acid sequence of SEQ ID NO:128; and (c) CDR-H3 comprising the amino acid sequence of SEQ ID NO:129. In another aspect, the antibody comprises a VH domain comprising the following CDRs (a) CDR-H1 comprising the amino acid sequence of SEQ ID NO: 127; (b) CDR-H2 comprising the amino acid sequence of SEQ ID NO:128; and (c) CDR-H3 comprising the amino acid sequence of SEQ ID NO: 129; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 133 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO:134, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:135, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO: 136 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 142. In one aspect, an anti-S-HBs antibody comprises a heavy chain variable domain (VH) sequence having at least 95%, sequence identity to the amino acid sequence of SEQ ID NO:142. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 142. In certain aspects, substitutions, insertions, or deletions occur in regions outside the CDRs (i.e., in the FRs). Optionally, the anti-S-HBs antibody comprises the VH sequence in SEQ ID NO: 142, including post-translational modifications of that sequence. In a particular aspect, the VH comprises one, two or three CDRs selected from: (a) CDR-H1, comprising the amino acid sequence of SEQ ID NO 127, (b) CDR-H2, comprising the amino acid sequence of SEQ ID NO: 128, and (c) CDR-H3, comprising the amino acid sequence of SEQ ID NO: 129.

In another aspect, an anti-S-HBs antibody comprises one or more of the heavy chain CDR sequences of the VH of SEQ ID NO:142. In one aspect, an anti-S-HBs antibody comprises one or more (preferably all three) of the heavy chain CDR amino acid sequences of the VH domain of SEQ ID NO:142 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 142. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:130; (b) CDR-L2 comprising the amino acid sequence of SEQ ID NO: 131; and (c) CDR-L3 comprising the amino acid sequence of SEQ ID NO:132. In another aspect, the antibody comprises a VL domain comprising the following CDRs (a) CDR-L1 comprising the amino acid sequence of SEQ ID NO:130; (b) CDR-L2 comprising the amino acid sequence of SEQ ID NO:131; and (c) CDR-L3 comprising the amino acid sequence of SEQ ID NO: 132; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 137 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:138 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:139 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4)

of SEQ ID NO:140 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:141. In one aspect, an anti-S-HBs antibody comprises a light chain variable domain (VL) sequence having at least 95% sequence identity to the amino acid sequence of SEQ ID NO:141. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:141. In certain aspects, the substitutions, insertions, or deletions occur in regions outside the CDRs (i.e., in the FRs). Optionally, the anti-S-HBs antibody comprises the VL sequence in SEQ ID NO: 141, including post-translational modifications of that sequence. In a particular aspect, the VL comprises one, two or three CDRs selected from: (a) CDR-L1, comprising the amino acid sequence of SEQ ID NO:130, (b) CDR-L2, comprising the amino acid sequence of SEQ ID NO:131, and (c) CDR-L3, comprising the amino acid sequence of SEQ ID NO:132.

In another embodiment, an anti-S-HBs antibody comprises one or more of the CDR sequences of the VL of SEQ ID NO:141. In one aspect, an anti-S-HBs antibody comprises one or more (preferably all three) of the light chain CDR amino acid sequences of the VL domain of SEQ ID NO: 141 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:141. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:129; and a VL domain comprising CDR-L3 of SEQ ID NO: 132. Optionally the VH domain further comprises CDR-H2 of SEQ ID NO: 128.

In another exemplary embodiment, the antibody comprises:

i) a VH domain comprising the following CDRs (a) CDR-H1 comprising the amino acid sequence of SEQ ID NO:127; (b) CDR-H2 comprising the amino acid sequence of SEQ ID NO: 128; and (c) CDR-H3 comprising the amino acid sequence of SEQ ID NO:129; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:130; (b) CDR-L2 comprising the amino acid sequence of SEQ ID NO: 131; and (c) CDR-L3 comprising the amino acid sequence of SEQ ID NO:132; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 142; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 141.

In another exemplary embodiment, the anti-S-HBs antibody comprises (a) CDR-H1 comprising the amino acid sequence of SEQ ID NO:127; (b) CDR-H2 comprising the amino acid sequence of SEQ ID NO:128; (c) CDR-H3 comprising the amino acid sequence of SEQ ID NO: 129; (d) CDR-L1 comprising the amino acid sequence of SEQ ID NO:130; (e) CDR-L2 comprising the amino acid sequence of SEQ ID NO:131; and (f) CDR-L3 comprising the amino acid sequence of SEQ ID NO:132, and a VH domain having at least 90%, 91%, 92%, 93%, 94%, 95%, 96%, 97%, 98%, 99%, or 100% sequence identity to the amino acid sequence of SEQ ID NO: 142, and a VL domain having at least 90%, 91%, 92%, 93%, 94%, 95%, 96%, 97%, 98%, 99%, or 100% sequence identity to the amino acid sequence of SEQ ID NO:141. In one aspect, the VH domain has at least 95% sequence identity to the amino acid sequence of SEQ ID NO:142. In one aspect, the VL domain has at least 95% sequence identity to the amino acid sequence of SEQ ID NO 141. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:142 and a VL sequence of SEQ ID NO:141.

In one aspect, the antibody comprises the VH and VL sequences in SEQ ID NO: 142 and SEQ ID NO:141, respectively, including post-translational modifications of those sequences.

In a further aspect, the antibody may comprise the full length light chain of SEQ ID NO: 143 and/or the full length heavy chain of SEQ ID NO: 144 or 270.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 142 and a VL sequence of SEQ ID NO:141. In certain aspects, an antibody is provided that binds to one or more of the following residues of S-HBs of SEQ ID NO: 253: C137, C138 and/or C139. Optionally, the antibody also binds to C124, optionally further to W156, and optionally to one or more of N146, T148 and/or I152. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bv4.115 to S-HBs (e.g., of SEQ ID NO:253), when assessed in the same assay, e.g., an ELISA or flow cytometry assay.

Additionally or alternatively, antibodies as described in this section may have or retain at least 50%, 60%, 70%, 75%, 80%, 85%, 90%, 95% or 100% of the binding activity of reference antibody Bv4.115 to one or more of the proteins of SEQ ID NO: 254-262 (e.g., to at least SEQ ID NO: 257), optionally each of the proteins of SEQ ID NO: 254 to 262, when assessed in the same assay, e.g., an ELISA or flow cytometry assay.

Reference antibody Bv4.115 has a VH sequence of SEQ ID NO: 142 and a VL sequence of SEQ ID NO:141. It has a full length heavy chain of SEQ ID NO: 144 or 270 and a full length light chain of SEQ ID NO: 143. SEQ ID NO: 270 comprises the IgG1 constant region expressed by vector LT615368.1, as used in the examples.

In some embodiments, the antibody as described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bv4.115 to the same antigen, when assessed in the same assay.

Additionally or alternatively, the antibody may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bv4.115 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bv4.115, as measured by ELISA or by flow cytometry. Alternatively or additionally, the antibody may bind one or more, or to each of the proteins of SEQ ID NO: 254-262, optionally at least to a protein of SEQ ID NO: 257, with an EC50 that is no more than 50, 10, 9, 8, 7, 6, 5, 4, 3, or 2 fold higher than, or is less than or equal to, the EC50 of reference antibody Bv4.115, as measured by ELISA or by flow cytometry.

In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D, e.g., with an IC50 value of ≤100 pg/ml, optionally ≤10 pg/ml.

In another embodiment, the antibody may have an IC50 value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the IC50 value of reference antibody Bv4.115 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the in vivo neutralizing activity of reference antibody Bv4.115 against HBV genotype A, B, C and/or D, optionally at least D, optionally all of A, B, C and D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bv4.115 against HBV genotype A, B, C and/or D, optionally at least D, optionally all of A, B, C and D, when assessed using the same assay (e.g., an assay as described herein).

I.

In one aspect, the invention provides an antibody comprising a VH domain comprising at least one, at least two, or all three VH CDR sequences selected from (a) CDR-H1 comprising the amino acid sequence of SEQ ID NO:145; (b) CDR-H2 comprising the amino acid sequence of SEQ ID NO:146; and (c) CDR-H3 comprising the amino acid sequence of SEQ ID NO:147. In another aspect, the antibody comprises a VH domain comprising the following CDRs (a) CDR-H1 comprising the amino acid sequence of SEQ ID NO:145; (b) CDR-H2 comprising the amino acid sequence of SEQ ID NO:146; and (c) CDR-H3 comprising the amino acid sequence of SEQ ID NO: 147; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 151 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO:152, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:153, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO: 154 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:160. In one aspect, an anti-S-HBs antibody comprises a heavy chain variable domain (VH) sequence having at least 95%, sequence identity to the amino acid sequence of SEQ ID NO:160. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 160. In certain aspects, substitutions, insertions, or deletions occur in regions outside the CDRs (i.e., in the FRs). Optionally, the anti-S-HBs antibody comprises the VH sequence in SEQ ID NO: 160, including post-translational modifications of that sequence. In a particular aspect, the VH comprises one, two or three CDRs selected from: (a) CDR-H1, comprising the amino acid sequence of SEQ ID NO 145, (b) CDR-H2, comprising the amino acid sequence of SEQ ID NO: 146, and (c) CDR-H3, comprising the amino acid sequence of SEQ ID NO: 147.

In another aspect, an anti-S-HBs antibody comprises one or more of the heavy chain CDR sequences of the VH of SEQ ID NO:160. In one aspect, an anti-S-HBs antibody comprises one or more (preferably all three) of the heavy chain CDR amino acid sequences of the VH domain of SEQ ID NO: 160 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 160. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:148; (b) CDR-L2 comprising the amino acid sequence of SEQ ID NO: 149; and (c) CDR-L3 comprising the amino acid sequence of SEQ ID NO:150. In another aspect, the antibody comprises a VL domain comprising the following CDRs (a) CDR-L1 comprising the amino acid sequence of SEQ ID NO:148; (b) CDR-L2 comprising the amino acid sequence of SEQ ID NO:149; and (c) CDR-L3 comprising the amino acid sequence of SEQ ID NO: 150; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 155 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:156 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:157 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:158 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:159. In one aspect, an anti-S-HBs antibody comprises a light chain variable domain (VL) sequence having at least 95% sequence identity to the amino acid sequence of SEQ ID NO: 159. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:159. In certain aspects, the substitutions, insertions, or deletions occur in regions outside the CDRs (i.e., in the FRs). Optionally, the anti-S-HBs antibody comprises the VL sequence in SEQ ID NO: 159, including post-translational modifications of that sequence. In a particular aspect, the VL comprises one, two or three CDRs selected from: (a) CDR-L1, comprising the amino acid sequence of SEQ ID NO:148, (b) CDR-L2, comprising the amino acid sequence of SEQ ID NO:149, and (c) CDR-L3, comprising the amino acid sequence of SEQ ID NO:150.

In another embodiment, an anti-S-HBs antibody comprises one or more of the CDR sequences of the VL of SEQ ID NO:159. In one aspect, an anti-S-HBs antibody comprises one or more (preferably all three) of the light chain CDR amino acid sequences of the VL domain of SEQ ID NO: 159 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:159. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO: 147; and a VL domain comprising CDR-L3 of SEQ ID NO: 150. Optionally the VH domain further comprises CDR-H2 of SEQ ID NO: 146.

In another exemplary embodiment, the antibody comprises:

i) a VH domain comprising the following CDRs (a) CDR-H1 comprising the amino acid sequence of SEQ ID NO:145; (b) CDR-H2 comprising the amino acid sequence of SEQ ID NO: 146; and (c) CDR-H3 comprising the amino acid sequence of SEQ ID NO:147; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:148; (b) CDR-L2 comprising the amino acid sequence of SEQ ID NO: 149; and (c) CDR-L3 comprising the amino acid sequence of SEQ ID NO:150; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 160; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 159.

In another exemplary embodiment, the anti-S-HBs antibody comprises (a) CDR-H1 comprising the amino acid sequence of SEQ ID NO:145; (b) CDR-H2 comprising the amino acid sequence of SEQ ID NO:146; (c) CDR-H3 comprising the amino acid sequence of SEQ ID NO: 147; (d) CDR-L1 comprising the amino acid sequence of SEQ ID NO:148; (e) CDR-L2 comprising the amino acid sequence of SEQ ID NO:149; and (f) CDR-L3 comprising the amino acid sequence of SEQ ID NO:150, and a VH domain having at least 90%, 91%, 92%, 93%, 94%, 95%, 96%, 97%, 98%, 99%, or 100% sequence identity to the amino acid sequence of SEQ ID NO: 160, and a VL domain having at least 90%, 91%, 92%, 93%, 94%, 95%, 96%, 97%, 98%, 99%, or 100% sequence identity to the amino acid sequence of SEQ ID NO:159. In one aspect, the VH domain has at least 95% sequence identity to the amino acid sequence of SEQ ID NO:160. In one aspect, the VL domain has at least 95% sequence identity to the amino acid sequence of SEQ ID NO 159. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:160 and a VL sequence of SEQ ID NO:159.

In one aspect, the antibody comprises the VH and VL sequences in SEQ ID NO:160 and SEQ ID NO:159, respectively, including post-translational modifications of those sequences.

In a further aspect, the antibody may comprise the full length light chain of SEQ ID NO: 161 and/or the full length heavy chain of SEQ ID NO: 162 or 271.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 160 and a VL sequence of SEQ ID NO:159. In certain aspects, an antibody is provided that binds to one or more the following residues of S-HBs of SEQ ID NO: 253: C121, K141, D144, and/or G145. Optionally the antibody may further bind one or more of C139, C147, C149, I152 and/or W156. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bc1.229 to S-HBs (e.g., of SEQ ID NO:253), when assessed in the same assay, e.g., an ELISA or flow cytometry assay.

Additionally or alternatively, antibodies as described in this section may have or retain at least 50%, 60%, 70%, 75%, 80%, 85%, 90%, 95% or 100% of the binding activity of reference antibody Bc1.229 to one or more of the proteins of SEQ ID NO: 254-262 (e.g., to at least SEQ ID NO: 257), optionally each of the proteins of SEQ ID NO: 254 to 262, when assessed in the same assay, e.g., an ELISA or flow cytometry assay.

Reference antibody Bc1.229 has a VH sequence of SEQ ID NO: 160 and a VL sequence of SEQ ID NO:159. It has a full length heavy chain of SEQ ID NO 162 or 271 and a full length light chain of SEQ ID NO: 161. SEQ ID NO: 271 comprises the IgG1 constant region expressed by vector LT615368.1, as used in the examples.

In some embodiments, the antibody as described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bc1.229 to the same antigen, when assessed in the same assay.

Additionally or alternatively, the antibody may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bc1.229 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bc1.229, as measured by ELISA or by flow cytometry. Alternatively or additionally, the antibody may bind one or more, or to each of the proteins of SEQ ID NO: 254-262, optionally at least to a protein of SEQ ID NO: 257, with an EC50 that is no more than 50, 10, 9, 8, 7, 6, 5, 4, 3, or 2 fold higher than, or is less than or equal to, the EC50 of reference antibody Bc1.229, as measured by ELISA or by flow cytometry.

In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D, e.g., with an IC50 value of ≤1 ng/ml, optionally ≤100 pg/ml.

In another embodiment, the antibody may have an $IC_{50}$ value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the IC50 value of reference antibody Bc1.229 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the in vivo neutralizing activity of reference antibody Bc1.229 against HBV genotype A, B, C and/or D, optionally at least D, optionally all of A, B, C and D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bc1.229 against HBV genotype A, B, C and/or D, optionally at least D, optionally all of A, B, C and D, when assessed using the same assay (e.g., an assay as described herein).

J.

In one aspect, the invention provides an antibody comprising a VH domain comprising at least one, at least two, or all three VH CDR sequences selected from (a) CDR-H1 comprising the amino acid sequence of SEQ ID NO:163; (b) CDR-H2 comprising the amino acid sequence of SEQ ID NO:164; and (c) CDR-H3 comprising the amino acid sequence of SEQ ID NO:165. In another aspect, the antibody comprises a VH domain comprising the following CDRs (a) CDR-H1 comprising the amino acid sequence of SEQ ID NO:163; (b) CDR-H2 comprising the amino acid sequence of SEQ ID NO:164; and (c) CDR-H3 comprising the amino acid sequence of SEQ ID NO: 165; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 169 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO:170, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:171, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:172 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 178. In one aspect, an anti-S-HBs antibody comprises a heavy chain variable domain (VH) sequence having at least 95%, sequence identity to the amino acid sequence of SEQ ID NO:178. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 178. In certain aspects, substitutions, insertions, or deletions occur in regions outside the CDRs (i.e., in the FRs). Optionally, the anti-S-HBs antibody comprises the VH sequence in SEQ ID NO: 178, including post-translational modifications of that sequence. In a particular aspect, the VH comprises one, two or three CDRs selected from: (a) CDR-H1, comprising the amino acid sequence of SEQ ID NO 163, (b) CDR-H2, comprising the amino acid sequence of SEQ ID NO: 164, and (c) CDR-H3, comprising the amino acid sequence of SEQ ID NO: 165.

In another aspect, an anti-S-HBs antibody comprises one or more of the heavy chain CDR sequences of the VH of SEQ ID NO:178. In one aspect, an anti-S-HBs antibody comprises one or more (preferably all three) of the heavy chain CDR amino acid sequences of the VH domain of SEQ ID NO:178 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:178. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:166; (b) CDR-L2 comprising the amino acid sequence of SEQ ID NO: 167; and (c) CDR-L3 comprising the amino acid sequence of SEQ ID NO:168. In another aspect, the antibody comprises a VL domain comprising the following CDRs (a) CDR-L1 comprising the amino acid sequence of SEQ ID NO:166; (b) CDR-L2 comprising the amino acid sequence of SEQ ID NO: 167; and (c) CDR-L3 comprising the amino acid sequence of SEQ ID NO: 168; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 173 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:174 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:175 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:176 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 177. In one aspect, an anti-S-HBs antibody comprises a light chain variable domain (VL) sequence having at least 95% sequence identity to the amino acid sequence of SEQ ID NO: 177. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:177. In certain aspects, the substitutions, insertions, or deletions occur in regions outside the CDRs (i.e., in the FRs). Optionally, the anti-S-HBs antibody comprises the VL sequence in SEQ ID NO:177, including post-translational modifications of that sequence. In a particular aspect, the VL comprises one, two or three CDRs selected from: (a) CDR-L1, comprising the amino acid sequence of SEQ ID NO:166, (b) CDR-L2, comprising the amino acid sequence of SEQ ID NO:167, and (c) CDR-L3, comprising the amino acid sequence of SEQ ID NO:168.

In another embodiment, an anti-S-HBs antibody comprises one or more of the CDR sequences of the VL of SEQ ID NO:177. In one aspect, an anti-S-HBs antibody comprises one or more (preferably all three) of the light chain CDR amino acid sequences of the VL domain of SEQ ID NO: 177 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:177. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO: 165; and a VL domain comprising CDR-L3 of SEQ ID NO: 168. Optionally the VH domain further comprises CDR-H2 of SEQ ID NO: 164.

In another exemplary embodiment, the antibody comprises:

i) a VH domain comprising the following CDRs (a) CDR-H1 comprising the amino acid sequence of SEQ ID NO:163; (b) CDR-H2 comprising the amino acid sequence of SEQ ID NO: 164; and (c) CDR-H3 comprising the amino acid sequence of SEQ ID NO:165; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:166; (b) CDR-L2 comprising the amino acid sequence of SEQ ID NO: 167; and (c) CDR-L3 comprising the amino acid sequence of SEQ ID NO:168; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 178; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 177.

In another exemplary embodiment, the anti-S-HBs antibody comprises (a) CDR-H1 comprising the amino acid sequence of SEQ ID NO:163; (b) CDR-H2 comprising the amino acid sequence of SEQ ID NO:164; (c) CDR-H3 comprising the amino acid sequence of SEQ ID NO: 165; (d) CDR-L1 comprising the amino acid sequence of SEQ ID NO:166; (e) CDR-L2 comprising the amino acid sequence of SEQ ID NO:167; and (f) CDR-L3 comprising the amino acid sequence of SEQ ID NO:168, and a VH domain having at least 90%, 91%, 92%, 93%, 94%, 95%, 96%, 97%, 98%, 99%, or 100% sequence identity to the amino acid sequence of SEQ ID NO: 178, and a VL domain having at least 90%, 91%, 92%, 93%, 94%, 95%, 96%, 97%, 98%, 99%, or 100% sequence identity to the amino acid sequence of SEQ ID NO:177. In one aspect, the VH domain has at least 95% sequence identity to the amino acid sequence of SEQ ID NO:178. In one aspect, the VL domain has at least 95% sequence identity to the amino acid sequence of SEQ ID NO 177. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:178 and a VL sequence of SEQ ID NO:177.

In one aspect, the antibody comprises the VH and VL sequences in SEQ ID NO: 178 and SEQ ID NO:177, respectively, including post-translational modifications of those sequences.

In a further aspect, the antibody may comprise the full length light chain of SEQ ID NO: 179 and/or the full length heavy chain of SEQ ID NO: 180 or 272.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 178 and a VL sequence of SEQ ID NO:177. In certain aspects, an antibody is provided that binds to the following residues of S-HBs of SEQ ID NO: 253: C121, C138, C139, C147 and/or C149. Optionally the antibody may additionally bind to one or more of L109, R122, T123, C124, M133, Y134, S136, K141 and/or I152. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bc8.159 to S-HBs (e.g., of SEQ ID NO:253), when assessed in the same assay, e.g., an ELISA assay or a flow cytometry assay.

Additionally or alternatively, antibodies as described in this section may have or retain at least 50%, 60%, 70%, 75%, 80%, 85%, 90%, 95% or 100% of the binding activity of reference antibody Bc8.159 to one or more of the proteins of SEQ ID NO: 254-262 (e.g., to at least SEQ ID NO: 257), optionally each of the proteins of SEQ ID NO: 254 to 262, when assessed in the same assay, e.g., an ELISA assay or a flow cytometry assay.

Reference antibody Bc8.159 has a VH sequence of SEQ ID NO:178 and a VL sequence of SEQ ID NO:177. It has a full length heavy chain of SEQ ID NO: 180 or 272 and a full length light chain of SEQ ID NO: 179. SEQ ID NO: 272 comprises the IgG1 constant region expressed by vector LT615368.1, as used in the examples.

In some embodiments, the antibody as described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bc8.159 to the same antigen, when assessed in the same assay.

Additionally or alternatively, the antibody may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bc8.159 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bc8.159, as measured by ELISA or by flow cytometry. Alternatively or additionally, the antibody may bind one or more, or to each of the proteins of SEQ ID NO: 254-262, optionally at least to a protein of SEQ ID NO: 257, with an EC50 that is no more than 50, 10, 9, 8, 7, 6, 5, 4, 3, or 2 fold higher than, or is less than or equal to, the EC50 of reference antibody Bc8.159, as measured by ELISA or by flow cytometry.

In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D, e.g., with an IC50 value of ≤1 ng/ml, optionally ≤100 pg/ml.

In another embodiment, the antibody may have an IC50 value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the IC50 value of reference antibody Bc8.159 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the in vivo neutralizing activity of reference antibody Bc8.159 against HBV genotype A, B, C and/or D, optionally at least D, optionally all of A, B, C and D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bc8.159 against HBV genotype A, B, C and/or D, optionally at least D, optionally all of A, B, C and D, when assessed using the same assay (e.g., an assay as described herein).

K.

In one aspect, the invention provides an antibody comprising a VH domain comprising at least one, at least two, or all three VH CDR sequences selected from (a) CDR-H1 comprising the amino acid sequence of SEQ ID NO:181; (b) CDR-H2 comprising the amino acid sequence of SEQ ID NO:182; and (c) CDR-H3 comprising the amino acid sequence of SEQ ID NO:183. In another aspect, the antibody comprises a VH domain comprising the following CDRs (a) CDR-H1 comprising the amino acid sequence of SEQ ID NO:181; (b) CDR-H2 comprising the amino acid sequence of SEQ ID NO:182; and (c) CDR-H3 comprising the amino acid sequence of SEQ ID NO: 183; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 187 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO:188, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:189, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:190 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 196. In one aspect, an anti-S-HBs antibody comprises a heavy chain variable domain (VH) sequence having at least 95%, sequence identity to the amino acid sequence of SEQ ID NO: 196. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 196. In certain aspects, substitutions, insertions, or deletions occur in regions outside the CDRs (i.e., in the FRs). Optionally, the anti-S-HBs antibody comprises the VH sequence in SEQ ID NO: 196, including post-translational modifications of that sequence. In a particular aspect, the VH comprises one, two or three CDRs selected from: (a) CDR-H1, comprising the amino acid sequence of SEQ ID NO 181, (b) CDR-H2, comprising the amino acid sequence of SEQ ID NO: 182, and (c) CDR-H3, comprising the amino acid sequence of SEQ ID NO: 183.

In another aspect, an anti-S-HBs antibody comprises one or more of the heavy chain CDR sequences of the VH of SEQ ID NO:196. In one aspect, an anti-S-HBs antibody comprises one or more (preferably all three) of the heavy chain CDR amino acid sequences of the VH domain of SEQ ID NO:196 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO: 196. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:184; (b) CDR-L2 comprising the amino acid sequence of SEQ ID NO: 185; and (c) CDR-L3 comprising the amino acid sequence of SEQ ID NO:186. In another aspect, the antibody comprises a VL domain comprising the following CDRs (a) CDR-L1 comprising the amino acid sequence of SEQ ID NO:184; (b) CDR-L2 comprising the amino acid sequence of SEQ ID NO:185; and (c) CDR-L3 comprising the amino acid sequence of SEQ ID NO: 186; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 191 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:192 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:193 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:194 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 195. In one aspect, an anti-S-HBs antibody comprises a light chain variable domain (VL) sequence having at least 95% sequence identity to the amino acid sequence of SEQ ID NO:195. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:195. In certain aspects, the substitutions, insertions, or deletions occur in regions outside the CDRs (i.e., in the FRs). Optionally, the anti-S-HBs antibody comprises the VL sequence in SEQ ID NO: 195, including post-translational modifications of that sequence. In a particular aspect, the VL comprises one, two or three CDRs selected from: (a) CDR-L1, comprising the amino acid sequence of SEQ ID NO:184, (b) CDR-L2, comprising the amino acid sequence of SEQ ID NO:185, and (c) CDR-L3, comprising the amino acid sequence of SEQ ID NO:186.

In another embodiment, an anti-S-HBs antibody comprises one or more of the CDR sequences of the VL of SEQ ID NO:195. In one aspect, an anti-S-HBs antibody comprises one or more (preferably all three) of the light chain CDR amino acid sequences of the VL domain of SEQ ID NO: 195 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:195. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:183; and a VL domain comprising CDR-L3 of SEQ ID NO: 186. Optionally the VH domain further comprises CDR-H2 of SEQ ID NO: 182.

In another exemplary embodiment, the antibody comprises:

i) a VH domain comprising the following CDRs (a) CDR-H1 comprising the amino acid sequence of SEQ ID NO:181; (b) CDR-H2 comprising the amino acid sequence of SEQ ID NO: 182; and (c) CDR-H3 comprising the amino acid sequence of SEQ ID NO:183; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:184; (b) CDR-L2 comprising the amino acid sequence of SEQ ID NO: 185; and (c) CDR-L3 comprising the amino acid sequence of SEQ ID NO:186; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 196; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 195.

In another exemplary embodiment, the anti-S-HBs antibody comprises (a) CDR-H1 comprising the amino acid sequence of SEQ ID NO:181; (b) CDR-H2 comprising the amino acid sequence of SEQ ID NO:182; (c) CDR-H3 comprising the amino acid sequence of SEQ ID NO: 183; (d) CDR-L1 comprising the amino acid sequence of SEQ ID NO:184; (e) CDR-L2 comprising the amino acid sequence of SEQ ID NO:185; and (f) CDR-L3 comprising the amino acid sequence of SEQ ID NO:186, and a VH domain having at least 90%, 91%, 92%, 93%, 94%, 95%, 96%, 97%, 98%, 99%, or 100% sequence identity to the amino acid sequence of SEQ ID NO: 196, and a VL domain having at least 90%, 91%, 92%, 93%, 94%, 95%, 96%, 97%, 98%, 99%, or 100% sequence identity to the amino acid sequence of SEQ ID NO:195. In one aspect, the VH domain has at least 95% sequence identity to the amino acid sequence of SEQ ID NO:196. In one aspect, the VL domain has at least 95% sequence identity to the amino acid sequence of SEQ ID NO 195. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:196 and a VL sequence of SEQ ID NO:195.

In one aspect, the antibody comprises the VH and VL sequences in SEQ ID NO: 196 and SEQ ID NO:195, respectively, including post-translational modifications of those sequences.

In a further aspect, the antibody may comprise the full length light chain of SEQ ID NO: 197 and/or the full length heavy chain of SEQ ID NO: 198 or 273.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 196 and a VL sequence of SEQ ID NO:195. In certain aspects, an antibody is provided that binds to the following residues of S-HBs of SEQ ID NO: 253: C121, C124, C137, C138, C139, C147 and/or C149, optionally also to I152. Optionally the antibody further binds to one or more of V106, P108, W156 and/or F161. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bc1.128 to S-HBs (e.g., of SEQ ID NO:253), when assessed in the same assay e.g., an ELISA assay or a flow cytometry assay.

Additionally or alternatively, antibodies as described in this section may have or retain at least 50%, 60%, 70%, 75%, 80%, 85%, 90%, 95% or 100% of the binding activity of reference antibody Bc1.128 to one or more of the proteins of SEQ ID NO: 254-262 (e.g., to at least SEQ ID NO: 257), optionally each of the proteins of SEQ ID NO: 254 to 262, when assessed in the same assay e.g., an ELISA assay or a flow cytometry assay.

Reference antibody Bc1.128 has a VH sequence of SEQ ID NO: 196 and a VL sequence of SEQ ID NO:195. It has a full length heavy chain of SEQ ID NO: 198 or 273 and a full length light chain of SEQ ID NO: 197. SEQ ID NO: 273 comprises the IgG1 constant region expressed by vector LT615368.1, as used in the examples.

In some embodiments, the antibody described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bc1.128 to the same antigen, when assessed in the same assay.

Additionally or alternatively, the antibody may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bc1.128 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bc1.128, as measured by ELISA or by flow cytometry. Alternatively or additionally, the antibody may bind one or more, or to each of the proteins of SEQ ID NO: 254-262, optionally at least to a protein of SEQ ID NO: 257, with an EC50 that is no more than 50, 10, 9, 8, 7, 6, 5, 4, 3, or 2 fold higher than, or is less than or equal to, the EC50 of reference antibody Bc1.128, as measured by ELISA or by flow cytometry.

In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D, e.g., with an IC50 value of ≤10 ng/ml, optionally ≤1 ng/ml.

In another embodiment, the antibody may have an $IC_{50}$ value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the $IC_{50}$ value of reference antibody Bc1.128 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the in vivo neutralizing activity of reference antibody Bc1.128 against HBV genotype A, B, C and/or D, optionally at least D, optionally all of A, B, C and D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bc1.128 against HBV genotype A, B, C and/or D, optionally at least D, optionally all of A, B, C and D, when assessed using the same assay (e.g., an assay as described herein).

L.

In one aspect, the invention provides an antibody comprising a VH domain comprising at least one, at least two, or all three VH CDR sequences selected from (a) CDR-H1 comprising the amino acid sequence of SEQ ID NO:199; (b) CDR-H2 comprising the amino acid sequence of SEQ ID NO:200; and (c) CDR-H3 comprising the amino acid sequence of SEQ ID NO:201. In another aspect, the antibody comprises a VH domain comprising the following CDRs (a) CDR-H1 comprising the amino acid sequence of SEQ ID NO:199; (b) CDR-H2 comprising the amino acid sequence of SEQ ID NO:200; and (c) CDR-H3 comprising the amino acid sequence of SEQ ID NO: 201; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 205 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO:206, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:207, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:208 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:214. In one aspect, an anti-S-HBs antibody comprises a heavy chain variable domain (VH) sequence having at least 95%, sequence identity to the amino acid sequence of SEQ ID NO: 214. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 214. In certain aspects, substitutions, insertions, or deletions occur in regions outside the CDRs (i.e., in the FRs). Optionally, the anti-S-HBs antibody comprises the VH sequence in SEQ ID NO: 214, including post-translational modifications of that sequence. In a particular aspect, the VH comprises one, two or three CDRs selected from: (a) CDR-H1, comprising the amino acid sequence of SEQ ID NO 199, (b) CDR-H2, comprising the amino acid sequence of SEQ ID NO: 200, and (c) CDR-H3, comprising the amino acid sequence of SEQ ID NO: 201.

In another aspect, an anti-S-HBs antibody comprises one or more of the heavy chain CDR sequences of the VH of SEQ ID NO:214. In one aspect, an anti-S-HBs antibody comprises one or more (preferably all three) of the heavy chain CDR amino acid sequences of the VH domain of SEQ ID NO:214 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:214. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:202; (b) CDR-L2 comprising the amino acid sequence of SEQ ID NO: 203; and (c) CDR-L3 comprising the amino acid sequence of SEQ ID NO:204. In another aspect, the antibody comprises a VL domain comprising the following CDRs (a) CDR-L1 comprising the amino acid sequence of SEQ ID NO:202; (b) CDR-L2 comprising the amino acid sequence of SEQ ID NO:203; and (c) CDR-L3 comprising the amino acid sequence of SEQ ID NO: 204; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 209 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:210 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:211 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:212 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:213. In one aspect, an anti-S-HBs antibody comprises a light chain variable domain (VL) sequence having at least 95% sequence identity to the amino acid sequence of SEQ ID NO:213. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:213. In certain aspects, the substitutions, insertions, or deletions occur in regions outside the CDRs (i.e., in the FRs). Optionally, the anti-S-HBs antibody comprises the VL sequence in SEQ ID NO:213, including post-translational modifications of that sequence. In a particular aspect, the VL comprises one, two or three CDRs selected from: (a) CDR-L1, comprising the amino acid sequence of SEQ ID NO:202, (b) CDR-L2, comprising the amino acid sequence of SEQ ID NO:203, and (c) CDR-L3, comprising the amino acid sequence of SEQ ID NO:204.

In another embodiment, an anti-S-HBs antibody comprises one or more of the CDR sequences of the VL of SEQ ID NO:213. In one aspect, an anti-S-HBs antibody comprises one or more (preferably all three) of the light chain CDR amino acid sequences of the VL domain of SEQ ID NO: 213 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:213. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:201; and a VL domain comprising CDR-L3 of SEQ ID NO: 204. Optionally the VH domain further comprises CDR-H2 of SEQ ID NO: 200.

In another exemplary embodiment, the antibody comprises:

i) a VH domain comprising the following CDRs (a) CDR-H1 comprising the amino acid sequence of SEQ ID NO:199; (b) CDR-H2 comprising the amino acid sequence of SEQ ID NO: 200; and (c) CDR-H3 comprising the amino acid sequence of SEQ ID NO:201; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:202; (b) CDR-L2 comprising the amino acid sequence of SEQ ID NO: 203; and (c) CDR-L3 comprising the amino acid sequence of SEQ ID NO:204; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 214; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 213.

In another exemplary embodiment, the anti-S-HBs antibody comprises (a) CDR-H1 comprising the amino acid sequence of SEQ ID NO:199; (b) CDR-H2 comprising the amino acid sequence of SEQ ID NO:200; (c) CDR-H3 comprising the amino acid sequence of SEQ ID NO: 201; (d) CDR-L1 comprising the amino acid sequence of SEQ ID NO:202; (e) CDR-L2 comprising the amino acid sequence of SEQ ID NO:203; and (f) CDR-L3 comprising the amino acid sequence of SEQ ID NO:204, and a VH domain having at least 90%, 91%, 92%, 93%, 94%, 95%, 96%, 97%, 98%, 99%, or 100% sequence identity to the amino acid sequence of SEQ ID NO: 214, and a VL domain having at least 90%, 91%, 92%, 93%, 94%, 95%, 96%, 97%, 98%, 99%, or 100% sequence identity to the amino acid sequence of SEQ ID NO:213. In one aspect, the VH domain has at least 95% sequence identity to the amino acid sequence of SEQ ID NO:214. In one aspect, the VL domain has at least 95% sequence identity to the amino acid sequence of SEQ ID NO: 213. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:214 and a VL sequence of SEQ ID NO:213.

In one aspect, the antibody comprises the VH and VL sequences in SEQ ID NO:214 and SEQ ID NO:213, respectively, including post-translational modifications of those sequences.

In a further aspect, the antibody may comprise the full length light chain of SEQ ID NO: 215 and/or the full length heavy chain of SEQ ID NO: 216 or 274.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 214 and a VL sequence of SEQ ID NO:213. In certain aspects, an antibody is provided that binds to residue F179 of S-HBs of SEQ ID NO:253. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bc4.204 to S-HBs (e.g., of SEQ ID NO: 253), when assessed in the same assay e.g., an ELISA assay or a flow cytometry assay. Additionally or alternatively, antibodies as described in this section may have or retain at least 50%, 60%, 70%, 75%, 80%, 85%, 90%, 95% or 100% of the binding activity of reference antibody Bc4.204 to proteins having the sequence of SEQ ID NO: 254, 255, 256, 257, 258, 260 and/or 262, when assessed in the same assay, optionally at least to SEQ ID NO: 257 e.g., an ELISA assay or a flow cytometry assay.

Reference antibody Bc4.204 has a VH sequence of SEQ ID NO:214 and a VL sequence of SEQ ID NO:213. It has a full length heavy chain of SEQ ID NO: 216 or 274 and a full length light chain of SEQ ID NO: 215. SEQ ID NO: 274 comprises the IgG1 constant region expressed by vector LT615368.1, as used in the examples.

In some embodiments, the antibody described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bc4.204 to the same antigen, when assessed in the same assay. Additionally or alternatively, the antibody may bind to one or more of SEQ ID NO: 254, 255, 256, 257, 258, 260 and/or 262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bc4.204 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bc4.204, as measured by ELISA or by flow cytometry. Alternatively or additionally, the antibody may bind one or more, or to each of, the proteins having the sequence of SEQ ID NO: 254, 255, 256, 257, 258, 260 and/or 262, optionally at least to a protein of SEQ ID NO: 257, with an EC50 that is no more than 50, 10, 9, 8, 7, 6, 5, 4, 3, or 2 fold higher than, or is less than or equal to, the EC50 of reference antibody Bc4.204, as measured by ELISA or by flow cytometry.

In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D, e.g., with an IC50 value of ≤10 ng/ml, optionally ≤1 ng/ml.

In another embodiment, the antibody may have an IC50 value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the IC50 value of reference antibody Bc4.204 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the in vivo neutralizing activity of reference antibody Bc4.204 against HBV genotype A, B, C and/or D, optionally at least D, optionally all of A, B, C and D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bc4.204 against HBV genotype A, B, C and/or D, optionally at least D, optionally all of A, B, C and D, when assessed using the same assay (e.g., an assay as described herein).

M.

In one aspect, the invention provides an antibody comprising a VH domain comprising at least one, at least two, or all three VH CDR sequences selected from (a) CDR-H1 comprising the amino acid sequence of SEQ ID NO:217; (b) CDR-H2 comprising the amino acid sequence of SEQ ID NO:218; and (c) CDR-H3 comprising the amino acid sequence of SEQ ID NO:219. In another aspect, the antibody comprises a VH domain comprising the following CDRs (a) CDR-H1 comprising the amino acid sequence of SEQ ID NO:217; (b) CDR-H2 comprising the amino acid sequence of SEQ ID NO:218; and (c) CDR-H3 comprising the amino acid sequence of SEQ ID NO: 219; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 223 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO:224, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:225, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:226 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:232. In one aspect, an anti-S-HBs antibody comprises a heavy chain variable domain (VH) sequence having at least 95%, sequence identity to the amino acid sequence of SEQ ID NO: 232. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 232. In certain aspects, substitutions, insertions, or deletions occur in regions outside the CDRs (i.e., in the FRs). Optionally, the anti-S-HBs antibody comprises the VH sequence in SEQ ID NO: 232, including post-translational modifications of that sequence. In a particular aspect, the VH comprises one, two or three CDRs selected from: (a) CDR-H1, comprising the amino acid sequence of SEQ ID NO 217, (b) CDR-H2, comprising the amino acid sequence of SEQ ID NO: 218, and (c) CDR-H3, comprising the amino acid sequence of SEQ ID NO: 219.

In another aspect, an anti-S-HBs antibody comprises one or more of the heavy chain CDR sequences of the VH of SEQ ID NO:232. In one aspect, an anti-S-HBs antibody comprises one or more (preferably all three) of the heavy chain CDR amino acid sequences of the VH domain of SEQ ID NO:232 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:232. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:220; (b) CDR-L2 comprising the amino acid sequence of SEQ ID NO: 221; and (c) CDR-L3 comprising the amino acid sequence of SEQ ID NO:222. In another aspect, the antibody comprises a VL domain comprising the following CDRs (a) CDR-L1 comprising the amino acid sequence of SEQ ID NO:220; (b) CDR-L2 comprising the amino acid sequence of SEQ ID NO:221; and (c) CDR-L3 comprising the amino acid sequence of SEQ ID NO: 222; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 227 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:228 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:229 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:230 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:231. In one aspect, an anti-S-HBs antibody comprises a light chain variable domain (VL) sequence having at least 95% sequence identity to the amino acid sequence of SEQ ID NO:231. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:231. In certain aspects, the substitutions, insertions, or deletions occur in regions outside the CDRs (i.e., in the FRs). Optionally, the anti-S-HBs antibody comprises the VL sequence in SEQ ID NO:231, including post-translational modifications of that sequence. In a particular aspect, the VL comprises one, two or three CDRs selected from: (a) CDR-L1, comprising the amino acid sequence of SEQ ID NO:220, (b) CDR-L2, comprising the amino acid sequence of SEQ ID NO:221, and (c) CDR-L3, comprising the amino acid sequence of SEQ ID NO:222.

In another embodiment, an anti-S-HBs antibody comprises one or more of the CDR sequences of the VL of SEQ ID NO:231. In one aspect, an anti-S-HBs antibody comprises one or more (preferably all three) of the light chain CDR amino acid sequences of the VL domain of SEQ ID NO: 231 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:231. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:219; and a VL domain comprising CDR-L3 of SEQ ID NO: 222. Optionally the VH domain further comprises CDR-H2 of SEQ ID NO: 218.

In another exemplary embodiment, the antibody comprises:

i) a VH domain comprising the following CDRs (a) CDR-H1 comprising the amino acid sequence of SEQ ID NO:217; (b) CDR-H2 comprising the amino acid sequence of SEQ ID NO: 218; and (c) CDR-H3 comprising the amino acid sequence of SEQ ID NO:219; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:220; (b) CDR-L2 comprising the amino acid sequence of SEQ ID NO: 221; and (c) CDR-L3 comprising the amino acid sequence of SEQ ID NO:222; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VI) sequence having at least 90%, 91%, 92%, 93%, 94%, 95%, 96%, 97%, 98%, 99%, or 100% sequence identity to the amino acid sequence of SEQ ID NO: 232; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 231.

In another exemplary embodiment, the anti-S-HBs antibody comprises (a) CDR-H1 comprising the amino acid sequence of SEQ ID NO:217; (b) CDR-H2 comprising the amino acid sequence of SEQ ID NO:218; (c) CDR-H3 comprising the amino acid sequence of SEQ ID NO: 219; (d) CDR-L1 comprising the amino acid sequence of SEQ ID NO:220; (e) CDR-L2 comprising the amino acid sequence of SEQ ID NO:221; and (f) CDR-L3 comprising the amino acid sequence of SEQ ID NO:222, and a VH domain having at least 90%, 91%, 92%, 93%, 94%, 95%, 96%, 97%, 98%, 99%, or 100% sequence identity to the amino acid sequence of SEQ ID NO: 232, and a VL domain having at least 90%, 91%, 92%, 93%, 94%, 95%, 96%, 97%, 98%, 99%, or 100% sequence identity to the amino acid sequence of SEQ ID NO:231. In one aspect, the VH domain has at least 95% sequence identity to the amino acid sequence of SEQ ID NO:232. In one aspect, the VL domain has at least 95% sequence identity to the amino acid sequence of SEQ ID NO: 231. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:232 and a VL sequence of SEQ ID NO:231.

In one aspect, the antibody comprises the VH and VL sequences in SEQ ID NO:232 and SEQ ID NO:231, respectively, including post-translational modifications of those sequences.

In a further aspect, the antibody may comprise the full length light chain of SEQ ID NO: 233 and/or the full length heavy chain of SEQ ID NO: 234 or 275.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 232 and a VL sequence of SEQ ID NO:231. In certain aspects, an antibody is provided that binds to the following residues of S-HBs of SEQ ID NO: 253: W165 and/or R169, and optionally M103. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bc1.263 to S-HBs (e.g., of SEQ ID NO: 253), when assessed in the same assay, e.g., an ELISA assay or a flow cytometry assay.

Additionally or alternatively, antibodies as described in this section may have or retain at least 50%, 60%, 70%, 75%, 80%, 85%, 90%, 95% or 100% of the binding activity of reference antibody Bc1.263 to one or more of the proteins of SEQ ID NO: 254-262 (e.g., to at least SEQ ID NO: 257), optionally to each of the proteins of SEQ ID NO: 254 to 262, when assessed in the same assay, e.g., an ELISA assay or a flow cytometry assay.

Reference antibody Bc1.263 has a VH sequence of SEQ ID NO:232 and a VL sequence of SEQ ID NO:231. It has a full length heavy chain of SEQ ID NO: 234 or 275 and a full length light chain of SEQ ID NO: 233. SEQ ID NO: 275 comprises the IgG1 constant region expressed by vector LT615368.1, as used in the examples.

In some embodiments, the antibody as described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bc1.263 to the same antigen, when assessed in the same assay.

Additionally or alternatively, the antibody may bind to one or more of SEQ ID NO: 254-262 (e.g., to at least SEQ ID NO: 257), optionally each of the proteins of SEQ ID NO: 254-262, with a $K_D$ value which is no more than 50, 10, 9, 8, 7, 6, 5, 4, 3, or 2 fold higher than, or is less than or equal to, the $K_D$ value of reference antibody Bc1.263 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bc1.263, as measured by ELISA or by flow cytometry. Alternatively or additionally, the antibody may bind one or more, or to each of the proteins of SEQ ID NO: 254-262, optionally at least to a protein of SEQ ID NO: 257, with an EC50 that is no more than 50, 10, 9, 8, 7, 6, 5, 4, 3, or 2 fold higher than, or is less than or equal to, the EC50 of reference antibody Bc1.263, as measured by ELISA or by flow cytometry.

In some embodiments antibodies as described in this section may have or retain in vitro neutralizing activity against HBV genotype A, B, C and/or D, optionally all of A, B, C and D. For example, antibodies as described in this section may have or retain in vitro neutralizing activity against HBV genotype D, e.g., with an IC50 value of ≤100 pg/ml, optionally ≤10 pg/ml.

In another embodiment, the antibody may have an $IC_{50}$ value for neutralization of HBV genotype A, B, C and/or D, optionally at least D, optionally all of A, B, C and D, which is no more than 50, 10, 9, 8, 7, 6, 5, 4, 3, or 2 fold higher than, or is less than or equal to, the $IC_{50}$ value of reference antibody Bc1.263 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the neutralizing activity of reference antibody Bc1.263 against HBV genotype A, B, C and/or D, optionally at least D, optionally all of A, B, C and D, when assessed using the same assay (e.g., an assay as described herein).

Optionally the antibody can suppress virus viremia in vivo e.g., in an individual infected with HBV genotype A, B, C or D, optionally D. Optionally, the antibody may have or retain at least 50%, 60%, 70%, 75%, 80%, 85%, 90%, 95% or 100% of the in vivo viremia suppressing activity of reference antibody Bc1.263 against HBV genotype A, B, C and/or D, optionally at least D, optionally all of A, B, C and D, when assessed using the same assay (e.g., an assay as described herein).

N.

In one aspect, the invention provides an antibody comprising a VH domain comprising at least one, at least two, or all three VH CDR sequences selected from (a) CDR-H1 comprising the amino acid sequence of SEQ ID NO:235; (b) CDR-H2 comprising the amino acid sequence of SEQ ID NO:236; and (c) CDR-H3 comprising the amino acid sequence of SEQ ID NO:237. In another aspect, the antibody comprises a VH domain comprising the following CDRs (a) CDR-H1 comprising the amino acid sequence of SEQ ID NO:235; (b) CDR-H2 comprising the amino acid sequence of SEQ ID NO:236; and (c) CDR-H3 comprising the amino acid sequence of SEQ ID NO: 237; or a variant thereof in which one, two or three amino acids in one or more of CDR-H1, CDR-H2 or CDR-H3 are substituted with another amino acid.

In one aspect, the VH domain may further comprise one or more heavy chain framework sequences selected from (a) a heavy chain frame work region 1 (HC-FR1) of SEQ ID NO: 241 or a variant having at least 85%, 86%, 87%, 88%, 89%, 90%, 91%, 92%, 93%, 94%, 95%, 96%, 97%, 98% or 99% sequence identity thereto, (b) a heavy chain frame work region 2 (HC-FR2) of SEQ ID NO:242, or a variant having at least 85%, 86%, 87%, 88%, 89%, 90%, 91%, 92%, 93%, 94%, 95%, 96%, 97%, 98% or 99% sequence identity thereto (c) a heavy chain frame work region 3 (HC-FR3) SEQ ID NO:243, or a variant having at least 85%, 86%, 87%, 88%, 89%, 90%, 91%, 92%, 93%, 94%, 95%, 96%, 97%, 98% or 99% sequence identity thereto and (d) a heavy chain frame work region 4 (HC-FR4) of SEQ ID NO:244 or a variant having at least 85%, 86%, 87%, 88%, 89%, 90%, 91%, 92%, 93%, 94%, 95%, 96%, 97%, 98% or 99% sequence identity thereto. Optionally, the VH domain comprises each of the heavy chain framework sequences as defined in (a) to (d). Optionally the percentage sequence identity is 95%. Optionally the percentage sequence identity is 98%.

In another aspect, an anti-S-HBs antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:250. In one aspect, an anti-S-HBs antibody comprises a heavy chain variable domain (VH) sequence having at least 95%, sequence identity to the amino acid sequence of SEQ ID NO: 250. In certain aspects, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO: 250. In certain aspects, substitutions, insertions, or deletions occur in regions outside the CDRs (i.e., in the FRs). Optionally, the anti-S-HBs antibody comprises the VH sequence in SEQ ID NO: 250, including post-translational modifications of that sequence. In a particular aspect, the VH comprises one, two or three CDRs selected from: (a) CDR-H1, comprising the amino acid sequence of SEQ ID NO 235, (b) CDR-H2, comprising the amino acid sequence of SEQ ID NO: 236, and (c) CDR-H3, comprising the amino acid sequence of SEQ ID NO: 237.

In another aspect, an anti-S-HBs antibody comprises one or more of the heavy chain CDR sequences of the VH of SEQ ID NO:250. In one aspect, an anti-S-HBs antibody comprises one or more (preferably all three) of the heavy chain CDR amino acid sequences of the VH domain of SEQ ID NO:250 and a framework of at least 85%, 86%, 87%, 88%, 89%, 90%, 91%, 92%, 93%, 94%, 95%, 96%, 97%, 98%, 99% sequence identity to the framework amino acid sequence of the VH domain of SEQ ID NO:250. Optionally the sequence identity is 95% or 98%.

In another aspect, the invention provides an antibody comprising a VL domain comprising at least one, at least two, or all three VL CDR sequences selected from (a) CDR-L1 comprising the amino acid sequence of SEQ ID NO:238; (b) CDR-L2 comprising the amino acid sequence of SEQ ID NO: 239; and (c) CDR-L3 comprising the amino acid sequence of SEQ ID NO:240. In another aspect, the antibody comprises a VL domain comprising the following CDRs (a) CDR-L1 comprising the amino acid sequence of SEQ ID NO:238; (b) CDR-L2 comprising the amino acid sequence of SEQ ID NO:239; and (c) CDR-L3 comprising the amino acid sequence of SEQ ID NO: 240; or a variant thereof in which one, two or three amino acids in one or more of CDR-L1, CDR-L2 or CDR-L3 are substituted with another amino acid.

In one aspect, the anti-S-HBs antibody VL domain may further comprise one or more light chain framework sequences selected from (a) a light chain frame work region 1 (LC-FR1) of SEQ ID NO: 245 or a variant having at least 85%, 86%, 87%, 88%, 89%, 90%, 91%, 92%, 93%, 94%, 95%, 96%, 97%, 98% or 99% sequence identity thereto, (b) a light chain frame work region 2 (LC-FR2) of SEQ ID NO:246 or a variant having at least 85%, 86%, 87%, 88%, 89%, 90%, 91%, 92%, 93%, 94%, 95%, 96%, 97%, 98% or 99% sequence identity thereto, (c) a light chain frame work region 3 (LC-FR3) of SEQ ID NO:247 or a variant having at least 85%, 86%, 87%, 88%, 89%, 90%, 91%, 92%, 93%, 94%, 95%, 96%, 97%, 98% or 99% sequence identity thereto, and (d) a light chain frame work region 4 (LC-FR4) of SEQ ID NO:248 or a variant having at least 85%, 86%, 87%, 88%, 89%, 90%, 91%, 92%, 93%, 94%, 95%, 96%, 97%, 98% or 99% sequence identity thereto. Optionally, the VL domain comprises each of the light chain framework sequences as defined in (a) to (d). Optionally the percentage sequence identity is 95%. Optionally the percentage sequence identity is 98%.

In another aspect, an anti-S-HBs antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO:249. In one aspect, an anti-S-HBs antibody comprises a light chain variable domain (VL) sequence having at least 95% sequence identity to the amino acid sequence of SEQ ID NO:249. In certain aspects, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-S-HBs antibody comprising that sequence retains the ability to bind to S-HBs. In certain aspects, a total of 1 to 10 amino acids have been substituted, inserted and/or deleted in SEQ ID NO:249. In certain aspects, the substitutions, insertions, or deletions occur in regions outside the CDRs (i.e., in the FRs). Optionally, the anti-S-HBs antibody comprises the VL sequence in SEQ ID NO:249, including post-translational modifications of that sequence. In a particular aspect, the VL comprises one, two or three CDRs selected from: (a) CDR-L1, comprising the amino acid sequence of SEQ ID NO:238, (b) CDR-L2, comprising the amino acid sequence of SEQ ID NO:239, and (c) CDR-L3, comprising the amino acid sequence of SEQ ID NO:240.

In another embodiment, an anti-S-HBs antibody comprises one or more of the CDR sequences of the VL of SEQ ID NO:249. In one aspect, an anti-S-HBs antibody comprises one or more (preferably all three) of the light chain CDR amino acid sequences of the VL domain of SEQ ID NO: 249 and a framework of at least 85%, 86%, 87%, 88%, 89%, 90%, 91%, 92%, 93%, 94%, 95%, 96%, 97%, 98%, 99% sequence identity to the framework amino acid sequence of the VL domain of SEQ ID NO:249. Optionally the sequence identity is 95% or 98%.

In another aspect, an anti-S-HBs antibody is provided, wherein the antibody comprises a VH sequence as in any of the aspects provided above, and a VL sequence as in any of the aspects provided above.

For instance, in one exemplary embodiment, the antibody comprises a VH domain comprising CDR-H3 of SEQ ID NO:237; and a VL domain comprising CDR-L3 of SEQ ID NO: 240. Optionally the VH domain further comprises CDR-H2 of SEQ ID NO: 236.

In another exemplary embodiment, the antibody comprises:

i) a VH domain comprising the following CDRs (a) CDR-H1 comprising the amino acid sequence of SEQ ID NO:235; (b) CDR-H2 comprising the amino acid sequence of SEQ ID NO: 236; and (c) CDR-H3 comprising the amino acid sequence of SEQ ID NO:237; or a variant thereof in which one, two or three amino acids in one or more of CDR-H1, CDR-H2 or CDR-H3 are substituted with another amino acid; and ii) a VL domain comprising the following CDRs (a) CDR-L1 comprising the amino acid sequence of SEQ ID NO:238; (b) CDR-L2 comprising the amino acid sequence of SEQ ID NO: 239; and (c) CDR-L3 comprising the amino acid sequence of SEQ ID NO:240; or a variant thereof in which one, two or three amino acids in one or more of CDR-L1, CDR-L2 or CDR-L3 are substituted with another amino acid.

In another exemplary embodiment, the antibody comprises:

i) a heavy chain variable domain (VH) sequence having at least 90%, 91%, 92%, 93%, 94%, 95%, 96%, 97%, 98%, 99%, or 100% sequence identity to the amino acid sequence of SEQ ID NO: 250; and ii) a light chain variable domain (VL) sequence having at least 90%, 91%, 92%, 93%, 94%, 95%, 96%, 97%, 98%, 99%, or 100% sequence identity to the amino acid sequence of SEQ ID NO: 249.

In another exemplary embodiment, the anti-S-HBs antibody comprises (a) CDR-H1 comprising the amino acid sequence of SEQ ID NO:235; (b) CDR-H2 comprising the amino acid sequence of SEQ ID NO:236; (c) CDR-H3 comprising the amino acid sequence of SEQ ID NO: 237; (d) CDR-L1 comprising the amino acid sequence of SEQ ID NO:238; (e) CDR-L2 comprising the amino acid sequence of SEQ ID NO:239; and (f) CDR-L3 comprising the amino acid sequence of SEQ ID NO:240, and a VH domain having at least 90%, 91%, 92%, 93%, 94%, 95%, 96%, 97%, 98%, 99%, or 100% sequence identity to the amino acid sequence of SEQ ID NO: 250, and a VL domain having at least 90%, 91%, 92%, 93%, 94%, 95%, 96%, 97%, 98%, 99%, or 100% sequence identity to the amino acid sequence of SEQ ID NO:249. In one aspect, the VH domain has at least 95% sequence identity to the amino acid sequence of SEQ ID NO:250. In one aspect, the VL domain has at least 95% sequence identity to the amino acid sequence of SEQ ID NO: 249. In one embodiment, the antibody specifically binds to S-HBs. In another embodiment, the antibody binds to S-HBs having a dissociation constant (KD) that is up to 10 fold reduced or up to 10 fold increased when compared to the dissociation constant (KD) of an antibody comprising a VH sequence of SEQ ID NO:250 and a VL sequence of SEQ ID NO:249.

In one aspect, the antibody comprises the VH and VL sequences in SEQ ID NO:250 and SEQ ID NO:249, respectively, including post-translational modifications of those sequences.

In a further aspect, the antibody may comprise the full length light chain of SEQ ID NO: 251 and/or the full length heavy chain of SEQ ID NO: 252 or 276.

In a further aspect, the invention provides an antibody that binds to the same epitope as the anti-S-HBs antibody provided herein. For example, in certain aspects, an antibody is provided that binds to the same epitope as an anti-S-HBs antibody comprising a VH sequence of SEQ ID NO: 250 and a VL sequence of SEQ ID NO:249. In certain aspects, an antibody is provided that binds to the following residues of S-HBs of SEQ ID NO: 253: C124, C137, C138 and/or C139; optionally R122, C149, and/or I152; and optionally W156. The antibody may comprise any of the sequences as defined above.

In a further aspect, the invention provides an antibody that competes for binding to S-HBs with an anti-S-HBs antibody provided herein.

Antibodies as described in this section may, in some embodiments, have or retain at least 50%, 60%, 70%, 75%, 80%, 85%, 90%, 95% or 100% of the binding activity of a reference antibody Bv4.105 to S-HBs (e.g., of SEQ ID NO:253), when assessed in the same assay, e.g., an ELISA assay or a flow cytometry assay.

Additionally or alternatively, antibodies as described in this section may have or retain at least 50%, 60%, 70%, 75%, 80%, 85%, 90%, 95% or 100% of the binding activity of reference antibody Bv4.105 to one or more, optionally each of the proteins of SEQ ID NO: 257, 258, 259, 260, and/or 261, optionally at least to SEQ ID NO: 257, when assessed in the same assay e.g., an ELISA assay or a flow cytometry assay.

Reference antibody Bv4.105 has a VH sequence of SEQ ID NO:250 and a VL sequence of SEQ ID NO:249. It has a full length heavy chain of SEQ ID NO: 252 or 276 and a full length light chain of SEQ ID NO: 251. SEQ ID NO: 276 comprises the IgG1 constant region expressed by vector LT615368.1, as used in the examples.

In some embodiments, the antibody described in this section may bind to S-HBs (e.g., of SEQ ID NO: 253) with a $K_D$ value which is no more than 50, 10, 9, 8, 7, 6, 5, 4, 3, or 2 fold higher than, or is less than or equal to, the $K_D$ value of reference antibody Bv4.105 to the same antigen, when assessed in the same assay.

Additionally or alternatively, the antibody may bind to one or more, optionally each of the proteins of SEQ ID NO: 257, 258, 259, 260, and/or 261, optionally at least to SEQ ID NO: 257, with a $K_D$ value which is no more than 50, 10, 9, 8, 7, 6, 5, 4, 3, or 2 fold higher than, or is less than or equal to, the $K_D$ value of reference antibody Bv4.105 to the same antigen, when assessed in the same assay.

In some embodiments, the antibody as described in this section may bind to S-HBs (e.g., of SEQ ID NO: 253) with an EC50 that is no more than 50, 10, 9, 8, 7, 6, 5, 4, 3, or 2 fold higher than, or is less than or equal to, the EC50 of reference antibody Bv4.105, as measured by ELISA or by flow cytometry. Alternatively or additionally, the antibody may bind to one or more, optionally each, of the proteins of SEQ ID NO: 257, 258, 259, 260, and/or 261, optionally at least to SEQ ID NO: 257, with an EC50 that is no more than 50, 10, 9, 8, 7, 6, 5, 4, 3, or 2 fold higher than, or is less than or equal to, the EC50 of reference antibody Bv4.105, as measured by ELISA or by flow cytometry.

In some embodiments antibodies as described in this section may have or retain in vitro neutralizing activity against HBV genotype D, E, F, and/or H, optionally all of genotypes D, E, F and H. For example, antibodies as described in this section may have or retain in vitro neutralizing activity against HBV genotype D, e.g., with an IC50 value of ≤100 pg/ml, optionally ≤10 pg/ml.

In another embodiment, the antibody may have an IC50 value for neutralization of HBV genotype D, E, F, G and/or H, optionally at least D, optionally all of D, E, F, G and/or H, which is no more than 50, 10, 9, 8, 7, 6, 5, 4, 3, or 2 fold higher than, or is less than or equal to, the IC50 value of reference antibody Bv4.105 against the same genotype, when assessed using the same assay (e.g., an in vitro neutralization assay as described herein).

In another embodiment, the antibody may have or retain at least 50%, 60%, 70%, 75%, 80%, 85%, 90%, 95% or 100% of the neutralizing activity of reference antibody Bv4.105 against HBV genotype D, E, F, G and/or H, optionally at least D, optionally all of D, E, F, G and H, when assessed using the same assay (e.g., an assay as described herein).

Optionally the antibody can suppress virus viremia in vivo e.g., in an individual infected with HBV genotype D, E, F, G or H, optionally D. Optionally, the antibody may have or retain at least 50%, 60%, 70%, 75%, 80%, 85%, 90%, 95% or 100% of the in vivo viremia suppressing activity of reference antibody Bv4.105 against HBV genotype D, E, F, G and/or H, optionally at least D, optionally all of D, E, F, G and H, when assessed using the same assay (e.g., an assay as described herein).

In general, an anti-S-HBs antibody according to any aspect of the present invention (including any of A-N above) may be a monoclonal antibody, including a chimeric, humanized or human antibody. In one aspect, an anti-S-HBs antibody is an antibody fragment, e.g., a Fv, Fab, Fab', scFv, diabody, or F(ab') 2 fragment.

In another general aspect, the antibody may be a full-length antibody, e.g., an intact IgG1, IgG2, IgG3 antibody or other antibody class or isotype as defined herein.

The C-terminal lysine (Lys447) of the full-length antibody may be either present or absent. In another aspect, the C-terminal glycine (Gly446) and the C-terminal lysine (Lys447) may be either present or absent.

In a further aspect, an anti-S-HBs antibody according to any of the above aspects may incorporate any of the features, singly or in combination, as described in Sections 1-7 below:

1. Antibody Affinity

In certain aspects, an antibody provided herein has a dissociation constant (KD) against the target protein of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In other aspects, an antibody provided herewith has or retains a $K_D$ which is which is no more than 50, 10, 9, 8, 7, 6, 5, 4, 3, or 2 fold higher than, or is less than or equal to, the $K_D$ value of a reference antibody against the target protein when assessed in the same assay, wherein the reference antibody is selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105.

In one aspect, $K_D$ is measured using a BIACORE® surface plasmon resonance assay. For example, an assay using a BIACORE®-2000 or a BIACORE®-3000 (BIAcore, Inc., Piscataway, NJ) is performed at 25° C. with immobilized antigen CM5 chips at ~10 response units (RU). In one aspect, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (KD) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

In another aspect, ELISA can be used to calculate $K_D$ values, e.g., as described in Friguet et al J Immunol. Methods (1985) 77 (2): 305-19.

2. Antibody Fragments

In certain aspects, an antibody provided herein is an antibody fragment.

In one aspect, the antibody fragment is a Fab, Fab', Fab'-SH, or F(ab') 2 fragment, in particular a Fab fragment. Papain digestion of intact antibodies produces two identical antigen-binding fragments, called "Fab" fragments containing each the heavy- and light-chain variable domains (VH and VL, respectively) and also the constant domain of the light chain (CL) and the first constant domain of the heavy chain (CH1). The term "Fab fragment" thus refers to an antibody fragment comprising a light chain comprising a VL domain and a CL domain, and a heavy chain fragment comprising a VH domain and a CH1 domain. "Fab' fragments" differ from Fab fragments by the addition of residues at the carboxy terminus of the CH1 domain including one or more cysteines (SEQ ID NO: 285) from the antibody hinge region. Fab'-SH are Fab' fragments in which the cysteine residue(s) of the constant domains bear a free thiol group. Pepsin treatment yields an $F(ab')_2$ fragment that has two antigen-binding sites (two Fab fragments) and a part of the Fc region. For discussion of Fab and $F(ab')_2$ fragments comprising salvage receptor binding epitope residues and having increased in vivo half-life, see U.S. Pat. No. 5,869,046.

In another aspect, the antibody fragment is a diabody, a triabody or a tetrabody. "Diabodies" are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90:6444-6448 (1993). Triabodies and tetrabodies are also described in Hudson et al., Nat. Med. 9:129-134 (2003).

In a further aspect, the antibody fragment is a single chain Fab fragment. A "single chain Fab fragment" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab fragments are stabilized via the natural disulfide bond between the CL domain and the CH1 domain. In addition, these single chain Fab fragments might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Plückthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as recombinant production by recombinant host cells (e.g., *E. coli*), as described herein.

3. Chimeric and Humanized Antibodies

In certain aspects, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain aspects, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region. In some aspects, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain aspects, an antibody provided herein is a human antibody. Human antibodies can be produced using various techniques known in the art. Human antibodies are described generally in van Dijk and van de Winkel, Curr. Opin. Pharmacol. 5:368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133:3001 (1984); Brodeur et al., *Monoclonal Antibody Production Techniques and Applications*, pp. 51-63 (Marcel Dekker, Inc., New York, 1987); and Boerner et al., *J. Immunol.,* 147:86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26 (4): 265-268 (2006) (describing human-human hybridomas). Human hybridoma technology (Trioma technology) is also described in Vollmers and Brandlein, *Histology and Histopathology,* 20 (3): 927-937 (2005) and Vollmers and Brandlein, *Methods and Findings in Experimental and Clinical Pharmacology,* 27 (3): 185-91 (2005).

Human antibodies may also be generated by isolating variable domain sequences selected from human-derived phage display libraries. Such variable domain sequences may then be combined with a desired human constant domain. Techniques for selecting human antibodies from antibody libraries are described below.

5. Library-Derived Antibodies

In certain aspects, an antibody provided herein is derived from a library. Antibodies of the invention may be isolated by screening combinatorial libraries for antibodies with the desired activity or activities. Methods for screening combinatorial libraries are reviewed, e.g., in Lerner et al. in *Nature Reviews* 16:498-508 (2016). For example, a variety of methods are known in the art for generating phage display libraries and screening such libraries for antibodies possessing the desired binding characteristics. Such methods are reviewed, e.g., in Frenzel et al. in *mAbs* 8:1177-1194 (2016); Bazan et al. in *Human Vaccines and Immunotherapeutics* 8:1817-1828 (2012) and Zhao et al. in *Critical Reviews in Biotechnology* 36:276-289 (2016) as well as in Hoogenboom et al. in *Methods in Molecular Biology* 178:1-37 (O'Brien et al., ed., Human Press, Totowa, NJ, 2001) and in Marks and Bradbury in *Methods in Molecular Biology* 248:161-175 (Lo, ed., Human Press, Totowa, NJ, 2003).

In certain phage display methods, repertoires of VH and VL genes are separately cloned by polymerase chain reaction (PCR) and recombined randomly in phage libraries, which can then be screened for antigen-binding phage as described in Winter et al. in *Annual Review of Immunology* 12:433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. in *EMBO Journal* 12:725-734 (1993). Furthermore, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in *Journal of Molecular Biology* 227:381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936.

Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in *Methods in Molecular Biology* 503:135-56 (2012) and in Cherf et al. in *Methods in Molecular biology* 1319: 155-175 (2015) as well as in Zhao et al. in *Methods in Molecular Biology* 889:73-84 (2012). Methods for ribosome display are described, e.g., in He et al. in *Nucleic Acids Research* 25:5132-5134 (1997) and in Hanes et al. in PNAS 94:4937-4942 (1997).

Antibodies or antibody fragments isolated from human antibody libraries are considered human antibodies or human antibody fragments herein.

6. Multispecific Antibodies

In certain aspects, an antibody provided herein is a multispecific antibody, e.g., a bispecific antibody. "Multispecific antibodies" are monoclonal antibodies that have binding specificities for at least two different sites, i.e., different epitopes on different antigens or different epitopes on the same antigen. In certain aspects, the multispecific antibody has three or more binding specificities. In certain aspects, one of the binding specificities is for S-HBs and the other specificity is for any other antigen. In certain aspects, bispecific antibodies may bind to two (or more) different epitopes of S-HBs. Multispecific (e.g., bispecific) antibodies may also be used to localize cytotoxic agents or cells to cells which express S-HBs. Multispecific antibodies may be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305:537 (1983)) and "knob-in-hole" engineering (see, e.g., U.S. U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., *Science,* 229:81 (1985)); using leucine zippers to produce bi-specific antibodies (see, e.g., Kostelny et al., *J. Immunol.,* 148 (5): 1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147:60 (1991).

Engineered antibodies with three or more antigen binding sites, including for example, "Octopus antibodies", or DVD-Ig are also included herein (see, e.g., WO 2001/77342 and WO 2008/024715). Other examples of multispecific antibodies with three or more antigen binding sites can be found in WO 2010/115589, WO 2010/112193, WO 2010/136172, WO 2010/145792, and WO 2013/026831. The bispecific antibody or antigen binding fragment thereof also includes a "Dual Acting FAb" or "DAF" comprising an antigen binding site that binds to S-HBs as well as another different antigen, or two different epitopes of S-HBs (see, e.g., US 2008/0069820 and WO 2015/095539).

Multi-specific antibodies may also be provided in an asymmetric form with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). In one aspect, the multispecific antibody comprises a cross-Fab fragment. The term "cross-Fab fragment" or "xFab fragment" or "crossover Fab fragment" refers to a Fab fragment, wherein either the variable regions or the constant regions of the heavy and light chain are exchanged. A cross-Fab fragment comprises a polypeptide chain composed of the light chain variable region (VL) and the heavy chain constant region 1 (CH1), and a polypeptide chain composed of the heavy chain variable region (VH) and the light chain constant region (CL). Asymmetrical Fab arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., Mol Immunol 67 (2015) 95-106).

A particular type of multispecific antibodies, also included herein, are bispecific antibodies designed to simultaneously bind to a surface antigen on a target cell, e.g., an infected cell and to an activating, invariant component of the T cell receptor (TCR) complex, such as CD3, for retargeting of T cells to kill target cells. Hence, in certain aspects, an antibody provided herein is a multispecific antibody, particularly a bispecific antibody, wherein one of the binding specificities is for S-HBs and the other is for CD3.

Examples of bispecific antibody formats that may be useful for this purpose include, but are not limited to, the so-called "BiTE" (bispecific T cell engager) molecules wherein two scFv molecules are fused by a flexible linker (see, e.g., WO 2004/106381, WO 2005/061547, WO 2007/042261, and WO 2008/119567, Nagorsen and Bäuerle, Exp Cell Res 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO 2013/026839, WO 2016/020309; Bacac et al., Oncoimmunology 5 (8) (2016) e1203498.

7. Antibody Variants

In certain aspects, amino acid sequence variants of the antibodies provided herein are contemplated. For example, it may be desirable to alter the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain aspects, antibody variants having one or more amino acid substitutions are provided. Sites of interest for substitutional mutagenesis include the CDRs and FRs. Conservative substitutions are shown in Table 1 under the heading of "preferred substitutions". More substantial changes are provided in Table 1 under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for a member of another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more. CDR residues are mutated and the variant antibodies displayed on phage and screened for a particular biological activity (e.g., binding affinity).

Alterations (e.g., substitutions) may be made in CDRs, e.g., to improve antibody affinity. Such alterations may be made in CDR "hotspots", i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some aspects of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain aspects, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in the CDRs. Such alterations may, for example, be outside of antigen contacting residues in the CDRs. In certain variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT (antibody directed enzyme prodrug therapy)) or a polypeptide which increases the serum half-life of the antibody.

b) Glycosylation Variants

In certain aspects, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the invention may be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e.g. complex, hybrid and high mannose structures) as measured by MALDI-TOF mass spectrometry, as described in WO 2006/082515, for example. Asn297 refers to the asparagine residue located at about position 297 in the Fc region (EU numbering of Fo region residues); however, Asn297 may also be located about +3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.,* 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain aspects, the invention contemplates an antibody variant that possesses some but not all effector functions, which make it a desirable candidate for applications in which the half life of the antibody in vivo is important yet certain effector functions (such as complement-dependent cytotoxicity (CDC) and antibody-dependent cell-mediated cytotoxicity (ADCC)) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FCγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18 (12): 1759-1769 (2006); WO 2013/120929 A1).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9 (2): 6591-6604 (2001).)

In certain aspects, an antibody variant comprises an Fc region with one or more amino acid substitutions which improve ADCC, e.g., substitutions at positions 298, 333, and/or 334 of the Fc region (EU numbering of residues).

In certain aspects, an antibody variant comprises an Fc region with one or more amino acid substitutions which diminish FcγR binding, e.g., substitutions at positions 234 and 235 of the Fc region (EU numbering of residues). In one aspect, the substitutions are L234A and L235A (LALA). In certain aspects, the antibody variant further comprises D265A and/or P329G in an Fc region derived from a human $IgG_1$ Fc region. In one aspect, the substitutions are L234A, L235A and P329G (LALA-PG) in an Fc region derived from a human IgG1 Fc region. (See, e.g., WO 2012/130831). In another aspect, the substitutions are L234A, L235A and D265A (LALA-DA) in an Fc region derived from a human $IgG_1$ Fc region.

In some aspects, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164:4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (See, e.g., U.S. Pat. No. 7,371,826; Dall'Acqua, W. F., et al. J. Biol. Chem. 281 (2006) 23514-23524).

Fc region residues critical to the mouse Fc-mouse FcRn interaction have been identified by site-directed mutagenesis (see e.g. Dall'Acqua, W. F., et al. J. Immunol 169 (2002) 5171-5180). Residues I253, H310, H433, N434, and H435 (EU numbering of residues) are involved in the interaction (Medesan, C., et al., Eur. J. Immunol. 26 (1996) 2533; Firan, M., et al., Int. Immunol. 13 (2001) 993; Kim, J. K., et al., Eur. J. Immunol. 24 (1994) 542). Residues I253, H310, and H435 were found to be critical for the interaction of human Fc with murine FcRn (Kim, J. K., et al., Eur. J. Immunol. 29 (1999) 2819). Studies of the human Fc-human FcRn complex have shown that residues 1253, S254, H435, and Y436 are crucial for the interaction (Firan, M., et al., Int. Immunol. 13 (2001) 993; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

In certain aspects, an antibody variant comprises an Fc region (in some embodiments an Fc region of IgG1) with one or more amino acid substitutions, which reduce FcRn binding, e.g., substitutions at positions 253, and/or 310, and/or 435 of the Fc-region (EU numbering of residues). In certain aspects, the antibody variant comprises an Fc region with the amino acid substitutions at positions 253, 310 and 435. In one aspect, the substitutions are I253A, H310A and H435A in an Fc region derived from a human IgG1 Fc-region. See, e.g., Grevys, A., et al., J. Immunol. 194 (2015) 5497-5508.

In certain aspects, an antibody variant comprises an Fc region (in some embodiments an Fc region of IgG1) with one or more amino acid substitutions, which reduce FcRn binding, e.g., substitutions at positions 310, and/or 433, and/or 436 of the Fc region (EU numbering of residues). In certain aspects, the antibody variant comprises an Fc region with the amino acid substitutions at positions 310, 433 and 436. In one aspect, the substitutions are H310A, H433A and Y436A in an Fc region derived from a human IgG1 Fc-region. (See, e.g., WO 2014/177460 A1).

In certain aspects, an antibody variant comprises an Fc region (in some embodiments an Fc region of IgG1) with one or more amino acid substitutions which increase FcRn binding, e.g., substitutions at positions 252, and/or 254, and/or 256 of the Fc region (EU numbering of residues). In certain aspects, the antibody variant comprises an Fc region with amino acid substitutions at positions 252, 254, and 256. In one aspect, the substitutions are M252Y, S254T and T256E in an Fc region derived from a human $IgG_1$ Fc-region. See also Duncan & Winter, *Nature* 322:738-40 (1988); U.S. Pat. Nos. 5,648,260; 5,624,821; and WO 94/29351 concerning other examples of Fc region variants.

In certain further aspects, an antibody variant comprises an Fc region (in some embodiments an Fc region of IgG1) with one or more amino acid substitutions which increase FcRn binding, e.g., substitutions at positions 428 and/or 434 and/or 436 of the Fc region (EU numbering of residues). In certain aspects, the antibody variant comprises an Fc region with amino acid substitutions at positions 428, 434, and 436. In one aspect, the substitutions are M428L, N434A and Y436T in an Fc region derived from a human IgG1 Fc-region. In another aspect, the antibody variant comprises an Fc region with amino acid substitution at position 434, e.g., N434A.

In certain further aspect, an antibody variant comprises an Fc region (in some embodiments an Fc region of IgG1) with one or more amino acid substitutions which increase FcRn binding, e.g., a substitutions at position 307 and/or 434, e.g., T307H and/or N434H, e.g., T307H and N434H.

In certain specific embodiments the antibody variant comprises a heavy chain as set out herein, modified by the substitutions i) M252Y, S254T and T256E; ii) M428L, N434A and Y436T; iii) N434A; or iv) T307H and N434H.

For instance, the antibody may comprise the light chain of SEQ ID NO: 17 and the heavy chain of SEQ ID NO: 18 or 263 modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO:35 and a heavy chain of SEQ ID NO:36 or 264, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO:53 and a heavy chain of SEQ ID NO: 54 or 265, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO:71 and a heavy chain of SEQ ID NO: 72 or 266, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO:89 and a heavy chain of SEQ ID NO: 90 or 267, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO: 107 and a heavy chain of SEQ ID NO: 108 or 268, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO: 125 and a heavy chain of SEQ ID NO: 126 or 269, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO: 143 and a heavy chain of SEQ ID NO: 144 or 270, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO: 161 and a heavy chain of SEQ ID NO: 162 or 271, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO: 179 and a heavy chain of SEQ ID NO: 180 or 272, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO: 197 and a heavy chain of SEQ ID NO: 198 or 273, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO: 215 and a heavy chain of SEQ ID NO: 216 or 274, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO: 233 and a heavy chain of SEQ ID NO: 234 or 275, modified by substitutions selected from the group consisting of i) M252Y, S254T and T256E; ii) M428L, N434A and Y436T; iii) N434A; and iv) T307H and N434H.

In another specific embodiment, the antibody may comprise a light chain of SEQ ID NO: 251 and a heavy chain of SEQ ID NO: 252 or 276, modified by substitutions selected from the group consisting of i) M252Y, S254T and T256E; ii) M428L, N434A and Y436T; iii) N434A; and iv) T307H and N434H.

The C-terminus of the heavy chain of the antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, an antibody comprising a heavy chain including a C-terminal CH3 domain as specified herein, comprises the C-terminal glycine-lysine dipeptide (G446 and K447, EU index numbering of amino acid positions). In one aspect of all aspects as reported herein, an antibody comprising a heavy chain including a C-terminal CH3 domain, as specified herein, comprises a C-terminal glycine residue (G446, EU index numbering of amino acid positions).

d) Cysteine Engineered Antibody Variants

In certain aspects, it may be desirable to create cysteine engineered antibodies, e.g., THIOMAB™ antibodies, in which one or more residues of an antibody are substituted with cysteine residues. In particular aspects, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 8,30,930, 7,855,275, 9,000,130, or WO 2016040856.

e) Antibody Derivatives

In certain aspects, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

B. Recombinant Methods and Compositions

Antibodies may be produced using recombinant methods and compositions, e.g., as described in U.S. Pat. No. 4,816,567. For these methods one or more isolated nucleic acid(s) encoding an antibody are provided.

In case of a native antibody or native antibody fragment two nucleic acids are required, one for the light chain or a fragment thereof and one for the heavy chain or a fragment thereof. Such nucleic acid(s) encode an amino acid sequence comprising the VL and/or an amino acid sequence comprising the VH of the antibody (e.g., the light and/or heavy chain(s) of the antibody). These nucleic acids can be on the same expression vector or on different expression vectors.

In case of a bispecific antibody with heterodimeric heavy chains four nucleic acids are required, one for the first light chain, one for the first heavy chain comprising the first heteromonomeric Fc-region polypeptide, one for the second light chain, and one for the second heavy chain comprising the second heteromonomeric Fc-region polypeptide. The four nucleic acids can be comprised in one or more nucleic acid molecules or expression vectors. Such nucleic acid(s) encode an amino acid sequence comprising the first VL and/or an amino acid sequence comprising the first VH including the first heteromonomeric Fc-region and/or an amino acid sequence comprising the second VL and/or an amino acid sequence comprising the second VH including the second heteromonomeric Fc-region of the antibody (e.g., the first and/or second light and/or the first and/or second heavy chains of the antibody). These nucleic acids can be on the same expression vector or on different expression vectors, normally these nucleic acids are located on two or three expression vectors, i.e. one vector can comprise more than one of these nucleic acids. Examples of these bispecific antibodies are CrossMabs (see, e.g., Schaefer, W. et al, PNAS, 108 (2011) 11187-1191). For example, one of the heteromonomeric heavy chain comprises the so-called "knob mutations" (T366W and optionally one of S354C or Y349C) and the other comprises the so-called "hole mutations" (T366S, L368A and Y407V and optionally Y349C or S354C) (see, e.g., Carter, P. et al., Immunotechnol. 2 (1996) 73) according to EU index numbering.

In one aspect, isolated nucleic acids encoding an antibody as used in the methods as reported herein are provided.

In one aspect, a method of making an anti-S-HBs antibody is provided, wherein the method comprises culturing a host cell comprising nucleic acid(s) encoding the antibody, as provided above, under conditions suitable for expression of the antibody, and optionally recovering the antibody from the host cell (or host cell culture medium).

For recombinant production of an anti-S-HBs antibody, nucleic acids encoding the antibody, e.g., as described above, are isolated and inserted into one or more vectors for further cloning and/or expression in a host cell. Such nucleic acids may be readily isolated and sequenced using conventional procedures (e.g., by using oligonucleotide probes that are capable of binding specifically to genes encoding the heavy and light chains of the antibody) or produced by recombinant methods or obtained by chemical synthesis.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, NJ (2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized", resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of (glycosylated) antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (as described, e.g., in Mather, J. P. et al., Annals N.Y. Acad. Sci. 383 (1982) 44-68); MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

In one aspect, the host cell is eukaryotic, e.g., a Chinese Hamster Ovary (CHO) cell or lymphoid cell (e.g., Y0, NS0, Sp20 cell).

C. Assays

Anti-S-HBs antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, flow cytometry, Western blot, etc.

S-HBs antigen for use in ELISA may be in the form of particles. Particles for use in an ELISA protocol may be provided by recombinant expression of antigen, e.g., S-HBs, in host cells and self-assembly of the antigen into particles. For instance, the antigen may be expressed in a yeast host cell such as *Pichia pastoris* or in a mammalian cell such as a Chinese Hamster Ovary (CHO) cell.

The ELISA assay may comprise the steps of i) coating an ELISA plate with S-HBs antigen ii) blocking the plate with BSA; iii) washing; iv) incubating with serial dilutions of IgG antibody; v) washing; vi) incubating with goat-anti-human IgG-HRP antibody; vii) developing the plate with HRP chromogenic substrate; and viii) measuring optical density at 405 nm (OD405 nM).

The binding activity measured by ELISA may be quantified as the area under the curve (AUC) as determined from the OD405 nM-concentration curve. Thus, the method may comprise ix) determining AUC from the OD405 nM-concentration curve. These values may be compared to compare the activity of a test antibody to a reference antibody, as a percentage. Alternatively, an EC50 value can be determined from the ELISA assay, as the concentration at which the half maximal value of OD450 nm is obtained.

A flow-cytometry assay may comprise the steps of i) expressing S-SBs in a human cell line; ii) fixing and permeabilizing the cells; iii) incubating the cells with IgG antibody; iv) washing; v) incubating the cells with AF647-conjugated goat anti-human IgG antibody; vi) washing and resuspending in PBS; and vii) determining % of bound S-HBs-expressing cells or the mean fluorescence intensity (MFI) by flow cytometry.

A serial dilution of antibody can be used to determine an EC50 in the flow cytometry assay. Alternatively, the values obtained for the % of bound S-HBs-expressing cells or the MFI may be compared to express the activity of a test antibody as a percentage of the activity a reference antibody, when the test antibody and the reference antibody are used at the same concentration, e.g., at 10 ug/ml or alternatively at the EC50 of the reference antibody (as determined in the flow cytometry assay), Where relative binding activity is assessed, the antibodies should be tested using the same method. They may also be assessed in the same format, e.g., both as IgGs. In such embodiments, the reference antibody will have the full length sequences for said reference antibody as provided herein. The binding activity of a test antibody comprising a VH and VL domain as defined herein (e.g., comprising a VH and/or VL domain which is a variant of that of the reference antibody) may be assessed in an IgG format comprising the constant domain and hinge sequences of the reference antibody.

Exemplary protocols are set out below.

Protocol 1

High-binding 96-well ELISA plates (Costar, Corning) are coated overnight with purified antigen (e.g., 125 ng/well in PBS). After washings (e.g., with 0.05% Tween 20-PBS (PBST)), plates are blocked 2 h with 2% BSA, 1 mM EDTA-PBST (Blocking solution), washed, and incubated with serially diluted antibody in PBS. After washings, plates are revealed by addition of goat HRP-conjugated anti-human IgG (e.g., 0.8 µg/ml final in blocking solution, Immunology Jackson ImmunoReseach) and HRP chromogenic substrate (e.g., ABTS solution, Euromedex). Optical density measurements are made at 405 nm (OD405 nm). Binding can be quantified as the area under the curve (AUC) from the OD405 nm-concentration curve, and the AUC of two antibodies can be compared to assess relative activity as a percentage. Alternatively, the EC50 of an antibody can be determined as the concentration at which the half maximal value of OD450 nm is obtained.

Experiments may be performed using HydroSpeed™ microplate washer and Sunrise™ microplate absorbance reader (Tecan Männedorf). A negative control antibody mGO53 and a suitable positive control such as HB1 (Kucinskaite-Kodze et al., 2016) may be included in each experiment.

Protocol 2

In an exemplary protocol for measuring binding activity using flow cytometry, a human cell line (e.g., Freestyle™ 293-F) is transfected with S-HBs-encoding vectors (0.65 µg plasmid DNA per $10^6$ cells), e.g., using the PEI-precipitation method as previously described (Lorin and Mouquet, 2015). Forty-eight hours post-transfection, transfected and non-transfected control cells are fixed and permeabilized e.g., using Cytofix/Cytoperm™ solution kit (BD Biosciences), and $0.5\times10^6$ cells are incubated with IgG antibodies for 45 min at 4° C. (e.g, in Perm/Wash™ solution; BD Biosciences). In one embodiment, the test and reference antibody are used at 10 ug/ml. In another embodiment, the test and reference antibody can be used at the EC50 of the reference antibody as determined in the flow cytometry assay. After washings, cells are incubated 20 min at 4° C. with AF647-conjugated goat anti-human IgG antibodies (1:1000 dilution; Thermo Fisher Scientific), washed and resuspended in PBS. The percentage of bound S-HBs-expressing cells and/or the mean fluorescence intensity (MFI) of the signals is assessed by flow cytometry, and the values obtained for two antibodies are compared to assess relative value as a percentage. Data may be acquired using a CytoFLEX flow cytometer (Beckman Coulter), and analyzed using FlowJo software (v10.3; FlowJo LLC).

Protocol 3

In an exemplary protocol for assessing EC50 using flow cytometry, a human cell line (e.g., Freestyle™ 293-F) is transfected with Ss-HBs-encoding vectors (0.65 µg plasmid DNA per $10^6$ cells), e.g., using the PEI-precipitation method as previously described (Lorin and Mouquet, 2015). Forty-eight hours post-transfection, transfected and non-transfected control cells are fixed and permeabilized e.g., using Cytofix/Cytoperm™ solution kit (BD Biosciences), and $0.5\times10^6$ cells are incubated with serial dilutions of IgG antibodies in PBS for 45 min at 4° C. (e.g in Perm/Wash™ solution; BD Biosciences). After washings, cells are incubated 20 min at 4° C. with AF647-conjugated goat anti-human IgG antibodies (1:1000 dilution; Thermo Fisher Scientific), washed and resuspended in PBS. The percentage of bound S-HBs-expressing cells or the mean fluorescence intensity (MFI) of the signals is be assessed by flow cytometry, and the EC50 is determined as the concentration at which the half maximal percentage of bound cells or MFI is obtained.

In another aspect, competition assays may be used to identify an antibody that competes with a reference antibody selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105 for binding to S-HBs. In certain aspects, such a competing antibody binds to the same epitope (e.g., a linear or a conformational epitope) that is bound by a reference antibody selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105. Detailed exemplary methods for mapping an epitope to which an antibody binds are provided in Morris (1996) "Epitope Mapping Protocols", in *Methods in Molecular Biology* vol. 66 (Humana Press, Totowa, NJ).

In an exemplary competition assay, immobilized S-HBs is incubated in a solution comprising a first labeled antibody that binds to S-HBs (e.g., a reference antibody selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105) and a second unlabeled antibody that is being tested for its ability to compete with the first antibody for binding to S-HBs. The second antibody may be present in a hybridoma supernatant. As a control, immobilized S-HBs is incubated in a solution comprising the first labeled antibody but not the second unlabeled antibody. After incubation under conditions permissive for binding of the first antibody to S-HBs, excess unbound antibody is removed, and the amount of label associated with immobilized S-HBs is measured. If the amount of label associated with immobilized S-HBs is substantially reduced in the test sample relative to the control sample, then that indicates that the second antibody is competing with the first antibody for binding to S-HBs. See Harlow and Lane (1988) *Antibodies: A Laboratory Manual* ch. 14 (Cold Spring Harbor Laboratory, Cold Spring Harbor, NY).

A further exemplary competition assay is a competition ELISA. Purified antibodies (e.g., a reference antibody selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105) are biotinylated using the EZ-Link Sulfo-NHS-Biotin kit (Thermo Fisher Scientific). Antigen or antigen-particle (e.g., rS-HBs)-coated plates are blocked, washed, incubated for 2 h with the biotinylated antibody (at a concentration 0.33 nM) in 1:2 serially diluted solutions of antibody competitors in PBS (IgG concentration range from 0.83 to 106.7 nM), and revealed using HRP-conjugated streptavidin. Experiments are performed using HydroSpeed™ microplate washer and Sunrise™ microplate absorbance reader (Tecan Männedorf), with optical density measurements made at 405 nm (OD405 nm).

2. Activity Assays

In one aspect, assays are provided for identifying anti-S-HBs antibodies thereof having biological activity. Biological activity may include, e.g., neutralizing activity in vitro or in vivo and/or the ability to reduce viremia in vivo. Antibodies having such biological activity in vivo and/or in vitro are also provided.

In vitro neutralizing activity may be inhibition of infection of primary human hepatocytes or human hepatocyte cell lines by HBV. This may be determined as a reduction in the supernatant S-HBs as compared to the absence of antibody. In vivo neutralizing activity may be determined as a reduction in circulating S-HBs animals infected with HBV, e.g., mice or humans.

Reduction of viral viremia can be determined as a reduction in HBV DNA in the serum of an HBV infected animal, e.g., mouse or human.

Antibodies may for instance have an IC50 value for in vitro inhibition of infectivity by HBV of a particular genotype e.g., genotype D, of ≤50 µg/ml, ≤10 µg/ml, ≤1 g/ml, ≤500 ng/ml, ≤100 ng/ml, ≤50 ng/ml, ≤10 ng/ml, ≤1 ng/ml, ≤500 pg/ml, ≤100 pg/ml, ≤50 pg/ml, ≤10 pg/ml or ≤1 pg/ml. In some embodiments, preferred antibodies may have a IC50 of ≤50 ng/ml, or ≤10 ng/ml. It may be preferred that the antibody has an IC50 of ≤1 ng/ml, ≤500 pg/ml or in some embodiments ≤100 pg/ml, ≤50 pg/ml, or ≤10 pg/ml. In some embodiments, a neutralizing antibody may have an IC50 value of ≤1 pg/ml, optionally ≤0.1 pg/ml.

In another embodiment, an antibody may have an IC50 value against a particular genotype, e.g., genotype D, which is no more than 50, 10, 9, 8, 7, 6, 5, 4, 3, or 2 fold higher than, or is less than or equal to, the IC50 value of a reference antibody against the same genotype, wherein the reference antibody is selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105 (when assessed in the same in vitro assay).

In another embodiment, an antibody may have or retain at least 50%, 60%, 70%, 75%, 80%, 85%, 90%, 95% or 100% of the neutralizing activity of a reference antibody to a particular HBV genotype, when assessed using the same assay (e.g., an in vivo assay as described herein).

In some embodiments, an antibody of the invention has or retains at least 50%, 60%, 70%, 75%, 80%, 85%, 90%, 95% or 100% of the in vivo neutralizing activity of a reference antibody against an HBV genotype A, B, C and/or D virus, wherein the reference antibody is selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105 . . . . In some embodiments, an antibodies of the invention has or retains at least 50%, 60%, 70%, 75%, 80%, 85%, 90%, 95% or 100% of the viremia-suppressing activity of a reference antibody against HBV genotype A, B, C and/or D viruses, wherein the reference antibody is selected from the group consisting of Bc1.187, Bv4.115, Bc8.159, Bv6.172, Bc1.229, Bc8.111, Bc1.128, Bc3.106, Bc1.180, Bv4.104, Bc8.104, Bc4.204, Bc1.263 and Bv4.105.

In certain aspects, an antibody of the invention is tested for such biological activity.

Exemplary in vitro neutralization assays are described below as protocol 4. An exemplary in vivo neutralization assay is described below as protocol 5. An exemplary assay for viremia suppression is described in protocol 6.

Where relative activities are assessed, the antibodies should be tested using the same method. The antibodies may both be assessed as IgGs: in such embodiments, the reference antibody will have the full length sequences for said reference antibody as provided herein. The binding activity of a test antibody comprising a VH and VL domain as defined herein (e.g., comprising a VH and/or VL domain which is a variant of that of the reference antibody) may be assessed in an IgG format comprising the constant domain and hinge sequences of the reference antibody.

Protocol 4 (for Assessing IC50 Values of In Vitro Neutralization)

In an exemplary protocol, the in vitro neutralizing activity of HBV antibodies is evaluated by incubating HBV virions (MOI 20-30) with serially diluted test antibodies for 1 h at room temperature. HBV-antibody mixtures are then added to hepatocytes in 96-well plates with a final concentration of 4% PEG 8000 (Sigma). Infected cells are incubated for 20 h at 37° C., and then washed 4 times with PBS to remove the HBV inoculum and refilled with complete media. Six days post-infection, in-supernatant S-HBs antigen content is quantified, e.g., using the S-HBs CLIA Kit (Autobio) according to the manufacturer's instructions. Neutralization activity is determined as the reduction in the supernatant S-HBs as compared to a control in the absence of antibodies. The IC50 value is the half maximal inhibitory concentration, measuring the inhibition of infectivity.

Cells may be primary human hepatocytes or human hepatocyte cell lines. Exemplary hepatocytes which may be used in the protocol are primary human hepatocytes (PHH) isolated from chimeric uPA/SCID mice with humanized livers by a collagenase perfusion method (Tateno et al., 2015), obtainable from PhoenixBio (Hiroshima, Japan). Further exemplary hepatocytes are the HepaRG cell line obtainable from Biopredic International (Saint-Gregoire, France).

Protocol 5 (for Assessing Neutralizing Activity In Vivo)

In an exemplary protocol for assessing in vivo neutralization activity, circulating blood S-HBs levels are monitored in AAV-HBV-transduced mice treated once i.v. with 0.5 mg of test antibody. Circulating blood S-HBs is measured by ELISA. Neutralizing activity is determined as a reduction in the amount of circulating blood S-HBs at the nadir (maximum decrease).

Protocol 6 (for Assessing Viremia Suppression In Vivo)

AAV-HBV mice carrying high levels of circulating S-HBsAg (>$10^4$ IU/ml) are selected as subjects. A single intravenous (i.v.) injection of test antibodies is administered at 20 mg/kg. HBV DNA was purified from mouse sera using QIAamp Blood Mini kits (Qiagen, Germany), and quantified by quantitative PCR as previously described (Cougot et al., 2012). Viremia suppression activity is determined by assessing the amount of HBV DNA at the nadir (maximum decrease).

D. Methods and Compositions for Diagnostics and Detection

In certain aspects, any of the anti-S-HBs antibodies provided herein is useful for detecting the presence of S-HBs in a biological sample. The term "detecting" as used herein encompasses quantitative or qualitative detection. In certain aspects, a biological sample comprises a sample of blood, blood plasma or blood serum.

In one aspect, an anti-S-HBs antibody for use in a method of diagnosis or detection is provided. In a further aspect, a method of detecting the presence of S-HBs in a biological sample is provided. In certain aspects, the method comprises contacting the biological sample with an anti-S-HBs antibody as described herein under conditions permissive for binding of the anti-S-HBs antibody to S-HBs, and detecting whether a complex is formed between the anti-S-HBs antibody and S-HBs. Such method may be an in vitro or in vivo method. In one aspect, an anti-S-HBs antibody is used to select subjects eligible for therapy with an anti-S-HBs antibody, e.g., where S-HBs is a biomarker for selection of patients.

Exemplary disorders that may be diagnosed using an antibody of the invention include hepatitis B, for instance chronic hepatitis B.

In certain aspects, labeled anti-S-HBs antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

E. Pharmaceutical Compositions

In a further aspect, provided are pharmaceutical compositions comprising any of the antibodies provided herein, e.g., for use in any of the below therapeutic methods. In one aspect, a pharmaceutical composition comprises any of the antibodies provided herein and a pharmaceutically acceptable carrier. In another aspect, a pharmaceutical composition comprises any of the antibodies provided herein and at least one additional therapeutic agent, e.g., as described below.

Pharmaceutical compositions of an anti-S-HBs antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized compositions or aqueous solutions. Pharmaceutically acceptable carriers are generally nontoxic to recipients at the dosages and concentrations employed, and include, but are not limited to: buffers such as histidine, phosphate, citrate, acetate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Halozyme, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody compositions are described in U.S. Pat. No. 6,267,958. Aqueous antibody compositions include those described in U.S. Pat. No. 6,171,586 and WO 2006/044908, the latter compositions including a histidine-acetate buffer.

The pharmaceutical composition herein may also contain more than one active ingredients as desired for the particular indication being treated, preferably those with complementary activities that do not adversely affect each other. For example, it may be desirable to further provide one or more additional therapeutic agents selected from: an antiviral medication such as a nucleotide analog reverse-transcriptase inhibitor or a nucleoside analogue, e.g., entecavir, tenofovir disoproxil fumarate, tenofovir alafenamide, lamivudine, adefovir or telbivudine; an siRNA targeted to an HBV sequence; an agent aiming at restoring the host's innate and adaptive immune responses, e.g., INFα or pegylated-IFNα; a therapeutic vaccine such as GS-4774, ABX-203, TG-1050, INO-1800; a TLR agonist such as an anti-TLR antibody, lipopeptide, lipopolysaccharide, Poly I:C (Polyriboinosinic-polyribocytidylic acid), Poly ICLC (Poly I:C-poly-l-lysine), imiquimod, GSK2245035, GSK2445053, RO6864018, RO7020531, GS-9620, GS-9688, 852A (Synthetic imidazoquinoline mimicking viral ssRNA), Resiquimod, VTX-2337 (Small-molecule selective TLR8 agonist mimicking viral ssRNA), *Bacillus* Calmette-Guérin (BCG), MPL (monophosphoryl lipid A) and/or CpG oligodeoxynucleotide; and/or a checkpoint inhibitor such as an antibody (e.g., an antagonist or blocking antibody), e.g., targeted against CTLA4 (e.g., ipilimumab, tremelimumab), PD-1 (e.g., nivolumab, pidilizumab), PD-L1 (e.g., MPDL3280A, MEDI4736, MSB0010718C), TIM-3, 2B4, A2AR, B7-H3, B7-H4, BTLA, IDO, KIR, LAG3, NOX2, VISTA, SIGLEC7 or SIGLEC9 (Fanning et al., 2019; Gehring and Protzer, 2019; Maini and Burton, 2019). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Pharmaceutical compositions for sustained-release may be prepared. Suitable examples of sustained-release preparations include semipermeable matrices of solid hydrophobic polymers containing the antibody, which matrices are in the form of shaped articles, e.g., films, or microcapsules.

The pharmaceutical compositions to be used for in vivo administration are generally sterile. Sterility may be readily accomplished, e.g., by filtration through sterile filtration membranes.

F. Therapeutic Methods and Routes of Administration

Any of the anti-S-HBs antibodies provided herein may be used in therapeutic methods.

In one aspect, an anti-S-HBs antibody for use as a medicament is provided. In further aspects, an anti-S-HBs antibody for use in treating hepatitis B is provided, e.g., for use in treating chronic hepatitis B virus infection. In certain aspects, an anti-S-HBs antibody for use in a method of treatment is provided. In certain aspects, the invention provides an anti-S-HBs antibody for use in a method of treating an individual having hepatitis B, e.g., chronic hepatitis B virus infection, comprising administering to the individual an effective amount of the anti-S-HBs antibody. In one such aspect, the method further comprises administering to the individual an effective amount of at least one additional therapeutic agent (e.g., one, two, three, four, five, or six additional therapeutic agents), e.g., as described below. In further aspects, the invention provides an anti-S-HBs antibody for use in reducing hepatitis B viral load, reducing detectable serum HBsAg or providing HBV functional cure. In certain aspects, the invention provides an anti-S-HBs antibody for use in a method of reducing hepatitis B viral load, reducing detectable serum HBsAg or providing HBV functional cure in an individual, comprising administering to the individual an effective amount of the anti-S-HBs antibody to reduce the viral load, reduce detectable serum HBsAg or provide HBV functional cure. HBV functional cure refers to seroclearance of hepatitis B surface antigen (HBsAg), i.e., the absence of detectable HBsAg in the serum. An "individual" according to any of the above aspects is preferably a human.

In a further aspect, the invention provides for the use of an anti-S-HBs antibody in the manufacture or preparation of a medicament. In one aspect, the medicament is for treatment of hepatitis B, e.g., chronic hepatitis B. In a further aspect, the medicament is for use in a method of treating hepatitis B, e.g., chronic hepatitis B, comprising administering to an individual having said condition an effective amount of the medicament. In one such aspect, the method further comprises administering to the individual an effective amount of at least one additional therapeutic agent, e.g., as described below. In a further aspect, the medicament is for reducing hepatitis B viral load, reducing detectable serum HBsAg or providing HBV functional cure. In a further aspect, the medicament is for use in a method of reducing hepatitis B viral load, reducing detectable serum HBsAg or providing HBV functional cure in an individual comprising administering to the individual an effective amount of the medicament to reduce the viral load, reduce the detectable serum HBsAg or provide HBV functional cure. An "individual" according to any of the above aspects may be a human.

In a further aspect, the invention provides a method for treating hepatitis B, e.g., chronic hepatitis B. In one aspect, the method comprises administering to an individual having hepatitis B, e.g., chronic hepatitis B an effective amount of an anti-S-HBs antibody. In one such aspect, the method further comprises administering to the individual an effective amount of at least one additional therapeutic agent, as described below.

An "individual" according to any of the above aspects may be a human.

In a further aspect, the invention provides a method for reducing hepatitis B viral load, reducing detectable serum HBsAg or providing HBV functional cure. In one aspect, the method comprises administering to the individual an effective amount of an anti-S-HBs antibody to reduce the viral load/reduce the detectable serum HBsAg/provide a functional cure. In one aspect, an "individual" is a human.

In a further aspect, the invention provides pharmaceutical compositions comprising any of the anti-S-HBs antibodies provided herein, e.g., for use in any of the above therapeutic methods. In one aspect, a pharmaceutical composition comprises any of the anti-S-HBs antibodies provided herein and a pharmaceutically acceptable carrier. In another aspect, a pharmaceutical composition comprises any of the anti-S-HBs antibodies provided herein and at least one additional therapeutic agent, e.g., as described below.

Antibodies of the invention can be administered alone or used in a combination therapy. For instance, the combination therapy includes administering an antibody of the invention and administering at least one additional therapeutic agent (e.g. one, two, three, four, five, or six additional therapeutic agents). In certain aspects, the combination therapy comprises administering an antibody of the invention and administering at least one additional therapeutic agent, such as: an antiviral medication such as a nucleotide analog reverse-transcriptase inhibitor or a nucleoside analogue, e.g., entecavir, tenofovir disoproxil fumarate, tenofovir alafenamide, lamivudine, adefovir or telbivudine; an siRNA targeted to the HBV sequence; an agent aiming at restoring the host's innate and adaptive immune responses, e.g., INFα or pegylated-IFNα; a therapeutic vaccine such as GS-4774, ABX-203, TG-1050, INO-1800; a TLR agonist such as an anti-TLR antibody, lipopeptide, lipopolysaccharide, Poly I:C (Polyriboinosinic-polyribocytidylic acid), Poly ICLC (Poly I:C-poly-l-lysine), imiquimod, GSK2245035, GSK2445053, RO6864018, RO7020531, GS-9620, GS-9688, 852A (Synthetic imidazoquinoline mimicking viral ssRNA), Resiquimod, VTX-2337 (Small-molecule selective TLR8 agonist mimicking viral ssRNA), *Bacillus* Calmette-Guérin (BCG), MPL (monophosphoryl lipid A) and/or CpG oligodeoxynucleotide; and/or a checkpoint inhibitor such as an antibody (e.g., an antagonist or blocking antibody), e.g., targeted against CTLA4 (e.g., ipilimumab, tremelimumab), PD-1 (e.g., nivolumab, pidilizumab), PD-L1 (e.g., MPDL3280A, MEDI4736, MSB0010718C), TIM-3, 2B4, A2AR, B7-H3, B7-H4, BTLA, IDO, KIR, LAG3, NOX2, VISTA, SIGLEC7 or SIGLEC9 (Fanning et al., 2019; Gehring and Protzer, 2019; Maini and Burton, 2019).

Such combination therapies noted above encompass combined administration (where two or more therapeutic agents are included in the same or separate pharmaceutical compositions), and separate administration, in which case, administration of the antibody of the invention can occur prior to, simultaneously, and/or following, administration of the additional therapeutic agent or agents. In one aspect, administration of the anti-S-HBs antibody and administration of an additional therapeutic agent occur within about one month, or within about one, two or three weeks, or within about one, two, three, four, five, or six days, of each other. In one aspect, the antibody and additional therapeutic agent are administered to the patient on Day 1 of the treatment.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the pharmaceutical composition, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. The progress of this therapy is easily monitored by conventional techniques and assays.

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this aspect of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

SEQUENCES

Amino acids shown in parentheses in the below table can be present or absent.

| SEQ ID NO | Description | Sequence |
|---|---|---|
| 1 | Bc1.187 CDR-H1 | NYGMQ |
| 2 | Bc1.187 CDR-H2 | IIWADGTKQYYGDSVKG |
| 3 | Bc1.187 CDR-H3 | DGLYASAPNDV |
| 4 | Bc1.187 CDR-L1 | RASQRISTYLN |
| 5 | Bc1.187-CDR-L2 | GASSLQS |
| 6 | Bc1.187 CDR-L3 | QQTYTLPPN |
| 7 | Bc1.187 H-FW1 | QVQLVESGGGVVQPGRSLRLSCEASGFTFS |
| 8 | Bc1.187 H-FW2 | WVRQAPGKGLEWVA |
| 9 | Bc1.187 H-FW3 | FTISRDNFKNTLYLQMNSLRGEDTAMYFCAR |
| 10 | Bc1.187 H-FW4 | WGQGTLVTVSS |
| 11 | Bc1.187 L-FW1 | DIQMTQSPSSLSAYVGDRVTITC |
| 12 | Bc1.187 L-FW2 | WYHQRPGKSPSLLIY |
| 13 | Bc1.187 L-FW3 | GVPSRFSASASGTDFTLTISSLRPEDLGTYYC |
| 14 | Bc1.187 L-FW4 | SGGGTKVEIK |
| 15 | Bc1.187 VL | DIQMTQSPSSLSAYVGDRVTITCRASQRISTYLNWYHQRPGKSPSLLIYGASSLQSGVPSRFSASASGTDFTLTIS<br>SLRPEDLGTYYCQQTYTLPPNSGGGTKVEIK |
| 16 | Bc1.187 VH | QVQLVESGGGVVQPGRSLRLSCEASGFTFSNYGMQWVRQAPGKGLEWVAIIWADGTKQYYGDSVKGRFTISRDNEK<br>NTLYLQMNSLRGEDTAMYFCARDGLYASAPNDVWGQGTLVTVSS |
| 17 | Bc1.187 full length light chain | DIQMTQSPSSLSAYVGDRVTITCRASQRISTYLNWYHQRPGKSPSLLIYGASSLQSGVPSRFSASASGTDFTLTIS<br>SLRPEDLGTYYCQQTYTLPPNSGGGTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| 18 | Bc1.187 full length heavy chain | QVQLVESGGGVVQPGRSLRLSCEASGFTFSNYGMQWVRQAPGKGLEWVAIIWADGTKQYYGDSVKGRFTISRDNFK<br>NTLYLQMNSLRGEDTAMYFCARDGLYASAPNDVWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYVDGVEVHNAKTKPREEQYNSTYR<br>VVSVLTVLHQDWLNGKEYKCKVSNKALPAPIEKTISKAK(G)QPREPQVYTLPPSRDELTKNQVSLTCLVKGFYPS<br>DIAVEWESNGQPENNYKTTPPVLDSDGSFFLYSKLTVDKSRWQQGNVFSCSVMHEALHNHYTQKSLSLSPGK |
| 19 | Bc1.180 CDR-H1 | RSAVS |
| 20 | Bc1.180 CDR-H2 | RTIPLLRIAEYSQTFQG |
| 21 | Bc1.180 CDR-H3 | EGDGLDM |
| 22 | Bc1.180 CDR-L1 | RASQSVTSNYFA |
| 23 | Bc1.180-CDR-L2 | GASSRAT |
| 24 | Bc1.180 CDR-L3 | QQFGSLPYT |
| 25 | Bc1.180 H-FW1 | QVQLVQSGAEVKKPGSSVKVSCKASGGTFG |
| 26 | Bc1.180 H-FW2 | WVRHAPGQRLEWMG |
| 27 | Bc1.180 H-FW3 | RVTITADKFTNTVYMELRSLTYEDTAVYYCAR |

-continued

SEQUENCES
Amino acids shown in parentheses in the below table can be present or absent.

| SEQ ID NO | Description | Sequence |
|---|---|---|
| 28 | Bc1.180 H-FW4 | WGQGTMVTVSS |
| 29 | Bc1.180 L-FW1 | EIVLTQSPGTLSLSPGNRATLSC |
| 30 | Bc1.180 L-FW2 | WYQHKPGQAPRVLIY |
| 31 | Bc1.180 L-FW3 | GIPDRFSGSGSGTDFTLTISRLEPEDFAVYYC |
| 32 | Bc1.180 L-FW4 | FGQGTKLEIK |
| 33 | Bc1.180 VL | EIVLTQSPGTLSLSPGNRATLSCRASQSVTSNYFAWYQHKPGQAPRVLIYGASSRATGIPDRFSGSGSGTDFTLTISRLEPEDFAVYYCQQFGSLPYTFGQGTKLEIK |
| 34 | Bc1.180 VH | QVQLVQSGAEVKKPGSSVKVSCKASGGTFGRSAVSWVRHAPGQRLEWMGRTIPLLRIAEYSQTFQGRVTITADKFTNTVYMELRSLTYEDTAVYYCAREGDGLDMWGQGTMVTVSS |
| 35 | Bc1.180 full length light chain | EIVLTQSPGTLSLSPGNRATLSCRASQSVTSNYFAWYQHKPGQAPRVLIYGASSRATGIPDRFSGSGSGTDFTLTISRLEPEDFAVYYCQQFGSLPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 36 | Bc1.180 full length heavy chain | QVQLVQSGAEVKKPGSSVKVSCKASGGTFGRSAVSWVRHAPGQRLEWMGRTIPLLRIAEYSQTFQGRVTITADKFTNTVYMELRSLTYEDTAVYYCAREGDGLDMWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK(G)QPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 37 | Bc3.106 CDR-H1 | SYAMS |
| 38 | Bc3.106 CDR-H2 | AFSGTGGSTYYADSVKG |
| 39 | Bc3.106 CDR-H3 | DPGHTSNWRDNYQYYQMDV |
| 40 | Bc3.106 CDR-L1 | RASQGIRNDLG |
| 41 | Bc3.106-CDR-L2 | AASSLQS |
| 42 | Bc3.106 CDR-L3 | LQHNSYPRT |
| 43 | Bc3.106 H-FW1 | EVQLLESGGGLVQPGGSLRLSCTASGFTFG |
| 44 | Bc3.106 H-FW2 | WVRQAPGKGLKWVS |
| 45 | Bc3.106 H-FW3 | RFTISRDNSKNTLYLQMNNLRAEDTAVYFCAK |
| 46 | Bc3.106 H-FW4 | WGQGTTVTVSS |
| 47 | Bc3.106 L-FW1 | DIQMTQSPSSLSASVGDRVTITC |
| 48 | Bc3.106 L-FW2 | WYQQKPGKAPKRLIY |
| 49 | Bc3.106 L-FW3 | GVPSRFSGSGSGTEFTLTISSLQPEDFATYYC |
| 50 | Bc3.106 L-FW4 | FGQGTKVEIK |
| 51 | Bc3.106 VL | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPRTFGQGTKVEIK |
| 52 | Bc3.106 VH | EVQLLESGGGLVQPGGSLRLSCTASGFTFGSYAMSWVRQAPGKGLKWVSAFSGTGGSTYYADSVKGRFTISRDNSKNTLYLQMNNLRAEDTAVYFCAKDPGHTSNWRDNYQYYQMDVWGQGTTVTVSS |
| 53 | Bc3.106 full length light chain | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 54 | Bc3.106 full length heavy chain | EVQLLESGGGLVQPGGSLRLSCTASGFTFGSYAMSWVRQAPGKGLKWVSAFSGTGGSTYYADSVKGRFTISRDNSKNTLYLQMNNLRAEDTAVYFCAKDPGHTSNWRDNYQYYQMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLIVLHQDWLNGKEYKCKVSNKALPAPIEKTISKAK(G)QPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |

-continued

| SEQUENCES Amino acids shown in parentheses in the below table can be present or absent. | | |
|---|---|---|
| SEQ ID NO | Description | Sequence |
| 55 | Bv4.104 CDR-H1 | GYGMH |
| 56 | Bv4.104 CDR-H2 | FLWHDGTSKDYADSVKG |
| 57 | Bv4.104 CDR-H3 | EDYYDSNAFDY |
| 58 | Bv4.104 CDR-L1 | TGTSSDVGNYKSVS |
| 59 | Bv4.104-CDR-L2 | EGTQRPS |
| 60 | Bv4.104 CDR-L3 | CSYAGSSTWL |
| 61 | Bv4.104 H-FW1 | QVQLVESGGGVVQPGRSLRLSCAASGFTFS |
| 62 | Bv4.104 H-FW2 | WVRQAPGKGLEWVA |
| 63 | Bv4.104 H-FW3 | RFTISRDNSKNTLYMQMNSLRAEDTAVYYCAR |
| 64 | Bv4.104 H-FW4 | WGQGTLVTVSS |
| 65 | Bv4.104 L-FW1 | QSALTQPASVSGSPGQSITISC |
| 66 | Bv4.104 L-FW2 | WYQHHPGKAPKFMIY |
| 67 | Bv4.104 L-FW3 | GVSNRFSGSKSGNTASLTISGLQAEDEAHYYC |
| 68 | Bv4.104 L-FW4 | FGGGTKLTVL |
| 69 | Bv4.104 VL | QSALTQPASVSGSPGQSITISCTGTSSDVGNYKSVSWYQHHPGKAPKFMIYEGTQRPSGVSNRFSGSKSGNTASLT ISGLQAEDEAHYYCCSYAGSSTWLFGGGTKLTVL |
| 70 | Bv4.104 VH | QVQLVESGGGVVQPGRSLRLSCAASGFTFSGYGMHWVRQAPGKGLEWVAFLWHDGTSKDYADSVKGRFTISRDNSK NTLYMQMNSLRAEDTAVYYCAREDYYDSNAFDYWGQGTLVTVSS |
| 71 | Bv4.104 full length light chain | QSALTQPASVSGSPGQSITISCTGTSSDVGNYKSVSWYQHHPGKAPKFMIYEGTQRPSGVSNRFSGSKSGNTASLT ISGLQAEDEAHYYCCSYAGSSTWLFGGGTKLTVLGQPKAAPSVTLFPPSSEELQANKATLVCLISDFYPGAVTVAW KADSSPVKAGVETTTPSKQSNNKYAASSYLSLTPEQWKSHRSYSCQVTHEGSTVEKTVAPTECS |
| 72 | Bv4.104 full length heavy chain | QVQLVESGGGVVQPGRSLRLSCAASGFTFSGYGMHWVRQAPGKGLEWVAFLWHDGTSKDYADSVKGRFTISRDNSK NTLYMQMNSLRAEDTAVYYCAREDYYDSNAFDYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICNVNHKPSNTKVDKKVEPKSCDKTHT CPPCPAPELLGGPSVFLFPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAK(G)QPREPQVYTLPPSRDELTKNQVSLTCLVKGFYPS DIAVEWESNGQPENNYKTTPPVLDSDGSFFLYSKLTVDKSRWQQGNVFSCSVMHEALHNHYTQKSLSLSPGK |
| 73 | Bc8.111 CDR-H1 | RYAMS |
| 74 | Bc8.111 CDR-H2 | ATSGSGADTYYADSVKG |
| 75 | Bc8.111 CDR-H3 | PYMVAAVARTVDY |
| 76 | Bc8.111 CDR-L1 | TRSSGSIASNYVQ |
| 77 | Bc8.111-CDR-L2 | EDNERPS |
| 78 | Bc8.111 CDR-L3 | QSYESSNWV |
| 79 | Bc8.111 H-FW1 | EVQLVESGGGLVQPGGSLRLSCAASGFTFS |
| 80 | Bc8.111 H-FW2 | WVRQAPGKGLEWVS |
| 81 | Bc8.111 H-FW3 | RFTISRDNSKNTVYLQMNSLRADDTAFYYCAK |
| 82 | Bc8.111 H-FW4 | WGQGTLVTVSS |
| 83 | Bc8.111 L-FW1 | QSVLTQPHSVSESPGKTVTISC |
| 84 | Bc8.111 L-FW2 | WYQQRPGSAPTTVIY |
| 85 | Bc8.111 L-FW3 | GVPARFSGSIDSSSNSASLTISGLKTEDEADYYC |
| 86 | Bc8.111 L-FW4 | FGGGTKLTVL |

-continued

SEQUENCES
Amino acids shown in parentheses in the below table can be present or absent.

| SEQ ID NO | Description | Sequence |
|---|---|---|
| 87 | Bc8.111 VL | QSVLTQPHSVSESPGKTVTISCTRSSGSIASNYVQWYQQRPGSAPTTVIYEDNERPSGVPARFSGSIDSSSNSASLTISGLKTEDEADYYCQSYESSNWVFGGGTKLTVL |
| 88 | Bc8.111 VH | EVQLVESGGGLVQPGGSLRLSCAASGFTFSRYAMSWVRQAPGKGLEWVSATSGSGADTYYADSVKGRFTISRDNSKNTVYLQMNSLRADDTAFYYCAKDPYMVAAVARTVDYWGQGTLVTVSS |
| 89 | Bc8.111 full length light chain | QSVLTQPHSVSESPGKTVTISCTRSSGSIASNYVQWYQQRPGSAPTTVIYEDNERPSGVPARFSGSIDSSSNSASLTISGLKTEDEADYYCQSYESSNWVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| 90 | Bc8.111 full length heavy chain | EVQLVESGGGLVQPGGSLRLSCAASGFTFSRYAMSWVRQAPGKGLEWVSATSGSGADTYYADSVKGRFTISRDNSKNTVYLQMNSLRADDTAFYYCAKDPYMVAAVARTVDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK(G)QPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 91 | Bc8.104 CDR-H1 | NYGVT |
| 92 | Bc8.104 CDR-H2 | GIIPIFGTTNYAQKFLG |
| 93 | Bc8.104 CDR-H3 | QGSSTWFATLYAFPI |
| 94 | Bc8.104 CDR-L1 | RASQRVSGNYLA |
| 95 | Bc8.104-CDR-L2 | GASSRAT |
| 96 | Bc8.104 CDR-L3 | HQYGSSPPT |
| 97 | Bc8.104 H-FW1 | QVQLVQSGAEVKKAGSSVKVSCKAFGGTSN |
| 98 | Bc8.104 H-FW2 | WVRQAPGQGLQWMG |
| 99 | Bc8.104 H-FW3 | RVTITADKSTRTAYMELSSLRSEDTAVYYCAS |
| 100 | Bc8.104 H-FW4 | WGQGTMVTVSS |
| 101 | Bc8.104 L-FW1 | EIVLTQSPGTLSLSPGERATLSC |
| 102 | Bc8.104 L-FW2 | WYQQKVGQAPRLLIY |
| 103 | Bc8.104 L-FW3 | GIPDRFSGSGSGTDFTLTISRLQPEDFAVYSC |
| 104 | Bc8.104 L-FW4 | FGQGTKVEIK |
| 105 | Bc8.104 VL | EIVLTQSPGTLSLSPGERATLSCRASQRVSGNYLAWYQQKVGQAPRLLIYGASSRATGIPDRFSGSGSGTDFTLTISRLQPEDFAVYSCHQYGSSPPTFGQGTKVEIK |
| 106 | Bc8.104 VH | QVQLVQSGAEVKKAGSSVKVSCKAFGGTSNNYGVTWVRQAPGQGLQWMGGIIPIFGTTNYAQKFLGRVTITADKSTRTAYMELSSLRSEDTAVYYCASQGSSTWFATLYAFPIWGQGTMVTVSS |
| 107 | Bc8.104 full length light chain | EIVLTQSPGTLSLSPGERATLSCRASQRVSGNYLAWYQQKVGQAPRLLIYGASSRATGIPDRESGSGSGTDFTLTISRLQPEDFAVYSCHQYGSSPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 108 | Bc8.104 full length heavy chain | QVQLVQSGAEVKKAGSSVKVSCKAFGGTSNNYGVTWVRQAPGQGLQWMGGIIPIFGTTNYAQKFLGRVTITADKSTRTAYMELSSLRSEDTAVYYCASQGSSTWFATLYAFPIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK(G)QPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 109 | Bv6.172 CDR-H1 | NYWIT |
| 110 | Bv6.172 CDR-H2 | RIDTRDSYTNYSPSFQG |
| 111 | Bv6.172 CDR-H3 | LSTTYPLNYYGMDV |
| 112 | Bv6.172 CDR-L1 | TGSSSNIGANYDVN |
| 113 | Bv6.172-CDR-L2 | GNTNRPS |

-continued

| SEQ ID NO | Description | Sequence |
|---|---|---|
| | SEQUENCES Amino acids shown in parentheses in the below table can be present or absent. | |
| 114 | Bv6.172 CDR-L3 | QSYDTSLSGWV |
| 115 | Bv6.172 H-FW1 | EVQLVQSGAAVRKPGESLRISCQASGFSFT |
| 116 | Bv6.172 H-FW2 | WVRQRPGKGLEWMG |
| 117 | Bv6.172 H-FW3 | HVTISIDRSINTAYLQWSSLKASDTAMYYCAR |
| 118 | Bv6.172 H-FW4 | WGQGTTVTVSS |
| 119 | Bv6.172 L-FW1 | QSVLTQPPSVSGTPGQRVTISC |
| 120 | Bv6.172 L-FW2 | WYQQLPGTAPKVLIY |
| 121 | Bv6.172 L-FW3 | GVPDRFSGSKSGTSASLAITGLQAEDEADYYC |
| 122 | Bv6.172 L-FW4 | FGGGTKLTVL |
| 123 | Bv6.172 VL | QSVLTQPPSVSGTPGQRVTISCTGSSSNIGANYDVNWYQQLPGTAPKVLIYGNTNRPSGVPDRFSGSKSGTSASLA ITGLQAEDEADYYCQSYDTSLSGWVFGGGTKLTVL |
| 124 | Bv6.172 VH | EVQLVQSGAAVRKPGESLRISCQASGFSFTNYWITWVRQRPGKGLEWMGRIDTRDSYTNYSPSFQGHVTISIDRSI NTAYLQWSSLKASDTAMYYCARLSTTYPLNYYGMDVWGQGTTVTVSS |
| 125 | Bv6.172 full length light chain | QSVLTQPPSVSGTPGQRVTISCTGSSSNIGANYDVNWYQQLPGTAPKVLIYGNTNRPSGVPDRFSGSKSGTSASLA ITGLQAEDEADYYCQSYDTSLSGWVFGGGTKLTVLGQPKAAPSVTLFPPSSEELQANKATLVCLISDFYPGAVTVA WKADSSPVKAGVETTTPSKQSNNKYAASSYLSLTPEQWKSHRSYSCQVTHEGSTVEKTVAPTECS |
| 126 | Bv6.172 full length heavy chain | EVQLVQSGAAVRKPGESLRISCQASGFSFTNYWITWVRQRPGKGLEWMGRIDTRDSYTNYSPSFQGHVTISIDRSI NTAYLQWSSLKASDTAMYYCARLSTTYPLNYYGMDVWGQGTTVTVSSASTKGPSVFPLAPSSKSTSGGTAALGCLV KDYFPEPVTVSWNSGALTSGVHTFPAVLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAK(G)QPREPQVYTLPPSRDELTKNQVSLTCLVKGF YPSDIAVEWESNGQPENNYKTTPPVLDSDGSFFLYSKLTVDKSRWQQGNVFSCSVMHEALHNHYTQKSLSLSPGK |
| 127 | Bv4.115 CDR-H1 | NYHIH |
| 128 | Bv4.115 CDR-H2 | IINPRRLSTAYAPKFQG |
| 129 | Bv4.115 CDR-H3 | DAGDDTSGPFDS |
| 130 | Bv4.115 CDR-L1 | RASQSINTWLA |
| 131 | Bv4.115-CDR-L2 | KASSLES |
| 132 | Bv4.115 CDR-L3 | QQYNTFS |
| 133 | Bv4.115 H-FW1 | QVQLVQSGAEVKKPGSSVKVSCRSSGYRFT |
| 134 | Bv4.115 H-FW2 | WVRQAPGQGLEWVG |
| 135 | Bv4.115 H-FW3 | RVTMTRDTSTSTVYMELSSLRSDDTAVYYCAR |
| 136 | Bv4.115 H-FW4 | WGQGTLVTVSS |
| 137 | Bv4.115 L-FW1 | DIQMTQSPSTLSASVGDRVTITC |
| 138 | Bv4.115 L-FW2 | WYQQKPGKAPKLLIS |
| 139 | Bv4.115 L-FW3 | GVPSRFSGSGSGTEFTLSISSLQPDDFATYYC |
| 140 | Bv4.115 L-FW4 | FGQGTKLEIK |
| 141 | Bv4.115 VL | DIQMTQSPSTLSASVGDRVTITCRASQSINTWLAWYQQKPGKAPKLLISKASSLESGVPSRFSGSGSGTEFTLSIS SLQPDDFATYYCQQYNTFSFGQGTKLEIK |
| 142 | Bv4.115 VH | QVQLVQSGAEVKKPGSSVKVSCRSSGYRFTNYHIHWVRQAPGQGLEWVGIINPRRLSTAYAPKFQGRVTMTRDTST STVYMELSSLRSDDTAVYYCARDAGDDTSGPFDSWGQGTLVTVSS |

-continued

SEQUENCES
Amino acids shown in parentheses in the below table can be present or absent.

| SEQ ID NO | Description | Sequence |
|---|---|---|
| 143 | Bv4.115 full length light chain | DIQMTQSPSTLSASVGDRVTITCRASQSINTWLAWYQQKPGKAPKLLISKASSLESGVPSRFSGSGSGTEFTLSIS SLQPDDFATYYCQQYNTFSFGQGTKLEIKRTVAAPSVFIFPPSDEQLKSGTASVVCLLNNFYPREAKVQWKVDNAL QSGNSQESVTEQDSKDSTYSLSSTLILSKADYEKHKVYACEVTHQGLSSPVTKSFNRGEC |
| 144 | Bv4.115 full length heavy chain | QVQLVQSGAEVKKPGSSVKVSCRSSGYRFTNYHIHWVRQAPGQGLEWVGIINPRRLSTAYAPKFQGRVTMTRDTST STVYMELSSLRSDDTAVYYCARDAGDDTSGPFDSWGQGTLVTVSSASTKGPSVFPLAPSSKSTSGGTAALGCLVKD YFPEPVTVSWNSGALTSGVHTFPAVLQSSGLYSLSSVVTVPSSSLGTQTYICNVNHKPSNTKVDKKVEPKSCDKTH TCPPCPAPELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAK(G)QPREPQVYTLPPSRDELTKNQVSLTCLVKGFYP SDIAVEWESNGQPENNYKTTPPVLDSDGSFFLYSKLTVDKSRWQQGNVFSCSVMHEALHNHYTQKSLSLSPGK |
| 145 | Bc1.229 CDR-H1 | NYGMH |
| 146 | Bc1.229 CDR-H2 | VIWNDGSNKYYADSVKG |
| 147 | Bc1.229 CDR-H3 | EGLTSVTMLDS |
| 148 | Bc1.229 CDR-L1 | RASQYISSFLN |
| 149 | Bc1.229-CDR-L2 | VASSLQS |
| 150 | Bc1.229 CDR-L3 | QQSYSTPLFT |
| 151 | Bc1.229 H-FW1 | QVQLVESGGGVVQPGRSLRVSCAASGFTFS |
| 152 | Bc1.229 H-FW2 | WVRQAPGKGLEWLA |
| 153 | Bc1.229 H-FW3 | RFIISRDNSKNTLYLQMNSLGAEDTAMYYCAR |
| 154 | Bc1.229 H-FW4 | WGQGALVTVSS |
| 155 | Bc1.229 L-FW1 | DIQMTQSPSSLSASVGDRVTITC |
| 156 | Bc1.229 L-FW2 | WYQQKPGKAPKLLIH |
| 157 | Bc1.229 L-FW3 | GVPSRFSGSGSGTHFTLTISSLQPEDFATYYC |
| 158 | Bc1.229 L-FW4 | FGPGTKVDIK |
| 159 | Bc1.229 VL | DIQMTQSPSSLSASVGDRVTITCRASQYISSFLNWYQQKPGKAPKLLIHVASSLQSGVPSRFSGSGSGTHFTLTIS SLQPEDFATYYCQQSYSTPLFTFGPGTKVDIK |
| 160 | Bc1.229 VH | QVQLVESGGGVVQPGRSLRVSCAASGFTFSNYGMHWVRQAPGKGLEWLAVIWNDGSNKYYADSVKGRFIISRDNSK NTLYLQMNSLGAEDTAMYYCAREGLTSVTMLDSWGQGALVTVSS |
| 161 | Bc1.229 full length light chain | DIQMTQSPSSLSASVGDRVTITCRASQYISSFLNWYQQKPGKAPKLLIHVASSLQSGVPSRFSGSGSGTHFTLTIS SLQPEDFATYYCQQSYSTPLFTFGPGTKVDIKRTVAAPSVFIFPPSDEQLKSGTASVVCLLNNFYPREAKVQWKVD NALQSGNSQESVTEQDSKDSTYSLSSTLTLSKADYEKHKVYACEVTHQGLSSPVTKSFNRGEC |
| 162 | Bc1.229 full length heavy chain | QVQLVESGGGVVQPGRSLRVSCAASGFTFSNYGMHWVRQAPGKGLEWLAVIWNDGSNKYYADSVKGRFIISRDNSK NTLYLQMNSLGAEDTAMYYCAREGLTSVTMLDSWGQGALVTVSSASTKGPSVFPLAPSSKSTSGGTAALGCLVKDY FPEPVTVSWNSGALTSGVHTFPAVLQSSGLYSLSSVVTVPSSSLGTQTYICNVNHKPSNTKVDKKVEPKSCDKTHT CPPCPAPELLGGPSVFLFPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAK(G)QPREPQVYTLPPSRDELTKNQVSLTCLVKGFYPS DIAVEWESNGQPENNYKTTPPVLDSDGSFFLYSKLTVDKSRWQQGNVFSCSVMHEALHNHYTQKSLSLSPGK |
| 163 | Bc8.159 CDR-H1 | TNNWWS |
| 164 | Bc8.159 CDR-H2 | EIHHIGSTNYNPSLKS |
| 165 | Bc8.159 CDR-H3 | GRLGITRDRYYFDS |
| 166 | Bc8.159 CDR-L1 | QASQDISNYLN |
| 167 | Bc8.159-CDR-L2 | DTSSLER |
| 168 | Bc8.159 CDR-L3 | QQYYNLPHT |
| 169 | Bc8.159 H-FW1 | QVQLQESGPGLVKPSGTLSLTCAVSGGTIR |
| 170 | Bc8.159 H-FW2 | WVRQPPGKGLEWIG |

-continued

SEQUENCES
Amino acids shown in parentheses in the below table can be present or absent.

| SEQ ID NO | Description | Sequence |
|---|---|---|
| 171 | Bc8.159 H-FW3 | QVTISVDKSKNQFSLNLSSVTAADTALYYCVR |
| 172 | Bc8.159 H-FW4 | WGRGTLVTVSS |
| 173 | Bc8.159 L-FW1 | DIQMTQSPSPLSVSVGDRVTITC |
| 174 | Bc8.159 L-FW2 | WYQQKPGQAPKLLIY |
| 175 | Bc8.159 L-FW3 | GVPSRFSGSGSGTDFTLTISSLQPEDIATYHC |
| 176 | Bc8.159 L-FW4 | FGQGTKLEIK |
| 177 | Bc8.159 VL | DIQMTQSPSPLSVSVGDRVTITCQASQDISNYLNWYQQKPGQAPKLLIYDTSSLERGVPSRFSGSGSGTDFTLTIS SLQPEDIATYHCQQYYNLPHTFGQGTKLEIK |
| 178 | Bc8.159 VH | QVQLQESGPGLVKPSGTLSLTCAVSGGTIRTNNWWSWVRQPPGKGLEWIGEIHHIGSTNYNPSLKSQVTISVDKSK NQFSLNLSSVTAADTALYYCVRGRLGITRDRYYFDSWGRGTLVTVSS |
| 179 | Bc8.159 full length light chain | DIQMTQSPSPLSVSVGDRVTITCQASQDISNYLNWYQQKPGQAPKLLIYDTSSLERGVPSRFSGSGSGTDFTLTIS SLQPEDIATYHCQQYYNLPHTFGQGTKLEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSPVTKSFNRGEC |
| 180 | Bc8.159 full length heavy chain | QVQLQESGPGLVKPSGTLSLTCAVSGGTIRTNNWWSWVRQPPGKGLEWIGEIHHIGSTNYNPSLKSQVTISVDKSK NQFSLNLSSVTAADTALYYCVRGRLGITRDRYYFDSWGRGTLVTVSSASTKGPSVFPLAPSSKSTSGGTAALGCLV KDYFPEPVTVSWNSGALTSGVHTFPAVLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAK(G)QPREPQVYTLPPSRDELTKNQVSLTCLVKGF YPSDIAVEWESNGQPENNYKTTPPVLDSDGSFFLYSKLTVDKSRWQQGNVFSCSVMHEALHNHYTQKSLSLSPGK |
| 181 | Bc1.128 CDR-H1 | NYGMH |
| 182 | Bc1.128 CDR-H2 | FTIYDGSHKYYADSVKG |
| 183 | Bc1.128 CDR-H3 | DSNGFGVLS |
| 184 | Bc1.128 CDR-L1 | RASQGIRSDLG |
| 185 | Bc1.128-CDR-L2 | GASNLQR |
| 186 | Bc1.128 CDR-L3 | LQHNSFPWT |
| 187 | Bc1.128 H-FW1 | EVQLVESGGGVVQPGRSLRLSCAASGFIFS |
| 188 | Bc1.128 H-FW2 | WVRQAPGKGLEWVA |
| 189 | Bc1.128 H-FW3 | RFTISRDNSKNTLYLQMNSLRYEDTAVYYCAT |
| 190 | Bc1.128 H-FW4 | WGQGTLVTVSS |
| 191 | Bc1.128 L-FW1 | DIQLTQSPSSLSASVGDRVTITC |
| 192 | Bc1.128 L-FW2 | WYQQKPGKAPKRLIY |
| 193 | Bc1.128 L-FW3 | GVPSRFSGSGSGTEFTLTISSLQPEDFASYYC |
| 194 | Bc1.128 L-FW4 | FGQGTKVEIK |
| 195 | Bc1.128 VL | DIQLTQSPSSLSASVGDRVTITCRASQGIRSDLGWYQQKPGKAPKRLIYGASNLQRGVPSRFSGSGSGTEFTLTIS SLQPEDFASYYCLQHNSFPWTFGQGTKVEIK |
| 196 | Bc1.128 VH | EVQLVESGGGVVQPGRSLRLSCAASGFIFSNYGMHWVRQAPGKGLEWVAFTIYDGSHKYYADSVKGRFTISRDNSK NTLYLQMNSLRYEDTAVYYCATDSNGFGVLSWGQGTLVTVSS |
| 197 | Bc1.128 full length light chain | DIQLTQSPSSLSASVGDRVTITCRASQGIRSDLGWYQQKPGKAPKRLIYGASNLQRGVPSRFSGSGSGTEFTLTIS SLQPEDFASYYCLQHNSFPWTFGQGTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSPVTKSFNRGEC |

-continued

SEQUENCES
Amino acids shown in parentheses in the below table can be present or absent.

| SEQ ID NO | Description | Sequence |
|---|---|---|
| 198 | Bc1.128 full length heavy chain | EVQLVESGGGVVQPGRSLRLSCAASGFIFSNYGMHWVRQAPGKGLEWVAFTIYDGSHKYYADSVKGRFTISRDNSKNTLYLQMNSLRYEDTAVYYCATDSNGFGVLSWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK(G)QPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 199 | Bc4.204 CDR-H1 | SYGMN |
| 200 | Bc4.204 CDR-H2 | IIWFDGSQTYYGDSVKG |
| 201 | Bc4.204 CDR-H3 | GGAEESTNWRFLWVPRYYYYMDV |
| 202 | Bc4.204 CDR-L1 | IGTNSDFGRYDYVS |
| 203 | Bc4.204-CDR-L2 | DVSQRPS |
| 204 | Bc4.204 CDR-L3 | CSYAGSFNLV |
| 205 | Bc4.204 H-FW1 | QVQLVESGGGVVQPGRSLRLSCTASGFAFN |
| 206 | Bc4.204 H-FW2 | WVRQAPGKGLEWVA |
| 207 | Bc4.204 H-FW3 | RFTISRDRSTNTLFLQMNNLRADDTAMYYCAR |
| 208 | Bc4.204 H-FW4 | WGKGTTVTVSS |
| 209 | Bc4.204 L-FW1 | QSALTQPRSVSGSPGQSVTISC |
| 210 | Bc4.204 L-FW2 | WYQQHPDKAPKLLIY |
| 211 | Bc4.204 L-FW3 | GVPDRFSGSKSGYTASLIISGLQADDEAEYFC |
| 212 | Bc4.204 L-FW4 | FGGGTKVTVL |
| 213 | Bc4.204 VL | QSALTQPRSVSGSPGQSVTISCIGTNSDFGRYDYVSWYQQHPDKAPKLLIYDVSQRPSGVPDRFSGSKSGYTASLIISGLQADDEAEYFCCSYAGSFNLVFGGGTKVTVL |
| 214 | Bc4.204 VH | QVQLVESGGGVVQPGRSLRLSCTASGFAFNSYGMNWVRQAPGKGLEWVAIIWFDGSQTYYGDSVKGRFTISRDRSTNTLFLQMNNLRADDTAMYYCARGGAEESTNWRFLWVPRYYYYMDVWGKGTTVTVSS |
| 215 | Bc4.204 full length light chain | QSALTQPRSVSGSPGQSVTISCIGTNSDFGRYDYVSWYQQHPDKAPKLLIYDVSQRPSGVPDRFSGSKSGYTASLIISGLQADDEAEYFCCSYAGSFNLVFGGGTKVTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| 216 | Bc4.204 full length heavy chain | QVQLVESGGGVVQPGRSLRLSCTASGFAFNSYGMNWVRQAPGKGLEWVAIIWFDGSQTYYGDSVKGRFTISRDRSTNTLFLQMNNLRADDTAMYYCARGGAEESTNWRFLWVPRYYYYMDVWGKGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK(G)QPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 217 | Bc1.263 CDR-H1 | NYGVN |
| 218 | Bc1.263 CDR-H2 | KIIPILGIVNYAQKFQG |
| 219 | Bc1.263 CDR-H3 | DRGGKPLYSYGYGLDY |
| 220 | Bc1.263 CDR-L1 | RASLSVSTYLA |
| 221 | Bc1.263-CDR-L2 | DASKRAT |
| 222 | Bc1.263 CDR-L3 | QQRSTT |
| 223 | Bc1.263 H-FW1 | QVQLVQSGAEVKKPGSSVKVSCRASGGTFS |
| 224 | Bc1.263 H-FW2 | WVRQAPGQGLEWMG |
| 225 | Bc1.263 H-FW3 | RVTITADKSTSTAYMELSSLRSEDTAVYYCAR |

-continued

SEQUENCES
Amino acids shown in parentheses in the below table can be present or absent.

| SEQ ID NO | Description | Sequence |
|---|---|---|
| 226 | Bc1.263 H-FW4 | WGQGTLVTVSS |
| 227 | Bc1.263 L-FW1 | EIVLTQSPATLSLSPGERATLSC |
| 228 | Bc1.263 L-FW2 | WYQKKPGQPPRLLIY |
| 229 | Bc1.263 L-FW3 | GIPARFSGSGSGTDFTLTISSLEPEDFAVYYC |
| 230 | Bc1.263 L-FW4 | FGQGTKVEIK |
| 231 | Bc1.263 VL | EIVLTQSPATLSLSPGERATLSCRASLSVSTYLAWYQKKPGQPPRLLIYDASKRATGIPARFSGSGSGTDFTLTIS SLEPEDFAVYYCQQRSTTFGQGTKVEIK |
| 232 | Bc1.263 VH | QVQLVQSGAEVKKPGSSVKVSCRASGGTFSNYGVNWVRQAPGQGLEWMGKIIPILGIVNYAQKFQGRVTITADKST STAYMELSSLRSEDTAVYYCARDRGGKPLYSYGYGLDYWGQGTLVTVSS |
| 233 | Bc1.263 full length light chain | EIVLTQSPATLSLSPGERATLSCRASLSVSTYLAWYQKKPGQPPRLLIYDASKRATGIPARFSGSGSGTDFTLTIS SLEPEDFAVYYCQQRSTTFGQGTKVEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFNRGEC |
| 234 | Bc1.263 full length heavy chain | QVQLVQSGAEVKKPGSSVKVSCRASGGTFSNYGVNWVRQAPGQGLEWMGKIIPILGIVNYAQKFQGRVTITADKST STAYMELSSLRSEDTAVYYCARDRGGKPLYSYGYGLDYWGQGTLVTVSSASTKGPSVFPLAPSSKSTSGGTAALGC LVKDYFPEPVTVSWNSGALTSGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAK(G)QPREPQVYTLPPSRDELTKNQVSLTCLVK GFYPSDIAVEWESNGQPENNYKTTPPVLDSDGSFFLYSKLTVDKSRWQQGNVFSCSVMHEALHNHYTQKSLSLSPG K |
| 235 | Bv4.105 CDR-H1 | DYPIM |
| 236 | Bv4.105 CDR-H2 | FIRSKAYGGTAEYAASVKG |
| 237 | Bv4.105 CDR-H3 | EGGHSGFWSGFNKIPTFDY |
| 238 | Bv4.105 CDR-L1 | RASETIRTYLN |
| 239 | Bv4.105-CDR-L2 | AASSVQS |
| 240 | Bv4.105 CDR-L3 | QQSYTSPWVT |
| 24 | Bv4.105 H-FW1 | QVQLVESGGGLVQSGRSLRLSCSAFGFTFG |
| 242 | Bv4.105 H-FW2 | WVRLAPGKGLEWVG |
| 243 | Bv4.105 H-FW3 | RFTTSRDDSRSTAYLQMNSLKTEDTAVYYCTR |
| 244 | Bv4.105 H-FW4 | WGQGSLVTVSS |
| 245 | Bv4.105 L-FW1 | DIQMTQSPSSLSASIGDRVSITC |
| 246 | Bv4.105 L-FW2 | WYQHKPGKAPQLLIY |
| 247 | Bv4.105 L-FW3 | GVPSRFSGSGSGTDFTLTISNLQPEDFATYYC |
| 248 | Bv4.105 L-FW4 | FGPGTKVDIK |
| 249 | Bv4.105 VL | DIQMTQSPSSLSASIGDRVSITCRASETIRTYLNWYQHKPGKAPQLLIYAASSVQSGVPSRFSGSGSGTDFTLTIS NLQPEDFATYYCQQSYTSPWVTFGPGTKVDIK |
| 250 | Bv4.105 VH | QVQLVESGGGLVQSGRSLRLSCSAFGFTFGDYPIMWVRLAPGKGLEWVGFIRSKAYGGTAEYAASVKGRFTTSRDD SRSTAYLQMNSLKTEDTAVYYCTREGGHSGFWSGENKIPTFDYWGQGSLVTVSS |
| 251 | Bv4.105 full length light chain | DIQMTQSPSSLSASIGDRVSITCRASETIRTYLNWYQHKPGKAPQLLIYAASSVQSGVPSRFSGSGSGTDFTLTIS NLQPEDFATYYCQQSYTSPWVTFGPGTKVDIKRTVAAPSVFIFPPSDEQLKSGTASVVCLLNNFYPREAKVQWKVD NALQSGNSQESVTEQDSKDSTYSLSSTLTLSKADYEKHKVYACEVTHQGLSSPVTKSFNRGEC |
| 252 | Bv4.105 full length heavy chain | QVQLVESGGGLVQSGRSLRLSCSAFGFTFGDYPIMWVRLAPGKGLEWVGFIRSKAYGGTAEYAASVKGRFTTSRDD SRSTAYLQMNSLKTEDTAVYYCTREGGHSGFWSGFNKIPTFDYWGQGSLVTVSSASTKGPSVFPLAPSSKSTSGGT AALGCLVKDYFPEPVTVSWNSGALTSGVHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVVDVSHEDPEVKFNWYVDGVEVHNAKTKP |

-continued

SEQUENCES
Amino acids shown in parentheses in the below table can be present or absent.

| SEQ ID NO | Description | Sequence |
|---|---|---|
| | | REEQYNSTYRVVSVLTVLHQDWLNGKEYKCKVSNKALPAPIEKTISKAK(G)QPREPQVYTLPPSRDELTKNQVSL TCLVKGFYPSDIAVEWESNGQPENNYKTTPPVLDSDGSFFLYSKLTVDKSRWQQGNVFSCSVMHEALHNHYTQKSL SLSPGK |
| 253 | S-SHBs Genbank AAA45488.1 | MENITSGFLGPLLVLQAGFFLLTRILTIPQSLDSWWTSLNFLGGTTVCLGQNSQSPTSNH SPTSCPPTCPGYRWMCLRRFIIFLFILLLCLIFLLVLLDYQGMLPVCPLIPGSSTTSTGP CRTCMTTAQGTSMYPSCCCTKPSDGNCTCIPIPSSWAFGKFLWEWASARFSWLSLLVPFV QWFVGLSPTVWLSVIWMMWYWGPSLYSILSPFLPLLPIFFCLWVYI |
| 254 | ConsHBAg_A | MENITSGFLGPLLVLQAGFFLLTRILTIPQSLDSWWTSLNFLGGSPVCLGQNSQSPTSNHSPTSCPPI CPGYRWMCLRRFIIFLFILLLCLIFLLVLLDYQGMLPVCPLIPGSTTTSTGPCKTCTTPAQGNSMFPSCCCTKP TDGNCTCIPIPSSWAFAKYLWEWASVRFSWLSLLVPFVQWFVGLSPTVWLSAIWMMWYWGPSL YSIVSPFIPLLPIFFCLWVYI |
| 255 | ConsHBAg_B | MENIASGLLGPLLVLQAGFFLLTKILTIPQSLDSWWTSLNFLGGTPVCLGQNSQSQISSHSPTCCPPICPGYR WMCLRRFIIFLCILLLCLIFLLVLLDYQGMLPVCPLIPGSSTTSTGPCKTCTTPAQGTSMFPSCCCTKPTDGNC TCIPIPSSWAFAKYLWEWASVRFSWLSLLVPFVQWFVGLSPTVWLSVIWMMWFWGPSLYNILSPFMPLLPI FFCLWVYI |
| 256 | ConsHBAg_C | MENTTSGFLGPLLVLQAGFFLLTRILTIPQSLDSWWTSLNFLGGAPTCPGQNSQSPTSNHSPT SCPPICPGYRWMCLRRFIIFLFILLLCLIFLLVLLDYQGMLPVCPLLPGTSTTSTGPCKTCTIPAQGT SMFPSCCCTKPSDGNCTCIPIPSSWAFARFLWEWASVRFSWLSLLVPFVQWFVGLSPTVWLSVI WMMWYWGPSLYNILSPFLPLLPIFFCLWVYI |
| 257 | ConsHBAg_D | MENITSGFLGPLLVLQAGFFLLTRILTIPQSLDSWWTSLNFLGGTTVCLGQNSQSPTSNHSPTSCPPT CPGYRWMCLRRFIIFLFILLLCLIFLLVLLDYQGMLPVCPLIPGSSTTSTGPCRTCTTTAQGTSMYP SCCCTKPSDGNCTCIPIPSSWAFGKFLWEWASARFSWLSLLVPFVQWFVGLSPTVWLSVIWMMWYWGPSL YSILSPFLPLLPIFFCLWVYI |
| 258 | ConsHBAg_E | MESITSGFLGPLLVLQAGFFLLTKILTIPQSLDSWWTSLNFLGGAPVCLGQNSQSPTSNHSPTSCPPICPGYRW MCLRRFIIFLFILLLCLIFLLVLLDYQGMLPVCPLIPGSSTTSTGPCRTCTTLAQGTSMFPSCCCSKPSDGNCTC IPIPSSWAFGKFLWEWASARFSWLSLLVPFVQWFAGLSPTVWLSVIWMMWYWGPSLYNILSPFIPLLPIFFC LWVYI |
| 259 | ConsHBAg_F | MDNITSGLLGPLLVLQAVCFLLTKILTIPQSLDSWWTSLNFLGGLPGCPGQNSQSPTSNHLPTSCPPTCPGYR WMCLRRFIIFLFILLLCLIFLLVLLDYQGMLPVCPLLPGSTTTSTGPCKTCTTLAQGTSMFPSCCCSKPSDGNC TCIPIPSSWALGKYLWEWASARFSWLSLLVQFVQWCVGLSPTVWLLVIWMIWYWGPNLCSILSPFIPLLPIF CYLWVSI |
| 260 | ConsHBAg_G | MENITSGFLGPLLVLQAGFFLLTRILTIPQSLDSWWTSLNFLGGVPVCPGLNSQSPTSNHSPISCPPTCPGYRW MCLRRFIIFLFILLLCLIFLLVLLDYQGMLPVCPLIPGSSTTSTGPCKTCTTPAQGNSMYPSCCCTKPSDGNCT CIPIPSSWAFAKYLWEWASVRFSWLSLLVPFVQWFVGLSPTVWLSAIWMMWYWGPNLYNILSPFIPLLPIFF CLWVYI |
| 261 | ConsHBAg_H | MENITSGLLGPLLVLQAVCFLLTKILTIPQSLDSWWTSLNFLGVPPGCPGQNSQSPISNHLPTSCPPTCPGYR WMCLRRFIIFLFILLLCLIFLLVLLDYQGMLPVCPLLPGSTTTSTGPCKTCTTLAQGTSMFPSCCCTKPSDGNC TCIPIPSSWAFGKYLWEWASARFSWLSLLVQFVQWCVGLSPTVWLLVIWMIWYWGPNLCSILSPFIPLLPIF CYLWASI |
| 262 | ConsHBAg_I | MENITSGFLGPLLVLQAGFFLLTKILTIPQSLDSWWTSLNFLGGAPVCLGQNSQSPTSNHSPTSCPPICPGYR WMCLRRFIIFLFILLLCLIFLLVLLDYQGMLPVCPLIPGSSTTSTGPCKTCTTPAQGNSMYPSCCCTKPTDGNC TCIPIPSSWAFAKYLWEWASARFSWLSLLVPFVQWFVGLSPTVWLSVI WMMWYWGPSLYNILSPFIPLLPIFFCLWVYI |
| 263 | Bc1.187 full length heavy chain | QVQLVESGGGVVQPGRSLRLSCEASGFTFSNYGMQWVRQAPGKGLEWVAIIWADGTKQYYGDSVKGRFT ISRDNFKNTLYLQMNSLRGEDTAMYFCARDGLYASAPNDVWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPSNT KVDKRVEPKSCDKTHTCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSDGSFFLYSKLTVDKSRWQQGN VFSCSVMHEALHNHYTQKSLSLSPGK |
| 264 | Bc1.180 full length heavy chain | QVQLVQSGAEVKKPGSSVKVSCKASGGTFGRSAVSWVRHAPGQRLEWMGRTIPLLRIAEYSQTFQGRVTIT ADKFTNTVYMELRSLTYEDTAVYYCAREGDGLDMWGQGTMVTVSSASTKGPSVFPLAPSSKSTSGGTAA LGCLVKDYFPEPVTVSWNSGALTSGVHTFPAVLQSSGLYSLSSVVTVPSSSLGTQTYICNVNHKPSNTKVD KRVEPKSCDKTHTCPPCPAPELLGGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFFLYSKLTVDKSRWQQGNVFS CSVMHEALHNHYTQKSLSLSPGK |

-continued

SEQUENCES
Amino acids shown in parentheses in the below table can be present or absent.

| SEQ ID NO | Description | Sequence |
|---|---|---|
| 265 | Bc3.106 full length heavy chain | EVQLLESGGGLVQPGGSLRLSCTASGFTFGSYAMSWVRQAPGKGLKWVSAFSGTGGSTYYADSVKGRFTI SRDNSKNTLYLQMNNLRAEDTAVYFCAKDPGHTSNWRDNYQYYQMDVWGQGTTVTVSSASTKGPSVFP LAPSSKSTSGGTAALGCLVKDYFPEPVTVSWNSGALTSGVHTFPAVLQSSGLYSLSSVVTVPSSSLGTQTYI CNVNHKPSNTKVDKRVEPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAK GQPREPQVYTLPPSREEMTKNQVSLTCLVKGFYPSDIAVEWESNGQPENNYKTTPPVLDSDGSFFLYSKLTV DKSRWQQGNVFSCSVMHEALHNHYTQKSLSLSPGK |
| 266 | Bv4.104 full length heavy chain | QVQLVESGGGVVQPGRSLRLSCAASGFTFSGYGMHWVRQAPGKGLEWVAFLWHDGTSKDYADSVKGRF TISRDNSKNTLYMQMNSLRAEDTAVYYCAREDYYDSNAFDYWGQGTLVTVSSASTKGPSVFPLAPSSKST SGGTAALGCLVKDYFPEPVTVSWNSGALTSGVHTFPAVLQSSGLYSLSSVVTVPSSSLGTQTYICNVNHKPS NTKVDKRVEPKSCDKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFFLYSKLTVDKSRWQQ GNVFSCSVMHEALHNHYTQKSLSLSPGK |
| 267 | Bc8.111 full length heavy chain | EVQLVESGGGLVQPGGSLRLSCAASGFTFSRYAMSWVRQAPGKGLEWVSATSGSGADTYYADSVKGRFTI SRDNSKNTVYLQMNSLRADDTAFYYCAKDPYMVAAVARTVDYWGQGTLVTVSSASTKGPSVFPLAPSSK STSGGTAALGCLVKDYFPEPVTVSWNSGALTSGVHTFPAVLQSSGLYSLSSVVTVPSSSLGTQTYICNVNHK PSNTKVDKRVEPKSCDKTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEKTISKAKGQPREPQ VYTLPPSREEMTKNQVSLTCLVKGFYPSDIAVEWESNGQPENNYKTTPPVLDSDGSFFLYSKLTVDKSRWQ QGNVFSCSVMHEALHNHYTQKSLSLSPGK |
| 268 | Bc8.104 full length heavy chain | QVQLVQSGAEVKKAGSSVKVSCKAFGGTSNNYGVTWVRQAPGQGLQWMGGIIPIFGTTNYAQKFLGRVTI TADKSTRTAYMELSSLRSEDTAVYYCASQGSSTWFATLYAFPIWGQGTMVTVSSASTKGPSVFPLAPSSKS TSGGTAALGCLVKDYFPEPVTVSWNSGALTSGVHTFPAVLQSSGLYSLSSVVTVPSSSLGTQTYICNVNHKP SNTKVDKRVEPKSCDKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFFLYSKLTVDKSRWQQ GNVFSCSVMHEALHNHYTQKSLSLSPGK |
| 269 | Bv6.172 full length heavy chain | EVQLVQSGAAVRKPGESLRISCQASGFSFTNYWITWVRQRPGKGLEWMGRIDTRDSYTNYSPSFQGHVTISI DRSINTAYLQWSSLKASDTAMYYCARLSTTYPLNYYGMDVWGQGTTVTVSSASTKGPSVFPLAPSSKSTS GGTAALGCLVKDYFPEPVTVSWNSGALTSGVHTFPAVLQSSGLYSLSSVVTVPSSSLGTQTYICNVNHKPS NTKVDKRVEPKSCDKTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFFLYSKLTVDKSRWQQ GNVFSCSVMHEALHNHYTQKSLSLSPGK |
| 270 | Bv4.115 full length heavy chain | QVQLVQSGAEVKKPGSSVKVSCRSSGYRFTNYHIHWVRQAPGQGLEWVGIINPRRLSTAYAPKFQGRVTM TRDTSTSTVYMELSSLRSDDTAVYYCARDAGDDTSGPFDSWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPSNT KVDKRVEPKSCDKTHTCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSDGSFFLYSKLTVDKSRWQQGN VFSCSVMHEALHNHYTQKSLSLSPGK |
| 271 | Bc1.229 full length heavy chain | QVQLVESGGGVVQPGRSLRVSCAASGFTFSNYGMHWVRQAPGKGLEWLAVIWNDGSNKYYADSVKGRFI ISRDNSKNTLYLQMNSLGAEDTAMYYCAREGLTSVTMLDSWGQGALVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPSNT KVDKRVEPKSCDKTHTCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSDGSFFLYSKLTVDKSRWQQGN VFSCSVMHEALHNHYTQKSLSLSPGK |
| 272 | Bc8.159 full length heavy chain | QVQLQESGPGLVKPSGTLSLTCAVSGGTIRTNNWWSWVRQPPGKGLEWIGEIHHIGSTNYNPSLKSQVTISV DKSKNQFSLNLSSVTAADTALYYCVRGRLGITRDRYYFDSWGRGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPSNT KVDKRVEPKSCDKTHTCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSDGSFFLYSKLTVDKSRWQQGN VFSCSVMHEALHNHYTQKSLSLSPGK |
| 273 | Bc1.128 full length heavy chain | EVQLVESGGGVVQPGRSLRLSCAASGFIFSNYGMHWVRQAPGKGLEWVAFTIYDGSHKYYADSVKGRFTI SRDNSKNTLYLQMNSLRYEDTAVYYCATDSNGFGVLSWGQGTLVTVSSASTKGPSVFPLAPSSKSTSGGTA ALGCLVKDYFPEPVTVSWNSGALTSGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKAKGQPREPQVYTLP PSREEMTKNQVSLTCLVKGFYPSDIAVEWESNGQPENNYKTTPPVLDSDGSFFLYSKLTVDKSRWQQGNVF SCSVMHEALHNHYTQKSLSLSPGK |

-continued

SEQUENCES
Amino acids shown in parentheses in the below table can be present or absent.

| SEQ ID NO | Description | Sequence |
|---|---|---|
| 274 | Bc4.204 full length heavy chain | QVQLVESGGGVVQPGRSLRLSCTASGFAFNSYGMNWVRQAPGKGLEWVAIIWFDGSQTYYGDSVKGRFTI<br>SRDRSTNTLFLQMNNLRADDTAMYYCARGGAEESTNWRFLWVPRYYYYMDVWGKGTTVTVSSASTKGP<br>SVFPLAPSSKSTSGGTAALGCLVKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWLNGKEYKCKVSNKALPAPIEKTI<br>SKAKGQPREPQVYTLPPSREEMTKNQVSLTCLVKGFYPSDIAVEWESNGQPENNYKTTPPVLDSDGSFFLY<br>SKLTVDKSRWQQGNVFSCSVMHEALHNHYTQKSLSLSPGK |
| 275 | Bc1.263 full length heavy chain | QVQLVQSGAEVKKPGSSVKVSCRASGGTFSNYGVNWVRQAPGQGLEWMGKIIPILGIVNYAQKFQGRVTI<br>TADKSTSTAYMELSSLRSEDTAVYYCARDRGGKPLYSYGYGLDYWGQGTLVTVSSASTKGPSVFPLAPSS<br>KSTSGGTAALGCLVKDYFPEPVTVSWNSGALTSGVHTFPAVLQSSGLYSLSSVVTVPSSSLGTQTYICNVNH<br>KPSNTKVDKRVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIEKTISKAKGQPRE<br>PQVYTLPPSREEMTKNQVSLTCLVKGFYPSDIAVEWESNGQPENNYKTTPPVLDSDGSFFLYSKLTVDKSR<br>WQQGNVFSCSVMHEALHNHYTQKSLSLSPGK |
| 276 | Bv4.105 full length heavy chain | QVQLVESGGGLVQSGRSLRLSCSAFGFTFGDYPIMWVRLAPGKGLEWVGFIRSKAYGGTAEYAASVKGRF<br>TTSRDDSRSTAYLQMNSLKTEDTAVYYCTREGGHSGFWSGFNKIPTFDYWGQGSLVTVSSASTKGPSVFPL<br>APSSKSTSGGTAALGCLVKDYFPEPVTVSWNSGALTSGVHTFPAVLQSSGLYSLSSVVTVPSSSLGTQTYIC<br>NVNHKPSNTKVDKRVEPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPVLDSDGSFFLYSKLTVD<br>KSRWQQGNVFSCSVMHEALHNHYTQKSLSLSPGK |

IV. Examples

The following are examples of methods and compositions of the invention. It is understood that various other embodiments may be practiced, given the general description provided above.

Materials and Methods

Human Samples

Blood samples from HBV vaccinees and HBV seroconverters were obtained from the healthy donors cohort of the ICAReB biobanking platform (Institut Pasteur) under the CoSimmGen protocol approved by the French Agence Nationale de Sécurité du Médicament (ANSM) on May 24th 2012, and the Comité de Protection des Personnes (CPP) on Jan. 17, 2014. The main clinical-biological characteristics of the donors are summarized in FIG. 6. All samples from HBV vaccinees and seroconverters were obtained as part of the clinical research protocol RAPIVIB performed in accordance with and after ethical approval from all the French legislation and regulation authorities. The RAPIVIB protocol received approval from the Comité de Recherche Clinique of the Institut Pasteur on Jul. 30, 2015 (#2014-058), the ANSM on Apr. 29, 2015 (#150457B-41), the CPP Ile-de-France III on Jun. 10, 2015 (#2015-100220-49/3267). The protocol was subjected to the MR-001 reference methodology of the Commission Nationale de l'Informatique et des Libertés (CNIL). All donors gave written consent to participate in this study, and data were collected under pseudo-anonymized conditions using subject coding. Peripheral blood mononuclear cells (PBMC) were isolated from donors' blood using Ficoll® Plaque Plus (GE Healthcare), and plasma or serum IgG antibodies were purified by batch/gravity-flow affinity chromatography using protein G sepharose 4 fast flow beads (GE Healthcare, Chicago, IL).

Antigens and Antibody Controls

Native S-HBsAg purified from infected subjects and recombinant S-HBsAg particles (ayw subtype) were prepared and biotinylated by Roche. Recombinant HBsAg particles (ayw) were produced in Chinese hamster ovary cells (Aventis Pasteur, Val de Reuil, France) (Michel et al., 1984). Adw-subtype HBsAg particles (HBV genotype A) were produced in the yeast *Pichia pastoris* expression system, and purified (<95% purity) at the Center for Genetic Engineering and Biotechnology production facilities (CIGB, Havana, Cuba; a kind gift from Dr. J. Aguilar). Consensus genotype-specific S-HBs fragments were constructed by multiple amino acid alignment of individual HBV genotypic sequences (A, n=205; B, n=495; C, n=1322; D, n=382; E, n=314; F, n=271; G, n=6; H, n=40; I, n=7) using CLC Main Workbench 7 software (v7.5.3, QIAGEN Aarhus A/S). Codon-optimized nucleotide fragments encoding the consensus S-HBs, a G3S linker (SEQ ID NO: 277), 10×His (SEQ ID NO: 278)- and Avi-tags were cloned into pcDNA™3.1/Zeo$^{(+)}$ expression vector (Thermo Fisher Scientific) using Anza 5 and 11 restriction enzymes (Thermo Fisher Scientific). For the production of the transmembrane (TM) domains-deleted S-HBs protein (ΔTM-S-HBs), the same construct but with the S-HBs DNA fragment lacking TM1, TM3, TM4 domains, and having the TM2 replaced by a $(G_3S)_5$ (SEQ ID NO: 279) linker was generated. Disulfide-bridged S-HBs/D 122-137 (RTCTTTAQGTSMYPSC (SEQ ID NO: 280)) and 139-148 (CTKPSDGNCT (SEQ ID NO: 281)) loop peptides, and 3 amino acids-overlapping 12-mer peptides (n=24) encompassing the entire ConsD S-HBs region but one transmembrane domain 2 peptide with high hydrophobicity (IFLFILLLCLIF (SEQ ID NO: 282)) were synthetized and desalted (GenScript HK Limited). Non-HBV antibody mGO53 (Wardemann and Nussenzweig, 2007) was used as isotype control. As positive control, neutralizing murine HB1 antibody specific to the 119-GPCRTCT (SEQ ID NO: 283)-125 linear epitope of the "a" determinant of S-HBsAg (Kucinskaite-Kodze et al., 2016), was produced as a chimeric recombinant IgG1 with a human Fc using the expression-cloning system described below. Murine anti-pre-S2 antibody 1F6 (Kuttner et al., 1999) was produced as chimeric human Fab fragments to be used as capture molecules in the alanine scan mapping described below.

Single B-Cell FACS Sorting and Expression-Cloning of Antibodies

Peripheral blood human B cells were isolated from donors' PBMCs by CD19 MACS (Miltenyi Biotec), and stained with LIVE/DEAD fixable dead cell stain kit (Thermo Fisher Scientific). Purified B cells were then incubated for 30 min at 4° C. with biotinylated recombinant or native S-HBs antigens, washed with 1% FBS-PBS (FACS buffer), and incubated for 30 min at 4° C. with a cocktail of mouse anti-human antibodies (CD19 A700 (HIB19), IgG BV786 (G18-145), CD27 PE-CF594 (M-T271) (BD Biosciences), IgA FITC (IS11-8E10, Miltenyi Biotec)), and streptavidin R-PE conjugate (Thermo Fisher Scientific). Stained cells were washed and resuspended in 1 mM EDTA FACS buffer. Single S-HBs$^+$CD19$^+$IgG$^+$ B cells were sorted into 96-well PCR plates using a FACS Aria III sorter (Becton Dickinson, Franklin Lakes, NJ) as previously described (Tiller et al., 2008). Single-cell cDNA synthesis using SuperScript IV reverse transcriptase (Thermo Fisher Scientific) followed by nested-PCR amplifications of IgH, Igκ and Igλ genes, and sequences analyses for Ig gene features were performed as previously described (Tiller et al., 2008). For the reversion to germline (GL) of the selected antibodies, sequences were constructed by replacing the mutated $V_H$-($D_H$)-$J_H$ and $V_L$-$J_L$ gene segments with their GL counterparts as previously described (Mouquet et al., 2012). Purified digested PCR products were cloned into human Igγ1-, Igκ- or Igλ-expressing vectors (GenBank #LT615368.1, LT615369.1 and LT615370.1, respectively) as previously described (Tiller et al., 2008). Murine Igγ2- and Igκ-expression vectors were generated from the original IgG1-expression vectors (Tiller et al., 2008) by substituting the DNA sequences coding for the human Igγ1/Igκ constant regions of by the ones of the mouse Igγ2- and Igκ (synthetic DNA fragment, GeneArt, Thermo Fisher Scientific), and then used for the cloning of chimeric mGO53 and Bc1.187 antibodies. Recombinant antibodies were produced by transient co-transfection of Freestyle™ 293-F suspension cells (Thermo Fisher Scientific) using PEI-precipitation method as previously described (Lorin and Mouquet, 2015). Recombinant human IgG antibodies were purified by protein G affinity chromatography (Protein G Sepharose® 4 Fast Flow, GE Healthcare, Chicago, IL). Purified antibodies were dialyzed against PBS. Preparations for in vivo infusions were micro-filtered (Ultrafree®-CL devices-0.1 µm PVDF membrane, Merck-Millipore, Darmstadt, Germany), and checked for endotoxins levels using the ToxinSensor™ Chromogenic LAL Endotoxin Assay Kit (GenScript).

ELISAs

ELISAs were performed as previously described (Planchais et al., 2019). Briefly, high-binding 96-well ELISA plates (Costar, Corning) were coated overnight with purified rS-HBs and nS-HBs (125 ng/well in PBS). After washings with 0.05% Tween 20-PBS (PBST), plates were blocked 2 h with 2% BSA, 1 mM EDTA-PBST (Blocking solution), washed, and incubated with serially diluted purified serum IgG and recombinant monoclonal antibodies in PBS. For sandwich ELISAs, plates were coated overnight with purified IgG antibodies (250 ng/well in PBS), and treated as afore-mentioned prior to incubation with biotylinated-rS-HBs (100 ng/well in PBS) in PBS. After washings, plates were revealed by addition of goat HRP-conjugated anti-human IgG or HRP-conjugated streptavidin (0.8 µg/ml final in blocking solution, Immunology Jackson ImmunoReseach) and HRP chromogenic substrate (ABTS solution, Euromedex). For competition ELISAs, purified antibodies were biotinylated using the EZ-Link Sulfo-NHS-Biotin kit (Thermo Fisher Scientific). rS-HBs-coated plates were blocked, washed, incubated for 2 h with biotinylated antibodies (at a concentration 0.33 nM) in 1:2 serially diluted solutions of antibody competitors in PBS (IgG concentration range from 0.83 to 106.7 nM), and revealed using HRP-conjugated streptavidin. Experiments were performed using HydroSpeed™ microplate washer and Sunrise™ microplate absorbance reader (Tecan Männedorf), with optical density measurements made at 405 nm (OD405 nm). Binding of anti-S-HBs antibodies to cyclic and overlapping linear peptides was tested using the same procedure as previously described (Mouquet et al., 2006). All antibodies were tested in duplicate or triplicate in at least two independent experiments, which included mGO53 negative and appropriate positive controls.

Alanine Scan Mapping

Mutant HBV envelope proteins were produced by co-transfection of Huh-7 cells with the psVLD3 and pT7HB2.7 plasmids using FuGENE 6 reagent (Roche) as previously described (Salisse and Sureau, 2009). High-binding 96-well ELISA plates (Costar, Corning) were coated overnight with purified human S-HBs antibodies (0.5 µg/well in PBS). After PBST washings, and a 2 h-blocking step, plates were incubated 2 h with culture supernatants containing HBsAg wildtype and mutants proteins. After washings, plates were incubated 1 h with purified His-tagged 1F6 Fab fragments (125 ng/well), washed, and revealed by addition of rabbit HRP-conjugated anti-6×His (SEQ ID NO: 284)-tag antibodies (1:4,000-diluted in blocking solution, ab1187, Abcam) and HRP chromogenic substrate (ABTS solution, Euromedex) as described above. Percentage of binding was calculated following the formula: $([OD]^{mutant}/[OD]^{wildtype})\times 100$.

Flow Cytometry Binding Assay

Freestyle™ 293-F were transfected with S-HBs-encoding vectors (0.65 µg plasmid DNA per $10^6$ cells) using PEI-precipitation method as previously described (Lorin and Mouquet, 2015). Forty-eight hours post-transfection, transfected and non-transfected control cells were fixed and permeabilized using Cytofix/Cytoperm™ solution kit (BD Biosciences), and $0.5\times10^6$ cells were incubated with IgG antibodies for 45 min at 4° C. (10 µg/ml, excepted if specified otherwise, in Perm/Wash™ solution; BD Biosciences). After washings, cells were incubated 20 min at 4° C. with AF647-conjugated goat anti-human IgG antibodies (1:1000 dilution; Thermo Fisher Scientific), washed and resuspended in PBS. Data were acquired using a CytoFLEX flow cytometer (Beckman Coulter), and analyzed using FlowJo software (v10.3; FlowJo LLC).

Protein Microarrays

All experiments were performed at 4° C. using ProtoArray Human Protein Microarrays (Thermo Fisher Scientific). Microarrays were blocked for 1 h in blocking solution (Thermo Fisher), washed and incubated for 1 h 30 with IgG antibodies at 2.5 µg/ml as previously described (Planchais et al., 2019). After washings, arrays were incubated for 1 h 30 with AF647-conjugated goat anti-human IgG antibodies (at 1 µg/ml in PBS; Thermo Fisher Scientific), and revealed using GenePix 4000B microarray scanner (Molecular Devices) and GenePix Pro 6.0 software (Molecular Devices) as previously described (Planchais et al., 2019). Fluorescence intensities were quantified using Spotxel® software (SICASYS Software GmbH, Germany), and mean fluorescence intensity (MFI) signals for each antibody (from duplicate protein spots) was plotted against the reference antibody mGO53 (non polyreactive isotype control) using GraphPad Prism software (v8.1.2, GraphPad Prism Inc.). For each antibody, Z-scores were calculated using ProtoArray® Prospector software (v5.2.3, Thermo Fisher Scientific), and deviation (o) to the diagonal, and polyreactivity index (PI) values were calculated as previously described (Planchais et al., 2019). Antibodies were defined as polyreactive when PI>0.21.

HEp-2 Cell Binding Assays

Binding of human anti-S-HBs and control IgG antibodies (mGO53 and ED38 (Meffre et al., 2004; Wardemann et al., 2003)) to HEp-2 cell-expressing autoantigens were analyzed at 50 μg/ml by ELISA (AESKULISA® ANA-HEp-2, Aesku.Diagnostics, Wendelsheim, Germany), and indirect immunofluorescence assay (IFA) (ANA HEp-2 AeskuSlides®, Aesku.Diagnostics) following the manufacturer' instructions. IFA sections were examined using the fluorescence microscope Axio Imager 2 (Zeiss, Jena, Germany), and pictures were taken at magnification ×40 with 5000 ms-acquisition using ZEN imaging software (Zen 2.0 blue version, Zeiss) at the Imagopole platform (Institut Pasteur).

HBV Neutralization Assay

HepaRG and HepG2.2.15 cell lines were obtained respectively from Biopredic International (Saint-Gregoire, France), and Dr. Michael Nassal (University Hospital Freiburg, Germany). HepaRG cells were cultured in Williams E medium (Gibco®, Thermo Fisher Scientific) supplemented with 10% HepaRG growth supplement (Biopredic), and differentiated using 1.8% DMSO for at least 2 weeks before infection. Primary human hepatocytes (PHH) isolated from chimeric uPA/SCID mice with humanized livers by a collagenase perfusion method (Tateno et al., 2015) were obtained from PhoenixBio (Hiroshima, Japan). PHH were plated on type I collagen coated 96-well plates at a concentration of $7\times10^4$ cells per well in culture media provided by Phoenix Bio. HBV genotype D viruses were produced in HepG2.2.15 cell culture supernatant, and concentrated using polyethylene glycol precipitation (Hantz et al., 2009). HBV viruses from genotypes A to C were purified from HBV-containing serum (American Red Cross) by gradient ultracentrifugation. Briefly, 1.5 ml of serum was applied on an OptiPrep™ gradient (10-50%, Sigma), and centrifuged at 32,000 rpm for 3 h at 4° C. Fractions (2 ml) were collected and analyzed for HBs antigen expression using S-HBs CLIA Kit (Autobio) and qPCR quantification. Whole genome sequences of all purified virus isolates were obtained by ultra-deep sequencing (DDL Diagnostic Laboratory, Netherlands), and HBV genotypes were determined using the Hepatitis B Virus database HBVdb (http://hbvdb.ibcp.fr) (Hayer et al., 2013). The neutralizing activity of HBV antibodies was evaluated by incubating HBV virions (MOI 20-30) with serially diluted antibodies in HepaRG or PHH complete media for 1 h at room temperature. HBV-antibody mixtures were then added to the cells in 96-well plates with a final concentration of 4% PEG 8000 (Sigma). Infected cells were incubated for 20 h at 37° C., and then washed 4 times with PBS to remove the HBV inoculum and refilled with complete media. Six days post-infection, in-supernatant S-HBs antigen content was quantified using the S-HBs CLIA Kit (Autobio) according to the manufacturer's instructions.

HDV Neutralization Assay

In vitro neutralization assays were conducted using the HDV model as previously described (Sureau, 2010), except that NTCP-expressing Huh-106 cells substituted for HepaRG cells (Verrier et al., 2016). At day-1 post seeding, Huh-106 cells ($1\times10^5$ cells/20 mm diameter well) were exposed to $5\times10^7$ genome equivalents (ge) of HDV virions for 16 h, in the presence of 4% polyethylene glycol (PEG) 8000. To assay neutralization, the inoculums were mixed with 1:2 dilutions of 500 ng/ml of monoclonal antibodies, and the mixture was incubated for 1 h at 37° C. prior to inoculation. Cells were harvested at 9 days post-inoculation (dpi) for measurement of intracellular HDV RNA that served as a marker of infection. HDV RNA signals were detected by Northern blot analysis using a $^{32}$P-labeled RNA probe and quantified using a phosphorimager instrument r (BAS-1800 II; Fuji).

Chronic HBV Mouse Model

Chronic HBV infection was established in 6-8-week-old C57BL/6 mice (Janvier Labs, Le Genest-Saint-Isle, France) by a single intravenous injection (retro-orbital venous sinus) of $5\times10^{10}$ viral genome of an adeno-associated-virus serotype 2/8 carrying a replication competent HBV-DNA genome (Dion et al., 2013). Virus stocks were produced and titrated as virus genome equivalents (GE Healthcare) and focus-forming units per milliliter by the Plateforme de Thérapie Génique (INSERM U1089, Nantes, France). Six weeks post-transduction, antibodies (0.25, 0.5 or 1 mg per injection per mouse) were administrated intravenously to HBV-carrier mice. Blood samples were collected and stored at −20° C. Serum S-HBsAg and HBeAg levels were determined using Monolisa S-HBsAg ULTRA (Bio-Rad, France) ELISA kits and ETI-EBK Plus NO140 (Diasorin SA, Italy), respectively. Concentrations were calculated by reference to standard curves established with known concentrations of S-HBsAg (Architect S-HBsAg Calibrators, Bio-Rad, France) and of the Paul-Ehrlich-Institut standard and are expressed in IU/mL and PEI U/mL, respectively. HBV DNA was purified from mouse sera using QIAamp Blood Mini kits (Qiagen, Germany), and quantified by quantitative PCR as previously described (Cougot et al., 2012). Serial dilutions of the payw1.2 plasmid containing 1.2 copies of HBV genome were used as quantification standards. Results are expressed in IU/ml with a detection threshold at 1000 IU/ml. All experimental animal protocols have been reviewed and approved by the institutional animal care committee of Institut Pasteur for compliance with the French and European regulations on Animal Welfare and with Public Health Service recommendations (APAFIS #15408-2018060517005070 v1). All experiments with HBV infections were performed in an A3 animal facility.

HBV HUHEP Mouse Model

To generate the HUHEP model BALB/c Rag2$^{-/-}$IL-2Rγc$^{-/-}$NOD.sirpa upA$^{tg/tg}$ (BRGS-uPA) mice were intrasplenically injected with $7\times10^5$ freshly thawed human hepatocytes (BD Biosciences, Corning) (Strick-Marchand et al., 2015). Liver chimerism was determined on plasma samples with a species-specific human albumin (hAlb) ELISA (Bethyl Laboratories) and HUHEP mice with ≥100 microg/ml hAlb were intraperitoneally infected with $1\times10^7$ HBV genome equivalents (Dusseaux et al., 2017). HBV-infected mice with $>10^6$ HBV DNA copies/ml were given an intraperitoneal injection of either bNAb CH1-187 or an isotype control (mGO53) IgG every 3-4 days at 20 mg/kg mouse, or every week at 1 mg/mouse, or Entecavir (ETV) 0.3 mg/kg/day (Baraclude, BMS) delivered in MediDrop Sucralose (Clear H2O) per os. For the rebound phase mice were returned to drinking water. Animals were housed in isolators under pathogen-free conditions with humane care. Experiments were approved by an institutional ethical committee at the Institut Pasteur (Paris, France) and validated by the French Ministry of Education and Research (MENESR #02162.02).

Statistical Analyses

For Ig gene repertoire analyses, groups were compared using two-sided 2×2 and 2× 5 Fisher's Exact tests. The numbers of $V_H$, Vκ and Vλ mutations were compared across groups of antibodies using unpaired student t-test with Welch's correction. The volcano plot analysis was performed by comparing 206 individual antibody gene features between groups, and reporting for each parameter the Δmean (x axis) and the $-\log_{10}$ p-values given by the two-sided 2×2 Fisher's Exact test (y axis). Statistical analyses were performed using GraphPad Prism software (v8.1.2, GraphPad Prism Inc.), and SISA online tools for 2×5 Fisher test (http://www.quantitativeskills.com/sisa).

Figure 1B:
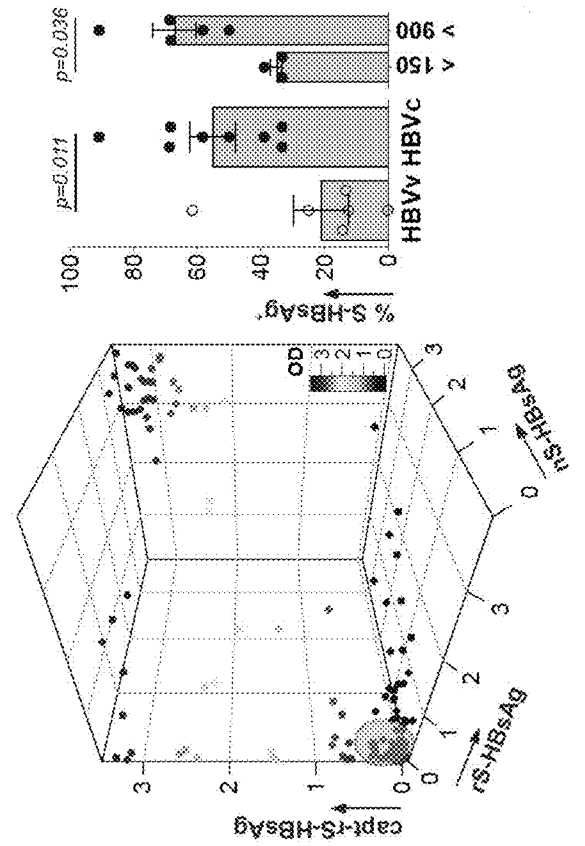
FIG. 1A-1E. S-HBs memory antibodies cloned from HBV vaccinees and controllers.
Figure 1A:
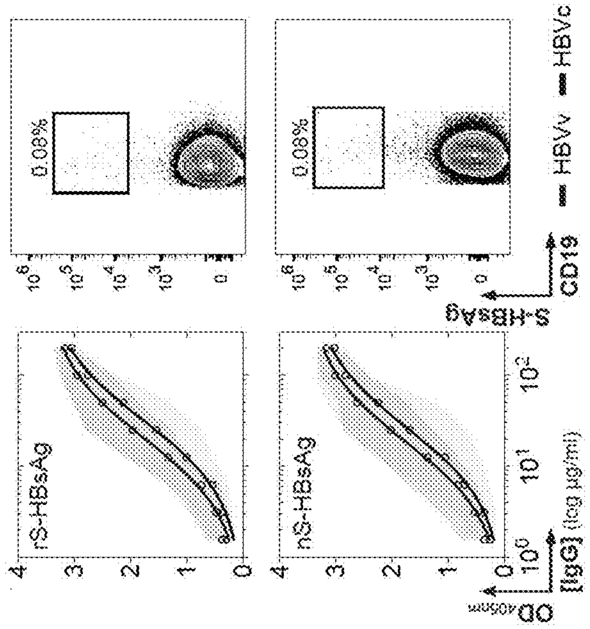
Figure 1C:
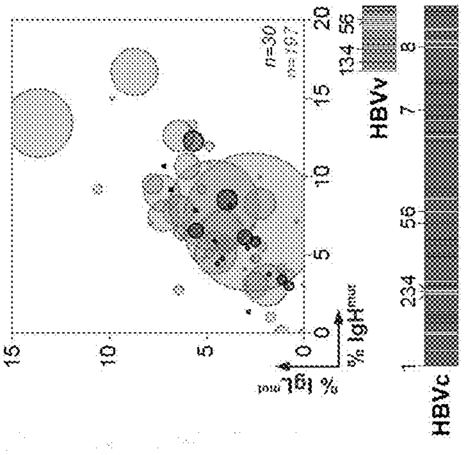
Figure 1D:
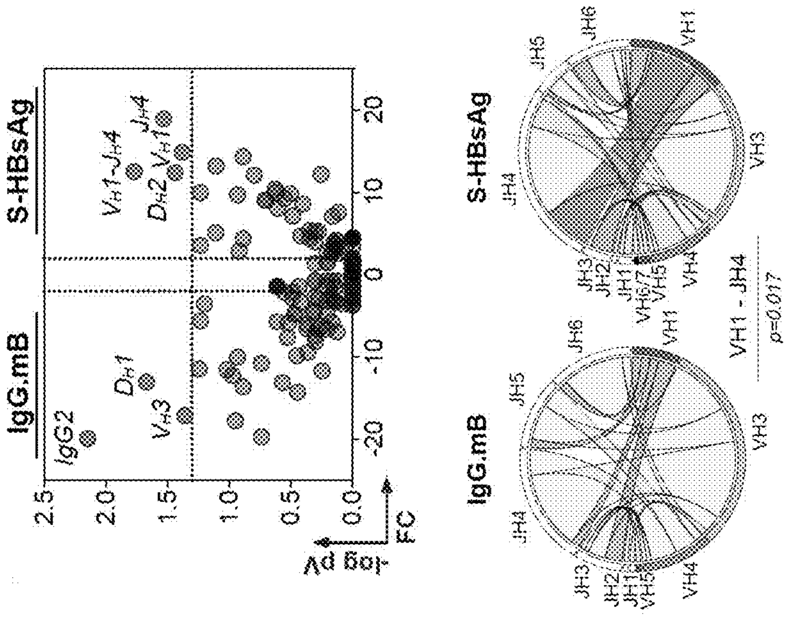
Figure 1E:
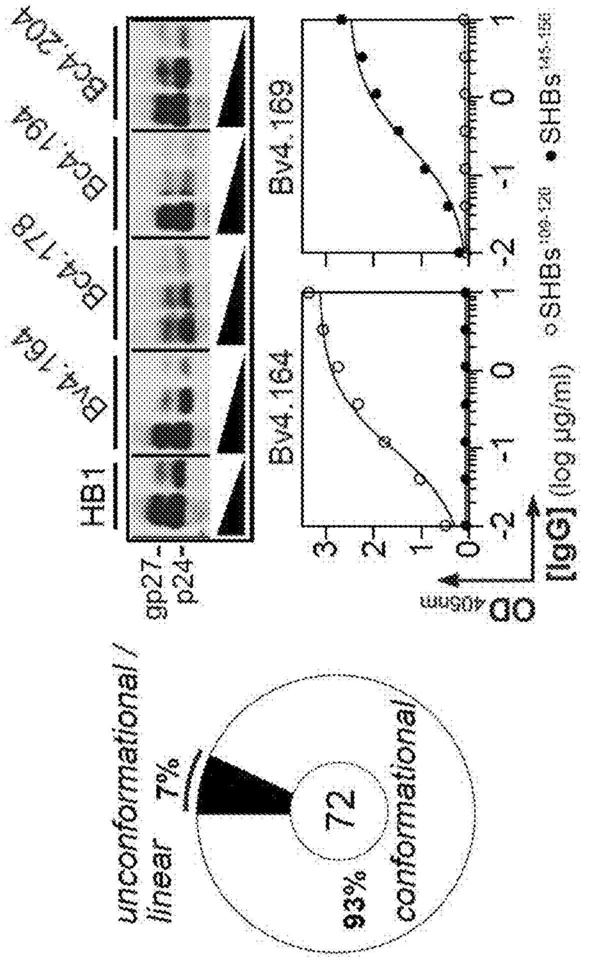
Figure 10A:
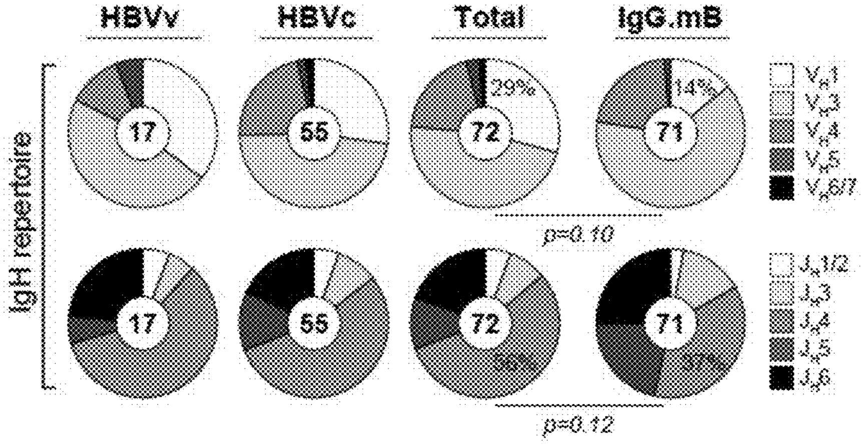
Figure 10B:
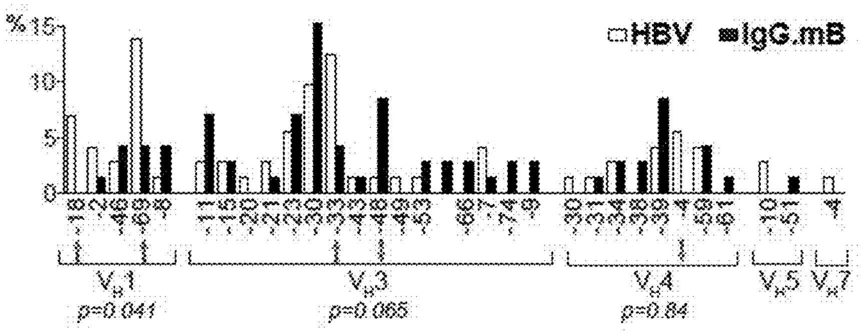
Figures 10C, 10D, 10E, 10F:
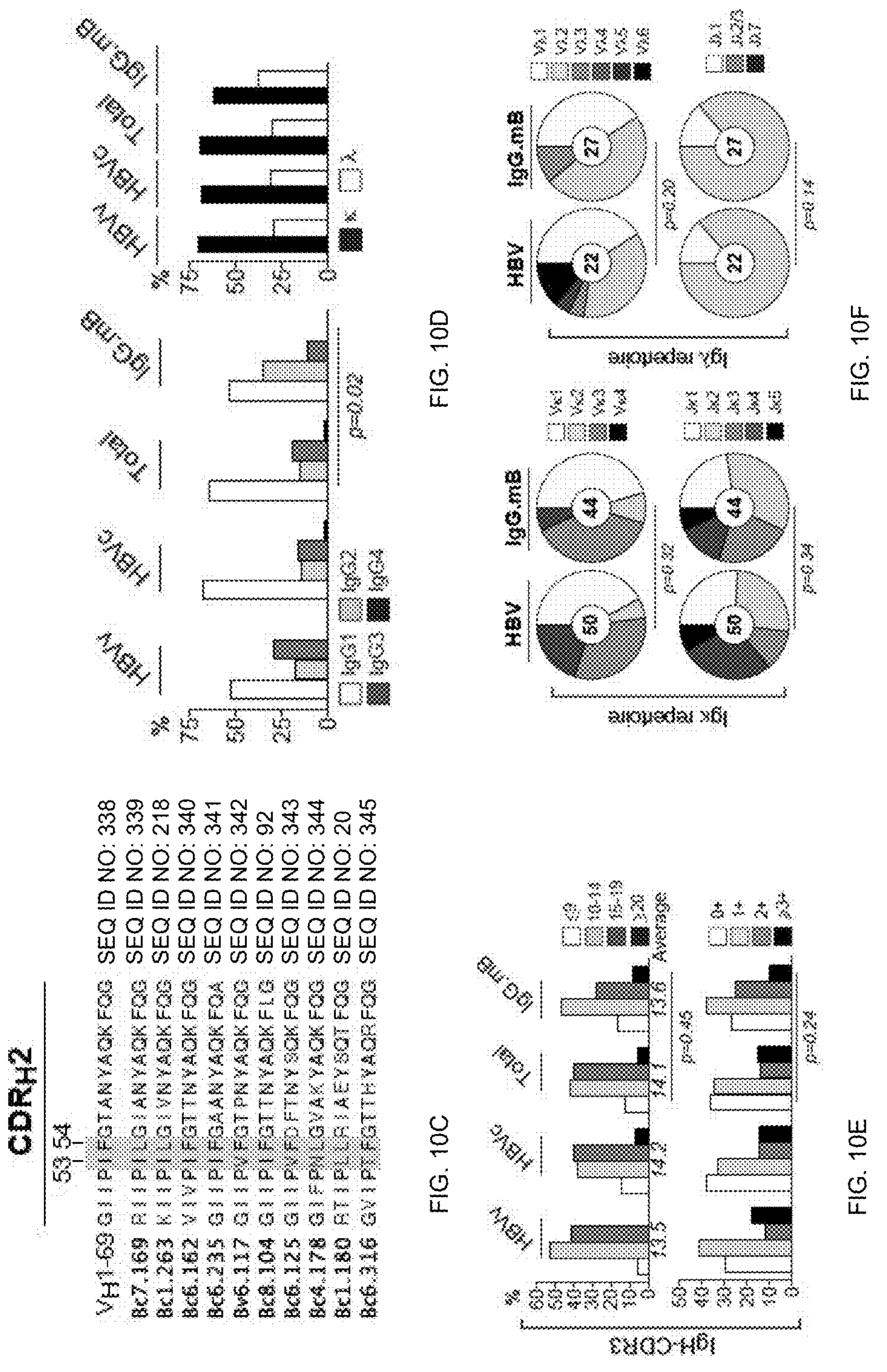
Figure 10G:
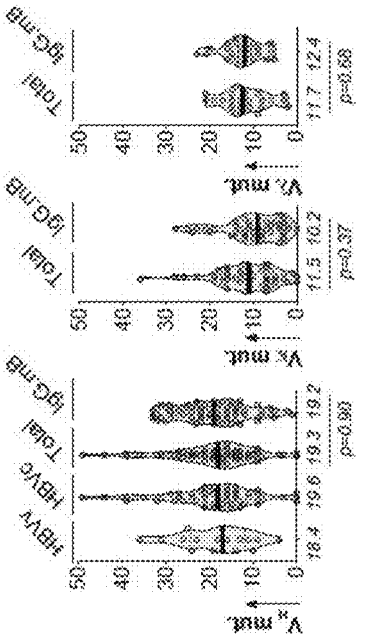
Figure 10H:
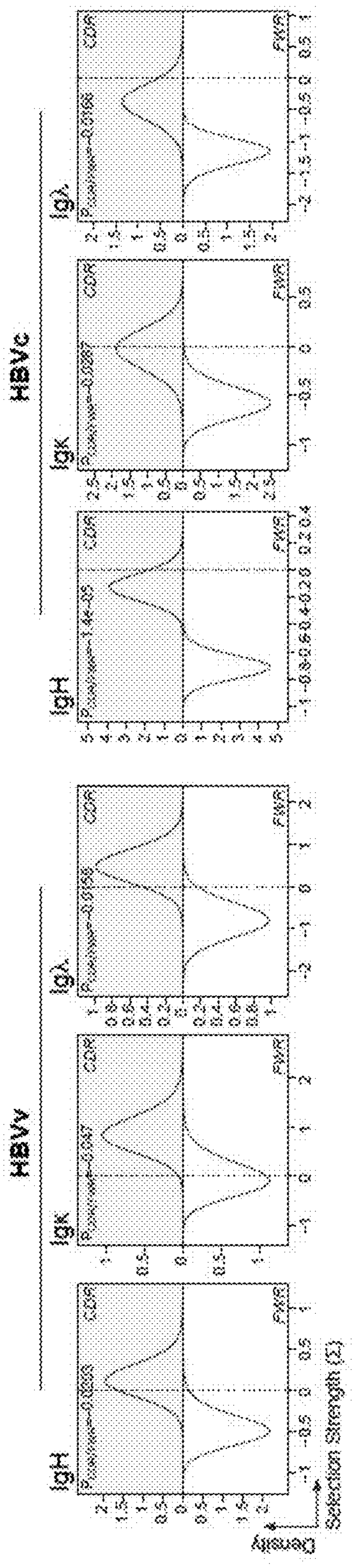

Example 1: Human S-HBs Monoclonal Antibodies from HBV Vaccinees and Controllers To characterize the memory B-cell antibody response to the HBV surface glycoproteins, peripheral blood B cells from six vaccinees and eight seroconverters with high serum anti-HBsAg IgG antibody titers (FIG. 6) were stained with fluorescently labeled recombinant or native S-HBs particles (FIG. 1A and FIG. 8A-8B). From the 3,452 S-HBs-binding IgG+ memory B cells captured by single-cell flow cytometric sorting, we produced a total of 170 unique human monoclonal antibodies by recombinant expression cloning (see above). ELISA binding analyses of S-HBs+ memory B-cell antibodies cloned from HBV vaccinees and controllers to S-HBs particles showed that only 21.1% (0-61.5%) and 55.2% (33.3-90.9%) were high-affinity to HBsAg, respectively (p=0.011, FIG. 1B and FIG. 9A-9B). In HBV controllers, high titers of circulating HBsAg antibodies were associated to a greater recovery of HBV-specific B cells (35.2% vs 64.7%, p=0.036). Bystander B cells lacking S-HBs-reactivity by ELISA were almost all polyreactive (not shown) and thus, may have been captured by interacting with non-envelope components of the viral particles. HBV-specific memory B cells were mainly part of clonal expansions and expressed somatically mutated immunoglobulin genes displaying antigen-driven maturation hallmarks (FIG. 1C, FIG. 10F and FIG. 10G). Comparison of immunoglobulin gene features with IgG+ memory B cells from healthy controls revealed an increased usage in the HBV-specific B-cell repertoire of VH1 (i.e. VH1-69 and VH1-18, p=0.041), JH4 (p=0.0017), and rearranged VH1 (DH) JH4 (p=0.017) genes, as well as IgG1/IgG3 subclass expression (p=0.019) (FIG. 1D, FIG. 7A-7B and FIG. 10A-10H). Among the HBV antibodies utilizing VH1-69 genes (14% of total), 60% possessed the germline-encoded phenylalanine at position 54 in the hydrophobic CRDH2 tip (FIG. 8C), which was shown to be essential for numerous human neutralizing antibodies against influenza virus, HCV and HIV-1 (Chen et al., 2019). Only four anti-S-HBs IgG antibodies (n=72) recognized denatured S-HBs antigens by immunoblotting and none bound to "a" determinant peptides whereas two reacted with linear epitopes flanking the "a" region (FIG. 11A-11C), indicating that most S-HBs memory antibodies target conformational epitopes (FIG. 1E). We conclude that the majority of human S-HBs IgG memory B cells express conformation-dependent IgG1 and IgG3 antibodies enriched in VH1-coding immunoglobulins.

Figure 2B:
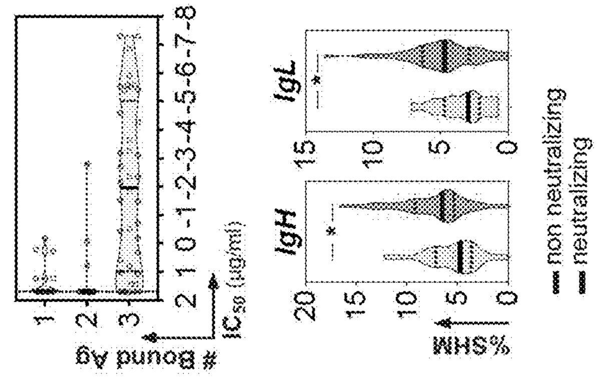
Figure 2A:
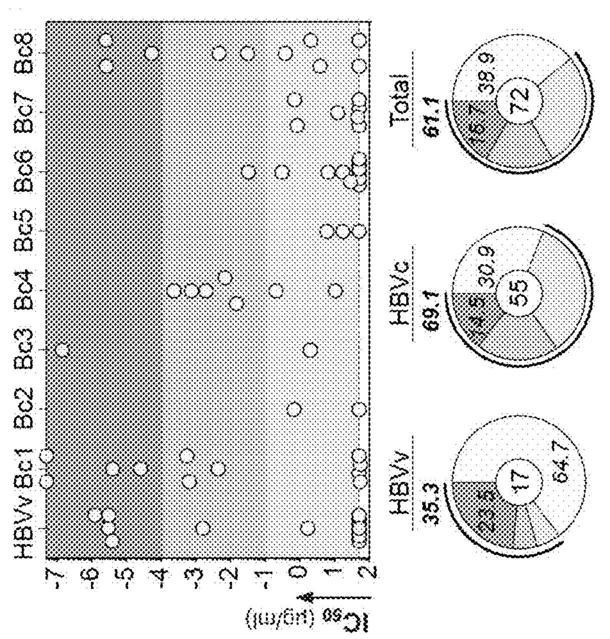
Figure 2C:
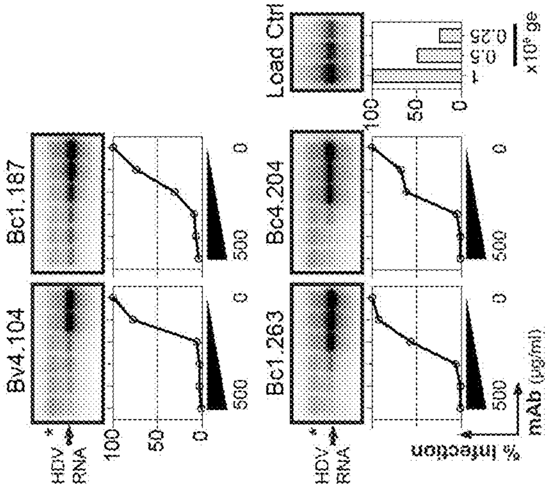

Example 2: In Vitro and In Vivo HBV Neutralization by Human S-HBs Memory B-Cell Antibodies To determine whether the S-HBs memory B-cell antibodies neutralize HBV, we measured their in vitro neutralizing activity against genotype D viruses in the HepaRG cell-based assay. Overall, 61% of the S-HBs antibodies blocked HBV infection with 50% inhibitory concentrations (IC50) ranging from 50 μg/ml down to 0.05 μg/ml (FIG. 2A, FIG. 7A-7B and FIG. 12A-12B). In HBV controllers, 69% of the antibodies were neutralizing including 35% of potent neutralizers with IC50 values below 50 ng/ml (FIG. 2A, and FIG. 7A-7B). S-HBs antibodies with higher hypermutation loads and broader reactivity to S-HBs antigens were more prone to inhibit HBV infection (FIG. 2B). HBV neutralizers equally expressed VH1-69 F54 and L54 alleles. Hepatitis delta virus (HDV) is a defective HBV-satellite virus of the Deltavirus genus coated with HBV envelope proteins (Sureau and Negro, 2016). We thus asked whether HBV neutralizing antibodies could also prevent HDV infection in vitro. As expected, selected antibodies neutralized HDV in the Huh-106 cell assay as efficiently as HBV (FIG. 2C).

Figure 2D:
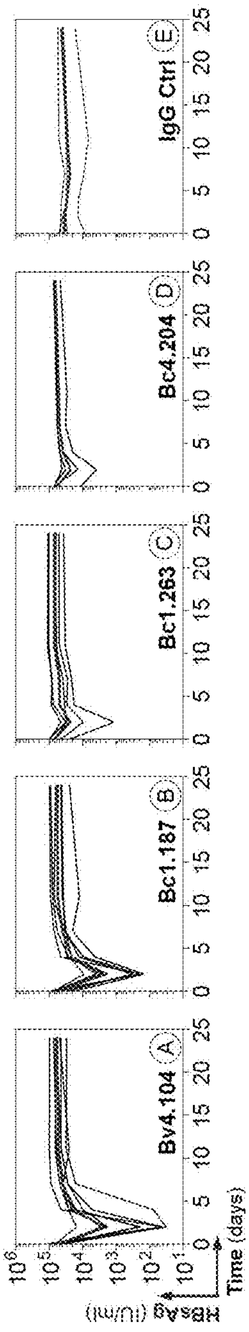
Figure 2E:
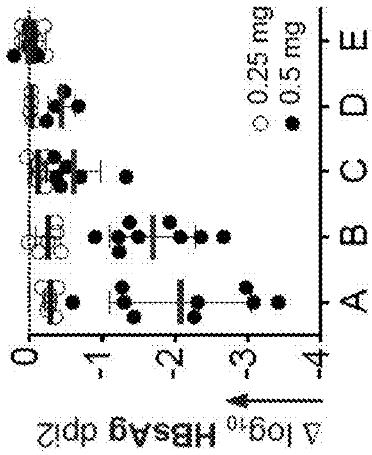
Figure 2F:
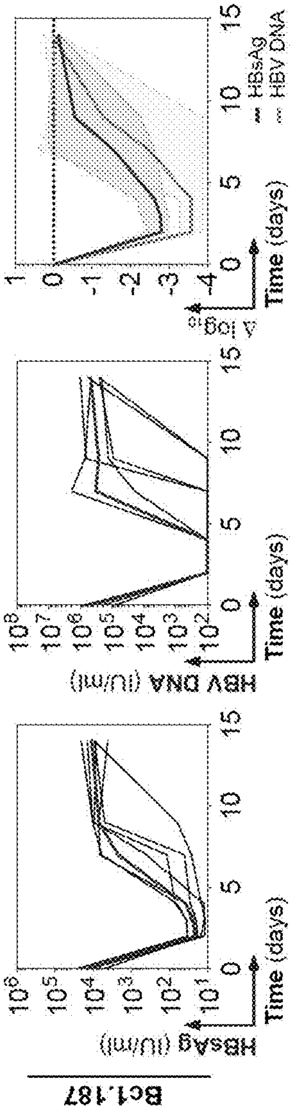

To evaluate the in vivo activity of neutralizing anti-S-HBs antibodies, we generated HBV-persistent mice based on the liver-targeted transduction of a recombinant HBV-encoding adeno-associated virus (AAV) (Dion et al., 2013). Four potent HBV neutralizers were selected and passively transferred into AAV-HBV mice carrying high levels of circulating S-HBsAg (>104 IU/ml). A single intravenous (i.v.) injection of antibodies at ~20 mg/kg led to a marked viremia drop 2 days post-injection (dpi), whereas treatments with a lower antibody dose had milder effects due to the rapid exhaustion of antibodies by outnumbering HBV particles (FIG. 2D, FIG. 2E and FIG. 13A-13B). The two most potent antibodies, Bc1.187 and Bv4.104, induced an average decrease of 1.7 and 2.1 log 10 at nadir (dpi2), respectively (FIG. 2E). A viral rebound 2 days post-drop accompanied antibody decay with a return to baseline levels of circulating HBsAg at dpi7 (FIG. 2D and FIG. 13B). As the decline of viremia in vivo was dependent on the amount of administrated antibody, we next thought to determine the effect of an increased dose of the HBV cross-neutralizing antibody Bc1.187. Viremic AAV-HBV mice receiving a single injection of Bc1.187 at ~40 mg/kg (1 mg i.v. per mouse) showed a maximum decrease of viremia of 2.8 log 10 in average at dpi2 (FIG. 2F), with HBsAg levels sustained below baseline for at least 12 days (FIG. 2F). In treated animals, HBV DNA loads followed the evolution of serum HBsAg titers and dropped of an average 3.6 log 10 to reach undetectable levels up to one week after the last Bc1.187 injection in 4 out 6 mice before viral rebound (FIG. 2F).

Figure 3B:
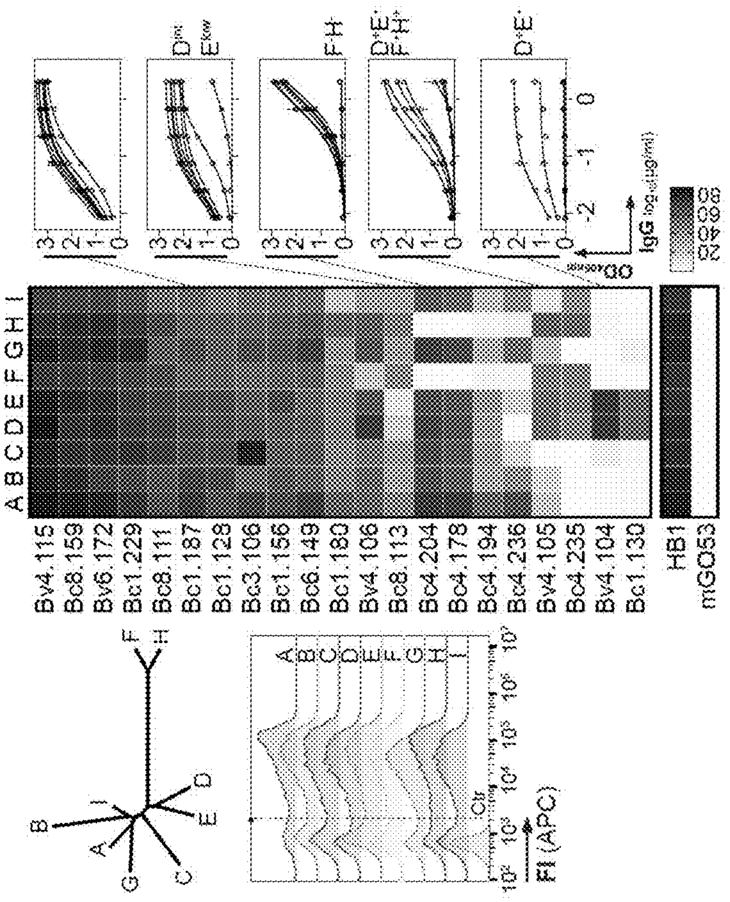
Figure 3A:
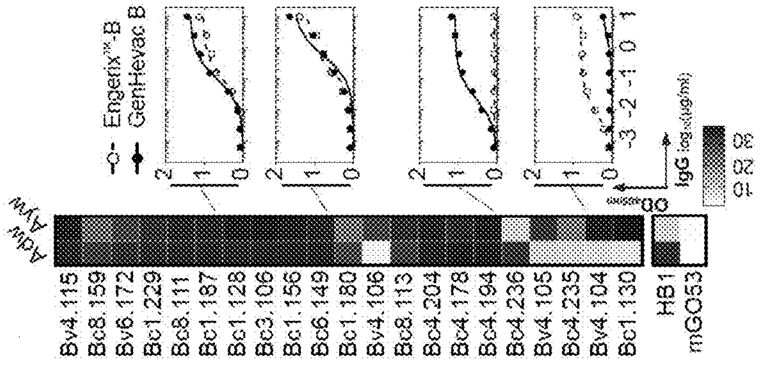
Figure 3D:
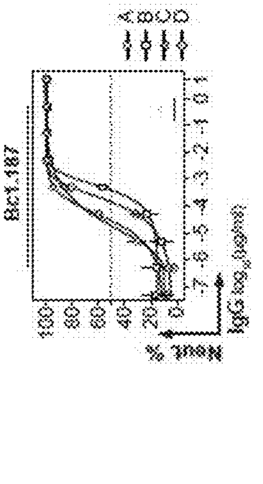
Figure 3E:
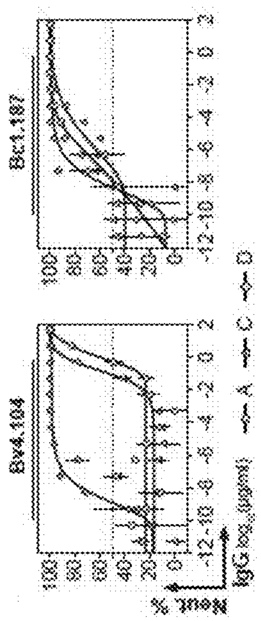
Figure 3C:
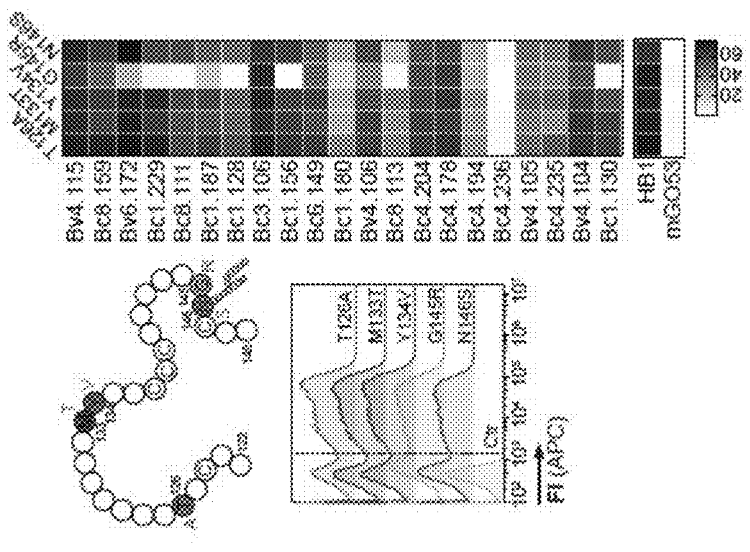

Example 3: Cross-Genotypic Activity of Potent Human HBV Neutralizing Antibodies HBV is classified into four major serotypes based on specific amino acid variations in the "a" determinant (adr, adw, ayr, ayw), and ten genotypes according to viral genome-based phylogeny (A to J) (Kato et al., 2016). Binding analyses showed that most potent HBV neutralizing antibodies (71%) are able to recognize both adw and ayw HBsAg particles used in GenHevac-B and Engerix-B vaccines, respectively (FIG. 3A). Importantly, about half of the neutralizers cross-reacted equally with consensus S-HBs proteins from 9 different genotypes (A to I) (FIG. 3B). The others displayed more heterogeneous binding profiles, with antibodies not reacting with F and H genotypes (19%, all from donor Bc4), or binding to D-F and H, or only to D and E (FIG. 3B). To validate that cross-genotypic HBV binding reflects cross-neutralization potential, we measured the in vitro neutralizing activity of the HBV cross-reactive neutralizer Bc1.187 against infection of primary human hepatocytes with HBV virions from genotypes A, B, C and D. As anticipated, Bc1.187 neutralized HBV viruses from all 4 genotypes although more efficiently genotype A and C than B and D (FIG. 3D). In the HepaRG cell assay, genotype A and C virions were also highly sensitive to Bc1.187 as opposed to Bv4.104 that consistent with its reactivity profile, only neutralized potently genotype D HBV (FIG. 3E).

In humans, several HBV escape mutations have been described, of which G145R is the most prevalent substitution in the S protein region (Chotiyaputta and Lok, 2009; Huang et al., 2012). We thus evaluated whether some of these mutations could affect HBV recognition by the potent neutralizers (FIG. 3E and FIG. 16). Significant decrease or loss of S-HBs binding was only detected with the G145R mutant protein for about half of the antibodies, indicating that the G145R mutation known to destabilize the "a" determinant antigenicity (Huang et al., 2012; Salisse and Sureau, 2009) can be detrimental to the neutralizing activity of some HBV antibodies. Mutant binding analyses also showed that none of the neutralizing antibodies interact with unique N-glycans on the S-HBs found at position N146 (FIG. 3E and FIG. 16). Collectively, these data show that S-HBs-specific memory B cells in HBV controllers can produce potent cross-neutralizing antibodies able to eliminate circulating HBsAg particles and suppress HBV viremia.

Example 4: Binding Features of Potent Human HBV Neutralizing Antibodies

Figure 4A:
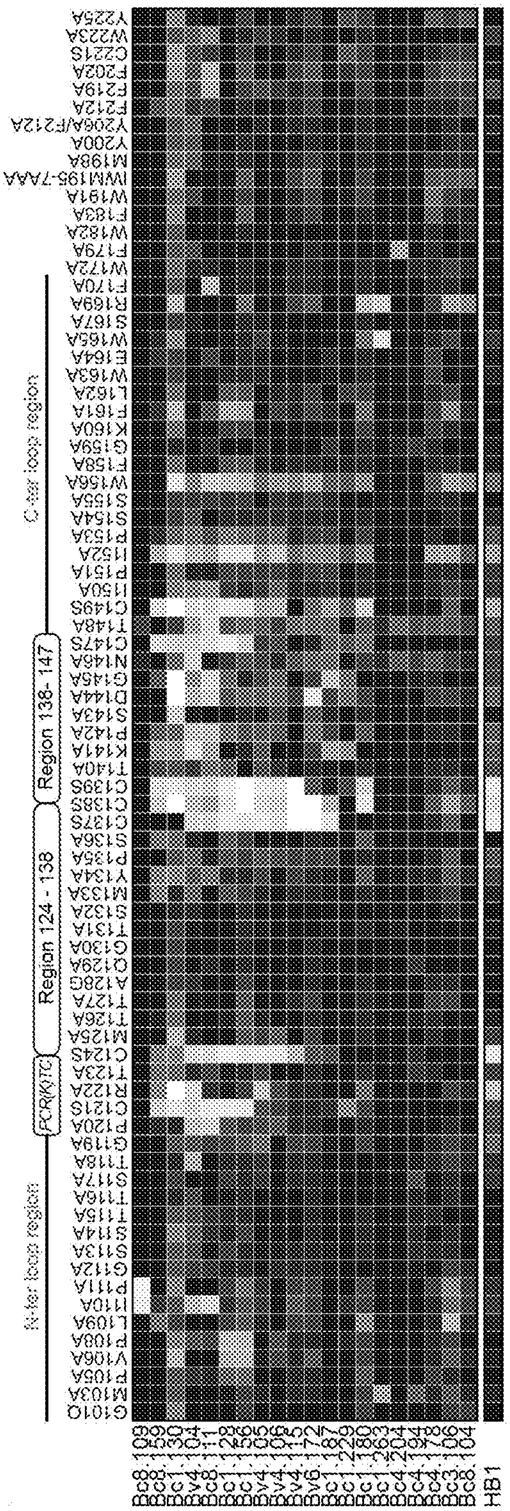
Figure 4B:
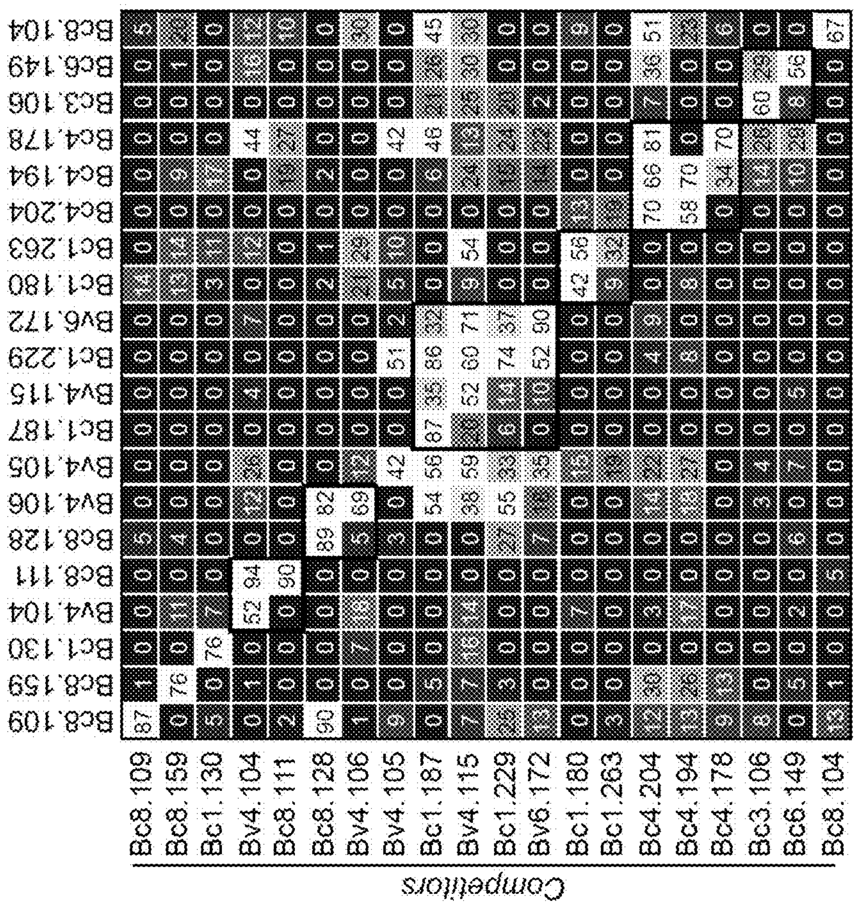
Figure 4C:
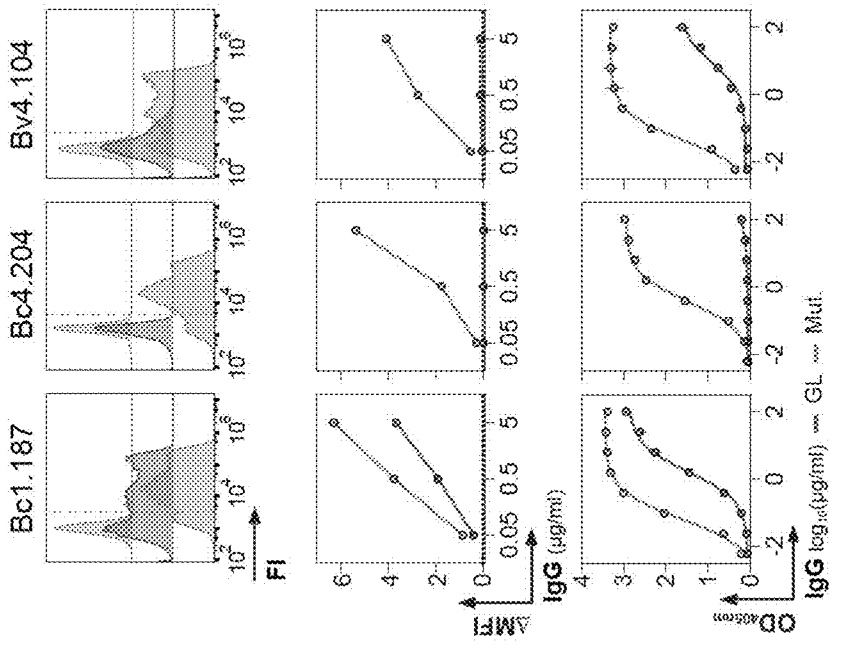

To map the epitopes targeted by potent neutralizing HBV antibodies, we performed alanine-scanning ELISA experiments using a library of mutant HBsAg proteins with substitutions covering the major hydrophilic region of HBsAg. Although all tested antibodies presented a unique recognition pattern, common binding profiles could be identified based on mutation sensitivity (FIG. 4A). Key epitopic regions were mostly found inside the "a" determinant but also outside in the N-terminal and C-terminal S-HBs region (Bc8.109 and Bc1.263, respectively). Some others could not be unambiguously identified (Bc4.204, Bc4.194, Bc4.178, Bc3.106 and Bc8.104) (FIG. 4A). Neutralizing epitopes in the "a" determinant were quite complex comprising major interacting residues either in the (i) "mini" and second loops (Bc8.159 and Bc1.130), (ii) first and second loops (Bv4.105 and Bv4.106), all 3 loops (Bv4.104, Bc8.111, Bc1.128 and Bc1.156), or mainly in the second loop (Bv4.115, Bv6.172, Bc1.187, Bc1.229 and Bc1.180) (FIG. 4A). Next, we performed competition S-HBs-binding ELISA analyses to evaluate the extent of overlap between neutralizing epitopes. In each aforementioned antibody class, cross-competition molecules were mostly found as independent tandems: Bv4.104/Bc8.111, Bc8.128/Bv4.106, Bc1.180/Bc1.263 and Bc3.106/Bc6.149 (FIG. 4C). The trio of neutralizers Bc4.194/Bc4.204/Bc4.178 recognized a common non-conformational epitope not well defined by the mapping (FIG. 1E, FIG. 4A and FIG. 4B), but likely located in the most distal portion of the HBsAg N- or C-terminus. In this regard, all 3 antibodies were unable to bind F and H genotypes, which principally diverge from the others in a region predicted to be the transmembrane domain 3 (Q178-Y225) (FIG. 11A-11C). Moreover, Bc4.204 had its binding decreased by the F179A mutation and also weakly bound to a linear peptide in C-ter (191-200) (FIG. 4A and FIG. 15A-15B). The larger epitopic cluster contained neutralizing antibodies having epitopes more centred on the second loop (Bv4.115, Bv6.172, Bc1.187, Bc1.229), but also able to interfere with the S-HBs binding of others neutralizers (FIG. 4B).

Figure 4D:
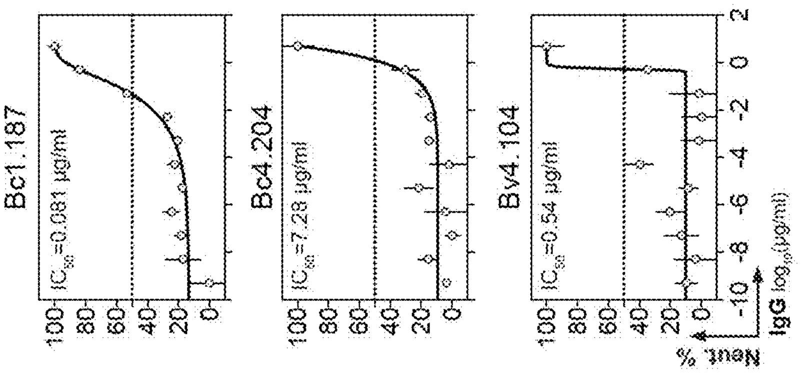
Figure 4E:
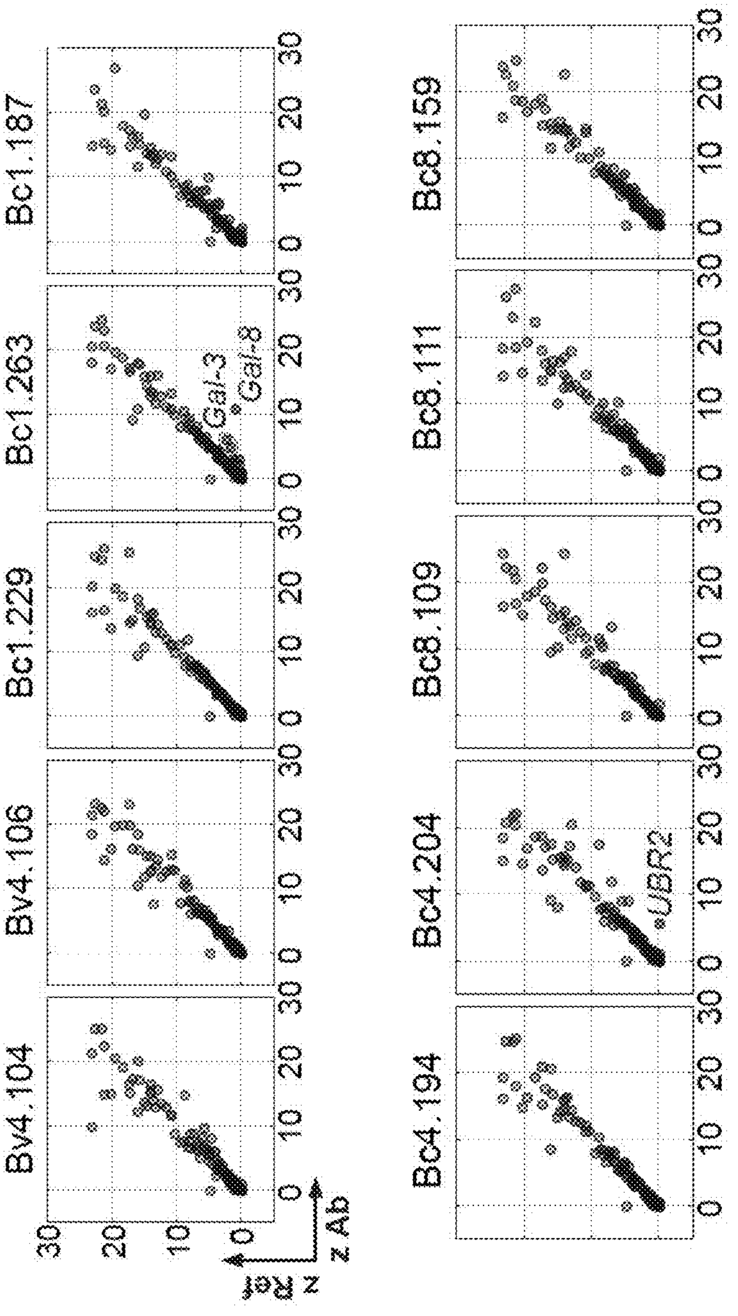

To examine whether somatic mutation contributes to the activity of HBV neutralizing antibodies, we reverted mutations in three representative potent neutralizers to produce their putative germline precursors (GL). Representative GL versions showed heterogeneous HBV recognition profiles: Bc4.204-GL failed reacting with S-HBs, whereas Bc1.187-GL and Bv4.104-GL still bound but with much lower relative affinities compared to their matured counterparts (FIG. 4C). GL IgGs displayed weak, as compared to the mutated antibodies, but significant inhibitory activities against in vitro HepaRG cell infection by genotype D HBV particularly, Bc1.187-GL with an IC50 of 0.08 μg/ml (FIG. 4D). This implies that although certain germline antibodies expressed by B-cell precursors can bind and neutralize HBV at a high concentration, somatic mutation is required for their high-affinity HBsAg binding and potent HBV neutralization.

Figure 18A:
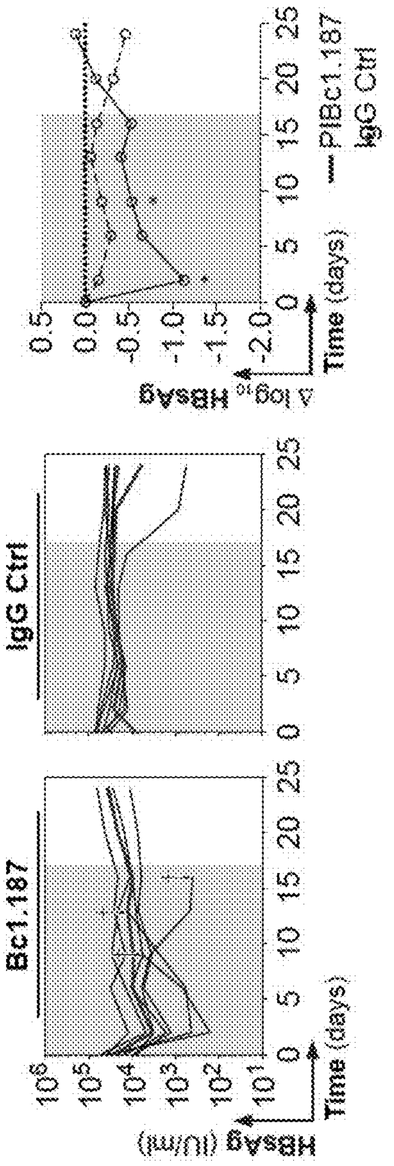
Figure 18B:
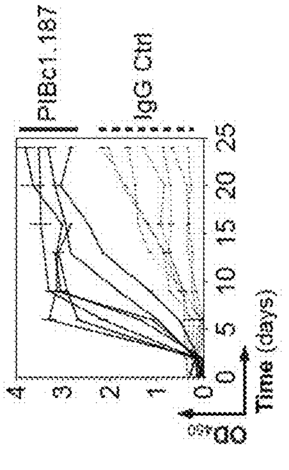
Figure 18C:
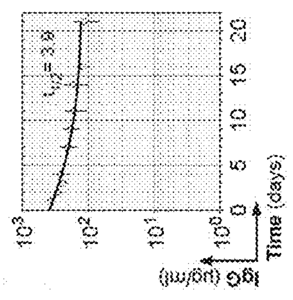
Figure 18D:
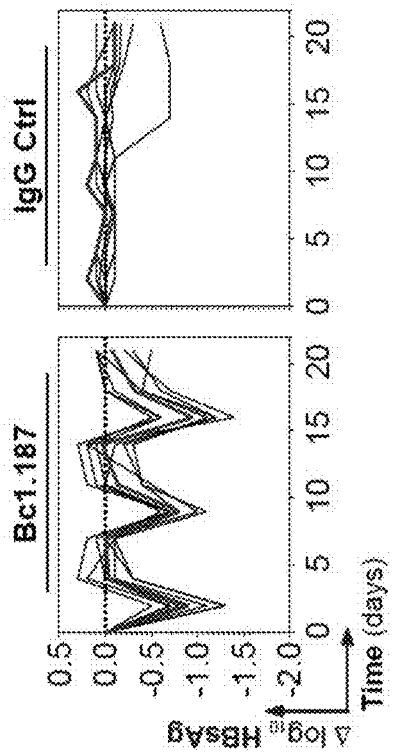
Figure 18E:
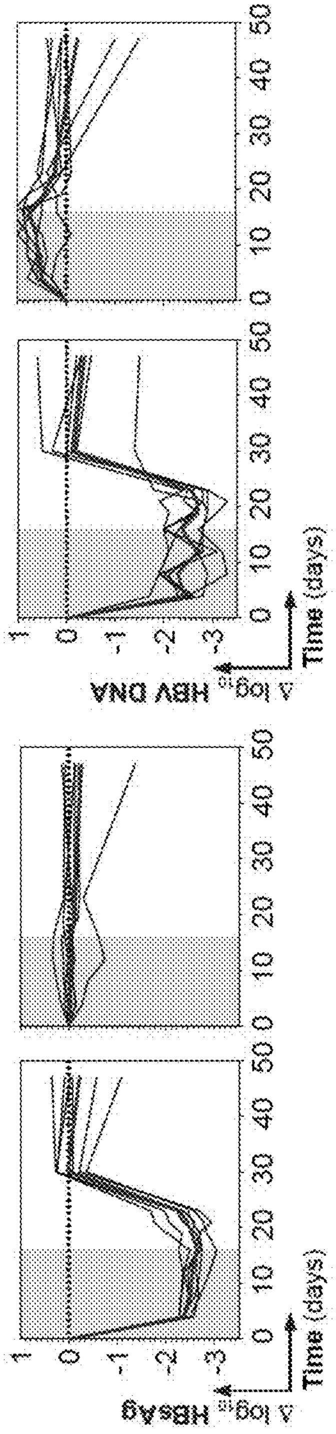

Human class-switched memory B cells including high affinity B-cell clones against viral antigens can cross-react with self-antigens (Andrews et al., 2015; Prigent et al., 2018; Prigent et al., 2016; Tiller et al., 2007). We thus evaluated the self-reactivity of 10 selected potent HBV neutralizers using clinical autoantibody assays (HEp-2 cells IFA and ELISA), and microarray immunoblotting (>9,000 human proteins). Apart from Bc1.263, none of the HBV neutralizers showed polyreactivity as measured by a global shift of the microarray fluorescence signals compared to the isotype control (FIG. 18A). Only Bc1.263 and Bc4.204 antibodies displayed a significant cross-reactivity (Z-scores>5) against galectin-3/-8 and E3 ubiquitin-protein ligase UBR2, respectively (FIG. 4D and FIG. 18B). No HBV neutralizers showed positive HEp-2 ELISA reactivity (FIG. 18C), although low (Bc1.187, Bc1.263) to moderate (Bc4.194, Bc4.204) binding to HEp-2 cell antigens were detected by IFA using high antibody concentrations (FIG. 18C).

Example 5: In Vivo HBV Suppression by Potent Cross-Neutralizing Antibody Bc1.187

To determine whether potent HBV neutralizers from natural controllers can stably suppress HBV viremia in vivo, AAV-HBV mice were treated for 17 days with Bc1.187 antibody (0.5 mg i.v., ~20 mg/kg, twice a week) (FIG. 19A). Viremic mice experienced a decrease in circulating HBsAg levels upon treatment with Bc1.187 but not with the isotype control (FIG. 19A). However, the development of murine anti-human IgG antibodies (referred as ADA, anti-drug antibodies) rapidly altered therapy effectiveness (FIG. 19B). To overcome or limit ADA production, we generated a chimeric version of Bc1.187 by combining the antibody's variable domains with the murine Igγ2a and IgK constant regions. The chimeric Bc1.187 antibody (c-Bc1.187) had a serum half-life of 3.9 days in non-transduced wildtype mice (FIG. 19C), and led to reproducible viremia drops when administrated weekly in AAV-HBV mice (0.88±0.07 log 10 in average at dpi2 during 3 consecutive weeks) (FIG. 19D).

Sixteen days of treatment with 0.5 mg i.v. injections of c-Bc1.187 every 2 days but not control antibody led to a loss of circulating HBsAg in all AAV-HBV mice from day 4 with an average 2.5 log 10 fold decrease compared to set-point (FIG. 5A). During c-Bc1.187 therapy, HBV viremia (as viral DNA IU/ml) was also drastically diminished by an average 2.5 log 10 fold and reached undetectable levels by day 21 in all but one mouse (FIG. 5A). HBsAg and HBV viremia were still suppressed for two weeks after the last antibody injection before rising back to baseline levels (FIG. 5A). As expected in this model, serum levels of HBe antigen, a surrogate marker for viral replication, remained unchanged during therapy (FIG. 5A).

We next wonder whether Bc1.187 could alter the natural course of HBV infection in vivo. BALB/c Rag2−/−SirpaN-ODAlb-uPAtg/tg mice stably engrafted with human hepatocytes (HUHEP) were infected with genotype D HBV. Once infection was established, mice received injections of Bc1.187 for 3 weeks, either bi-weekly (20 mg/kg per mouse) or weekly (50 mg/kg per mouse). In agreement with the AAV-HBV in vivo model, treatment with Bc1.187, but not non-HBV antibody and nucleoside reverse transcriptase inhibitor controls, induced a decrease of circulating HBsAg levels in viremic HUHEP mice by an average 2.1 and 2 log 10 fold at dpi21 for the 20 mg/kg and 50 mg/kg dosing regimen, respectively (FIG. 5B and FIG. 19A). However, HBV viremia declined more effectively in the group receiving weekly Bc1.187 injections of 50 mg/kg (average drop at dpi21 of 1.76 log 10 vs 0.64 log 10 for 20 mg/kg) (FIG. 5B). At the end of the follow-up, two mice with low pre-treatment viremia showed complete viral suppression in response to the 20 mg/kg dosing regimen (28.6%, n=7) (FIG. 5B and FIG. 19B). Circulating HBsAg levels dropped and remained undetectable for 2 weeks after the last injection of 50 mg/kg Bc1.187 in 60% of the mice (n=5). Of these mice, one died, another experienced viral rebound and the last still controlled the infection for more than a month post-treatment before HBV viremia reappearance (FIG. 5B and FIG. 19B). Circulating levels of HBeAg were also diminished upon Bc1.187 antibody treatment but to a lower extent compared to HBsAg (average fold changes at dpi21 0.26 log 10 for 20 mg/kg and 0.49 log 10 for 50 mg/kg) (FIG. 5B). Serum titres of human albumin remained unchanged during the monitoring period (FIG. 19C), indicating that engraftments were stable and not affected by treatments.

Summary

Rare individuals can naturally clear chronic hepatitis B virus (HBV) infection and acquire protection from re-infection as conferred by vaccination. To examine the protective humoral response against HBV, we cloned human antibodies to the viral surface glycoprotein S-SHBs from memory B cells of HBV vaccinees and controllers. We find that S-SHBs memory B cells from natural controllers produce mainly neutralizing antibodies able to cross-react with several viral genotypes. Human neutralizing HBV antibodies are encoded by a diverse set of immunoglobulin genes and recognize various conformational epitopes on the S-SHBs antigen. Strikingly, monotherapy in HBV mouse models with a potent cross-neutralizer isolated from a controller, Bc1.187, suppress viremia in vivo and lead to post-therapy control of the infection in some animals. Thus, neutralizing S-SHBs antibodies may play a key role in the spontaneous control of HBV and represent promising immunotherapeutics for achieving HBV functional cure in chronically infected humans.

Results for certain antibodies described herein are summarized below, in table 2. This summarizes results from FIG. 3A-3E. Accordingly, "serotype" data reports the ELISA reactivity of HBV neutralizing antibodies against Adw and Ayw genotype D S-HBs proteins (measured as AUC values from FIG. 14). "Cross-genotype binding" reports the reactivity of HBV neutralizing antibodies against S-HBs antigens from the indicated genotypes, as % of bound S-HBs-expressing cells determined by flow cytometry. "Mutants binding" is the same as for "cross genotype binding" but for S-HBs mutant proteins depicted. IC50 values are for neutralizing activity against infection of primary human hepatocytes by HBV viruses from genotype D. Table 3 provides EC50 values calculated from ELISA graphs showing the reactivity of selected antibodies against recombinant HBV vaccines Engerix-B (Ayw) and GenHevac (Adw) (FIG. 3A-3E).

TABLE 2

| | Serotype binding (AUC) | | Cross-genotype binding | | | | | | | | | Mutants binding | | | | | HBV-gD in vitro neutralization |
|---|---|---|---|---|---|---|---|---|---|---|---|---|---|---|---|---|---|
| | Adw | Ayw | A | B | C | D | E | F | G | H | I | T126A | M133T | Y134V | G145R | N146S | (IC50 μg/ml) |
| Bv4.115 | 36 | 37 | 88 | 83 | 82 | 89 | 85 | 73 | 83 | 77 | 71 | 71 | 67 | 66 | 60 | 67 | 3.87E-06 |
| Bc8.159 | 32 | 25 | 85 | 79 | 76 | 76 | 79 | 73 | 79 | 79 | 68 | 70 | 58 | 61 | 48 | 61 | 5.28E-05 |
| Bv6.172 | 34 | 31 | 83 | 71 | 76 | 78 | 77 | 72 | 82 | 79 | 69 | 75 | 71 | 69 | 24 | 77 | 3.06E-06 |
| Bc1.229 | 35 | 34 | 75 | 68 | 76 | 73 | 71 | 68 | 79 | 74 | 64 | 70 | 62 | 67 | 3 | 56 | 2.53E-05 |
| Bc8.111 | 35 | 36 | 65 | 64 | 72 | 71 | 68 | 66 | 60 | 67 | 52 | 55 | 54 | 56 | 0 | 55 | 2.51E-06 |
| Bc1.187 | 36 | 35 | 73 | 70 | 67 | 66 | 66 | 58 | 64 | 59 | 54 | 60 | 52 | 57 | 17 | 48 | 5.00E-08 |
| Bc1.128 | 35 | 37 | 64 | 67 | 67 | 64 | 65 | 58 | 58 | 59 | 47 | 53 | 48 | 47 | 0 | 46 | 5.44E-04 |
| Bc3.106 | 36 | 37 | 70 | 55 | 83 | 62 | 59 | 55 | 65 | 59 | 53 | 71 | 66 | 69 | 67 | 63 | 1.39E-07 |
| Bc1.180 | 30 | 23 | 57 | 45 | 43 | 47 | 46 | 42 | 39 | 55 | 22 | 38 | 25 | 25 | 14 | 27 | 5.00E-08 |
| Bv4.104 | 7 | 37 | 1 | 1 | 5 | 73 | 73 | 1 | 1 | 1 | 1 | 64 | 64 | 60 | 54 | 63 | 1.21E-06 |
| Bc8.104 | ND | ND | ND | ND | ND | ND | ND | ND | ND | ND | ND | ND | ND | ND | ND | ND | 2.61E-06 |
| Bc4-204 | 36 | 36 | 74 | 65 | 65 | 68 | 65 | 0 | 71 | 1 | 58 | 60 | 59 | 57 | 55 | 53 | 2.29E-04 |
| Bc1.263 | ND | ND | ND | ND | ND | ND | ND | ND | ND | ND | ND | ND | ND | ND | ND | ND | 3.96E-06 |
| Bv4.105 | 8 | 33 | 16 | 1 | 5 | 52 | 51 | 46 | 24 | 55 | 10 | 45 | 39 | 46 | 40 | 43 | 2.95E-06 |

TABLE 3

| | Serotype binding (EC50 ug/ml) | |
|---|---|---|
| | Adw | Ayw |
| Bv4.115 | 0.0277 | 0.0051 |
| Bc8.159 | 0.0108 | 0.7844 |

TABLE 3-continued

| | Serotype binding (EC50 ug/ml) | |
|---|---|---|
| | Adw | Ayw |
| Bv6.172 | 0.0065 | 0.0040 |
| Bc1.229 | 0.0261 | 0.0123 |
| Bc8.111 | 0.0089 | 0.0095 |
| Bc1.187 | 0.0049 | 0.0035 |
| Bc1.128 | 0.0072 | 0.0057 |
| Bc3.106 | 0.0421 | 0.0193 |
| Bc1.180 | 0.0653 | 0.3095 |
| Bv4.104 | 6.5840 | 0.0046 |
| Bc8.104 | ND | ND |
| Bc4-204 | 0.0156 | 0.0150 |
| Bc1.263 | ND | ND |
| Bv4.105 | 8.9210 | 0.0048 |

Discussion

In chronic HBV infection, most HBsAg-specific B cells are atypical memory lymphocytes presenting several B-cell dysfunctions such as an altered capacity to differentiate into antibody-producing cells and thus, to potentially produce HBV neutralizing antibodies (Burton et al., 2018; Salimzadeh et al., 2018). In contrast, circulating B cells in individuals who resolved the infection, both during the acute and chronic phase, secrete HBsAg antibodies likely participating in the seroconversion (Salimzadeh et al., 2018; Xu et al., 2015). To characterize memory B-cells directed against the HBV surface antigen in immune donors, we investigated the molecular and functional properties of recombinant human antibodies cloned from single S-HBs-specific IgG$^{+}$ circulating in the blood of HBV controllers and vaccinees. Our study reveals that despite a moderate enrichment in $V_H1$-$J_H4$-encoding clones, circulating S-HBs-specific memory B cells from HBV controllers, but also from vaccinees, express a diverse gene repertoire of immunoglobulins recognizing mostly conformational epitopes on the HBV surface glycoproteins. The majority of anti-S-HBs IgGs cloned from controllers could neutralize HBV in vitro, with some being active at very low concentrations, including against HDV infection. Potent neutralizers evaluated in vivo also showed antiviral effects by decreasing both serum HBsAg level and HBV viremia, suggesting that in infected humans these antibodies may be functionally important. The majority of HBV neutralizing antibodies were broadly reactive against various viral genotypes and recognized epitopes located in the "a" determinant although others were also mapped outside this region. Several neutralizing epitopes were identified including a main region involving the S-HBs second loop recognized by the potent cross-neutralizing antibody Bc1.187. A single passive infusion of Bc1.187 was particularly effective in vivo in a mouse model of chronic HBV infection to completely suppress for a few days serum HBsAg and HBV viremia. Interestingly, we showed here that the germline version of Bc1.187 could still bind and neutralize HBV with an $IC_{50}$<0.1 μg/ml. This suggests that B-cell precursors expressing such immunoglobulins could rapidly affinity matured and thus, be readily active in neutralizing HBV.

Current therapies for treating chronic HBV infection include potent direct antivirals and PEG-IFNα. However, antiviral treatments have no significant impact on the serum HBsAg levels due principally to defective sub-viral particles outnumbering infectious HBV virions. To bypass the immune tolerance observed in chronically infected individuals, and induce effective anti-HBV antibody responses is therefore still a major challenge. One promising strategy is the development of immunotherapies based on the use of potent HBV neutralizing antibodies (Corti et al., 2018; Gao et al., 2017; Tu and Urban, 2018). Preclinical models in mice and monkeys, as well as several phase I clinical trials in chronically-infected humans have shown the in vivo efficacy of neutralizing HBV monoclonal antibodies, which when administrated in infected recipients altered the course of infection by suppressing HBsAg and reducing HBV DNA content (Eren et al., 2000; Galun et al., 2002; Lee et al., 2019; Lever et al., 1990; Li et al., 2017; van Nunen et al., 2001; Zhang et al., 2016; Zhu et al., 2016). In this study, we showed using two different mouse models that treating viremic animals with a potent human cross-neutralizing antibody had profound effects on HBV infection. Bc1.187 therapy induced a rapid loss and/or substantial decrease of circulating HBsAg and HBV DNA that persisted in most mice for several days to few weeks post-treatment. In vivo experiments also demonstrated that low viremia-bearing mice could clear HBV infection upon Bc1.187 antibody treatment. Antibodies are versatile immune effectors. Besides neutralization, they can exert a variety of immunological effector functions such as antibody dependent cellular cytotoxicity (ADCC), which allow the killing of infected cells by innate immune cells such as Natural Killer cells (NK). The ADCC activity is a key component of the therapeutic property of human neutralizing antibodies to viruses such as HIV-1 and influenza (Bruel et al., 2016; DiLillo et al., 2014). Early on, complement-dependent lysis and ADCC have been involved in the hepatocytes killing activity of murine anti-S-HBs antibodies using in vitro and in vivo systems (Shouval et al., 1982a; Shouval et al., 1982b). More recently, a human neutralizing HBV antibody against the pre-S1 region has been shown to exert therapeutic activity with sustained virological suppression in part, by eliciting Fc-dependent effector functions (Li et al., 2017). Finally, antibody therapy by engaging the host immune system can lead to a stimulation of immune responses, a property better appreciated and known as vaccine-like effects (Pelegrin et al., 2015), a property that could be essential in breaking HBV-induced immune tolerance. Hence, we propose that in addition to blocking de novo infection and possibly eliminating infected hepatocytes via Fc-dependent mechanisms, some of the potent human cross-neutralizing HBV antibodies described here could be used in chronically infected patients to greatly reduce serum HBsAg level. Such antibodies could indeed act as a powerful "antigenic sink", which when combined with therapies aiming at restoring the host's innate and adaptive immune responses, i.e., INFα, therapeutic vaccines, TLR agonists, checkpoint inhibitors (Fanning et al., 2019; Gehring and Protzer, 2019; Maini and Burton, 2019) could facilitate viral clearance and eventually lead to a long-term control of HBV infection.

Example 6-In-Vitro and In Vivo Pharmacokinetic (PK) Assessment of Bc1.187 and Bc1.187 Engineered Constructs An in vitro pulse-chase assay to measure antibody recycling and transcytosis (Antibody Recycling and Clearance (ARC) Assay) was used to flag potential clearance liabilities driven by two known mechanisms: 1) non-specific clearance-driven by non-specific binding/internalization into cells (ARC-score at pH=7.4), and 2) FcRn-mediated effects (ARC-score at pH=6 and ARC-fold shift). This assay provides an assessment of these parameters relative to controls that have shown IgG-like pharmacokinetics in human (for a further description of the assay, see *MAbs.* 2017 July; 9 (5): 781-791. doi: 10.1080/19420862.2017.1320008). Wild-type IgG1 Bc1.187 displayed an ARC-score of 0.28 and 4.97 at pH 7.4 and pH 6, respectively, leading to an ARC-fold shift of 17.8. These values indicate a low potential for non-specific binding/internalization into cells, and an FcRn-recycling in line with IgG-molecules. Similar constructs that are based on Bc1.187 IgG, but with additional FcRn-modifications to enhance FcRn-binding (and recycling) were also assessed in the assay, and the results are summarized in Table 4. The data show that FcRn-engineering can increase the ARC-fold shift, which is predictive for lower clearance in vivo.

A second in vitro assay, the Large molecule Unspecific Clearance Assay (LUCA) was used to assess antibody clearance in human primary endothelial cells. This assay relates the rate of mAb uptake into endothelial cells expressing endogenous amounts of FcRn, and provides a relative LUCA rate that is resulting from unspecific uptake, FcRn-recycling, and protein degradation. Bc1.187 has a relative LUCA rate of 0.05, indicating a rate of cellular accumulation in between standardization compounds, motavizumab-YTE (rel. LUCA rate of 0) and CD20-TCB (rel. LUCA rate of 1). This also points to predicted IgG-like properties for Bc1.187 in human. Additionally FcRn-engineered constructs based on Bc1.187 were tested in the assay, and the results are summarized in Table 4. As for the ARC-assay, it is predicted that FcRn-engineered constructs have a lower clearance in vivo.

Lastly, the in vivo pharmacokinetics of wild-type Bc1.187 IgG and FcRn-engineered Bc1.187 IgG constructs were assessed in transgenic mice expressing human neonatal Fc receptor (huFcRn-Tg mice), as these mice have shown to be predictive for human PK. (For further description of the mouse models, see 28. Proetzel et al. *Methods.* 2014; 65:148-53; Roopenian et al. *Methods Mol Biol.* 2016; 1438: 103-14; Avery L B et al. *MAbs.* 2016; 8:1064-78). All constructs were administered intravenously at a dose of 5 mg/kg, and the clearance parameters are summarized in Table 4. For all tested constructs, a clearance in the typical range for IgGs in these mice was observed. Taken together these in vitro and in vivo pharmacokinetics benchmarking studies indicate that neutralizing antibodies based on the Bc1.187 sequence are likely to display IgG-like pharmacokinetics in human. Protein engineering can lead to lower predicted clearance, which would confer significant advantages for neutralizing antibodies, as it is expected to translate to longer duration of HBsAg-neutralization, or longer dosing intervals in the clinic (i.e. increased convenience and compliance).

TABLE 4 summary of in vitro and in vivo assays to assess clearance processes

| | In vitro assays | | | | In vivo hFcRn-Tg |
|---|---|---|---|---|---|
| | ARC-assay | | | Luca-assay | mice |
| | ARC-score @pH = 6 | ARC-score @pH = 7.4 | ARC-fold shift | Relative LUCA rate | Clearance (mL/day/kg) |
| Bc1.187_huIgG1_wt | 4.97 | 0.28 | 17.8 | 0.05 | 8.70 |
| Bc1.187_huIgG1 YTE | 28.2 | 0.55 | 51.1 | −0.22 | 5.29 |
| Bc1.187_huIgG1_HH | 18.6 | 0.60 | 31.3 | −0.14 | 8.30 |
| Bc1.187_huIgG1_LAT | 20.9 | 0.55 | 38.4 | −0.25 | 6.24 |
| Bc1.187_huIgG1_N434A | 17.9 | 0.26 | 69.5 | −0.14 | 9.08 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An antibody that binds to small hepatitis B virus surface antigen (S-HBs), wherein the antibody comprises:

(i) a heavy chain variable domain (VH) comprising (a) CDR-H1 comprising the amino acid sequence of SEQ ID NO:1, (b) CDR-H2 comprising the amino acid sequence of SEQ ID NO:2, and (c) CDR-H3 comprising the amino acid sequence of SEQ ID NO:3, and a light chain variable domain (VL) comprising (d) CDR-L1 comprising the amino acid sequence of SEQ ID NO: 4, (e) CDR-L2 comprising the amino acid sequence of SEQ ID NO:5, and (f) CDR-L3 comprising the amino acid sequence of SEQ ID NO:6; or (ii) a heavy chain variable domain (VH) comprising (a) CDR-H1 comprising the amino acid sequence of SEQ ID NO:19, (b) CDR-H2 comprising the amino acid sequence of SEQ ID NO: 20, and (c) CDR-H3 comprising the amino acid sequence of SEQ ID NO:21, and a light chain variable domain (VL) comprising (d) CDR-L1 comprising the amino acid sequence of SEQ ID NO:22, (e) CDR-L2 comprising the amino acid sequence of SEQ ID NO:23, and (f) CDR-L3 comprising the amino acid sequence of SEQ ID NO:24; or (iii) a heavy chain variable domain (VH) comprising (a) CDR-H1 comprising the amino acid sequence of SEQ ID NO:37, (b) CDR-H2 comprising the amino acid sequence of SEQ ID NO: 38, and (c) CDR-H3 comprising the amino acid sequence of SEQ ID NO:39, and a light chain variable domain (VL) comprising (d) CDR-L1 comprising the amino acid sequence of SEQ ID NO:40, (e) CDR-L2 comprising the amino acid sequence of SEQ ID NO:41, and (f) CDR-L3 comprising the amino acid sequence of SEQ ID NO:42; or (iv) a heavy chain variable domain (VH) comprising (a) CDR-H1 comprising the amino acid sequence of SEQ ID NO:55, (b) CDR-H2 comprising the amino acid sequence of SEQ ID NO: 56, and (c) CDR-H3 comprising the amino acid sequence of SEQ ID NO:57, and a light chain variable domain (VL) comprising (d) CDR-L1 comprising the amino acid sequence of SEQ ID NO:58, (e) CDR-L2 comprising the amino acid sequence of SEQ ID NO:59, and (f) CDR-L3 comprising the amino acid sequence of SEQ ID NO:60; or (v) a heavy chain variable domain (VH) comprising (a) CDR-H1 comprising the amino acid sequence of SEQ ID NO:73, (b) CDR-H2 comprising the amino acid sequence of SEQ ID NO: 74, and (c) CDR-H3 comprising the amino acid sequence of SEQ ID NO:75, and a light chain variable domain (VL) comprising (d) CDR-L1 comprising the amino acid sequence of SEQ ID NO:76, (e) CDR-L2 comprising the amino acid sequence of SEQ ID NO:77, and (f) CDR-L3 comprising the amino acid sequence of SEQ ID NO:78; or (vi) a heavy chain variable domain (VH) comprising (a) CDR-H1 comprising the amino acid sequence of SEQ ID NO:91, (b) CDR-H2 comprising the amino acid sequence of SEQ ID NO: 92, and (c) CDR-H3 comprising the amino acid sequence of SEQ ID NO:93, and a light chain variable domain (VL) comprising (d) CDR-L1 comprising the amino acid sequence of SEQ ID NO:94, (e) CDR-L2 comprising the amino acid sequence of SEQ ID NO:95, and (f) CDR-L3 comprising the amino acid sequence of SEQ ID NO:96; or (vii) a heavy chain variable domain (VH) comprising (a) CDR-H1 comprising the amino acid sequence of SEQ ID NO:109, (b) CDR-H2 comprising the amino acid sequence of SEQ ID NO: 110, and (c) CDR-H3 comprising the amino acid sequence of SEQ ID NO:111, and a light chain variable domain (VL) comprising (d) CDR-L1 comprising the amino acid sequence of SEQ ID NO:112, (e) CDR-L2 comprising the amino acid sequence of SEQ ID NO:113, and (f) CDR-L3 comprising the amino acid sequence of SEQ ID NO:114; or (viii) a heavy chain variable domain (VH) comprising (a) CDR-H1 comprising the amino acid sequence of SEQ ID NO: 127, (b) CDR-H2 comprising the amino acid sequence of SEQ ID NO: 128, and (c) CDR-H3 comprising the amino acid sequence of SEQ ID NO:129, and a light chain variable domain (VL) comprising (d) CDR-L1 comprising the amino acid sequence of SEQ ID NO:130, (e) CDR-L2 comprising the amino acid sequence of SEQ ID NO:131, and (f) CDR-L3 comprising the amino acid sequence of SEQ ID NO:132; or (ix) a heavy chain variable domain (VH) comprising (a) CDR-H1 comprising the amino acid sequence of SEQ ID NO:145, (b) CDR-H2 comprising the amino acid sequence of SEQ ID NO: 146, and (c) CDR-H3 comprising the amino acid sequence of SEQ ID NO:147, and a light chain variable domain (VL) comprising (d) CDR-L1 comprising the amino acid sequence of SEQ ID NO:148, (e) CDR-L2 comprising the amino acid sequence of SEQ ID NO:149, and (f) CDR-L3 comprising the amino acid sequence of SEQ ID NO: 150; or (x) a heavy chain variable domain (VH) comprising (a) CDR-H1 comprising the amino acid sequence of SEQ ID NO:163, (b) CDR-H2 comprising the amino acid sequence of SEQ ID NO: 164, and (c) CDR-H3 comprising the amino acid sequence of SEQ ID NO:165, and a light chain variable domain (VL) comprising (d) CDR-L1 comprising the amino acid sequence of SEQ ID NO:166, (e) CDR-L2 comprising the amino acid sequence of SEQ ID NO:167, and (f) CDR-L3 comprising the amino acid sequence of SEQ ID NO:168; or (xi) a heavy chain variable domain (VH) comprising (a) CDR-H1 comprising the amino acid sequence of SEQ ID NO:181, (b) CDR-H2 comprising the amino acid sequence of SEQ ID NO: 182, and (c) CDR-H3 comprising the amino acid sequence of SEQ ID NO:183, and a light chain variable domain (VL) comprising (d) CDR-L1 comprising the amino acid sequence of SEQ ID NO:184, (e) CDR-L2 comprising the amino acid sequence of SEQ ID NO:185, and (f) CDR-L3 comprising the amino acid sequence of SEQ ID NO: 186; or (xii) a heavy chain variable domain (VH) comprising (a) CDR-H1 comprising the amino acid sequence of SEQ ID NO:199, (b) CDR-H2 comprising the amino acid sequence of SEQ ID NO: 200, and (c) CDR-H3 comprising the amino acid sequence of SEQ ID NO:201, and a light chain variable domain (VL) comprising (d) CDR-L1 comprising the amino acid sequence of SEQ ID NO:202, (e) CDR-L2 comprising the amino acid sequence of SEQ ID NO:203, and (f) CDR-L3 comprising the amino acid sequence of SEQ ID NO:204; or (xiii) a heavy chain variable domain (VH) comprising (a) CDR-H1 comprising the amino acid sequence of SEQ ID NO:217, (b) CDR-H2 comprising the amino acid sequence of SEQ ID NO: 218, and (c) CDR-H3 comprising the amino acid sequence of SEQ ID NO:219, and a light chain variable domain (VL) comprising (d) CDR-L1 comprising the amino acid sequence of SEQ ID NO:220, (e) CDR-L2 comprising the amino acid sequence of SEQ ID NO:221, and (f) CDR-L3 comprising the amino acid sequence of SEQ ID NO:222; or (xiv) a heavy chain variable domain (VH) comprising (a) CDR-H1 comprising the amino acid sequence of SEQ ID NO:235, (b) CDR-H2 comprising the amino acid sequence of SEQ ID NO: 236, and (c) CDR-H3 comprising the amino acid sequence of SEQ ID NO:237, and a light chain variable domain (VL) comprising (d) CDR-L1 comprising the amino acid sequence of SEQ ID NO:238, (e) CDR-L2 comprising the amino acid sequence of SEQ ID NO:239, and (f) CDR-L3 comprising the amino acid sequence of SEQ ID NO:240.

2. The antibody of claim 1, wherein the antibody comprises:

(a) a VH sequence of SEQ ID NO: 34 and a VL sequence of SEQ ID NO: 33; or (b) a VH sequence of SEQ ID NO: 52 and a VL sequence of SEQ ID NO: 51; or (c) a VH sequence of SEQ ID NO: 70 and a VL sequence of SEQ ID NO: 69; or (d) a VH sequence of SEQ ID NO: 88 and a VL sequence of SEQ ID NO: 87; or (e) a VH sequence of SEQ ID NO: 106 and a VL sequence of SEQ ID NO: 105; or (f) a VH sequence of SEQ ID NO: 124 and a VL sequence of SEQ ID NO: 123; or (g) a VH sequence of SEQ ID NO: 142 and a VL sequence of SEQ ID NO: 141; or (h) a VH sequence of SEQ ID NO: 160 and a VL sequence of SEQ ID NO: 159; or (i) a VH sequence of SEQ ID NO: 178 and a VL sequence of SEQ ID NO: 177; or (j) a VH sequence of SEQ ID NO: 196 and a VL sequence of SEQ ID NO: 195; or (k) a VH sequence of SEQ ID NO: 214 and a VL sequence of SEQ ID NO: 213; or (l) a VH sequence of SEQ ID NO: 232 and a VL sequence of SEQ ID NO: 231; or (m) a VH sequence of SEQ ID NO: 250 and a VL sequence of SEQ ID NO: 249.

3. An antibody that binds to small hepatitis B virus surface antigen (S-HBs), wherein the antibody comprises a heavy chain variable domain (VH) comprising (a) CDR-H1 comprising the amino acid sequence of SEQ ID NO:1, (b) CDR-H2 comprising the amino acid sequence of SEQ ID NO:2, and (c) CDR-H3 comprising the amino acid sequence of SEQ ID NO:3, and a light chain variable domain (VL) comprising (d) CDR-L1 comprising the amino acid sequence of SEQ ID NO:4, (e) CDR-L2 comprising the amino acid sequence of SEQ ID NO:5, and (f) CDR-L3 comprising the amino acid sequence of SEQ ID NO:6.

4. The antibody of claim 3, comprising a sequence selected from the group consisting of (a) a VH sequence having at least 95% sequence identity to the amino acid sequence of SEQ ID NO:16;

(b) a VL sequence having at least 95% sequence identity to the amino acid sequence of SEQ ID NO:15; and (c) a VH sequence as defined in (a) and a VL sequence as defined in (b).

5. The antibody of claim 3, comprising a VH sequence of SEQ ID NO: 16 and a VL sequence of SEQ ID NO: 15.

6. The antibody of claim 3, which has neutralizing activity against a genome D HBV in vivo or in vitro.

7. The antibody of claim 3, which is a monoclonal antibody.

8. The antibody of claim 3, which is a human or chimeric antibody.

9. The antibody of claim 3, which is an antibody fragment that binds S-HBs.

10. The antibody of claim 3, which is a full-length IgG antibody.

11. The antibody of claim 3 comprising a heavy chain of SEQ ID NO:18 or 263 and a light chain of SEQ ID NO:17.

12. The antibody of claim 10, comprising an Fc region with one or more substitutions therein which improve binding of the Fc region to FcRn.

13. The antibody of claim 12, wherein said substitutions are selected from the group consisting of:

i) M252Y, S254T and T256E;
ii) M428L, N434A and Y436T;
iii) N434A; and
iv) T307H and N434H.

14. An antibody of claim 13, comprising a light chain of SEQ ID NO: 17 and a heavy chain of SEQ ID NO: 18 or 263 modified by substitutions selected from the group consisting of:

i) M252Y, S254T and T256E;
ii) M428L, N434A and Y436T;
iii) N434A; and
iv) T307H and N434H.

15. An isolated nucleic acid encoding the antibody of claim 3.

16. A host cell comprising the nucleic acid of claim 15.

17. A method of producing an antibody that binds to S-HBs comprising culturing the host cell of claim 16 under conditions suitable for the expression of the antibody.

18. The method of claim 17, further comprising recovering the antibody from the host cell.

19. A pharmaceutical composition comprising the antibody of claim 3 and a pharmaceutically acceptable carrier.

20. The pharmaceutical composition of claim 19, further comprising an additional therapeutic agent.

21. The pharmaceutical composition of claim 20, wherein the additional therapeutic agent is selected from: an siRNA targeted to an HBV sequence; a nucleotide analog reverse-transcriptase inhibitor or a nucleoside analogue, INFα or pegylated INF-α; a therapeutic vaccine; a TLR agonist; and/or a checkpoint inhibitor.

22. A method of treating an individual having hepatitis B comprising administering to the individual an effective amount of the antibody of claim 3.

23. The method of claim 22 further comprising administering an additional therapeutic agent to the individual.

24. The method of claim 23, wherein the additional therapeutic agent is selected from the group consisting of: an siRNA targeted to an HBV sequence; a nucleotide analog reverse-transcriptase inhibitor or a nucleoside analogue; INFα or pegylated IFN-α; a therapeutic vaccine; a TLR agonist; and/or a checkpoint inhibitor.

25. The method of claim 22, wherein said hepatitis B is chronic hepatitis B.

* * * * *

SEQUENCE LISTING

```
<160> NUMBER OF SEQ ID NOS: 434

<210> SEQ ID NO 1
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 1

Asn Tyr Gly Met Gln
1               5


<210> SEQ ID NO 2
<211> LENGTH: 17
```

<212> TYPE: PRT
<213> ORGANISM: Artificial Sequence
<220> FEATURE:
<223> OTHER INFORMATION: The sequence is artificially synthesized

<400> SEQUENCE: 2

Ile Ile Trp Ala Asp Gly Thr Lys Gln Tyr Tyr Gly Asp Ser Val Lys
1 5 10 15

Gly

<210> SEQ ID NO 3
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 3

Asp Gly Leu Tyr Ala Ser Ala Pro Asn Asp Val
1 5 10

<210> SEQ ID NO 4
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 4

Arg Ala Ser Gln Arg Ile Ser Thr Tyr Leu Asn
1 5 10

<210> SEQ ID NO 5
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 5

Gly Ala Ser Ser Leu Gln Ser
1 5

<210> SEQ ID NO 6
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 6

Gln Gln Thr Tyr Thr Leu Pro Pro Asn
1 5

<210> SEQ ID NO 7
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 7

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser
20 25 30

<210> SEQ ID NO 8
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 8

Trp Val Arg Gln Ala Pro Gly Lys Gly Leu Glu Trp Val Ala
1 5 10

<210> SEQ ID NO 9
<211> LENGTH: 31
<212> TYPE: PRT
<213> ORGANISM: Artificial Sequence
<220> FEATURE:
<223> OTHER INFORMATION: The sequence is artificially synthesized

<400> SEQUENCE: 9

Phe Thr Ile Ser Arg Asp Asn Phe Lys Asn Thr Leu Tyr Leu Gln Met
1 5 10 15

Asn Ser Leu Arg Gly Glu Asp Thr Ala Met Tyr Phe Cys Ala Arg
20 25 30

<210> SEQ ID NO 10
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 10

Trp Gly Gln Gly Thr Leu Val Thr Val Ser Ser
1 5 10

<210> SEQ ID NO 11
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 11

Asp Ile Gln Met Thr Gln Ser Pro Ser Ser Leu Ser Ala Tyr Val Gly
1 5 10 15

Asp Arg Val Thr Ile Thr Cys
20

<210> SEQ ID NO 12
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 12

Trp Tyr His Gln Arg Pro Gly Lys Ser Pro Ser Leu Leu Ile Tyr
1 5 10 15

<210> SEQ ID NO 13
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 13

Gly Val Pro Ser Arg Phe Ser Ala Ser Ala Ser Gly Thr Asp Phe Thr
1               5                   10                  15

Leu Thr Ile Ser Ser Leu Arg Pro Glu Asp Leu Gly Thr Tyr Tyr Cys
            20                  25                  30

<210> SEQ ID NO 14
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 14

Ser Gly Gly Gly Thr Lys Val Glu Ile Lys
1               5                   10

<210> SEQ ID NO 15
<211> LENGTH: 107
<212> TYPE: PRT
<213> ORGANISM: Artificial Sequence
<220> FEATURE:
<223> OTHER INFORMATION: The sequence is artificially synthesized

<400> SEQUENCE: 15

Asp Ile Gln Met Thr Gln Ser Pro Ser Ser Leu Ser Ala Tyr Val Gly
1               5                   10                  15

Asp Arg Val Thr Ile Thr Cys Arg Ala Ser Gln Arg Ile Ser Thr Tyr
            20                  25                  30

Leu Asn Trp Tyr His Gln Arg Pro Gly Lys Ser Pro Ser Leu Leu Ile
        35                  40                  45

Tyr Gly Ala Ser Ser Leu Gln Ser Gly Val Pro Ser Arg Phe Ser Ala
    50                  55                  60

Ser Ala Ser Gly Thr Asp Phe Thr Leu Thr Ile Ser Ser Leu Arg Pro
65                  70                  75                  80

Glu Asp Leu Gly Thr Tyr Tyr Cys Gln Gln Thr Tyr Thr Leu Pro Pro
                85                  90                  95

Asn Ser Gly Gly Gly Thr Lys Val Glu Ile Lys
            100                 105

<210> SEQ ID NO 16
<211> LENGTH: 120
<212> TYPE: PRT
<213> ORGANISM: Artificial Sequence
<220> FEATURE:
<223> OTHER INFORMATION: The sequence is artificially synthesized

<400> SEQUENCE: 16

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Asn Tyr
            20                  25                  30

Gly Met Gln Trp Val Arg Gln Ala Pro Gly Lys Gly Leu Glu Trp Val
        35                  40                  45

Ala Ile Ile Trp Ala Asp Gly Thr Lys Gln Tyr Tyr Gly Asp Ser Val
    50                  55                  60

Lys Gly Arg Phe Thr Ile Ser Arg Asp Asn Phe Lys Asn Thr Leu Tyr
65                  70                  75                  80

Leu Gln Met Asn Ser Leu Arg Gly Glu Asp Thr Ala Met Tyr Phe Cys

```
                85                  90                  95

Ala Arg Asp Gly Leu Tyr Ala Ser Ala Pro Asn Asp Val Trp Gly Gln
            100                 105                 110

Gly Thr Leu Val Thr Val Ser Ser
        115                 120


<210> SEQ ID NO 17
<211> LENGTH: 214
<212> TYPE: PRT
<213> ORGANISM: Artificial Sequence
<220> FEATURE:
<223> OTHER INFORMATION: The sequence is artificially synthesized

<400> SEQUENCE: 17

Asp Ile Gln Met Thr Gln Ser Pro Ser Ser Leu Ser Ala Tyr Val Gly
1               5                   10                  15

Asp Arg Val Thr Ile Thr Cys Arg Ala Ser Gln Arg Ile Ser Thr Tyr
            20                  25                  30

Leu Asn Trp Tyr His Gln Arg Pro Gly Lys Ser Pro Ser Leu Leu Ile
        35                  40                  45

Tyr Gly Ala Ser Ser Leu Gln Ser Gly Val Pro Ser Arg Phe Ser Ala
    50                  55                  60

Ser Ala Ser Gly Thr Asp Phe Thr Leu Thr Ile Ser Ser Leu Arg Pro
65                  70                  75                  80

Glu Asp Leu Gly Thr Tyr Tyr Cys Gln Gln Thr Tyr Thr Leu Pro Pro
                85                  90                  95

Asn Ser Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 18
<211> LENGTH: 450
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (344)..(344)
<223> OTHER INFORMATION: Xaa can be  Gly or absent

<400> SEQUENCE: 18

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Asn Tyr
            20                  25                  30
```

```
Gly Met Gln Trp Val Arg Gln Ala Pro Gly Lys Gly Leu Glu Trp Val
        35                  40                  45

Ala Ile Ile Trp Ala Asp Gly Thr Lys Gln Tyr Tyr Gly Asp Ser Val
    50                  55                  60

Lys Gly Arg Phe Thr Ile Ser Arg Asp Asn Phe Lys Asn Thr Leu Tyr
65                  70                  75                  80

Leu Gln Met Asn Ser Leu Arg Gly Glu Asp Thr Ala Met Tyr Phe Cys
                85                  90                  95

Ala Arg Asp Gly Leu Tyr Ala Ser Ala Pro Asn Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Xaa Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly Lys
450

<210> SEQ ID NO 19
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 19

Arg Ser Ala Val Ser
1 5

<210> SEQ ID NO 20
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 20

Arg Thr Ile Pro Leu Leu Arg Ile Ala Glu Tyr Ser Gln Thr Phe Gln
1 5 10 15

Gly

<210> SEQ ID NO 21
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 21

Glu Gly Asp Gly Leu Asp Met
1 5

<210> SEQ ID NO 22
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 22

Arg Ala Ser Gln Ser Val Thr Ser Asn Tyr Phe Ala
1 5 10

<210> SEQ ID NO 23
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 23

Gly Ala Ser Ser Arg Ala Thr
1 5

<210> SEQ ID NO 24
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 24

Gln Gln Phe Gly Ser Leu Pro Tyr Thr
1 5

<210> SEQ ID NO 25
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 25

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Gly
20 25 30

<210> SEQ ID NO 26
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 26

Trp Val Arg His Ala Pro Gly Gln Arg Leu Glu Trp Met Gly
1 5 10

<210> SEQ ID NO 27
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 27

Arg Val Thr Ile Thr Ala Asp Lys Phe Thr Asn Thr Val Tyr Met Glu
1 5 10 15

Leu Arg Ser Leu Thr Tyr Glu Asp Thr Ala Val Tyr Tyr Cys Ala Arg
20 25 30

<210> SEQ ID NO 28
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 28

Trp Gly Gln Gly Thr Met Val Thr Val Ser Ser
1 5 10

<210> SEQ ID NO 29
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 29

Glu Ile Val Leu Thr Gln Ser Pro Gly Thr Leu Ser Leu Ser Pro Gly
1 5 10 15

Asn Arg Ala Thr Leu Ser Cys
20

<210> SEQ ID NO 30
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 30

```
Trp Tyr Gln His Lys Pro Gly Gln Ala Pro Arg Val Leu Ile Tyr
1               5                   10                  15
```

<210> SEQ ID NO 31
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 31

```
Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30
```

<210> SEQ ID NO 32
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 32

```
Phe Gly Gln Gly Thr Lys Leu Glu Ile Lys
1               5                   10
```

<210> SEQ ID NO 33
<211> LENGTH: 108
<212> TYPE: PRT
<213> ORGANISM: Artificial Sequence
<220> FEATURE:
<223> OTHER INFORMATION: The sequence is artificially synthesized

<400> SEQUENCE: 33

```
Glu Ile Val Leu Thr Gln Ser Pro Gly Thr Leu Ser Leu Ser Pro Gly
1               5                   10                  15

Asn Arg Ala Thr Leu Ser Cys Arg Ala Ser Gln Ser Val Thr Ser Asn
            20                  25                  30

Tyr Phe Ala Trp Tyr Gln His Lys Pro Gly Gln Ala Pro Arg Val Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Leu Pro
                85                  90                  95

Tyr Thr Phe Gly Gln Gly Thr Lys Leu Glu Ile Lys
            100                 105
```

<210> SEQ ID NO 34
<211> LENGTH: 116
<212> TYPE: PRT
<213> ORGANISM: Artificial Sequence
<220> FEATURE:
<223> OTHER INFORMATION: The sequence is artificially synthesized

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Arg Ser
            20                  25                  30

Ala Val Ser Trp Val Arg His Ala Pro Gly Gln Arg Leu Glu Trp Met
        35                  40                  45

Gly Arg Thr Ile Pro Leu Leu Arg Ile Ala Glu Tyr Ser Gln Thr Phe
    50                  55                  60

Gln Gly Arg Val Thr Ile Thr Ala Asp Lys Phe Thr Asn Thr Val Tyr
65                  70                  75                  80

Met Glu Leu Arg Ser Leu Thr Tyr Glu Asp Thr Ala Val Tyr Tyr Cys
                85                  90                  95

Ala Arg Glu Gly Asp Gly Leu Asp Met Trp Gly Gln Gly Thr Met Val
            100                 105                 110

Thr Val Ser Ser
        115

<210> SEQ ID NO 35
<211> LENGTH: 215
<212> TYPE: PRT
<213> ORGANISM: Artificial Sequence
<220> FEATURE:
<223> OTHER INFORMATION: The sequence is artificially synthesized

<400> SEQUENCE: 35

Glu Ile Val Leu Thr Gln Ser Pro Gly Thr Leu Ser Leu Ser Pro Gly
1               5                   10                  15

Asn Arg Ala Thr Leu Ser Cys Arg Ala Ser Gln Ser Val Thr Ser Asn
            20                  25                  30

Tyr Phe Ala Trp Tyr Gln His Lys Pro Gly Gln Ala Pro Arg Val Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Leu Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 36
<211> LENGTH: 446
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (340)..(340)
<223> OTHER INFORMATION: Xaa can be Gly or absent

<400> SEQUENCE: 36

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Arg Ser
            20                  25                  30

Ala Val Ser Trp Val Arg His Ala Pro Gly Gln Arg Leu Glu Trp Met
        35                  40                  45

Gly Arg Thr Ile Pro Leu Leu Arg Ile Ala Glu Tyr Ser Gln Thr Phe
    50                  55                  60

Gln Gly Arg Val Thr Ile Thr Ala Asp Lys Phe Thr Asn Thr Val Tyr
65                  70                  75                  80

Met Glu Leu Arg Ser Leu Thr Tyr Glu Asp Thr Ala Val Tyr Tyr Cys
                85                  90                  95

Ala Arg Glu Gly Asp Gly Leu Asp Met Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Xaa Gln Pro Arg Glu Pro Gln Val Tyr Thr Leu Pro Pro
            340                 345                 350
```

Ser Arg Asp Glu Leu Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 37
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 37

Ser Tyr Ala Met Ser
1 5

<210> SEQ ID NO 38
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 38

Ala Phe Ser Gly Thr Gly Gly Ser Thr Tyr Tyr Ala Asp Ser Val Lys
1 5 10 15

Gly

<210> SEQ ID NO 39
<211> LENGTH: 19
<212> TYPE: PRT
<213> ORGANISM: Artificial Sequence
<220> FEATURE:
<223> OTHER INFORMATION: The sequence is artificially synthesized

<400> SEQUENCE: 39

Asp Pro Gly His Thr Ser Asn Trp Arg Asp Asn Tyr Gln Tyr Tyr Gln
1 5 10 15

Met Asp Val

<210> SEQ ID NO 40
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 40

Arg Ala Ser Gln Gly Ile Arg Asn Asp Leu Gly
1 5 10

<210> SEQ ID NO 41
<211> LENGTH: 7
<212> TYPE: PRT

<213> ORGANISM: Artificial Sequence
<220> FEATURE:
<223> OTHER INFORMATION: The sequence is artificially synthesized

<400> SEQUENCE: 41

Ala Ala Ser Ser Leu Gln Ser
1 5

<210> SEQ ID NO 42
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 42

Leu Gln His Asn Ser Tyr Pro Arg Thr
1 5

<210> SEQ ID NO 43
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 43

Glu Val Gln Leu Leu Glu Ser Gly Gly Gly Leu Val Gln Pro Gly Gly
1 5 10 15

Ser Leu Arg Leu Ser Cys Thr Ala Ser Gly Phe Thr Phe Gly
20 25 30

<210> SEQ ID NO 44
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 44

Trp Val Arg Gln Ala Pro Gly Lys Gly Leu Lys Trp Val Ser
1 5 10

<210> SEQ ID NO 45
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 45

Arg Phe Thr Ile Ser Arg Asp Asn Ser Lys Asn Thr Leu Tyr Leu Gln
1 5 10 15

Met Asn Asn Leu Arg Ala Glu Asp Thr Ala Val Tyr Phe Cys Ala Lys
20 25 30

<210> SEQ ID NO 46
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 46

Trp Gly Gln Gly Thr Thr Val Thr Val Ser Ser
1 5 10

<210> SEQ ID NO 47
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 47

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 48
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 48

```
Trp Tyr Gln Gln Lys Pro Gly Lys Ala Pro Lys Arg Leu Ile Tyr
1               5                   10                  15
```

<210> SEQ ID NO 49
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 49

```
Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 50
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 50

```
Phe Gly Gln Gly Thr Lys Val Glu Ile Lys
1               5                   10
```

<210> SEQ ID NO 51
<211> LENGTH: 107
<212> TYPE: PRT
<213> ORGANISM: Artificial Sequence
<220> FEATURE:
<223> OTHER INFORMATION: The sequence is artificially synthesized

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
```

```
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105


<210> SEQ ID NO 52
<211> LENGTH: 128
<212> TYPE: PRT
<213> ORGANISM: Artificial Sequence
<220> FEATURE:
<223> OTHER INFORMATION: The sequence is artificially synthesized

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Gly Ser Tyr
            20                  25                  30

Ala Met Ser Trp Val Arg Gln Ala Pro Gly Lys Gly Leu Lys Trp Val
        35                  40                  45

Ser Ala Phe Ser Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Phe Cys
                85                  90                  95

Ala Lys Asp Pro Gly His Thr Ser Asn Trp Arg Asp Asn Tyr Gln Tyr
            100                 105                 110

Tyr Gln Met Asp Val Trp Gly Gln Gly Thr Thr Val Thr Val Ser Ser
        115                 120                 125


<210> SEQ ID NO 53
<211> LENGTH: 214
<212> TYPE: PRT
<213> ORGANISM: Artificial Sequence
<220> FEATURE:
<223> OTHER INFORMATION: The sequence is artificially synthesized

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 54
<211> LENGTH: 458
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (352)..(352)
<223> OTHER INFORMATION: Xaa can be  Gly or absent

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Gly Ser Tyr
            20                  25                  30

Ala Met Ser Trp Val Arg Gln Ala Pro Gly Lys Gly Leu Lys Trp Val
        35                  40                  45

Ser Ala Phe Ser Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Phe Cys
                85                  90                  95

Ala Lys Asp Pro Gly His Thr Ser Asn Trp Arg Asp Asn Tyr Gln Tyr
            100                 105                 110

Tyr Gln Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255
```

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu
290 295 300

Glu Gln Tyr Asn Ser Thr Tyr Arg Val Val Ser Val Leu Thr Val Leu
305 310 315 320

His Gln Asp Trp Leu Asn Gly Lys Glu Tyr Lys Cys Lys Val Ser Asn
325 330 335

Lys Ala Leu Pro Ala Pro Ile Glu Lys Thr Ile Ser Lys Ala Lys Xaa
340 345 350

Gln Pro Arg Glu Pro Gln Val Tyr Thr Leu Pro Pro Ser Arg Asp Glu
355 360 365

Leu Thr Lys Asn Gln Val Ser Leu Thr Cys Leu Val Lys Gly Phe Tyr
370 375 380

Pro Ser Asp Ile Ala Val Glu Trp Glu Ser Asn Gly Gln Pro Glu Asn
385 390 395 400

Asn Tyr Lys Thr Thr Pro Pro Val Leu Asp Ser Asp Gly Ser Phe Phe
405 410 415

Leu Tyr Ser Lys Leu Thr Val Asp Lys Ser Arg Trp Gln Gln Gly Asn
420 425 430

Val Phe Ser Cys Ser Val Met His Glu Ala Leu His Asn His Tyr Thr
435 440 445

Gln Lys Ser Leu Ser Leu Ser Pro Gly Lys
450 455

<210> SEQ ID NO 55
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 55

Gly Tyr Gly Met His
1 5

<210> SEQ ID NO 56
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 56

Phe Leu Trp His Asp Gly Thr Ser Lys Asp Tyr Ala Asp Ser Val Lys
1 5 10 15

Gly

<210> SEQ ID NO 57
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 57

Glu Asp Tyr Tyr Asp Ser Asn Ala Phe Asp Tyr 1 5 10

<210> SEQ ID NO 58
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 58

Thr Gly Thr Ser Ser Asp Val Gly Asn Tyr Lys Ser Val Ser
1 5 10

<210> SEQ ID NO 59
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 59

Glu Gly Thr Gln Arg Pro Ser
1 5

<210> SEQ ID NO 60
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 60

Cys Ser Tyr Ala Gly Ser Ser Thr Trp Leu
1 5 10

<210> SEQ ID NO 61
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 61

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser
20 25 30

<210> SEQ ID NO 62
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 62

Trp Val Arg Gln Ala Pro Gly Lys Gly Leu Glu Trp Val Ala
1 5 10

<210> SEQ ID NO 63
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 63

Arg Phe Thr Ile Ser Arg Asp Asn Ser Lys Asn Thr Leu Tyr Met Gln
1 5 10 15

Met Asn Ser Leu Arg Ala Glu Asp Thr Ala Val Tyr Tyr Cys Ala Arg
20 25 30

<210> SEQ ID NO 64
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 64

Trp Gly Gln Gly Thr Leu Val Thr Val Ser Ser
1 5 10

<210> SEQ ID NO 65
<211> LENGTH: 22
<212> TYPE: PRT
<213> ORGANISM: Artificial Sequence
<220> FEATURE:
<223> OTHER INFORMATION: The sequence is artificially synthesized

<400> SEQUENCE: 65

Gln Ser Ala Leu Thr Gln Pro Ala Ser Val Ser Gly Ser Pro Gly Gln
1 5 10 15

Ser Ile Thr Ile Ser Cys
20

<210> SEQ ID NO 66
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 66

Trp Tyr Gln His His Pro Gly Lys Ala Pro Lys Phe Met Ile Tyr
1 5 10 15

<210> SEQ ID NO 67
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 67

Gly Val Ser Asn Arg Phe Ser Gly Ser Lys Ser Gly Asn Thr Ala Ser
1 5 10 15

Leu Thr Ile Ser Gly Leu Gln Ala Glu Asp Glu Ala His Tyr Tyr Cys
20 25 30

<210> SEQ ID NO 68
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 68

Phe Gly Gly Gly Thr Lys Leu Thr Val Leu
1 5 10

<210> SEQ ID NO 69
<211> LENGTH: 110
<212> TYPE: PRT
<213> ORGANISM: Artificial Sequence
<220> FEATURE:
<223> OTHER INFORMATION: The sequence is artificially synthesized

<400> SEQUENCE: 69

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Asn Tyr
20 25 30

Lys Ser Val Ser Trp Tyr Gln His His Pro Gly Lys Ala Pro Lys Phe
35 40 45

Met Ile Tyr Glu Gly Thr Gln Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala His Tyr Tyr Cys Cys Ser Tyr Ala Gly Ser
85 90 95

Ser Thr Trp Leu Phe Gly Gly Gly Thr Lys Leu Thr Val Leu
100 105 110

<210> SEQ ID NO 70
<211> LENGTH: 120
<212> TYPE: PRT
<213> ORGANISM: Artificial Sequence
<220> FEATURE:
<223> OTHER INFORMATION: The sequence is artificially synthesized

<400> SEQUENCE: 70

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Gly Tyr
20 25 30

Gly Met His Trp Val Arg Gln Ala Pro Gly Lys Gly Leu Glu Trp Val
35 40 45

Ala Phe Leu Trp His Asp Gly Thr Ser Lys Asp Tyr Ala Asp Ser Val
50 55 60

Lys Gly Arg Phe Thr Ile Ser Arg Asp Asn Ser Lys Asn Thr Leu Tyr
65 70 75 80

Met Gln Met Asn Ser Leu Arg Ala Glu Asp Thr Ala Val Tyr Tyr Cys
85 90 95

Ala Arg Glu Asp Tyr Tyr Asp Ser Asn Ala Phe Asp Tyr Trp Gly Gln
100 105 110

Gly Thr Leu Val Thr Val Ser Ser
115 120

<210> SEQ ID NO 71
<211> LENGTH: 216
<212> TYPE: PRT
<213> ORGANISM: Artificial Sequence
<220> FEATURE:
<223> OTHER INFORMATION: The sequence is artificially synthesized

<400> SEQUENCE: 71

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Asn Tyr
20 25 30

```
Lys Ser Val Ser Trp Tyr Gln His His Pro Gly Lys Ala Pro Lys Phe
        35                  40                  45

Met Ile Tyr Glu Gly Thr Gln Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala His Tyr Tyr Cys Cys Ser Tyr Ala Gly Ser
                85                  90                  95

Ser Thr Trp Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 72
<211> LENGTH: 450
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (344)..(344)
<223> OTHER INFORMATION: Xaa can be  Gly or absent

<400> SEQUENCE: 72

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Phe Leu Trp His Asp Gly Thr Ser Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Met Gln Met Asn Ser Leu Arg Ala Glu Asp Thr Ala Val Tyr Tyr Cys
                85                  90                  95

Ala Arg Glu Asp Tyr Tyr Asp Ser Asn Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Xaa Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 73
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 73

Arg Tyr Ala Met Ser
1               5


<210> SEQ ID NO 74
<211> LENGTH: 17
<212> TYPE: PRT
<213> ORGANISM: Artificial Sequence
<220> FEATURE:
<223> OTHER INFORMATION: The sequence is artificially synthesized
```

<400> SEQUENCE: 74

Ala Thr Ser Gly Ser Gly Ala Asp Thr Tyr Tyr Ala Asp Ser Val Lys
1               5                   10                  15

Gly

<210> SEQ ID NO 75
<211> LENGTH: 13
<212> TYPE: PRT
<213> ORGANISM: Artificial Sequence
<220> FEATURE:
<223> OTHER INFORMATION: The sequence is artificially synthesized

<400> SEQUENCE: 75

Pro Tyr Met Val Ala Ala Val Ala Arg Thr Val Asp Tyr
1               5                   10

<210> SEQ ID NO 76
<211> LENGTH: 13
<212> TYPE: PRT
<213> ORGANISM: Artificial Sequence
<220> FEATURE:
<223> OTHER INFORMATION: The sequence is artificially synthesized

<400> SEQUENCE: 76

Thr Arg Ser Ser Gly Ser Ile Ala Ser Asn Tyr Val Gln
1               5                   10

<210> SEQ ID NO 77
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 77

Glu Asp Asn Glu Arg Pro Ser
1               5

<210> SEQ ID NO 78
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 78

Gln Ser Tyr Glu Ser Ser Asn Trp Val
1               5

<210> SEQ ID NO 79
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 80
<211> LENGTH: 14

<212> TYPE: PRT
<213> ORGANISM: Artificial Sequence
<220> FEATURE:
<223> OTHER INFORMATION: The sequence is artificially synthesized

<400> SEQUENCE: 80

```
Trp Val Arg Gln Ala Pro Gly Lys Gly Leu Glu Trp Val Ser
1               5                   10
```

<210> SEQ ID NO 81
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 81

```
Arg Phe Thr Ile Ser Arg Asp Asn Ser Lys Asn Thr Val Tyr Leu Gln
1               5                   10                  15

Met Asn Ser Leu Arg Ala Asp Asp Thr Ala Phe Tyr Tyr Cys Ala Lys
            20                  25                  30
```

<210> SEQ ID NO 82
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 82

```
Trp Gly Gln Gly Thr Leu Val Thr Val Ser Ser
1               5                   10
```

<210> SEQ ID NO 83
<211> LENGTH: 22
<212> TYPE: PRT
<213> ORGANISM: Artificial Sequence
<220> FEATURE:
<223> OTHER INFORMATION: The sequence is artificially synthesized

<400> SEQUENCE: 83

```
Gln Ser Val Leu Thr Gln Pro His Ser Val Ser Glu Ser Pro Gly Lys
1               5                   10                  15

Thr Val Thr Ile Ser Cys
            20
```

<210> SEQ ID NO 84
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 84

```
Trp Tyr Gln Gln Arg Pro Gly Ser Ala Pro Thr Thr Val Ile Tyr
1               5                   10                  15
```

<210> SEQ ID NO 85
<211> LENGTH: 34
<212> TYPE: PRT
<213> ORGANISM: Artificial Sequence
<220> FEATURE:
<223> OTHER INFORMATION: The sequence is artificially synthesized

<400> SEQUENCE: 85

```
Gly Val Pro Ala Arg Phe Ser Gly Ser Ile Asp Ser Ser Ser Asn Ser
```

```
1               5                   10                  15

Ala Ser Leu Thr Ile Ser Gly Leu Lys Thr Glu Asp Glu Ala Asp Tyr
            20                  25                  30

Tyr Cys


<210> SEQ ID NO 86
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 86

Phe Gly Gly Gly Thr Lys Leu Thr Val Leu
1               5                   10


<210> SEQ ID NO 87
<211> LENGTH: 110
<212> TYPE: PRT
<213> ORGANISM: Artificial Sequence
<220> FEATURE:
<223> OTHER INFORMATION: The sequence is artificially synthesized

<400> SEQUENCE: 87

Gln Ser Val Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Glu Arg Pro Ser Gly Val Pro Ala Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Glu Ser
                85                  90                  95

Ser Asn Trp Val Phe Gly Gly Gly Thr Lys Leu Thr Val Leu
            100                 105                 110


<210> SEQ ID NO 88
<211> LENGTH: 123
<212> TYPE: PRT
<213> ORGANISM: Artificial Sequence
<220> FEATURE:
<223> OTHER INFORMATION: The sequence is artificially synthesized

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ala Thr Ser Gly Ser Gly Ala Asp Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Asp Asp Thr Ala Phe Tyr Tyr Cys
                85                  90                  95
```

```
Ala Lys Asp Pro Tyr Met Val Ala Ala Val Ala Arg Thr Val Asp Tyr
            100                 105                 110

Trp Gly Gln Gly Thr Leu Val Thr Val Ser Ser
        115                 120


<210> SEQ ID NO 89
<211> LENGTH: 216
<212> TYPE: PRT
<213> ORGANISM: Artificial Sequence
<220> FEATURE:
<223> OTHER INFORMATION: The sequence is artificially synthesized

<400> SEQUENCE: 89

Gln Ser Val Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Glu Arg Pro Ser Gly Val Pro Ala Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Glu Ser
                85                  90                  95

Ser Asn Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 90
<211> LENGTH: 453
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (347)..(347)
<223> OTHER INFORMATION: Xaa can be  Gly or absent

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
```

```
        35                  40                  45

Ser Ala Thr Ser Gly Ser Gly Ala Asp Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Asp Asp Thr Ala Phe Tyr Tyr Cys
                85                  90                  95

Ala Lys Asp Pro Tyr Met Val Ala Ala Val Ala Arg Thr Val Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Xaa Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 91
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 91

Asn Tyr Gly Val Thr
1 5

<210> SEQ ID NO 92
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 92

Gly Ile Ile Pro Ile Phe Gly Thr Thr Asn Tyr Ala Gln Lys Phe Leu
1 5 10 15

Gly

<210> SEQ ID NO 93
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 93

Gln Gly Ser Ser Thr Trp Phe Ala Thr Leu Tyr Ala Phe Pro Ile
1 5 10 15

<210> SEQ ID NO 94
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 94

Arg Ala Ser Gln Arg Val Ser Gly Asn Tyr Leu Ala
1 5 10

<210> SEQ ID NO 95
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 95

Gly Ala Ser Ser Arg Ala Thr
1 5

<210> SEQ ID NO 96
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 96

His Gln Tyr Gly Ser Ser Pro Pro Thr 1 5

<210> SEQ ID NO 97
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 97

Gln Val Gln Leu Val Gln Ser Gly Ala Glu Val Lys Lys Ala Gly Ser
1 5 10 15

Ser Val Lys Val Ser Cys Lys Ala Phe Gly Gly Thr Ser Asn
20 25 30

<210> SEQ ID NO 98
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 98

Trp Val Arg Gln Ala Pro Gly Gln Gly Leu Gln Trp Met Gly
1 5 10

<210> SEQ ID NO 99
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 99

Arg Val Thr Ile Thr Ala Asp Lys Ser Thr Arg Thr Ala Tyr Met Glu
1 5 10 15

Leu Ser Ser Leu Arg Ser Glu Asp Thr Ala Val Tyr Tyr Cys Ala Ser
20 25 30

<210> SEQ ID NO 100
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 100

Trp Gly Gln Gly Thr Met Val Thr Val Ser Ser
1 5 10

<210> SEQ ID NO 101
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 101

Glu Ile Val Leu Thr Gln Ser Pro Gly Thr Leu Ser Leu Ser Pro Gly
1 5 10 15

Glu Arg Ala Thr Leu Ser Cys
20

<210> SEQ ID NO 102
<211> LENGTH: 15

```
<212> TYPE: PRT
<213> ORGANISM: Artificial Sequence
<220> FEATURE:
<223> OTHER INFORMATION: The sequence is artificially synthesized

<400> SEQUENCE: 102

Trp Tyr Gln Gln Lys Val Gly Gln Ala Pro Arg Leu Leu Ile Tyr
1               5                   10                  15


<210> SEQ ID NO 103
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 103

Gly Ile Pro Asp Arg Phe Ser Gly Ser Gly Ser Gly Thr Asp Phe Thr
1               5                   10                  15

Leu Thr Ile Ser Arg Leu Gln Pro Glu Asp Phe Ala Val Tyr Ser Cys
            20                  25                  30


<210> SEQ ID NO 104
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 104

Phe Gly Gln Gly Thr Lys Val Glu Ile Lys
1               5                   10


<210> SEQ ID NO 105
<211> LENGTH: 108
<212> TYPE: PRT
<213> ORGANISM: Artificial Sequence
<220> FEATURE:
<223> OTHER INFORMATION: The sequence is artificially synthesized

<400> SEQUENCE: 105

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Gly Asn
            20                  25                  30

Tyr Leu Ala Trp Tyr Gln Gln Lys Val Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Gln
65                  70                  75                  80

Pro Glu Asp Phe Ala Val Tyr Ser Cys His Gln Tyr Gly Ser Ser Pro
                85                  90                  95

Pro Thr Phe Gly Gln Gly Thr Lys Val Glu Ile Lys
            100                 105


<210> SEQ ID NO 106
<211> LENGTH: 124
<212> TYPE: PRT
<213> ORGANISM: Artificial Sequence
<220> FEATURE:
<223> OTHER INFORMATION: The sequence is artificially synthesized

<400> SEQUENCE: 106
```

```
Gln Val Gln Leu Val Gln Ser Gly Ala Glu Val Lys Lys Ala Gly Ser
1               5                   10                  15

Ser Val Lys Val Ser Cys Lys Ala Phe Gly Gly Thr Ser Asn Asn Tyr
            20                  25                  30

Gly Val Thr Trp Val Arg Gln Ala Pro Gly Gln Gly Leu Gln Trp Met
        35                  40                  45

Gly Gly Ile Ile Pro Ile Phe Gly Thr Thr Asn Tyr Ala Gln Lys Phe
    50                  55                  60

Leu Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Gln Gly Ser Ser Thr Trp Phe Ala Thr Leu Tyr Ala Phe Pro
            100                 105                 110

Ile Trp Gly Gln Gly Thr Met Val Thr Val Ser Ser
        115                 120


<210> SEQ ID NO 107
<211> LENGTH: 215
<212> TYPE: PRT
<213> ORGANISM: Artificial Sequence
<220> FEATURE:
<223> OTHER INFORMATION: The sequence is artificially synthesized

<400> SEQUENCE: 107

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Gly Asn
            20                  25                  30

Tyr Leu Ala Trp Tyr Gln Gln Lys Val Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Gln
65                  70                  75                  80

Pro Glu Asp Phe Ala Val Tyr Ser Cys His Gln Tyr Gly Ser Ser Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 108
```

```
<211> LENGTH: 454
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (348)..(348)
<223> OTHER INFORMATION: Xaa can be  Gly or absent

<400> SEQUENCE: 108

Gln Val Gln Leu Val Gln Ser Gly Ala Glu Val Lys Lys Ala Gly Ser
1               5                   10                  15

Ser Val Lys Val Ser Cys Lys Ala Phe Gly Gly Thr Ser Asn Asn Tyr
            20                  25                  30

Gly Val Thr Trp Val Arg Gln Ala Pro Gly Gln Gly Leu Gln Trp Met
        35                  40                  45

Gly Gly Ile Ile Pro Ile Phe Gly Thr Thr Asn Tyr Ala Gln Lys Phe
    50                  55                  60

Leu Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Gln Gly Ser Ser Thr Trp Phe Ala Thr Leu Tyr Ala Phe Pro
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Xaa Gln Pro Arg Glu
            340                 345                 350

Pro Gln Val Tyr Thr Leu Pro Pro Ser Arg Asp Glu Leu Thr Lys Asn
```

```
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 109
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 109

Asn Tyr Trp Ile Thr
1               5


<210> SEQ ID NO 110
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 110

Arg Ile Asp Thr Arg Asp Ser Tyr Thr Asn Tyr Ser Pro Ser Phe Gln
1               5                   10                  15

Gly


<210> SEQ ID NO 111
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 111

Leu Ser Thr Thr Tyr Pro Leu Asn Tyr Tyr Gly Met Asp Val
1               5                   10


<210> SEQ ID NO 112
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 112

Thr Gly Ser Ser Ser Asn Ile Gly Ala Asn Tyr Asp Val Asn
1               5                   10


<210> SEQ ID NO 113
<211> LENGTH: 7
<212> TYPE: PRT
<213> ORGANISM: Artificial Sequence
```

<220> FEATURE:
<223> OTHER INFORMATION: The sequence is artificially synthesized

<400> SEQUENCE: 113

Gly Asn Thr Asn Arg Pro Ser
1 5

<210> SEQ ID NO 114
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 114

Gln Ser Tyr Asp Thr Ser Leu Ser Gly Trp Val
1 5 10

<210> SEQ ID NO 115
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 115

Glu Val Gln Leu Val Gln Ser Gly Ala Ala Val Arg Lys Pro Gly Glu
1 5 10 15

Ser Leu Arg Ile Ser Cys Gln Ala Ser Gly Phe Ser Phe Thr
20 25 30

<210> SEQ ID NO 116
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 116

Trp Val Arg Gln Arg Pro Gly Lys Gly Leu Glu Trp Met Gly
1 5 10

<210> SEQ ID NO 117
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 117

His Val Thr Ile Ser Ile Asp Arg Ser Ile Asn Thr Ala Tyr Leu Gln
1 5 10 15

Trp Ser Ser Leu Lys Ala Ser Asp Thr Ala Met Tyr Tyr Cys Ala Arg
20 25 30

<210> SEQ ID NO 118
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 118

Trp Gly Gln Gly Thr Thr Val Thr Val Ser Ser
1 5 10

<210> SEQ ID NO 119
<211> LENGTH: 22
<212> TYPE: PRT
<213> ORGANISM: Artificial Sequence
<220> FEATURE:
<223> OTHER INFORMATION: The sequence is artificially synthesized

<400> SEQUENCE: 119

Gln Ser Val Leu Thr Gln Pro Pro Ser Val Ser Gly Thr Pro Gly Gln
1 5 10 15

Arg Val Thr Ile Ser Cys
20

<210> SEQ ID NO 120
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 120

Trp Tyr Gln Gln Leu Pro Gly Thr Ala Pro Lys Val Leu Ile Tyr
1 5 10 15

<210> SEQ ID NO 121
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 121

Gly Val Pro Asp Arg Phe Ser Gly Ser Lys Ser Gly Thr Ser Ala Ser
1 5 10 15

Leu Ala Ile Thr Gly Leu Gln Ala Glu Asp Glu Ala Asp Tyr Tyr Cys
20 25 30

<210> SEQ ID NO 122
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 122

Phe Gly Gly Gly Thr Lys Leu Thr Val Leu
1 5 10

<210> SEQ ID NO 123
<211> LENGTH: 111
<212> TYPE: PRT
<213> ORGANISM: Artificial Sequence
<220> FEATURE:
<223> OTHER INFORMATION: The sequence is artificially synthesized

<400> SEQUENCE: 123

Gln Ser Val Leu Thr Gln Pro Pro Ser Val Ser Gly Thr Pro Gly Gln
1 5 10 15

Arg Val Thr Ile Ser Cys Thr Gly Ser Ser Ser Asn Ile Gly Ala Asn
20 25 30

Tyr Asp Val Asn Trp Tyr Gln Gln Leu Pro Gly Thr Ala Pro Lys Val
35 40 45

Leu Ile Tyr Gly Asn Thr Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Thr Ser
85 90 95

Leu Ser Gly Trp Val Phe Gly Gly Gly Thr Lys Leu Thr Val Leu
100 105 110

<210> SEQ ID NO 124
<211> LENGTH: 123
<212> TYPE: PRT
<213> ORGANISM: Artificial Sequence
<220> FEATURE:
<223> OTHER INFORMATION: The sequence is artificially synthesized

<400> SEQUENCE: 124

Glu Val Gln Leu Val Gln Ser Gly Ala Ala Val Arg Lys Pro Gly Glu
1 5 10 15

Ser Leu Arg Ile Ser Cys Gln Ala Ser Gly Phe Ser Phe Thr Asn Tyr
20 25 30

Trp Ile Thr Trp Val Arg Gln Arg Pro Gly Lys Gly Leu Glu Trp Met
35 40 45

Gly Arg Ile Asp Thr Arg Asp Ser Tyr Thr Asn Tyr Ser Pro Ser Phe
50 55 60

Gln Gly His Val Thr Ile Ser Ile Asp Arg Ser Ile Asn Thr Ala Tyr
65 70 75 80

Leu Gln Trp Ser Ser Leu Lys Ala Ser Asp Thr Ala Met Tyr Tyr Cys
85 90 95

Ala Arg Leu Ser Thr Thr Tyr Pro Leu Asn Tyr Tyr Gly Met Asp Val
100 105 110

Trp Gly Gln Gly Thr Thr Val Thr Val Ser Ser
115 120

<210> SEQ ID NO 125
<211> LENGTH: 217
<212> TYPE: PRT
<213> ORGANISM: Artificial Sequence
<220> FEATURE:
<223> OTHER INFORMATION: The sequence is artificially synthesized

<400> SEQUENCE: 125

Gln Ser Val Leu Thr Gln Pro Pro Ser Val Ser Gly Thr Pro Gly Gln
1 5 10 15

Arg Val Thr Ile Ser Cys Thr Gly Ser Ser Ser Asn Ile Gly Ala Asn
20 25 30

Tyr Asp Val Asn Trp Tyr Gln Gln Leu Pro Gly Thr Ala Pro Lys Val
35 40 45

Leu Ile Tyr Gly Asn Thr Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Thr Ser
85 90 95

Leu Ser Gly Trp Val Phe Gly Gly Gly Thr Lys Leu Thr Val Leu Gly
100 105 110

Gln Pro Lys Ala Ala Pro Ser Val Thr Leu Phe Pro Pro Ser Ser Glu
115 120 125

Glu Leu Gln Ala Asn Lys Ala Thr Leu Val Cys Leu Ile Ser Asp Phe

```
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 126
<211> LENGTH: 453
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (347)..(347)
<223> OTHER INFORMATION: Xaa can be  Gly or absent

<400> SEQUENCE: 126

Glu Val Gln Leu Val Gln Ser Gly Ala Ala Val Arg Lys Pro Gly Glu
1               5                   10                  15

Ser Leu Arg Ile Ser Cys Gln Ala Ser Gly Phe Ser Phe Thr Asn Tyr
            20                  25                  30

Trp Ile Thr Trp Val Arg Gln Arg Pro Gly Lys Gly Leu Glu Trp Met
        35                  40                  45

Gly Arg Ile Asp Thr Arg Asp Ser Tyr Thr Asn Tyr Ser Pro Ser Phe
    50                  55                  60

Gln Gly His Val Thr Ile Ser Ile Asp Arg Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Thr Thr Tyr Pro Leu Asn Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Xaa Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 127
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 127

Asn Tyr His Ile His
1               5


<210> SEQ ID NO 128
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 128

Ile Ile Asn Pro Arg Arg Leu Ser Thr Ala Tyr Ala Pro Lys Phe Gln
1               5                   10                  15

Gly


<210> SEQ ID NO 129
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 129

Asp Ala Gly Asp Asp Thr Ser Gly Pro Phe Asp Ser
1               5                   10
```

<210> SEQ ID NO 130
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 130

Arg Ala Ser Gln Ser Ile Asn Thr Trp Leu Ala
1 5 10

<210> SEQ ID NO 131
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 131

Lys Ala Ser Ser Leu Glu Ser
1 5

<210> SEQ ID NO 132
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 132

Gln Gln Tyr Asn Thr Phe Ser
1 5

<210> SEQ ID NO 133
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 133

Gln Val Gln Leu Val Gln Ser Gly Ala Glu Val Lys Lys Pro Gly Ser
1 5 10 15

Ser Val Lys Val Ser Cys Arg Ser Ser Gly Tyr Arg Phe Thr
20 25 30

<210> SEQ ID NO 134
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 134

Trp Val Arg Gln Ala Pro Gly Gln Gly Leu Glu Trp Val Gly
1 5 10

<210> SEQ ID NO 135
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 135

Arg Val Thr Met Thr Arg Asp Thr Ser Thr Ser Thr Val Tyr Met Glu
1 5 10 15

Leu Ser Ser Leu Arg Ser Asp Asp Thr Ala Val Tyr Tyr Cys Ala Arg
20 25 30

<210> SEQ ID NO 136
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 136

Trp Gly Gln Gly Thr Leu Val Thr Val Ser Ser
1 5 10

<210> SEQ ID NO 137
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 137

Asp Ile Gln Met Thr Gln Ser Pro Ser Thr Leu Ser Ala Ser Val Gly
1 5 10 15

Asp Arg Val Thr Ile Thr Cys
20

<210> SEQ ID NO 138
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 138

Trp Tyr Gln Gln Lys Pro Gly Lys Ala Pro Lys Leu Leu Ile Ser
1 5 10 15

<210> SEQ ID NO 139
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 139

Gly Val Pro Ser Arg Phe Ser Gly Ser Gly Ser Gly Thr Glu Phe Thr
1 5 10 15

Leu Ser Ile Ser Ser Leu Gln Pro Asp Asp Phe Ala Thr Tyr Tyr Cys
20 25 30

<210> SEQ ID NO 140
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 140

Phe Gly Gln Gly Thr Lys Leu Glu Ile Lys
1 5 10

<210> SEQ ID NO 141

<211> LENGTH: 105
<212> TYPE: PRT
<213> ORGANISM: Artificial Sequence
<220> FEATURE:
<223> OTHER INFORMATION: The sequence is artificially synthesized

<400> SEQUENCE: 141

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Thr Trp
            20                  25                  30

Leu Ala Trp Tyr Gln Gln Lys Pro Gly Lys Ala Pro Lys Leu Leu Ile
        35                  40                  45

Ser Lys Ala Ser Ser Leu Glu Ser Gly Val Pro Ser Arg Phe Ser Gly
    50                  55                  60

Ser Gly Ser Gly Thr Glu Phe Thr Leu Ser Ile Ser Ser Leu Gln Pro
65                  70                  75                  80

Asp Asp Phe Ala Thr Tyr Tyr Cys Gln Gln Tyr Asn Thr Phe Ser Phe
                85                  90                  95

Gly Gln Gly Thr Lys Leu Glu Ile Lys
            100                 105

<210> SEQ ID NO 142
<211> LENGTH: 121
<212> TYPE: PRT
<213> ORGANISM: Artificial Sequence
<220> FEATURE:
<223> OTHER INFORMATION: The sequence is artificially synthesized

<400> SEQUENCE: 142

Gln Val Gln Leu Val Gln Ser Gly Ala Glu Val Lys Lys Pro Gly Ser
1               5                   10                  15

Ser Val Lys Val Ser Cys Arg Ser Ser Gly Tyr Arg Phe Thr Asn Tyr
            20                  25                  30

His Ile His Trp Val Arg Gln Ala Pro Gly Gln Gly Leu Glu Trp Val
        35                  40                  45

Gly Ile Ile Asn Pro Arg Arg Leu Ser Thr Ala Tyr Ala Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Asp Ala Gly Asp Asp Thr Ser Gly Pro Phe Asp Ser Trp Gly
            100                 105                 110

Gln Gly Thr Leu Val Thr Val Ser Ser
        115                 120

<210> SEQ ID NO 143
<211> LENGTH: 212
<212> TYPE: PRT
<213> ORGANISM: Artificial Sequence
<220> FEATURE:
<223> OTHER INFORMATION: The sequence is artificially synthesized

<400> SEQUENCE: 143

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Thr Trp
            20                  25                  30

Leu Ala Trp Tyr Gln Gln Lys Pro Gly Lys Ala Pro Lys Leu Leu Ile
35 40 45

Ser Lys Ala Ser Ser Leu Glu Ser Gly Val Pro Ser Arg Phe Ser Gly
50 55 60

Ser Gly Ser Gly Thr Glu Phe Thr Leu Ser Ile Ser Ser Leu Gln Pro
65 70 75 80

Asp Asp Phe Ala Thr Tyr Tyr Cys Gln Gln Tyr Asn Thr Phe Ser Phe
85 90 95

Gly Gln Gly Thr Lys Leu Glu Ile Lys Arg Thr Val Ala Ala Pro Ser
100 105 110

Val Phe Ile Phe Pro Pro Ser Asp Glu Gln Leu Lys Ser Gly Thr Ala
115 120 125

Ser Val Val Cys Leu Leu Asn Asn Phe Tyr Pro Arg Glu Ala Lys Val
130 135 140

Gln Trp Lys Val Asp Asn Ala Leu Gln Ser Gly Asn Ser Gln Glu Ser
145 150 155 160

Val Thr Glu Gln Asp Ser Lys Asp Ser Thr Tyr Ser Leu Ser Ser Thr
165 170 175

Leu Thr Leu Ser Lys Ala Asp Tyr Glu Lys His Lys Val Tyr Ala Cys
180 185 190

Glu Val Thr His Gln Gly Leu Ser Ser Pro Val Thr Lys Ser Phe Asn
195 200 205

Arg Gly Glu Cys
210

<210> SEQ ID NO 144
<211> LENGTH: 451
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (345)..(345)
<223> OTHER INFORMATION: Xaa can be Gly or absent

<400> SEQUENCE: 144

Gln Val Gln Leu Val Gln Ser Gly Ala Glu Val Lys Lys Pro Gly Ser
1 5 10 15

Ser Val Lys Val Ser Cys Arg Ser Ser Gly Tyr Arg Phe Thr Asn Tyr
20 25 30

His Ile His Trp Val Arg Gln Ala Pro Gly Gln Gly Leu Glu Trp Val
35 40 45

Gly Ile Ile Asn Pro Arg Arg Leu Ser Thr Ala Tyr Ala Pro Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Asp Asp Thr Ala Val Tyr Tyr Cys
85 90 95

Ala Arg Asp Ala Gly Asp Asp Thr Ser Gly Pro Phe Asp Ser Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Xaa Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 145
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 145

Asn Tyr Gly Met His
1               5


<210> SEQ ID NO 146
<211> LENGTH: 17
<212> TYPE: PRT
<213> ORGANISM: Artificial Sequence
<220> FEATURE:
<223> OTHER INFORMATION: The sequence is artificially synthesized
```

<400> SEQUENCE: 146

Val Ile Trp Asn Asp Gly Ser Asn Lys Tyr Tyr Ala Asp Ser Val Lys
1 5 10 15

Gly

<210> SEQ ID NO 147
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 147

Glu Gly Leu Thr Ser Val Thr Met Leu Asp Ser
1 5 10

<210> SEQ ID NO 148
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 148

Arg Ala Ser Gln Tyr Ile Ser Ser Phe Leu Asn
1 5 10

<210> SEQ ID NO 149
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 149

Val Ala Ser Ser Leu Gln Ser
1 5

<210> SEQ ID NO 150
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 150

Gln Gln Ser Tyr Ser Thr Pro Leu Phe Thr
1 5 10

<210> SEQ ID NO 151
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 151

Gln Val Gln Leu Val Glu Ser Gly Gly Gly Val Val Gln Pro Gly Arg
1 5 10 15

Ser Leu Arg Val Ser Cys Ala Ala Ser Gly Phe Thr Phe Ser
20 25 30

<210> SEQ ID NO 152
<211> LENGTH: 14
<212> TYPE: PRT

<213> ORGANISM: Artificial Sequence
<220> FEATURE:
<223> OTHER INFORMATION: The sequence is artificially synthesized

<400> SEQUENCE: 152

Trp Val Arg Gln Ala Pro Gly Lys Gly Leu Glu Trp Leu Ala
1 5 10

<210> SEQ ID NO 153
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 153

Arg Phe Ile Ile Ser Arg Asp Asn Ser Lys Asn Thr Leu Tyr Leu Gln
1 5 10 15

Met Asn Ser Leu Gly Ala Glu Asp Thr Ala Met Tyr Tyr Cys Ala Arg
20 25 30

<210> SEQ ID NO 154
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 154

Trp Gly Gln Gly Ala Leu Val Thr Val Ser Ser
1 5 10

<210> SEQ ID NO 155
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 155

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 156
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 156

Trp Tyr Gln Gln Lys Pro Gly Lys Ala Pro Lys Leu Leu Ile His
1 5 10 15

<210> SEQ ID NO 157
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 157

Gly Val Pro Ser Arg Phe Ser Gly Ser Gly Ser Gly Thr His Phe Thr
1 5 10 15

Leu Thr Ile Ser Ser Leu Gln Pro Glu Asp Phe Ala Thr Tyr Tyr Cys
20 25 30

<210> SEQ ID NO 158
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 158

Phe Gly Pro Gly Thr Lys Val Asp Ile Lys
1 5 10

<210> SEQ ID NO 159
<211> LENGTH: 108
<212> TYPE: PRT
<213> ORGANISM: Artificial Sequence
<220> FEATURE:
<223> OTHER INFORMATION: The sequence is artificially synthesized

<400> SEQUENCE: 159

Asp Ile Gln Met Thr Gln Ser Pro Ser Ser Leu Ser Ala Ser Val Gly
1 5 10 15

Asp Arg Val Thr Ile Thr Cys Arg Ala Ser Gln Tyr Ile Ser Ser Phe
20 25 30

Leu Asn Trp Tyr Gln Gln Lys Pro Gly Lys Ala Pro Lys Leu Leu Ile
35 40 45

His Val Ala Ser Ser Leu Gln Ser Gly Val Pro Ser Arg Phe Ser Gly
50 55 60

Ser Gly Ser Gly Thr His Phe Thr Leu Thr Ile Ser Ser Leu Gln Pro
65 70 75 80

Glu Asp Phe Ala Thr Tyr Tyr Cys Gln Gln Ser Tyr Ser Thr Pro Leu
85 90 95

Phe Thr Phe Gly Pro Gly Thr Lys Val Asp Ile Lys
100 105

<210> SEQ ID NO 160
<211> LENGTH: 120
<212> TYPE: PRT
<213> ORGANISM: Artificial Sequence
<220> FEATURE:
<223> OTHER INFORMATION: The sequence is artificially synthesized

<400> SEQUENCE: 160

Gln Val Gln Leu Val Glu Ser Gly Gly Gly Val Val Gln Pro Gly Arg
1 5 10 15

Ser Leu Arg Val Ser Cys Ala Ala Ser Gly Phe Thr Phe Ser Asn Tyr
20 25 30

Gly Met His Trp Val Arg Gln Ala Pro Gly Lys Gly Leu Glu Trp Leu
35 40 45

Ala Val Ile Trp Asn Asp Gly Ser Asn Lys Tyr Tyr Ala Asp Ser Val
50 55 60

Lys Gly Arg Phe Ile Ile Ser Arg Asp Asn Ser Lys Asn Thr Leu Tyr
65 70 75 80

Leu Gln Met Asn Ser Leu Gly Ala Glu Asp Thr Ala Met Tyr Tyr Cys
85 90 95

Ala Arg Glu Gly Leu Thr Ser Val Thr Met Leu Asp Ser Trp Gly Gln
100 105 110

Gly Ala Leu Val Thr Val Ser Ser
        115                 120

<210> SEQ ID NO 161
<211> LENGTH: 215
<212> TYPE: PRT
<213> ORGANISM: Artificial Sequence
<220> FEATURE:
<223> OTHER INFORMATION: The sequence is artificially synthesized

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Ser Ser Phe
            20                  25                  30

Leu Asn Trp Tyr Gln Gln Lys Pro Gly Lys Ala Pro Lys Leu Leu Ile
        35                  40                  45

His Val Ala Ser Ser Leu Gln Ser Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 162
<211> LENGTH: 450
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (344)..(344)
<223> OTHER INFORMATION: Xaa can be Gly or absent

<400> SEQUENCE: 162

Gln Val Gln Leu Val Glu Ser Gly Gly Gly Val Val Gln Pro Gly Arg
1               5                   10                  15

Ser Leu Arg Val Ser Cys Ala Ala Ser Gly Phe Thr Phe Ser Asn Tyr
            20                  25                  30

Gly Met His Trp Val Arg Gln Ala Pro Gly Lys Gly Leu Glu Trp Leu
        35                  40                  45

Ala Val Ile Trp Asn Asp Gly Ser Asn Lys Tyr Tyr Ala Asp Ser Val

```
    50                  55                  60

Lys Gly Arg Phe Ile Ile Ser Arg Asp Asn Ser Lys Asn Thr Leu Tyr
65                  70                  75                  80

Leu Gln Met Asn Ser Leu Gly Ala Glu Asp Thr Ala Met Tyr Tyr Cys
                85                  90                  95

Ala Arg Glu Gly Leu Thr Ser Val Thr Met Leu Asp Ser Trp Gly Gln
            100                 105                 110

Gly Ala Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Xaa Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 163

<211> LENGTH: 6
<212> TYPE: PRT
<213> ORGANISM: Artificial Sequence
<220> FEATURE:
<223> OTHER INFORMATION: The sequence is artificially synthesized

<400> SEQUENCE: 163

Thr Asn Asn Trp Trp Ser
1               5

<210> SEQ ID NO 164
<211> LENGTH: 16
<212> TYPE: PRT
<213> ORGANISM: Artificial Sequence
<220> FEATURE:
<223> OTHER INFORMATION: The sequence is artificially synthesized

<400> SEQUENCE: 164

Glu Ile His His Ile Gly Ser Thr Asn Tyr Asn Pro Ser Leu Lys Ser
1               5                   10                  15

<210> SEQ ID NO 165
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 165

Gly Arg Leu Gly Ile Thr Arg Asp Arg Tyr Tyr Phe Asp Ser
1               5                   10

<210> SEQ ID NO 166
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 166

Gln Ala Ser Gln Asp Ile Ser Asn Tyr Leu Asn
1               5                   10

<210> SEQ ID NO 167
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 167

Asp Thr Ser Ser Leu Glu Arg
1               5

<210> SEQ ID NO 168
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 168

Gln Gln Tyr Tyr Asn Leu Pro His Thr
1               5

<210> SEQ ID NO 169
<211> LENGTH: 30

<212> TYPE: PRT
<213> ORGANISM: Artificial Sequence
<220> FEATURE:
<223> OTHER INFORMATION: The sequence is artificially synthesized

<400> SEQUENCE: 169

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Thr Ile Arg
            20                  25                  30
```

<210> SEQ ID NO 170
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 170

```
Trp Val Arg Gln Pro Pro Gly Lys Gly Leu Glu Trp Ile Gly
1               5                   10
```

<210> SEQ ID NO 171
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 171

```
Gln Val Thr Ile Ser Val Asp Lys Ser Lys Asn Gln Phe Ser Leu Asn
1               5                   10                  15

Leu Ser Ser Val Thr Ala Ala Asp Thr Ala Leu Tyr Tyr Cys Val Arg
            20                  25                  30
```

<210> SEQ ID NO 172
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 172

```
Trp Gly Arg Gly Thr Leu Val Thr Val Ser Ser
1               5                   10
```

<210> SEQ ID NO 173
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 173

```
Asp Ile Gln Met Thr Gln Ser Pro Ser Pro Leu Ser Val Ser Val Gly
1               5                   10                  15

Asp Arg Val Thr Ile Thr Cys
            20
```

<210> SEQ ID NO 174
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 174

Trp Tyr Gln Gln Lys Pro Gly Gln Ala Pro Lys Leu Leu Ile Tyr
1 5 10 15

<210> SEQ ID NO 175
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 175

Gly Val Pro Ser Arg Phe Ser Gly Ser Gly Ser Gly Thr Asp Phe Thr
1 5 10 15

Leu Thr Ile Ser Ser Leu Gln Pro Glu Asp Ile Ala Thr Tyr His Cys
20 25 30

<210> SEQ ID NO 176
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 176

Phe Gly Gln Gly Thr Lys Leu Glu Ile Lys
1 5 10

<210> SEQ ID NO 177
<211> LENGTH: 107
<212> TYPE: PRT
<213> ORGANISM: Artificial Sequence
<220> FEATURE:
<223> OTHER INFORMATION: The sequence is artificially synthesized

<400> SEQUENCE: 177

Asp Ile Gln Met Thr Gln Ser Pro Ser Pro Leu Ser Val Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Gln Ala Pro Lys Leu Leu Ile
35 40 45

Tyr Asp Thr Ser Ser Leu Glu Arg Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr His Cys Gln Gln Tyr Tyr Asn Leu Pro His
85 90 95

Thr Phe Gly Gln Gly Thr Lys Leu Glu Ile Lys
100 105

<210> SEQ ID NO 178
<211> LENGTH: 123
<212> TYPE: PRT
<213> ORGANISM: Artificial Sequence
<220> FEATURE:
<223> OTHER INFORMATION: The sequence is artificially synthesized

<400> SEQUENCE: 178

Gln Val Gln Leu Gln Glu Ser Gly Pro Gly Leu Val Lys Pro Ser Gly
1 5 10 15

Thr Leu Ser Leu Thr Cys Ala Val Ser Gly Gly Thr Ile Arg Thr Asn

```
            20                  25                  30

Asn Trp Trp Ser Trp Val Arg Gln Pro Pro Gly Lys Gly Leu Glu Trp
        35                  40                  45

Ile Gly Glu Ile His His Ile Gly Ser Thr Asn Tyr Asn Pro Ser Leu
    50                  55                  60

Lys Ser Gln Val Thr Ile Ser Val Asp Lys Ser Lys Asn Gln Phe Ser
65                  70                  75                  80

Leu Asn Leu Ser Ser Val Thr Ala Ala Asp Thr Ala Leu Tyr Tyr Cys
                85                  90                  95

Val Arg Gly Arg Leu Gly Ile Thr Arg Asp Arg Tyr Tyr Phe Asp Ser
            100                 105                 110

Trp Gly Arg Gly Thr Leu Val Thr Val Ser Ser
        115                 120


<210> SEQ ID NO 179
<211> LENGTH: 214
<212> TYPE: PRT
<213> ORGANISM: Artificial Sequence
<220> FEATURE:
<223> OTHER INFORMATION: The sequence is artificially synthesized

<400> SEQUENCE: 179

Asp Ile Gln Met Thr Gln Ser Pro Ser Pro Leu Ser Val Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Gln Ala Pro Lys Leu Leu Ile
        35                  40                  45

Tyr Asp Thr Ser Ser Leu Glu Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr His Cys Gln Gln Tyr Tyr Asn Leu Pro His
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 180
<211> LENGTH: 453
<212> TYPE: PRT
<213> ORGANISM: Artificial Sequence
<220> FEATURE:
<223> OTHER INFORMATION: The sequence is artificially synthesized
```

<220> FEATURE:
<221> NAME/KEY: VARIANT
<222> LOCATION: (347)..(347)
<223> OTHER INFORMATION: Xaa can be Gly or absent

<400> SEQUENCE: 180

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Thr Ile Arg Thr Asn
            20                  25                  30

Asn Trp Trp Ser Trp Val Arg Gln Pro Pro Gly Lys Gly Leu Glu Trp
        35                  40                  45

Ile Gly Glu Ile His His Ile Gly Ser Thr Asn Tyr Asn Pro Ser Leu
    50                  55                  60

Lys Ser Gln Val Thr Ile Ser Val Asp Lys Ser Lys Asn Gln Phe Ser
65                  70                  75                  80

Leu Asn Leu Ser Ser Val Thr Ala Ala Asp Thr Ala Leu Tyr Tyr Cys
                85                  90                  95

Val Arg Gly Arg Leu Gly Ile Thr Arg Asp Arg Tyr Tyr Phe Asp Ser
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Xaa Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380
```

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 181
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 181

Asn Tyr Gly Met His
1 5

<210> SEQ ID NO 182
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 182

Phe Thr Ile Tyr Asp Gly Ser His Lys Tyr Tyr Ala Asp Ser Val Lys
1 5 10 15

Gly

<210> SEQ ID NO 183
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 183

Asp Ser Asn Gly Phe Gly Val Leu Ser
1 5

<210> SEQ ID NO 184
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 184

Arg Ala Ser Gln Gly Ile Arg Ser Asp Leu Gly
1 5 10

<210> SEQ ID NO 185
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 185

Gly Ala Ser Asn Leu Gln Arg
1               5

<210> SEQ ID NO 186
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 186

Leu Gln His Asn Ser Phe Pro Trp Thr
1               5

<210> SEQ ID NO 187
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 187

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser
            20                  25                  30

<210> SEQ ID NO 188
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 188

Trp Val Arg Gln Ala Pro Gly Lys Gly Leu Glu Trp Val Ala
1               5                   10

<210> SEQ ID NO 189
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 189

Arg Phe Thr Ile Ser Arg Asp Asn Ser Lys Asn Thr Leu Tyr Leu Gln
1               5                   10                  15

Met Asn Ser Leu Arg Tyr Glu Asp Thr Ala Val Tyr Tyr Cys Ala Thr
            20                  25                  30

<210> SEQ ID NO 190
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 190

Trp Gly Gln Gly Thr Leu Val Thr Val Ser Ser
1               5                   10

<210> SEQ ID NO 191
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 191

Asp Ile Gln Leu Thr Gln Ser Pro Ser Ser Leu Ser Ala Ser Val Gly
1 5 10 15

Asp Arg Val Thr Ile Thr Cys
20

<210> SEQ ID NO 192
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 192

Trp Tyr Gln Gln Lys Pro Gly Lys Ala Pro Lys Arg Leu Ile Tyr
1 5 10 15

<210> SEQ ID NO 193
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 193

Gly Val Pro Ser Arg Phe Ser Gly Ser Gly Ser Gly Thr Glu Phe Thr
1 5 10 15

Leu Thr Ile Ser Ser Leu Gln Pro Glu Asp Phe Ala Ser Tyr Tyr Cys
20 25 30

<210> SEQ ID NO 194
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 194

Phe Gly Gln Gly Thr Lys Val Glu Ile Lys
1 5 10

<210> SEQ ID NO 195
<211> LENGTH: 107
<212> TYPE: PRT
<213> ORGANISM: Artificial Sequence
<220> FEATURE:
<223> OTHER INFORMATION: The sequence is artificially synthesized

<400> SEQUENCE: 195

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Arg Ser Asp
20 25 30

Leu Gly Trp Tyr Gln Gln Lys Pro Gly Lys Ala Pro Lys Arg Leu Ile
35 40 45

Tyr Gly Ala Ser Asn Leu Gln Arg Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Ser Tyr Tyr Cys Leu Gln His Asn Ser Phe Pro Trp

```
                85                  90                  95

Thr Phe Gly Gln Gly Thr Lys Val Glu Ile Lys
            100                 105


<210> SEQ ID NO 196
<211> LENGTH: 118
<212> TYPE: PRT
<213> ORGANISM: Artificial Sequence
<220> FEATURE:
<223> OTHER INFORMATION: The sequence is artificially synthesized

<400> SEQUENCE: 196

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Asn Tyr
            20                  25                  30

Gly Met His Trp Val Arg Gln Ala Pro Gly Lys Gly Leu Glu Trp Val
        35                  40                  45

Ala Phe Thr Ile Tyr Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Tyr Glu Asp Thr Ala Val Tyr Tyr Cys
                85                  90                  95

Ala Thr Asp Ser Asn Gly Phe Gly Val Leu Ser Trp Gly Gln Gly Thr
            100                 105                 110

Leu Val Thr Val Ser Ser
        115


<210> SEQ ID NO 197
<211> LENGTH: 214
<212> TYPE: PRT
<213> ORGANISM: Artificial Sequence
<220> FEATURE:
<223> OTHER INFORMATION: The sequence is artificially synthesized

<400> SEQUENCE: 197

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Asp
            20                  25                  30

Leu Gly Trp Tyr Gln Gln Lys Pro Gly Lys Ala Pro Lys Arg Leu Ile
        35                  40                  45

Tyr Gly Ala Ser Asn Leu Gln Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ser Tyr Tyr Cys Leu Gln His Asn Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 198
<211> LENGTH: 448
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (342)..(342)
<223> OTHER INFORMATION: Xaa can be  Gly or absent

<400> SEQUENCE: 198

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Asn Tyr
            20                  25                  30

Gly Met His Trp Val Arg Gln Ala Pro Gly Lys Gly Leu Glu Trp Val
        35                  40                  45

Ala Phe Thr Ile Tyr Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Tyr Glu Asp Thr Ala Val Tyr Tyr Cys
                85                  90                  95

Ala Thr Asp Ser Asn Gly Phe Gly Val Leu Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Xaa Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 199
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 199

Ser Tyr Gly Met Asn
1               5


<210> SEQ ID NO 200
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 200

Ile Ile Trp Phe Asp Gly Ser Gln Thr Tyr Tyr Gly Asp Ser Val Lys
1               5                   10                  15

Gly


<210> SEQ ID NO 201
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 201

Gly Gly Ala Glu Glu Ser Thr Asn Trp Arg Phe Leu Trp Val Pro Arg
1               5                   10                  15

Tyr Tyr Tyr Tyr Met Asp Val
            20


<210> SEQ ID NO 202
<211> LENGTH: 14
<212> TYPE: PRT
```

<213> ORGANISM: Artificial Sequence
<220> FEATURE:
<223> OTHER INFORMATION: The sequence is artificially synthesized

<400> SEQUENCE: 202

Ile Gly Thr Asn Ser Asp Phe Gly Arg Tyr Asp Tyr Val Ser
1               5                   10

<210> SEQ ID NO 203
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 203

Asp Val Ser Gln Arg Pro Ser
1               5

<210> SEQ ID NO 204
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 204

Cys Ser Tyr Ala Gly Ser Phe Asn Leu Val
1               5                   10

<210> SEQ ID NO 205
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 205

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Ala Phe Asn
            20                  25                  30

<210> SEQ ID NO 206
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 206

Trp Val Arg Gln Ala Pro Gly Lys Gly Leu Glu Trp Val Ala
1               5                   10

<210> SEQ ID NO 207
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 207

Arg Phe Thr Ile Ser Arg Asp Arg Ser Thr Asn Thr Leu Phe Leu Gln
1               5                   10                  15

Met Asn Asn Leu Arg Ala Asp Asp Thr Ala Met Tyr Tyr Cys Ala Arg
            20                  25                  30

<210> SEQ ID NO 208
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 208

```
Trp Gly Lys Gly Thr Thr Val Thr Val Ser Ser
1               5                   10
```

<210> SEQ ID NO 209
<211> LENGTH: 22
<212> TYPE: PRT
<213> ORGANISM: Artificial Sequence
<220> FEATURE:
<223> OTHER INFORMATION: The sequence is artificially synthesized

<400> SEQUENCE: 209

```
Gln Ser Ala Leu Thr Gln Pro Arg Ser Val Ser Gly Ser Pro Gly Gln
1               5                   10                  15

Ser Val Thr Ile Ser Cys
            20
```

<210> SEQ ID NO 210
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 210

```
Trp Tyr Gln Gln His Pro Asp Lys Ala Pro Lys Leu Leu Ile Tyr
1               5                   10                  15
```

<210> SEQ ID NO 211
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 211

```
Gly Val Pro Asp Arg Phe Ser Gly Ser Lys Ser Gly Tyr Thr Ala Ser
1               5                   10                  15

Leu Ile Ile Ser Gly Leu Gln Ala Asp Asp Glu Ala Glu Tyr Phe Cys
            20                  25                  30
```

<210> SEQ ID NO 212
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 212

```
Phe Gly Gly Gly Thr Lys Val Thr Val Leu
1               5                   10
```

<210> SEQ ID NO 213
<211> LENGTH: 110
<212> TYPE: PRT
<213> ORGANISM: Artificial Sequence
<220> FEATURE:
<223> OTHER INFORMATION: The sequence is artificially synthesized

<400> SEQUENCE: 213

Gln Ser Ala Leu Thr Gln Pro Arg Ser Val Ser Gly Ser Pro Gly Gln
1               5                   10                  15

Ser Val Thr Ile Ser Cys Ile Gly Thr Asn Ser Asp Phe Gly Arg Tyr
            20                  25                  30

Asp Tyr Val Ser Trp Tyr Gln Gln His Pro Asp Lys Ala Pro Lys Leu
        35                  40                  45

Leu Ile Tyr Asp Val Ser Gln Arg Pro Ser Gly Val Pro Asp Arg Phe
    50                  55                  60

Ser Gly Ser Lys Ser Gly Tyr Thr Ala Ser Leu Ile Ile Ser Gly Leu
65                  70                  75                  80

Gln Ala Asp Asp Glu Ala Glu Tyr Phe Cys Cys Ser Tyr Ala Gly Ser
                85                  90                  95

Phe Asn Leu Val Phe Gly Gly Gly Thr Lys Val Thr Val Leu
            100                 105                 110

<210> SEQ ID NO 214
<211> LENGTH: 132
<212> TYPE: PRT
<213> ORGANISM: Artificial Sequence
<220> FEATURE:
<223> OTHER INFORMATION: The sequence is artificially synthesized

<400> SEQUENCE: 214

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Ala Phe Asn Ser Tyr
            20                  25                  30

Gly Met Asn Trp Val Arg Gln Ala Pro Gly Lys Gly Leu Glu Trp Val
        35                  40                  45

Ala Ile Ile Trp Phe Asp Gly Ser Gln Thr Tyr Tyr Gly Asp Ser Val
    50                  55                  60

Lys Gly Arg Phe Thr Ile Ser Arg Asp Arg Ser Thr Asn Thr Leu Phe
65                  70                  75                  80

Leu Gln Met Asn Asn Leu Arg Ala Asp Asp Thr Ala Met Tyr Tyr Cys
                85                  90                  95

Ala Arg Gly Gly Ala Glu Glu Ser Thr Asn Trp Arg Phe Leu Trp Val
            100                 105                 110

Pro Arg Tyr Tyr Tyr Tyr Met Asp Val Trp Gly Lys Gly Thr Thr Val
        115                 120                 125

Thr Val Ser Ser
    130

<210> SEQ ID NO 215
<211> LENGTH: 216
<212> TYPE: PRT
<213> ORGANISM: Artificial Sequence
<220> FEATURE:
<223> OTHER INFORMATION: The sequence is artificially synthesized

<400> SEQUENCE: 215

Gln Ser Ala Leu Thr Gln Pro Arg Ser Val Ser Gly Ser Pro Gly Gln
1               5                   10                  15

Ser Val Thr Ile Ser Cys Ile Gly Thr Asn Ser Asp Phe Gly Arg Tyr
            20                  25                  30

Asp Tyr Val Ser Trp Tyr Gln Gln His Pro Asp Lys Ala Pro Lys Leu
        35                  40                  45

Leu Ile Tyr Asp Val Ser Gln Arg Pro Ser Gly Val Pro Asp Arg Phe
50 55 60

Ser Gly Ser Lys Ser Gly Tyr Thr Ala Ser Leu Ile Ile Ser Gly Leu
65 70 75 80

Gln Ala Asp Asp Glu Ala Glu Tyr Phe Cys Cys Ser Tyr Ala Gly Ser
85 90 95

Phe Asn Leu Val Phe Gly Gly Gly Thr Lys Val Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 216
<211> LENGTH: 462
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (356)..(356)
<223> OTHER INFORMATION: Xaa can be Gly or absent

<400> SEQUENCE: 216

Gln Val Gln Leu Val Glu Ser Gly Gly Gly Val Val Gln Pro Gly Arg
1 5 10 15

Ser Leu Arg Leu Ser Cys Thr Ala Ser Gly Phe Ala Phe Asn Ser Tyr
20 25 30

Gly Met Asn Trp Val Arg Gln Ala Pro Gly Lys Gly Leu Glu Trp Val
35 40 45

Ala Ile Ile Trp Phe Asp Gly Ser Gln Thr Tyr Tyr Gly Asp Ser Val
50 55 60

Lys Gly Arg Phe Thr Ile Ser Arg Asp Arg Ser Thr Asn Thr Leu Phe
65 70 75 80

Leu Gln Met Asn Asn Leu Arg Ala Asp Asp Thr Ala Met Tyr Tyr Cys
85 90 95

Ala Arg Gly Gly Ala Glu Glu Ser Thr Asn Trp Arg Phe Leu Trp Val
100 105 110

Pro Arg Tyr Tyr Tyr Tyr Met Asp Val Trp Gly Lys Gly Thr Thr Val
115 120 125

Thr Val Ser Ser Ala Ser Thr Lys Gly Pro Ser Val Phe Pro Leu Ala
130 135 140

Pro Ser Ser Lys Ser Thr Ser Gly Gly Thr Ala Ala Leu Gly Cys Leu
145 150 155 160

Val Lys Asp Tyr Phe Pro Glu Pro Val Thr Val Ser Trp Asn Ser Gly

```
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Xaa Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460


<210> SEQ ID NO 217
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 217

Asn Tyr Gly Val Asn
1               5


<210> SEQ ID NO 218
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 218
```

Lys Ile Ile Pro Ile Leu Gly Ile Val Asn Tyr Ala Gln Lys Phe Gln
1 5 10 15

Gly

<210> SEQ ID NO 219
<211> LENGTH: 16
<212> TYPE: PRT
<213> ORGANISM: Artificial Sequence
<220> FEATURE:
<223> OTHER INFORMATION: The sequence is artificially synthesized

<400> SEQUENCE: 219

Asp Arg Gly Gly Lys Pro Leu Tyr Ser Tyr Gly Tyr Gly Leu Asp Tyr
1 5 10 15

<210> SEQ ID NO 220
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 220

Arg Ala Ser Leu Ser Val Ser Thr Tyr Leu Ala
1 5 10

<210> SEQ ID NO 221
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 221

Asp Ala Ser Lys Arg Ala Thr
1 5

<210> SEQ ID NO 222
<211> LENGTH: 6
<212> TYPE: PRT
<213> ORGANISM: Artificial Sequence
<220> FEATURE:
<223> OTHER INFORMATION: The sequence is artificially synthesized

<400> SEQUENCE: 222

Gln Gln Arg Ser Thr Thr
1 5

<210> SEQ ID NO 223
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 223

Gln Val Gln Leu Val Gln Ser Gly Ala Glu Val Lys Lys Pro Gly Ser
1 5 10 15

Ser Val Lys Val Ser Cys Arg Ala Ser Gly Gly Thr Phe Ser
20 25 30

<210> SEQ ID NO 224
<211> LENGTH: 14
<212> TYPE: PRT
<213> ORGANISM: Artificial Sequence
<220> FEATURE:

<223> OTHER INFORMATION: The sequence is artificially synthesized

<400> SEQUENCE: 224

Trp Val Arg Gln Ala Pro Gly Gln Gly Leu Glu Trp Met Gly
1 5 10

<210> SEQ ID NO 225
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 225

Arg Val Thr Ile Thr Ala Asp Lys Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 226
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 226

Trp Gly Gln Gly Thr Leu Val Thr Val Ser Ser
1 5 10

<210> SEQ ID NO 227
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 227

Glu Ile Val Leu Thr Gln Ser Pro Ala Thr Leu Ser Leu Ser Pro Gly
1 5 10 15

Glu Arg Ala Thr Leu Ser Cys
20

<210> SEQ ID NO 228
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 228

Trp Tyr Gln Lys Lys Pro Gly Gln Pro Pro Arg Leu Leu Ile Tyr
1 5 10 15

<210> SEQ ID NO 229
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 229

Gly Ile Pro Ala Arg Phe Ser Gly Ser Gly Ser Gly Thr Asp Phe Thr
1 5 10 15

Leu Thr Ile Ser Ser Leu Glu Pro Glu Asp Phe Ala Val Tyr Tyr Cys 20 25 30

<210> SEQ ID NO 230
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 230

Phe Gly Gln Gly Thr Lys Val Glu Ile Lys
1 5 10

<210> SEQ ID NO 231
<211> LENGTH: 104
<212> TYPE: PRT
<213> ORGANISM: Artificial Sequence
<220> FEATURE:
<223> OTHER INFORMATION: The sequence is artificially synthesized

<400> SEQUENCE: 231

Glu Ile Val Leu Thr Gln Ser Pro Ala Thr Leu Ser Leu Ser Pro Gly
1 5 10 15

Glu Arg Ala Thr Leu Ser Cys Arg Ala Ser Leu Ser Val Ser Thr Tyr
20 25 30

Leu Ala Trp Tyr Gln Lys Lys Pro Gly Gln Pro Pro Arg Leu Leu Ile
35 40 45

Tyr Asp Ala Ser Lys Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Thr Thr Phe Gly
85 90 95

Gln Gly Thr Lys Val Glu Ile Lys
100

<210> SEQ ID NO 232
<211> LENGTH: 125
<212> TYPE: PRT
<213> ORGANISM: Artificial Sequence
<220> FEATURE:
<223> OTHER INFORMATION: The sequence is artificially synthesized

<400> SEQUENCE: 232

Gln Val Gln Leu Val Gln Ser Gly Ala Glu Val Lys Lys Pro Gly Ser
1 5 10 15

Ser Val Lys Val Ser Cys Arg Ala Ser Gly Gly Thr Phe Ser Asn Tyr
20 25 30

Gly Val Asn Trp Val Arg Gln Ala Pro Gly Gln Gly Leu Glu Trp Met
35 40 45

Gly Lys Ile Ile Pro Ile Leu Gly Ile Val Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Arg Gly Gly Lys Pro Leu Tyr Ser Tyr Gly Tyr Gly Leu
100 105 110

Asp Tyr Trp Gly Gln Gly Thr Leu Val Thr Val Ser Ser
115 120 125

<210> SEQ ID NO 233
<211> LENGTH: 211
<212> TYPE: PRT
<213> ORGANISM: Artificial Sequence
<220> FEATURE:
<223> OTHER INFORMATION: The sequence is artificially synthesized

<400> SEQUENCE: 233

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Leu Ser Val Ser Thr Tyr
            20                  25                  30

Leu Ala Trp Tyr Gln Lys Lys Pro Gly Gln Pro Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Thr Thr Phe Gly
                85                  90                  95

Gln Gly Thr Lys Val Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210
```

<210> SEQ ID NO 234
<211> LENGTH: 455
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (349)..(349)
<223> OTHER INFORMATION: Xaa can be Gly or absent

<400> SEQUENCE: 234

```
Gln Val Gln Leu Val Gln Ser Gly Ala Glu Val Lys Lys Pro Gly Ser
1               5                   10                  15

Ser Val Lys Val Ser Cys Arg Ala Ser Gly Gly Thr Phe Ser Asn Tyr
            20                  25                  30

Gly Val Asn Trp Val Arg Gln Ala Pro Gly Gln Gly Leu Glu Trp Met
        35                  40                  45

Gly Lys Ile Ile Pro Ile Leu Gly Ile Val Asn Tyr Ala Gln Lys Phe
    50                  55                  60
```

```
Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Gly Lys Pro Leu Tyr Ser Tyr Gly Tyr Gly Leu
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Xaa Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 235
<211> LENGTH: 5
<212> TYPE: PRT

<213> ORGANISM: Artificial Sequence
<220> FEATURE:
<223> OTHER INFORMATION: The sequence is artificially synthesized

<400> SEQUENCE: 235

Asp Tyr Pro Ile Met
1               5

<210> SEQ ID NO 236
<211> LENGTH: 19
<212> TYPE: PRT
<213> ORGANISM: Artificial Sequence
<220> FEATURE:
<223> OTHER INFORMATION: he sequence is artificially synthesized

<400> SEQUENCE: 236

Phe Ile Arg Ser Lys Ala Tyr Gly Gly Thr Ala Glu Tyr Ala Ala Ser
1               5                   10                  15

Val Lys Gly

<210> SEQ ID NO 237
<211> LENGTH: 19
<212> TYPE: PRT
<213> ORGANISM: Artificial Sequence
<220> FEATURE:
<223> OTHER INFORMATION: he sequence is artificially synthesized

<400> SEQUENCE: 237

Glu Gly Gly His Ser Gly Phe Trp Ser Gly Phe Asn Lys Ile Pro Thr
1               5                   10                  15

Phe Asp Tyr

<210> SEQ ID NO 238
<211> LENGTH: 11
<212> TYPE: PRT
<213> ORGANISM: Artificial Sequence
<220> FEATURE:
<223> OTHER INFORMATION: he sequence is artificially synthesized

<400> SEQUENCE: 238

Arg Ala Ser Glu Thr Ile Arg Thr Tyr Leu Asn
1               5                   10

<210> SEQ ID NO 239
<211> LENGTH: 7
<212> TYPE: PRT
<213> ORGANISM: Artificial Sequence
<220> FEATURE:
<223> OTHER INFORMATION: he sequence is artificially synthesized

<400> SEQUENCE: 239

Ala Ala Ser Ser Val Gln Ser
1               5

<210> SEQ ID NO 240
<211> LENGTH: 10
<212> TYPE: PRT
<213> ORGANISM: Artificial Sequence
<220> FEATURE:
<223> OTHER INFORMATION: he sequence is artificially synthesized

<400> SEQUENCE: 240

Gln Gln Ser Tyr Thr Ser Pro Trp Val Thr
1               5                   10

<210> SEQ ID NO 241
<211> LENGTH: 30
<212> TYPE: PRT
<213> ORGANISM: Artificial Sequence
<220> FEATURE:
<223> OTHER INFORMATION: he sequence is artificially synthesized

<400> SEQUENCE: 241

Gln Val Gln Leu Val Glu Ser Gly Gly Gly Leu Val Gln Ser Gly Arg
1               5                   10                  15

Ser Leu Arg Leu Ser Cys Ser Ala Phe Gly Phe Thr Phe Gly
            20                  25                  30

<210> SEQ ID NO 242
<211> LENGTH: 14
<212> TYPE: PRT
<213> ORGANISM: Artificial Sequence
<220> FEATURE:
<223> OTHER INFORMATION: he sequence is artificially synthesized

<400> SEQUENCE: 242

Trp Val Arg Leu Ala Pro Gly Lys Gly Leu Glu Trp Val Gly
1               5                   10

<210> SEQ ID NO 243
<211> LENGTH: 32
<212> TYPE: PRT
<213> ORGANISM: Artificial Sequence
<220> FEATURE:
<223> OTHER INFORMATION: he sequence is artificially synthesized

<400> SEQUENCE: 243

Arg Phe Thr Thr Ser Arg Asp Asp Ser Arg Ser Thr Ala Tyr Leu Gln
1               5                   10                  15

Met Asn Ser Leu Lys Thr Glu Asp Thr Ala Val Tyr Tyr Cys Thr Arg
            20                  25                  30

<210> SEQ ID NO 244
<211> LENGTH: 11
<212> TYPE: PRT
<213> ORGANISM: Artificial Sequence
<220> FEATURE:
<223> OTHER INFORMATION: he sequence is artificially synthesized

<400> SEQUENCE: 244

Trp Gly Gln Gly Ser Leu Val Thr Val Ser Ser
1               5                   10

<210> SEQ ID NO 245
<211> LENGTH: 23
<212> TYPE: PRT
<213> ORGANISM: Artificial Sequence
<220> FEATURE:
<223> OTHER INFORMATION: he sequence is artificially synthesized

<400> SEQUENCE: 245

Asp Ile Gln Met Thr Gln Ser Pro Ser Ser Leu Ser Ala Ser Ile Gly
1               5                   10                  15

Asp Arg Val Ser Ile Thr Cys
            20

<210> SEQ ID NO 246
<211> LENGTH: 15
<212> TYPE: PRT
<213> ORGANISM: Artificial Sequence
<220> FEATURE:

<223> OTHER INFORMATION: he sequence is artificially synthesized

<400> SEQUENCE: 246

Trp Tyr Gln His Lys Pro Gly Lys Ala Pro Gln Leu Leu Ile Tyr
1 5 10 15

<210> SEQ ID NO 247
<211> LENGTH: 32
<212> TYPE: PRT
<213> ORGANISM: Artificial Sequence
<220> FEATURE:
<223> OTHER INFORMATION: he sequence is artificially synthesized

<400> SEQUENCE: 247

Gly Val Pro Ser Arg Phe Ser Gly Ser Gly Ser Gly Thr Asp Phe Thr
1 5 10 15

Leu Thr Ile Ser Asn Leu Gln Pro Glu Asp Phe Ala Thr Tyr Tyr Cys
20 25 30

<210> SEQ ID NO 248
<211> LENGTH: 10
<212> TYPE: PRT
<213> ORGANISM: Artificial Sequence
<220> FEATURE:
<223> OTHER INFORMATION: he sequence is artificially synthesized

<400> SEQUENCE: 248

Phe Gly Pro Gly Thr Lys Val Asp Ile Lys
1 5 10

<210> SEQ ID NO 249
<211> LENGTH: 108
<212> TYPE: PRT
<213> ORGANISM: Artificial Sequence
<220> FEATURE:
<223> OTHER INFORMATION: he sequence is artificially synthesized

<400> SEQUENCE: 249

Asp Ile Gln Met Thr Gln Ser Pro Ser Ser Leu Ser Ala Ser Ile Gly
1 5 10 15

Asp Arg Val Ser Ile Thr Cys Arg Ala Ser Glu Thr Ile Arg Thr Tyr
20 25 30

Leu Asn Trp Tyr Gln His Lys Pro Gly Lys Ala Pro Gln Leu Leu Ile
35 40 45

Tyr Ala Ala Ser Ser Val Gln Ser Gly Val Pro Ser Arg Phe Ser Gly
50 55 60

Ser Gly Ser Gly Thr Asp Phe Thr Leu Thr Ile Ser Asn Leu Gln Pro
65 70 75 80

Glu Asp Phe Ala Thr Tyr Tyr Cys Gln Gln Ser Tyr Thr Ser Pro Trp
85 90 95

Val Thr Phe Gly Pro Gly Thr Lys Val Asp Ile Lys
100 105

<210> SEQ ID NO 250
<211> LENGTH: 130
<212> TYPE: PRT
<213> ORGANISM: Artificial Sequence
<220> FEATURE:
<223> OTHER INFORMATION: The sequence is artificially synthesized

<400> SEQUENCE: 250

Gln Val Gln Leu Val Glu Ser Gly Gly Gly Leu Val Gln Ser Gly Arg
1 5 10 15

Ser Leu Arg Leu Ser Cys Ser Ala Phe Gly Phe Thr Phe Gly Asp Tyr
20 25 30

Pro Ile Met Trp Val Arg Leu Ala Pro Gly Lys Gly Leu Glu Trp Val
35 40 45

Gly Phe Ile Arg Ser Lys Ala Tyr Gly Gly Thr Ala Glu Tyr Ala Ala
50 55 60

Ser Val Lys Gly Arg Phe Thr Thr Ser Arg Asp Asp Ser Arg Ser Thr
65 70 75 80

Ala Tyr Leu Gln Met Asn Ser Leu Lys Thr Glu Asp Thr Ala Val Tyr
85 90 95

Tyr Cys Thr Arg Glu Gly Gly His Ser Gly Phe Trp Ser Gly Phe Asn
100 105 110

Lys Ile Pro Thr Phe Asp Tyr Trp Gly Gln Gly Ser Leu Val Thr Val
115 120 125

Ser Ser
130

<210> SEQ ID NO 251
<211> LENGTH: 215
<212> TYPE: PRT
<213> ORGANISM: Artificial Sequence
<220> FEATURE:
<223> OTHER INFORMATION: he sequence is artificially synthesized

<400> SEQUENCE: 251

Asp Ile Gln Met Thr Gln Ser Pro Ser Ser Leu Ser Ala Ser Ile Gly
1 5 10 15

Asp Arg Val Ser Ile Thr Cys Arg Ala Ser Glu Thr Ile Arg Thr Tyr
20 25 30

Leu Asn Trp Tyr Gln His Lys Pro Gly Lys Ala Pro Gln Leu Leu Ile
35 40 45

Tyr Ala Ala Ser Ser Val Gln Ser Gly Val Pro Ser Arg Phe Ser Gly
50 55 60

Ser Gly Ser Gly Thr Asp Phe Thr Leu Thr Ile Ser Asn Leu Gln Pro
65 70 75 80

Glu Asp Phe Ala Thr Tyr Tyr Cys Gln Gln Ser Tyr Thr Ser Pro Trp
85 90 95

Val Thr Phe Gly Pro Gly Thr Lys Val Asp Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 252

```
<211> LENGTH: 460
<212> TYPE: PRT
<213> ORGANISM: Artificial Sequence
<220> FEATURE:
<223> OTHER INFORMATION: he sequence is artificially synthesized
<220> FEATURE:
<221> NAME/KEY: VARIANT
<222> LOCATION: (354)..(354)
<223> OTHER INFORMATION: Xaa can be  Gly or absent

<400> SEQUENCE: 252

Gln Val Gln Leu Val Glu Ser Gly Gly Gly Leu Val Gln Ser Gly Arg
1               5                   10                  15

Ser Leu Arg Leu Ser Cys Ser Ala Phe Gly Phe Thr Phe Gly Asp Tyr
            20                  25                  30

Pro Ile Met Trp Val Arg Leu Ala Pro Gly Lys Gly Leu Glu Trp Val
        35                  40                  45

Gly Phe Ile Arg Ser Lys Ala Tyr Gly Gly Thr Ala Glu Tyr Ala Ala
    50                  55                  60

Ser Val Lys Gly Arg Phe Thr Thr Ser Arg Asp Asp Ser Arg Ser Thr
65                  70                  75                  80

Ala Tyr Leu Gln Met Asn Ser Leu Lys Thr Glu Asp Thr Ala Val Tyr
                85                  90                  95

Tyr Cys Thr Arg Glu Gly Gly His Ser Gly Phe Trp Ser Gly Phe Asn
            100                 105                 110

Lys Ile Pro Thr Phe Asp Tyr Trp Gly Gln Gly Ser Leu Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Xaa Gln Pro Arg Glu Pro Gln Val Tyr Thr Leu Pro Pro Ser Arg
```

```
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460


<210> SEQ ID NO 253
<211> LENGTH: 226
<212> TYPE: PRT
<213> ORGANISM: Hepatitis B virus

<400> SEQUENCE: 253

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Met Thr Thr Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220

Tyr Ile
225


<210> SEQ ID NO 254
<211> LENGTH: 226
<212> TYPE: PRT
<213> ORGANISM: Artificial Sequence
<220> FEATURE:
```

<223> OTHER INFORMATION: The sequence is artificially synthesized

<400> SEQUENCE: 254

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile
225

<210> SEQ ID NO 255
<211> LENGTH: 226
<212> TYPE: PRT
<213> ORGANISM: Artificial Sequence
<220> FEATURE:
<223> OTHER INFORMATION: The sequence is artificially synthesized

<400> SEQUENCE: 255

Met Glu Asn Ile Ala Ser Gly Leu Leu Gly Pro Leu Leu Val Leu Gln
1               5                   10                  15

Ala Gly Phe Phe Leu Leu Thr Lys Ile Leu Thr Ile Pro Gln Ser Leu
            20                  25                  30

Asp Ser Trp Trp Thr Ser Leu Asn Phe Leu Gly Gly Thr Pro Val Cys
        35                  40                  45

Leu Gly Gln Asn Ser Gln Ser Gln Ile Ser Ser His Ser Pro Thr Cys
    50                  55                  60

Cys Pro Pro Ile Cys Pro Gly Tyr Arg Trp Met Cys Leu Arg Arg Phe
65                  70                  75                  80

Ile Ile Phe Leu Cys Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

```
Ser Ser Thr Thr Ser Thr Gly Pro Cys Lys Thr Cys Thr Thr Pro Ala
        115                 120                 125

Gln Gly Thr Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Phe Trp Gly Pro Ser Leu Tyr Asn Ile
        195                 200                 205

Leu Ser Pro Phe Met Pro Leu Leu Pro Ile Phe Phe Cys Leu Trp Val
    210                 215                 220

Tyr Ile
225


<210> SEQ ID NO 256
<211> LENGTH: 226
<212> TYPE: PRT
<213> ORGANISM: Artificial Sequence
<220> FEATURE:
<223> OTHER INFORMATION: The sequence is artificially synthesized

<400> SEQUENCE: 256

Met Glu Asn Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala Pro Thr Cys
        35                  40                  45

Pro Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Lys Thr Cys Thr Ile Pro Ala
        115                 120                 125

Gln Gly Thr Ser Met Phe Pro Ser Cys Cys Cys Thr Lys Pro Ser Asp
    130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Ser Pro Phe Leu Pro Leu Leu Pro Ile Phe Phe Cys Leu Trp Val
    210                 215                 220

Tyr Ile
225
```

<210> SEQ ID NO 257
<211> LENGTH: 226
<212> TYPE: PRT
<213> ORGANISM: Artificial Sequence
<220> FEATURE:
<223> OTHER INFORMATION: The sequence is artificially synthesized

<400> SEQUENCE: 257

Met Glu Asn Ile Thr Ser Gly Phe Leu Gly Pro Leu Leu Val Leu Gln
1 5 10 15

Ala Gly Phe Phe Leu Leu Thr Arg Ile Leu Thr Ile Pro Gln Ser Leu
20 25 30

Asp Ser Trp Trp Thr Ser Leu Asn Phe Leu Gly Gly Thr Thr Val Cys
35 40 45

Leu Gly Gln Asn Ser Gln Ser Pro Thr Ser Asn His Ser Pro Thr Ser
50 55 60

Cys Pro Pro Thr Cys Pro Gly Tyr Arg Trp Met Cys Leu Arg Arg Phe
65 70 75 80

Ile Ile Phe Leu Phe Ile Leu Leu Leu Cys Leu Ile Phe Leu Leu Val
85 90 95

Leu Leu Asp Tyr Gln Gly Met Leu Pro Val Cys Pro Leu Ile Pro Gly
100 105 110

Ser Ser Thr Thr Ser Thr Gly Pro Cys Arg Thr Cys Thr Thr Thr Ala
115 120 125

Gln Gly Thr Ser Met Tyr Pro Ser Cys Cys Cys Thr Lys Pro Ser Asp
130 135 140

Gly Asn Cys Thr Cys Ile Pro Ile Pro Ser Ser Trp Ala Phe Gly Lys
145 150 155 160

Phe Leu Trp Glu Trp Ala Ser Ala Arg Phe Ser Trp Leu Ser Leu Leu
165 170 175

Val Pro Phe Val Gln Trp Phe Val Gly Leu Ser Pro Thr Val Trp Leu
180 185 190

Ser Val Ile Trp Met Met Trp Tyr Trp Gly Pro Ser Leu Tyr Ser Ile
195 200 205

Leu Ser Pro Phe Leu Pro Leu Leu Pro Ile Phe Phe Cys Leu Trp Val
210 215 220

Tyr Ile
225

<210> SEQ ID NO 258
<211> LENGTH: 226
<212> TYPE: PRT
<213> ORGANISM: Artificial Sequence
<220> FEATURE:
<223> OTHER INFORMATION: The sequence is artificially synthesized

<400> SEQUENCE: 258

Met Glu Ser Ile Thr Ser Gly Phe Leu Gly Pro Leu Leu Val Leu Gln
1 5 10 15

Ala Gly Phe Phe Leu Leu Thr Lys Ile Leu Thr Ile Pro Gln Ser Leu
20 25 30

Asp Ser Trp Trp Thr Ser Leu Asn Phe Leu Gly Gly Ala Pro Val Cys
35 40 45

Leu Gly Gln Asn Ser Gln Ser Pro Thr Ser Asn His Ser Pro Thr Ser
50 55 60

Cys Pro Pro Ile Cys Pro Gly Tyr Arg Trp Met Cys Leu Arg Arg Phe

```
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Leu Ala
        115                 120                 125

Gln Gly Thr Ser Met Phe Pro Ser Cys Cys Cys Ser Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Ala Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Ser Pro Phe Ile Pro Leu Leu Pro Ile Phe Phe Cys Leu Trp Val
    210                 215                 220

Tyr Ile
225


<210> SEQ ID NO 259
<211> LENGTH: 226
<212> TYPE: PRT
<213> ORGANISM: Artificial Sequence
<220> FEATURE:
<223> OTHER INFORMATION: The sequence is artificially synthesized

<400> SEQUENCE: 259

Met Asp Asn Ile Thr Ser Gly Leu Leu Gly Pro Leu Leu Val Leu Gln
1               5                   10                  15

Ala Val Cys Phe Leu Leu Thr Lys Ile Leu Thr Ile Pro Gln Ser Leu
            20                  25                  30

Asp Ser Trp Trp Thr Ser Leu Asn Phe Leu Gly Gly Leu Pro Gly Cys
        35                  40                  45

Pro Gly Gln Asn Ser Gln Ser Pro Thr Ser Asn His Leu Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Ser Thr Thr Thr Ser Thr Gly Pro Cys Lys Thr Cys Thr Thr Leu Ala
        115                 120                 125

Gln Gly Thr Ser Met Phe Pro Ser Cys Cys Cys Ser Lys Pro Ser Asp
    130                 135                 140

Gly Asn Cys Thr Cys Ile Pro Ile Pro Ser Ser Trp Ala Leu Gly Lys
145                 150                 155                 160

Tyr Leu Trp Glu Trp Ala Ser Ala Arg Phe Ser Trp Leu Ser Leu Leu
                165                 170                 175

Val Gln Phe Val Gln Trp Cys Val Gly Leu Ser Pro Thr Val Trp Leu
            180                 185                 190

Leu Val Ile Trp Met Ile Trp Tyr Trp Gly Pro Asn Leu Cys Ser Ile
```

```
        195                 200                 205

Leu Ser Pro Phe Ile Pro Leu Leu Pro Ile Phe Cys Tyr Leu Trp Val
    210                 215                 220

Ser Ile
225
```

<210> SEQ ID NO 260
<211> LENGTH: 226
<212> TYPE: PRT
<213> ORGANISM: Artificial Sequence
<220> FEATURE:
<223> OTHER INFORMATION: The sequence is artificially synthesized

<400> SEQUENCE: 260

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Val Pro Val Cys
        35                  40                  45

Pro Gly Leu Asn Ser Gln Ser Pro Thr Ser Asn His Ser Pro Ile Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Lys Thr Cys Thr Thr Pro Ala
        115                 120                 125

Gln Gly Asn Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Asn Leu Tyr Asn Ile
        195                 200                 205

Leu Ser Pro Phe Ile Pro Leu Leu Pro Ile Phe Phe Cys Leu Trp Val
    210                 215                 220

Tyr Ile
225
```

<210> SEQ ID NO 261
<211> LENGTH: 226
<212> TYPE: PRT
<213> ORGANISM: Artificial Sequence
<220> FEATURE:
<223> OTHER INFORMATION: The sequence is artificially synthesized

<400> SEQUENCE: 261

```
Met Glu Asn Ile Thr Ser Gly Leu Leu Gly Pro Leu Leu Val Leu Gln
1               5                   10                  15

Ala Val Cys Phe Leu Leu Thr Lys Ile Leu Thr Ile Pro Gln Ser Leu
            20                  25                  30
```

```
Asp Ser Trp Trp Thr Ser Leu Asn Phe Leu Gly Val Pro Pro Gly Cys
        35                  40                  45

Pro Gly Gln Asn Ser Gln Ser Pro Ile Ser Asn His Leu Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Ser Thr Thr Thr Ser Thr Gly Pro Cys Lys Thr Cys Thr Thr Leu Ala
        115                 120                 125

Gln Gly Thr Ser Met Phe Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Tyr Leu Trp Glu Trp Ala Ser Ala Arg Phe Ser Trp Leu Ser Leu Leu
                165                 170                 175

Val Gln Phe Val Gln Trp Cys Val Gly Leu Ser Pro Thr Val Trp Leu
            180                 185                 190

Leu Val Ile Trp Met Ile Trp Tyr Trp Gly Pro Asn Leu Cys Ser Ile
        195                 200                 205

Leu Ser Pro Phe Ile Pro Leu Leu Pro Ile Phe Cys Tyr Leu Trp Ala
    210                 215                 220

Ser Ile
225


<210> SEQ ID NO 262
<211> LENGTH: 226
<212> TYPE: PRT
<213> ORGANISM: Artificial Sequence
<220> FEATURE:
<223> OTHER INFORMATION: The sequence is artificially synthesized

<400> SEQUENCE: 262

Met Glu Asn Ile Thr Ser Gly Phe Leu Gly Pro Leu Leu Val Leu Gln
1               5                   10                  15

Ala Gly Phe Phe Leu Leu Thr Lys Ile Leu Thr Ile Pro Gln Ser Leu
            20                  25                  30

Asp Ser Trp Trp Thr Ser Leu Asn Phe Leu Gly Gly Ala Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Lys Thr Cys Thr Thr Pro Ala
        115                 120                 125

Gln Gly Asn Ser Met Tyr Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160
```

```
Tyr Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Ser Pro Phe Ile Pro Leu Leu Pro Ile Phe Phe Cys Leu Trp Val
    210                 215                 220

Tyr Ile
225


<210> SEQ ID NO 263
<211> LENGTH: 450
<212> TYPE: PRT
<213> ORGANISM: Artificial Sequence
<220> FEATURE:
<223> OTHER INFORMATION: The sequence is artificially synthesized

<400> SEQUENCE: 263

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Asn Tyr
            20                  25                  30

Gly Met Gln Trp Val Arg Gln Ala Pro Gly Lys Gly Leu Glu Trp Val
        35                  40                  45

Ala Ile Ile Trp Ala Asp Gly Thr Lys Gln Tyr Tyr Gly Asp Ser Val
    50                  55                  60

Lys Gly Arg Phe Thr Ile Ser Arg Asp Asn Phe Lys Asn Thr Leu Tyr
65                  70                  75                  80

Leu Gln Met Asn Ser Leu Arg Gly Glu Asp Thr Ala Met Tyr Phe Cys
                85                  90                  95

Ala Arg Asp Gly Leu Tyr Ala Ser Ala Pro Asn Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 264
<211> LENGTH: 446
<212> TYPE: PRT
<213> ORGANISM: Artificial Sequence
<220> FEATURE:
<223> OTHER INFORMATION: The sequence is artificially synthesized

<400> SEQUENCE: 264

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Arg Ser
            20                  25                  30

Ala Val Ser Trp Val Arg His Ala Pro Gly Gln Arg Leu Glu Trp Met
        35                  40                  45

Gly Arg Thr Ile Pro Leu Leu Arg Ile Ala Glu Tyr Ser Gln Thr Phe
    50                  55                  60

Gln Gly Arg Val Thr Ile Thr Ala Asp Lys Phe Thr Asn Thr Val Tyr
65                  70                  75                  80

Met Glu Leu Arg Ser Leu Thr Tyr Glu Asp Thr Ala Val Tyr Tyr Cys
                85                  90                  95

Ala Arg Glu Gly Asp Gly Leu Asp Met Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

```
Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 265
<211> LENGTH: 458
<212> TYPE: PRT
<213> ORGANISM: Artificial Sequence
<220> FEATURE:
<223> OTHER INFORMATION: The sequence is artificially synthesized

<400> SEQUENCE: 265

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Gly Ser Tyr
            20                  25                  30

Ala Met Ser Trp Val Arg Gln Ala Pro Gly Lys Gly Leu Lys Trp Val
        35                  40                  45

Ser Ala Phe Ser Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Phe Cys
                85                  90                  95

Ala Lys Asp Pro Gly His Thr Ser Asn Trp Arg Asp Asn Tyr Gln Tyr
            100                 105                 110
```

Tyr Gln Met Asp Val Trp Gly Gln Gly Thr Thr Val Thr Val Ser Ser
115 120 125

Ala Ser Thr Lys Gly Pro Ser Val Phe Pro Leu Ala Pro Ser Ser Lys
130 135 140

Ser Thr Ser Gly Gly Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Gln Thr
195 200 205

Tyr Ile Cys Asn Val Asn His Lys Pro Ser Asn Thr Lys Val Asp Lys
210 215 220

Arg Val Glu Pro Lys Ser Cys Asp Lys Thr His Thr Cys Pro Pro Cys
225 230 235 240

Pro Ala Pro Glu Leu Leu Gly Gly Pro Ser Val Phe Leu Phe Pro Pro
245 250 255

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu
290 295 300

Glu Gln Tyr Asn Ser Thr Tyr Arg Val Val Ser Val Leu Thr Val Leu
305 310 315 320

His Gln Asp Trp Leu Asn Gly Lys Glu Tyr Lys Cys Lys Val Ser Asn
325 330 335

Lys Ala Leu Pro Ala Pro Ile Glu Lys Thr Ile Ser Lys Ala Lys Gly
340 345 350

Gln Pro Arg Glu Pro Gln Val Tyr Thr Leu Pro Pro Ser Arg Glu Glu
355 360 365

Met Thr Lys Asn Gln Val Ser Leu Thr Cys Leu Val Lys Gly Phe Tyr
370 375 380

Pro Ser Asp Ile Ala Val Glu Trp Glu Ser Asn Gly Gln Pro Glu Asn
385 390 395 400

Asn Tyr Lys Thr Thr Pro Pro Val Leu Asp Ser Asp Gly Ser Phe Phe
405 410 415

Leu Tyr Ser Lys Leu Thr Val Asp Lys Ser Arg Trp Gln Gln Gly Asn
420 425 430

Val Phe Ser Cys Ser Val Met His Glu Ala Leu His Asn His Tyr Thr
435 440 445

Gln Lys Ser Leu Ser Leu Ser Pro Gly Lys
450 455

<210> SEQ ID NO 266
<211> LENGTH: 450
<212> TYPE: PRT
<213> ORGANISM: Artificial Sequence
<220> FEATURE:
<223> OTHER INFORMATION: The sequence is artificially synthesized

<400> SEQUENCE: 266

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Gly Tyr
20 25 30

Gly Met His Trp Val Arg Gln Ala Pro Gly Lys Gly Leu Glu Trp Val
35 40 45

Ala Phe Leu Trp His Asp Gly Thr Ser Lys Asp Tyr Ala Asp Ser Val
50 55 60

Lys Gly Arg Phe Thr Ile Ser Arg Asp Asn Ser Lys Asn Thr Leu Tyr
65 70 75 80

Met Gln Met Asn Ser Leu Arg Ala Glu Asp Thr Ala Val Tyr Tyr Cys
85 90 95

Ala Arg Glu Asp Tyr Tyr Asp Ser Asn Ala Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro

```
        435                 440                 445

Gly Lys
    450


<210> SEQ ID NO 267
<211> LENGTH: 453
<212> TYPE: PRT
<213> ORGANISM: Artificial Sequence
<220> FEATURE:
<223> OTHER INFORMATION: The sequence is artificially synthesized

<400> SEQUENCE: 267

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ala Thr Ser Gly Ser Gly Ala Asp Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Asp Asp Thr Ala Phe Tyr Tyr Cys
                85                  90                  95

Ala Lys Asp Pro Tyr Met Val Ala Ala Val Ala Arg Thr Val Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
```

```
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 268
<211> LENGTH: 454
<212> TYPE: PRT
<213> ORGANISM: Artificial Sequence
<220> FEATURE:
<223> OTHER INFORMATION: The sequence is artificially synthesized

<400> SEQUENCE: 268

Gln Val Gln Leu Val Gln Ser Gly Ala Glu Val Lys Lys Ala Gly Ser
1               5                   10                  15

Ser Val Lys Val Ser Cys Lys Ala Phe Gly Gly Thr Ser Asn Asn Tyr
            20                  25                  30

Gly Val Thr Trp Val Arg Gln Ala Pro Gly Gln Gly Leu Gln Trp Met
        35                  40                  45

Gly Gly Ile Ile Pro Ile Phe Gly Thr Thr Asn Tyr Ala Gln Lys Phe
    50                  55                  60

Leu Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Gln Gly Ser Ser Thr Trp Phe Ala Thr Leu Tyr Ala Phe Pro
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
```

```
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 269
<211> LENGTH: 453
<212> TYPE: PRT
<213> ORGANISM: Artificial Sequence
<220> FEATURE:
<223> OTHER INFORMATION: The sequence is artificially synthesized

<400> SEQUENCE: 269

Glu Val Gln Leu Val Gln Ser Gly Ala Ala Val Arg Lys Pro Gly Glu
1               5                   10                  15

Ser Leu Arg Ile Ser Cys Gln Ala Ser Gly Phe Ser Phe Thr Asn Tyr
            20                  25                  30

Trp Ile Thr Trp Val Arg Gln Arg Pro Gly Lys Gly Leu Glu Trp Met
        35                  40                  45

Gly Arg Ile Asp Thr Arg Asp Ser Tyr Thr Asn Tyr Ser Pro Ser Phe
    50                  55                  60

Gln Gly His Val Thr Ile Ser Ile Asp Arg Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Thr Thr Tyr Pro Leu Asn Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
```

```
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 270
<211> LENGTH: 451
<212> TYPE: PRT
<213> ORGANISM: Artificial Sequence
<220> FEATURE:
<223> OTHER INFORMATION: The sequence is artificially synthesized

<400> SEQUENCE: 270

```
Gln Val Gln Leu Val Gln Ser Gly Ala Glu Val Lys Lys Pro Gly Ser
1               5                   10                  15

Ser Val Lys Val Ser Cys Arg Ser Ser Gly Tyr Arg Phe Thr Asn Tyr
            20                  25                  30

His Ile His Trp Val Arg Gln Ala Pro Gly Gln Gly Leu Glu Trp Val
        35                  40                  45

Gly Ile Ile Asn Pro Arg Arg Leu Ser Thr Ala Tyr Ala Pro Lys Phe
```

```
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Asp Ala Gly Asp Asp Thr Ser Gly Pro Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 271
```

<211> LENGTH: 450
<212> TYPE: PRT
<213> ORGANISM: Artificial Sequence
<220> FEATURE:
<223> OTHER INFORMATION: The sequence is artificially synthesized

<400> SEQUENCE: 271

Gln Val Gln Leu Val Glu Ser Gly Gly Gly Val Val Gln Pro Gly Arg
1 5 10 15

Ser Leu Arg Val Ser Cys Ala Ala Ser Gly Phe Thr Phe Ser Asn Tyr
20 25 30

Gly Met His Trp Val Arg Gln Ala Pro Gly Lys Gly Leu Glu Trp Leu
35 40 45

Ala Val Ile Trp Asn Asp Gly Ser Asn Lys Tyr Tyr Ala Asp Ser Val
50 55 60

Lys Gly Arg Phe Ile Ile Ser Arg Asp Asn Ser Lys Asn Thr Leu Tyr
65 70 75 80

Leu Gln Met Asn Ser Leu Gly Ala Glu Asp Thr Ala Met Tyr Tyr Cys
85 90 95

Ala Arg Glu Gly Leu Thr Ser Val Thr Met Leu Asp Ser Trp Gly Gln
100 105 110

Gly Ala Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Thr Cys Leu Val Lys Gly Phe Tyr Pro Ser Asp Ile Ala Val Glu Trp
370 375 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 272
<211> LENGTH: 453
<212> TYPE: PRT
<213> ORGANISM: Artificial Sequence
<220> FEATURE:
<223> OTHER INFORMATION: The sequence is artificially synthesized

<400> SEQUENCE: 272

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Thr Ile Arg Thr Asn
            20                  25                  30

Asn Trp Trp Ser Trp Val Arg Gln Pro Pro Gly Lys Gly Leu Glu Trp
        35                  40                  45

Ile Gly Glu Ile His His Ile Gly Ser Thr Asn Tyr Asn Pro Ser Leu
    50                  55                  60

Lys Ser Gln Val Thr Ile Ser Val Asp Lys Ser Lys Asn Gln Phe Ser
65                  70                  75                  80

Leu Asn Leu Ser Ser Val Thr Ala Ala Asp Thr Ala Leu Tyr Tyr Cys
                85                  90                  95

Val Arg Gly Arg Leu Gly Ile Thr Arg Asp Arg Tyr Tyr Phe Asp Ser
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 273
<211> LENGTH: 448
<212> TYPE: PRT
<213> ORGANISM: Artificial Sequence
<220> FEATURE:
<223> OTHER INFORMATION: The sequence is artificially synthesized

<400> SEQUENCE: 273

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Asn Tyr
            20                  25                  30

Gly Met His Trp Val Arg Gln Ala Pro Gly Lys Gly Leu Glu Trp Val
        35                  40                  45

Ala Phe Thr Ile Tyr Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Tyr Glu Asp Thr Ala Val Tyr Tyr Cys
                85                  90                  95

Ala Thr Asp Ser Asn Gly Phe Gly Val Leu Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

```
Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 274
<211> LENGTH: 462
<212> TYPE: PRT
<213> ORGANISM: Artificial Sequence
<220> FEATURE:
<223> OTHER INFORMATION: The sequence is artificially synthesized

<400> SEQUENCE: 274

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Ala Phe Asn Ser Tyr
            20                  25                  30

Gly Met Asn Trp Val Arg Gln Ala Pro Gly Lys Gly Leu Glu Trp Val
        35                  40                  45

Ala Ile Ile Trp Phe Asp Gly Ser Gln Thr Tyr Tyr Gly Asp Ser Val
    50                  55                  60

Lys Gly Arg Phe Thr Ile Ser Arg Asp Arg Ser Thr Asn Thr Leu Phe
65                  70                  75                  80

Leu Gln Met Asn Asn Leu Arg Ala Asp Asp Thr Ala Met Tyr Tyr Cys
                85                  90                  95

Ala Arg Gly Gly Ala Glu Glu Ser Thr Asn Trp Arg Phe Leu Trp Val
            100                 105                 110
```

```
Pro Arg Tyr Tyr Tyr Tyr Met Asp Val Trp Gly Lys Gly Thr Thr Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460


<210> SEQ ID NO 275
<211> LENGTH: 455
<212> TYPE: PRT
<213> ORGANISM: Artificial Sequence
<220> FEATURE:
<223> OTHER INFORMATION: The sequence is artificially synthesized

<400> SEQUENCE: 275

Gln Val Gln Leu Val Gln Ser Gly Ala Glu Val Lys Lys Pro Gly Ser
1               5                   10                  15
```

```
Ser Val Lys Val Ser Cys Arg Ala Ser Gly Gly Thr Phe Ser Asn Tyr
            20                  25                  30

Gly Val Asn Trp Val Arg Gln Ala Pro Gly Gln Gly Leu Glu Trp Met
        35                  40                  45

Gly Lys Ile Ile Pro Ile Leu Gly Ile Val Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Gly Lys Pro Leu Tyr Ser Tyr Gly Tyr Gly Leu
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430
```

Cys Ser Val Met His Glu Ala Leu His Asn His Tyr Thr Gln Lys Ser
435 440 445

Leu Ser Leu Ser Pro Gly Lys
450 455

<210> SEQ ID NO 276
<211> LENGTH: 460
<212> TYPE: PRT
<213> ORGANISM: Artificial Sequence
<220> FEATURE:
<223> OTHER INFORMATION: The sequence is artificially synthesized

<400> SEQUENCE: 276

Gln Val Gln Leu Val Glu Ser Gly Gly Gly Leu Val Gln Ser Gly Arg
1 5 10 15

Ser Leu Arg Leu Ser Cys Ser Ala Phe Gly Phe Thr Phe Gly Asp Tyr
20 25 30

Pro Ile Met Trp Val Arg Leu Ala Pro Gly Lys Gly Leu Glu Trp Val
35 40 45

Gly Phe Ile Arg Ser Lys Ala Tyr Gly Gly Thr Ala Glu Tyr Ala Ala
50 55 60

Ser Val Lys Gly Arg Phe Thr Thr Ser Arg Asp Asp Ser Arg Ser Thr
65 70 75 80

Ala Tyr Leu Gln Met Asn Ser Leu Lys Thr Glu Asp Thr Ala Val Tyr
85 90 95

Tyr Cys Thr Arg Glu Gly Gly His Ser Gly Phe Trp Ser Gly Phe Asn
100 105 110

Lys Ile Pro Thr Phe Asp Tyr Trp Gly Gln Gly Ser Leu Val Thr Val
115 120 125

Ser Ser Ala Ser Thr Lys Gly Pro Ser Val Phe Pro Leu Ala Pro Ser
130 135 140

Ser Lys Ser Thr Ser Gly Gly Thr Ala Ala Leu Gly Cys Leu Val Lys
145 150 155 160

Asp Tyr Phe Pro Glu Pro Val Thr Val Ser Trp Asn Ser Gly Ala Leu
165 170 175

Thr Ser Gly Val His Thr Phe Pro Ala Val Leu Gln Ser Ser Gly Leu
180 185 190

Tyr Ser Leu Ser Ser Val Val Thr Val Pro Ser Ser Ser Leu Gly Thr
195 200 205

Gln Thr Tyr Ile Cys Asn Val Asn His Lys Pro Ser Asn Thr Lys Val
210 215 220

Asp Lys Arg Val Glu Pro Lys Ser Cys Asp Lys Thr His Thr Cys Pro
225 230 235 240

Pro Cys Pro Ala Pro Glu Leu Leu Gly Gly Pro Ser Val Phe Leu Phe
245 250 255

Pro Pro Lys Pro Lys Asp Thr Leu Met Ile Ser Arg Thr Pro Glu Val
260 265 270

Thr Cys Val Val Val Asp Val Ser His Glu Asp Pro Glu Val Lys Phe
275 280 285

Asn Trp Tyr Val Asp Gly Val Glu Val His Asn Ala Lys Thr Lys Pro
290 295 300

Arg Glu Glu Gln Tyr Asn Ser Thr Tyr Arg Val Val Ser Val Leu Thr
305 310 315 320

Val Leu His Gln Asp Trp Leu Asn Gly Lys Glu Tyr Lys Cys Lys Val
325 330 335

```
Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460


<210> SEQ ID NO 277
<211> LENGTH: 4
<212> TYPE: PRT
<213> ORGANISM: Artificial Sequence
<220> FEATURE:
<223> OTHER INFORMATION: The sequence is artificially synthesized

<400> SEQUENCE: 277

Gly Gly Gly Ser
1


<210> SEQ ID NO 278
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 278

His His His His His His His His His His
1               5                   10


<210> SEQ ID NO 279
<211> LENGTH: 20
<212> TYPE: PRT
<213> ORGANISM: Artificial Sequence
<220> FEATURE:
<223> OTHER INFORMATION: The sequence is artificially synthesized

<400> SEQUENCE: 279

Gly Gly Gly Ser Gly Gly Gly Ser Gly Gly Gly Ser Gly Gly Gly Ser
1               5                   10                  15

Gly Gly Gly Ser
            20


<210> SEQ ID NO 280
<211> LENGTH: 16
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: DISULFID
<222> LOCATION: (3)..(16)
<223> OTHER INFORMATION: Disulfide bond

<400> SEQUENCE: 280
```

Arg Thr Cys Thr Thr Thr Ala Gln Gly Thr Ser Met Tyr Pro Ser Cys
1 5 10 15

<210> SEQ ID NO 281
<211> LENGTH: 10
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: DISULFID
<222> LOCATION: (1)..(9)
<223> OTHER INFORMATION: Disulfide bond

<400> SEQUENCE: 281

Cys Thr Lys Pro Ser Asp Gly Asn Cys Thr
1 5 10

<210> SEQ ID NO 282
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 282

Ile Phe Leu Phe Ile Leu Leu Leu Cys Leu Ile Phe
1 5 10

<210> SEQ ID NO 283
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 283

Gly Pro Cys Arg Thr Cys Thr
1 5

<210> SEQ ID NO 284
<211> LENGTH: 6
<212> TYPE: PRT
<213> ORGANISM: Artificial Sequence
<220> FEATURE:
<223> OTHER INFORMATION: The sequence is artificially synthesized

<400> SEQUENCE: 284

His His His His His His
1 5

<210> SEQ ID NO 285
<211> LENGTH: 4
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (4)..(4)
<223> OTHER INFORMATION: Cys residue can be repeated one or more times

<400> SEQUENCE: 285

Cys Cys Cys Cys
1

<210> SEQ ID NO 286

<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 286

Gln Gln Tyr Tyr Ser Thr Pro Tyr Thr
1 5

<210> SEQ ID NO 287
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 287

Asp Arg Asp Ile Gln Leu Pro Phe Gly Asp Phe Tyr Tyr Gly Met Asp
1 5 10 15

Val

<210> SEQ ID NO 288
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 288

Ala Thr His Tyr Lys Thr Gly Trp Tyr Asp Glu Asn Phe Gln His
1 5 10 15

<210> SEQ ID NO 289
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 289

Ala Thr Tyr Thr Arg Phe Gly Glu Thr Leu Gly Tyr Leu Asp Phe
1 5 10 15

<210> SEQ ID NO 290
<211> LENGTH: 13
<212> TYPE: PRT
<213> ORGANISM: Artificial Sequence
<220> FEATURE:
<223> OTHER INFORMATION: The sequence is artificially synthesized

<400> SEQUENCE: 290

Val Lys Ala Glu Gly Ala Thr Thr His Phe Phe Asp His
1 5 10

<210> SEQ ID NO 291
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 291

Glu Arg Ser Ile Arg Asp Leu Ala Phe Asp Ile
1 5 10

<210> SEQ ID NO 292
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 292

Gly Trp Gly Gly Asp Phe Gly Tyr
1               5

<210> SEQ ID NO 293
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 293

Leu Tyr Tyr Asp Ser Ser Asp Glu Arg Asn Tyr Phe Asp Tyr
1               5                   10

<210> SEQ ID NO 294
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 294

Asp Cys Gly Thr Ala Ser Cys Tyr Thr Gly His
1               5                   10

<210> SEQ ID NO 295
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 295

Ile Ile Val Pro Gly Ile Trp Arg Trp Phe Tyr Gly Met Asp Val
1               5                   10                  15

<210> SEQ ID NO 296
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 296

Gly Gly Thr Tyr Tyr Ser Ala Ser Gly Ser Pro Lys
1               5                   10

<210> SEQ ID NO 297
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 297

Val Ser Leu Val Arg Gly Val Thr Val Asp Tyr
1               5                   10

<210> SEQ ID NO 298

<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 298

Pro Arg Gly Arg Ser Ala Arg Gly Tyr Tyr His His Tyr Gly Met Asp
1 5 10 15

Val

<210> SEQ ID NO 299
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 299

Gly Gly Phe Thr Ile Phe Gly Val Ile Ile Pro Trp Phe Asp Pro
1 5 10 15

<210> SEQ ID NO 300
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 300

Leu Gly Ser Ser Val His Phe Tyr Phe Asp Ser
1 5 10

<210> SEQ ID NO 301
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 301

Val Arg Ser Ile Pro Ser Ala Ser Tyr Leu Asp Phe
1 5 10

<210> SEQ ID NO 302
<211> LENGTH: 16
<212> TYPE: PRT
<213> ORGANISM: Artificial Sequence
<220> FEATURE:
<223> OTHER INFORMATION: The sequence is artificially synthesized

<400> SEQUENCE: 302

Asp Arg Asn Arg Val Thr Thr Arg His Leu His His Ala Phe Asp Val
1 5 10 15

<210> SEQ ID NO 303
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 303

Ala Asn Leu Pro Leu Trp Phe Gly Glu Leu Asp Ser
1 5 10

<210> SEQ ID NO 304
<211> LENGTH: 13
<212> TYPE: PRT
<213> ORGANISM: Artificial Sequence
<220> FEATURE:
<223> OTHER INFORMATION: The sequence is artificially synthesized

<400> SEQUENCE: 304

Gly Pro Ser Gly Ser Ser Gly Tyr Trp Ala Leu Asp Asn
1 5 10

<210> SEQ ID NO 305
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 305

Asp Ser Asn Gly Tyr Gly Leu Asp Ser
1 5

<210> SEQ ID NO 306
<211> LENGTH: 16
<212> TYPE: PRT
<213> ORGANISM: Artificial Sequence
<220> FEATURE:
<223> OTHER INFORMATION: The sequence is artificially synthesized

<400> SEQUENCE: 306

Ala Phe Leu Leu Ser Ser Ser Trp Pro Thr Asp Asn Trp Phe His Pro
1 5 10 15

<210> SEQ ID NO 307
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 307

Ser Gln Asp Asn Leu Trp Phe Gly Ala Phe Gly Gly Gly Ser Phe Asp
1 5 10 15

Ile

<210> SEQ ID NO 308
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 308

Asp Leu Ala Met Pro Arg Trp Phe Phe Asn Leu
1 5 10

<210> SEQ ID NO 309
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 309

Val Val Arg Ala Val Thr Asn Tyr Tyr Tyr Tyr Tyr Tyr Tyr Met Asp
1 5 10 15

Val

<210> SEQ ID NO 310
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 310

Gly His Trp Gly Gln Phe Asp Ser
1 5

<210> SEQ ID NO 311
<211> LENGTH: 18
<212> TYPE: PRT
<213> ORGANISM: Artificial Sequence
<220> FEATURE:
<223> OTHER INFORMATION: The sequence is artificially synthesized

<400> SEQUENCE: 311

Ser Pro Glu Ala Pro Arg Leu Leu Arg Phe Leu Gln Trp Leu Tyr Phe
1 5 10 15

Asp Tyr

<210> SEQ ID NO 312
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 312

Asp Gln Ala Ala Thr Phe Trp Ser Ala Tyr Phe Arg Asn Trp Phe Asp
1 5 10 15

Pro

<210> SEQ ID NO 313
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 313

Gln Gln Tyr Tyr Ser Ser Pro Arg Thr
1 5

<210> SEQ ID NO 314
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 314

Ser Ser Phe Arg Ser Ala Pro Ile Ser Thr Val
1 5 10

<210> SEQ ID NO 315
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 315

Gln His Arg Ser Asn Trp Pro Pro
1 5

<210> SEQ ID NO 316
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 316

Gln Gln Tyr Tyr Thr Thr Pro Phe Thr
1 5

<210> SEQ ID NO 317
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 317

Gln Gln Tyr Asn Ser Leu Tyr Thr
1 5

<210> SEQ ID NO 318
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 318

Leu Gln Gly Ser His Trp Pro Leu Thr
1 5

<210> SEQ ID NO 319
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 319

Gln Gln Tyr Tyr Gly Ser Arg Leu Ser
1 5

<210> SEQ ID NO 320
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 320

Gln Gln Tyr Asn Asn Trp Pro Ile Thr
1 5

<210> SEQ ID NO 321
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 321

Gln Gln Val Lys Ser Tyr Pro Leu Thr
1 5

<210> SEQ ID NO 322
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 322

Gln Gln Tyr Asn Ser Phe Pro Tyr Thr
1 5

<210> SEQ ID NO 323
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 323

Glu Thr Trp Asp Ser Asn Thr Gln Val
1 5

<210> SEQ ID NO 324
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 324

Gln Ser Tyr Asp Ser Ser Leu Ser Gly Ser Tyr Val
1 5 10

<210> SEQ ID NO 325
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 325

Gln Gln Arg Ser Asn Trp Pro Pro Met Tyr Thr
1 5 10

<210> SEQ ID NO 326
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 326

Ala Ala Trp Asp Asp Ser Leu Phe Ala Tyr Ala
1 5 10

<210> SEQ ID NO 327
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 327

```
Ala Ala Trp Asp Asp Arg Leu Ser Gly Arg Val
1               5                   10


<210> SEQ ID NO 328
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 328

Gln Gln Tyr Gly Ser Ser Pro Trp Thr
1               5


<210> SEQ ID NO 329
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 329

Gln Gln Tyr Gly Ser Ser Leu Val Ile Thr
1               5                   10


<210> SEQ ID NO 330
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 330

Gln Gln Tyr Tyr Thr Thr Thr Tyr Thr
1               5


<210> SEQ ID NO 331
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 331

Ser Ser Tyr Ala Gly Ser Tyr Thr Phe Val Val
1               5                   10


<210> SEQ ID NO 332
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 332

Gln Gln Lys Arg Thr
1               5


<210> SEQ ID NO 333
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 333

Gln Gln Tyr Gly Ser Ser Pro Leu Ala
```

1 5

<210> SEQ ID NO 334
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 334

His Gln Tyr Gly Tyr Ser Ser Gly Ser
1 5

<210> SEQ ID NO 335
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 335

Gln Tyr Tyr Asn Asn Trp Pro Leu Gly
1 5

<210> SEQ ID NO 336
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 336

Gln Gln Ser Tyr Ser Phe Pro Ile Thr
1 5

<210> SEQ ID NO 337
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 337

Gln Gln Tyr Asn Asn Trp Pro Pro Ser Trp Thr
1 5 10

<210> SEQ ID NO 338
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 338

Gly Ile Ile Pro Ile Phe Gly Thr Ala Asn Tyr Ala Gln Lys Phe Gln
1 5 10 15

Gly

<210> SEQ ID NO 339
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 339

Arg Ile Ile Pro Ile Leu Gly Ile Ala Asn Tyr Ala Gln Lys Phe Gln
1 5 10 15

Gly

<210> SEQ ID NO 340
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 340

Val Ile Val Pro Ile Phe Gly Thr Thr Asn Tyr Ala Gln Lys Phe Gln
1 5 10 15

Gly

<210> SEQ ID NO 341
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 341

Gly Ile Ile Pro Ile Phe Gly Ala Ala Asn Tyr Ala Gln Lys Phe Gln
1 5 10 15

Ala

<210> SEQ ID NO 342
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 342

Gly Ile Ile Pro Val Phe Gly Thr Pro Asn Tyr Ala Gln Lys Phe Gln
1 5 10 15

Gly

<210> SEQ ID NO 343
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 343

Gly Ile Ile Pro Val Phe Asp Phe Thr Asn Tyr Ser Gln Lys Phe Gln
1 5 10 15

Gly

<210> SEQ ID NO 344
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 344

Gly Ile Phe Pro Asn Leu Gly Val Ala Lys Tyr Ala Gln Lys Phe Gln
1 5 10 15

Gly

<210> SEQ ID NO 345
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 345

Gly Val Ile Pro Thr Phe Gly Thr Thr His Tyr Ala Gln Arg Phe Gln
1 5 10 15

Gly

<210> SEQ ID NO 346
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 346

Met Glu Asn Ile Thr Ser Gly Phe Leu Gly Pro Leu
1 5 10

<210> SEQ ID NO 347
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 347

Gly Pro Leu Leu Val Leu Gln Ala Gly Phe Phe Leu
1 5 10

<210> SEQ ID NO 348
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 348

Phe Phe Leu Leu Thr Arg Ile Leu Thr Ile Pro Gln
1 5 10

<210> SEQ ID NO 349
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 349

Ile Pro Gln Ser Leu Asp Ser Trp Trp Thr Ser Leu
1 5 10

<210> SEQ ID NO 350
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 350

Thr Ser Leu Asn Phe Leu Gly Gly Thr Thr Val Cys 1 5 10

<210> SEQ ID NO 351
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 351

Thr Val Cys Leu Gly Gln Asn Ser Gln Ser Pro Thr
1 5 10

<210> SEQ ID NO 352
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 352

Ser Pro Thr Ser Asn His Ser Pro Thr Ser Cys Pro
1 5 10

<210> SEQ ID NO 353
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 353

Ser Cys Pro Pro Thr Cys Pro Gly Tyr Arg Trp Met
1 5 10

<210> SEQ ID NO 354
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 354

Arg Trp Met Cys Leu Arg Arg Phe Ile Ile Phe Leu
1 5 10

<210> SEQ ID NO 355
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 355

Leu Ile Phe Leu Leu Val Leu Leu Asp Tyr Gln Gly
1 5 10

<210> SEQ ID NO 356
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 356

Tyr Gln Gly Met Leu Pro Val Cys Pro Leu Ile Pro
1 5 10

<210> SEQ ID NO 357
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 357

Leu Ile Pro Gly Ser Ser Thr Thr Ser Thr Gly Pro
1 5 10

<210> SEQ ID NO 358
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 358

Thr Gly Pro Cys Arg Thr Cys Thr Thr Thr Ala Gln
1 5 10

<210> SEQ ID NO 359
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 359

Thr Ala Gln Gly Thr Ser Met Tyr Pro Ser Cys Cys
1 5 10

<210> SEQ ID NO 360
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 360

Ser Cys Cys Cys Thr Lys Pro Ser Asp Gly Asn Cys
1 5 10

<210> SEQ ID NO 361
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 361

Gly Asn Cys Thr Cys Ile Pro Ile Pro Ser Ser Trp
1 5 10

<210> SEQ ID NO 362
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 362

Ser Ser Trp Ala Phe Gly Lys Phe Leu Trp Glu Trp
1 5 10

<210> SEQ ID NO 363
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 363

Trp Glu Trp Ala Ser Ala Arg Phe Ser Trp Leu Ser
1 5 10

<210> SEQ ID NO 364
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 364

Trp Leu Ser Leu Leu Val Pro Phe Val Gln Trp Phe
1 5 10

<210> SEQ ID NO 365
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 365

Gln Trp Phe Val Gly Leu Ser Pro Thr Val Trp Leu
1 5 10

<210> SEQ ID NO 366
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 366

Val Trp Leu Ser Val Ile Trp Met Met Trp Tyr Trp
1 5 10

<210> SEQ ID NO 367
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 367

Trp Tyr Trp Gly Pro Ser Leu Tyr Ser Ile Leu Ser
1 5 10

<210> SEQ ID NO 368
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 368

Ile Leu Ser Pro Phe Leu Pro Leu Leu Pro Ile Phe
1 5 10

<210> SEQ ID NO 369
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 369

Pro Ile Phe Phe Cys Leu Trp Val Tyr Ile
1               5                   10

<210> SEQ ID NO 370
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 370

Val Lys Trp Leu Val Thr Thr Tyr Tyr Phe Asp Ser
1               5                   10

<210> SEQ ID NO 371
<211> LENGTH: 20
<212> TYPE: PRT
<213> ORGANISM: Artificial Sequence
<220> FEATURE:
<223> OTHER INFORMATION: The sequence is artificially synthesized

<400> SEQUENCE: 371

Glu Ser Arg Ser Arg Leu Gln Leu Trp Leu Arg Thr Tyr Tyr Asn Tyr
1               5                   10                  15

Tyr Met Gly Val
            20

<210> SEQ ID NO 372
<211> LENGTH: 13
<212> TYPE: PRT
<213> ORGANISM: Artificial Sequence
<220> FEATURE:
<223> OTHER INFORMATION: The sequence is artificially synthesized

<400> SEQUENCE: 372

Asp Gly Gly Arg Gly Phe Phe Glu Trp Thr Tyr Glu Tyr
1               5                   10

<210> SEQ ID NO 373
<211> LENGTH: 16
<212> TYPE: PRT
<213> ORGANISM: Artificial Sequence
<220> FEATURE:
<223> OTHER INFORMATION: The sequence is artificially synthesized

<400> SEQUENCE: 373

Asp Phe Gly Val Trp Gly Asn Tyr Tyr Asn Tyr Tyr Gly Met Asp Val
1               5                   10                  15

<210> SEQ ID NO 374
<211> LENGTH: 18
<212> TYPE: PRT
<213> ORGANISM: Artificial Sequence
<220> FEATURE:
<223> OTHER INFORMATION: The sequence is artificially synthesized

<400> SEQUENCE: 374

Asp His Ala Gln Thr Trp Trp Asn His Tyr Tyr His Tyr Tyr Gly Met
1               5                   10                  15

Asp Val

<210> SEQ ID NO 375
<211> LENGTH: 22
<212> TYPE: PRT
<213> ORGANISM: Artificial Sequence
<220> FEATURE:
<223> OTHER INFORMATION: The sequence is artificially synthesized

<400> SEQUENCE: 375

Ala Ser Gln Pro Gly Asn Asn Val Val Leu Arg Tyr Ser Asp Trp Leu
1 5 10 15

Leu Arg Pro Leu Asp Tyr
20

<210> SEQ ID NO 376
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 376

Asp Met Gly Gly Ser Phe Arg Leu Met Asp Tyr
1 5 10

<210> SEQ ID NO 377
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 377

Asp Lys Gly Thr Leu Trp Ser Gly Tyr Gln Asn Trp Ile Asp Pro
1 5 10 15

<210> SEQ ID NO 378
<211> LENGTH: 18
<212> TYPE: PRT
<213> ORGANISM: Artificial Sequence
<220> FEATURE:
<223> OTHER INFORMATION: The sequence is artificially synthesized

<400> SEQUENCE: 378

Gly Tyr Tyr Gly Ser Gly Ser Tyr Phe Ala Ser Gly Asn Asn Trp Phe
1 5 10 15

Asp Pro

<210> SEQ ID NO 379
<211> LENGTH: 16
<212> TYPE: PRT
<213> ORGANISM: Artificial Sequence
<220> FEATURE:
<223> OTHER INFORMATION: The sequence is artificially synthesized

<400> SEQUENCE: 379

Tyr Thr Asp Cys Thr Thr Thr Ser Cys Phe Ser Asn Trp Phe Asp Pro
1 5 10 15

<210> SEQ ID NO 380
<211> LENGTH: 17
<212> TYPE: PRT
<213> ORGANISM: Artificial Sequence
<220> FEATURE:

<223> OTHER INFORMATION: The sequence is artificially synthesized

<400> SEQUENCE: 380

Asp Arg Arg Tyr Tyr Asp Ser Gly Gly Tyr Pro Ser Gly Gly Met Asp
1 5 10 15

Val

<210> SEQ ID NO 381
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 381

Arg Gly Tyr Asn Thr Gly Trp Gly Gln Asp Tyr
1 5 10

<210> SEQ ID NO 382
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 382

Thr Leu Val Ala Gly Phe Asp Asn
1 5

<210> SEQ ID NO 383
<211> LENGTH: 18
<212> TYPE: PRT
<213> ORGANISM: Artificial Sequence
<220> FEATURE:
<223> OTHER INFORMATION: The sequence is artificially synthesized

<400> SEQUENCE: 383

Asp Arg Val Asp Lys Val Thr Thr Ser His Asp Ala Tyr Tyr Gly Leu
1 5 10 15

Asp Val

<210> SEQ ID NO 384
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 384

Gly Leu Tyr Ser Phe Tyr Asp Asp
1 5

<210> SEQ ID NO 385
<211> LENGTH: 18
<212> TYPE: PRT
<213> ORGANISM: Artificial Sequence
<220> FEATURE:
<223> OTHER INFORMATION: The sequence is artificially synthesized

<400> SEQUENCE: 385

Glu Gly Leu Pro Tyr Phe Asp Ser Ser Thr Tyr Tyr Tyr Asn Gly Leu
1 5 10 15

Asp Val

<210> SEQ ID NO 386
<211> LENGTH: 21
<212> TYPE: PRT
<213> ORGANISM: Artificial Sequence
<220> FEATURE:
<223> OTHER INFORMATION: The sequence is artificially synthesized

<400> SEQUENCE: 386

Ser Lys Ala Pro Asp Ser Thr Tyr Val Leu Arg Tyr Ile Asp Trp Tyr
1 5 10 15

Leu Pro Pro Asp Phe
20

<210> SEQ ID NO 387
<211> LENGTH: 16
<212> TYPE: PRT
<213> ORGANISM: Artificial Sequence
<220> FEATURE:
<223> OTHER INFORMATION: The sequence is artificially synthesized

<400> SEQUENCE: 387

Val Gly Tyr Cys Ser Ser Thr Ser Cys His Gly Pro Ile Phe Asp Tyr
1 5 10 15

<210> SEQ ID NO 388
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 388

Tyr Cys Ser Tyr Asn Cys Pro Gly Pro Leu Asp Tyr
1 5 10

<210> SEQ ID NO 389
<211> LENGTH: 7
<212> TYPE: PRT
<213> ORGANISM: Artificial Sequence
<220> FEATURE:
<223> OTHER INFORMATION: The sequence is artificially synthesized

<400> SEQUENCE: 389

Gly Leu Thr Ser Ala Asp Tyr
1 5

<210> SEQ ID NO 390
<211> LENGTH: 17
<212> TYPE: PRT
<213> ORGANISM: Artificial Sequence
<220> FEATURE:
<223> OTHER INFORMATION: The sequence is artificially synthesized

<400> SEQUENCE: 390

Asp His Arg Ser Arg Phe Leu Glu Trp Leu Leu Tyr His Tyr Phe Asp
1 5 10 15

Tyr

<210> SEQ ID NO 391
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 391

Asp Val Phe Ala Trp Ser Phe Asp Tyr
1 5

<210> SEQ ID NO 392
<211> LENGTH: 13
<212> TYPE: PRT
<213> ORGANISM: Artificial Sequence
<220> FEATURE:
<223> OTHER INFORMATION: The sequence is artificially synthesized

<400> SEQUENCE: 392

Gly Arg Gly Gly Ser Gly Ser Tyr Ser Pro Phe Asp Tyr
1 5 10

<210> SEQ ID NO 393
<211> LENGTH: 19
<212> TYPE: PRT
<213> ORGANISM: Artificial Sequence
<220> FEATURE:
<223> OTHER INFORMATION: The sequence is artificially synthesized

<400> SEQUENCE: 393

Gly Ser Gly Ser Phe Trp Ser Gly Ile Gly Tyr Tyr Tyr Tyr Tyr Ser
1 5 10 15

Met Asn Val

<210> SEQ ID NO 394
<211> LENGTH: 16
<212> TYPE: PRT
<213> ORGANISM: Artificial Sequence
<220> FEATURE:
<223> OTHER INFORMATION: The sequence is artificially synthesized

<400> SEQUENCE: 394

Gly Ala Pro Arg Tyr Phe Asp Trp Leu Phe Arg Asp Ala Phe Asp Ile
1 5 10 15

<210> SEQ ID NO 395
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 395

Leu Tyr Cys Thr Gly Gly Thr Cys Tyr Ala
1 5 10

<210> SEQ ID NO 396
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 396

Asp Pro Tyr Met Val Ala Ala Val Ala Arg Thr Val Asp Tyr
1 5 10

<210> SEQ ID NO 397
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 397

Lys Ala Thr Leu Ala Gly Thr Asp Gly Gly Tyr Phe Asp Tyr
1 5 10

<210> SEQ ID NO 398
<211> LENGTH: 13
<212> TYPE: PRT
<213> ORGANISM: Artificial Sequence
<220> FEATURE:
<223> OTHER INFORMATION: The sequence is artificially synthesized

<400> SEQUENCE: 398

Gly Ile Glu Gly Tyr Asn Tyr Ser Arg Tyr Phe Asp Phe
1 5 10

<210> SEQ ID NO 399
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 399

Asp Leu Asp Ser Ser Thr Tyr Trp Gly Asn Trp Phe Asp Pro
1 5 10

<210> SEQ ID NO 400
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 400

Asn Arg Leu Gly Thr Thr Arg Asp Arg Tyr Tyr Phe Asp Tyr
1 5 10

<210> SEQ ID NO 401
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 401

Glu Gly His Thr Ala Met Ala Thr Leu Asp Tyr
1 5 10

<210> SEQ ID NO 402
<211> LENGTH: 19
<212> TYPE: PRT
<213> ORGANISM: Artificial Sequence
<220> FEATURE:
<223> OTHER INFORMATION: The sequence is artificially synthesized

<400> SEQUENCE: 402

Thr Gly Pro Pro Phe Ser Lys Trp Leu His Met Ala Gly Glu Lys Tyr
1 5 10 15

Phe His Phe

<210> SEQ ID NO 403
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 403

Cys Ser Tyr Ala Gly Pro Tyr Asn Leu Gly Leu
1 5 10

<210> SEQ ID NO 404
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 404

Gln Gln Tyr His Ser Ala Pro Ala Leu Ser
1 5 10

<210> SEQ ID NO 405
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 405

Gly Thr Trp Asp Asn Ser Leu Arg Gly Val Val
1 5 10

<210> SEQ ID NO 406
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 406

Gln Gln Tyr Tyr Gly Ala Pro Leu Thr
1 5

<210> SEQ ID NO 407
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 407

Leu Leu Tyr Tyr Gly Gly Ser Trp Val
1 5

<210> SEQ ID NO 408
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 408

Gln Gln Tyr Ala Ile Leu Pro Leu Thr
1 5

<210> SEQ ID NO 409
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 409

Gln Gln Tyr Ser Ser Tyr Pro Leu Thr
1 5

<210> SEQ ID NO 410
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 410

Gln Gln Ser His Ser Phe Pro Leu Thr
1 5

<210> SEQ ID NO 411
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 411

Cys Ser Tyr Ala Gly Ser Phe Thr Tyr Val
1 5 10

<210> SEQ ID NO 412
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 412

Cys Ser Tyr Ala Gly Ser Asp Thr Phe Val Val
1 5 10

<210> SEQ ID NO 413
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 413

Gln Gln Tyr Asn Asn Trp Pro Arg Thr
1 5

<210> SEQ ID NO 414
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 414

Val Ala Trp Asp Asp Ser Leu Asn Val Val
1 5 10

<210> SEQ ID NO 415
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 415

Gln Gln Phe Tyr Ser Ser Pro Gln Thr
1 5

<210> SEQ ID NO 416
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 416

Gln Gln Val Asn Phe Tyr Pro Pro Trp Pro
1 5 10

<210> SEQ ID NO 417
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 417

Gly Thr Trp Asp Ser Ser Leu Ser Glu Pro Trp Val
1 5 10

<210> SEQ ID NO 418
<211> LENGTH: 13
<212> TYPE: PRT
<213> ORGANISM: Artificial Sequence
<220> FEATURE:
<223> OTHER INFORMATION: The sequence is artificially synthesized

<400> SEQUENCE: 418

Ala Ala Trp Asp Asp Ser Leu Asn Gly Arg Asn Val Val
1 5 10

<210> SEQ ID NO 419
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 419

Gln Gln Tyr Ser Thr Thr Pro Gln Thr
1 5

<210> SEQ ID NO 420
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 420

Ala Ala Trp Asp Asp Ser Leu Ser Gly Trp Val
1 5 10

<210> SEQ ID NO 421
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 421

Gln Gln Tyr Asn Gln Trp Pro Arg Thr 1 5

<210> SEQ ID NO 422
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 422

Gln Gln Tyr Asn Ser Tyr Ser Thr Trp Thr
1 5 10

<210> SEQ ID NO 423
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 423

Gln Gln Tyr Asn His Trp Pro Leu Thr
1 5

<210> SEQ ID NO 424
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 424

Gln Gln Gly Tyr Ser Trp Pro Leu Ser
1 5

<210> SEQ ID NO 425
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 425

Gln Gln Tyr Tyr Arg Thr Pro Phe Thr
1 5

<210> SEQ ID NO 426
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 426

Gln Gln Tyr Tyr Ser Thr Leu Tyr Thr
1 5

<210> SEQ ID NO 427
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 427

Leu Leu Tyr Tyr Gly Gly Ala Gln Leu Val
1 5 10

<210> SEQ ID NO 428
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 428

Met Gln Thr Leu Gln Met Tyr Thr
1 5

<210> SEQ ID NO 429
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 429

Gln Val Trp Asp Ser Asp Ser Asp His Val Val
1 5 10

<210> SEQ ID NO 430
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 430

Ser Ser Tyr Thr Leu Thr Ser Asp Arg Lys Thr Thr Thr Leu Val
1 5 10 15

<210> SEQ ID NO 431
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 431

Met Gln Ala Leu Gln Thr Pro Ile Thr
1 5

<210> SEQ ID NO 432
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 432

Gln Gln Tyr His Ser Leu Pro Leu Thr
1 5

<210> SEQ ID NO 433
<211> LENGTH: 10
<212> TYPE: PRT
<213> ORGANISM: Artificial Sequence
<220> FEATURE:
<223> OTHER INFORMATION: The sequence is artificially synthesized

<400> SEQUENCE: 433

Gln Gln Ser Tyr Ser Met Pro Lys Leu Thr
1 5 10

<210> SEQ ID NO 434
<211> LENGTH: 226
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (2)..(2)
<223> OTHER INFORMATION: Xaa can be Asp or Glu
<220> FEATURE:
<221> NAME/KEY: VARIANT
<222> LOCATION: (3)..(3)
<223> OTHER INFORMATION: Xaa can be Ser or Asn
<220> FEATURE:
<221> NAME/KEY: VARIANT
<222> LOCATION: (4)..(4)
<223> OTHER INFORMATION: Xaa can be Thr or Ile
<220> FEATURE:
<221> NAME/KEY: VARIANT
<222> LOCATION: (5)..(5)
<223> OTHER INFORMATION: Xaa can be Ala or Thr
<220> FEATURE:
<221> NAME/KEY: VARIANT
<222> LOCATION: (8)..(8)
<223> OTHER INFORMATION: Xaa can be Leu or Phe
<220> FEATURE:
<221> NAME/KEY: VARIANT
<222> LOCATION: (18)..(18)
<223> OTHER INFORMATION: Xaa can be Val or Gly
<220> FEATURE:
<221> NAME/KEY: VARIANT
<222> LOCATION: (19)..(19)
<223> OTHER INFORMATION: Xaa can be Cys or Phe
<220> FEATURE:
<221> NAME/KEY: VARIANT
<222> LOCATION: (24)..(24)
<223> OTHER INFORMATION: Xaa can be Arg or Lys
<220> FEATURE:
<221> NAME/KEY: VARIANT
<222> LOCATION: (44)..(44)
<223> OTHER INFORMATION: Xaa can be Val or Gly
<220> FEATURE:
<221> NAME/KEY: VARIANT
<222> LOCATION: (45)..(45)
<223> OTHER INFORMATION: Xaa can be Thr, Ala , Ser, Val , Leu or Pro
<220> FEATURE:
<221> NAME/KEY: VARIANT
<222> LOCATION: (46)..(46)
<223> OTHER INFORMATION: Xaa can be Pro or Thr
<220> FEATURE:
<221> NAME/KEY: VARIANT
<222> LOCATION: (47)..(47)
<223> OTHER INFORMATION: Xaa can be Thr, Gly or Val
<220> FEATURE:
<221> NAME/KEY: VARIANT
<222> LOCATION: (49)..(49)
<223> OTHER INFORMATION: Xaa can be Pro or Leu
<220> FEATURE:
<221> NAME/KEY: VARIANT
<222> LOCATION: (51)..(51)
<223> OTHER INFORMATION: Xaa can be Leu or Gln
<220> FEATURE:
<221> NAME/KEY: VARIANT
<222> LOCATION: (56)..(56)
<223> OTHER INFORMATION: Xaa can be Gln or Pro
<220> FEATURE:
<221> NAME/KEY: VARIANT
<222> LOCATION: (57)..(57)
<223> OTHER INFORMATION: Xaa can be Ile or Thr
<220> FEATURE:
<221> NAME/KEY: VARIANT
<222> LOCATION: (59)..(59)
<223> OTHER INFORMATION: Xaa can be Ser or Asn
<220> FEATURE:
<221> NAME/KEY: VARIANT
<222> LOCATION: (61)..(61)
<223> OTHER INFORMATION: Xaa can be Leu or Ser
<220> FEATURE:
<221> NAME/KEY: VARIANT
<222> LOCATION: (63)..(63)
<223> OTHER INFORMATION: Xaa can be Ile or Thr
<220> FEATURE:
<221> NAME/KEY: VARIANT
<222> LOCATION: (64)..(64)
<223> OTHER INFORMATION: Xaa can be Cys or Ser
<220> FEATURE:
<221> NAME/KEY: VARIANT
<222> LOCATION: (68)..(68)
<223> OTHER INFORMATION: Xaa can be Thr or Ile
<220> FEATURE:
<221> NAME/KEY: VARIANT
<222> LOCATION: (85)..(85)
<223> OTHER INFORMATION: Xaa can be Cys or Phe
<220> FEATURE:
<221> NAME/KEY: VARIANT
<222> LOCATION: (110)..(110)
<223> OTHER INFORMATION: Xaa can be Leu or Ile
<220> FEATURE:
<221> NAME/KEY: VARIANT
<222> LOCATION: (113)..(113)
<223> OTHER INFORMATION: Xaa can be Thr or Ser
<220> FEATURE:
<221> NAME/KEY: VARIANT
<222> LOCATION: (114)..(114)
<223> OTHER INFORMATION: Xaa can be Thr or Ser
<220> FEATURE:
<221> NAME/KEY: VARIANT
<222> LOCATION: (122)..(122)
<223> OTHER INFORMATION: Xaa can be Arg or Lys
<220> FEATURE:
<221> NAME/KEY: VARIANT
<222> LOCATION: (126)..(126)
<223> OTHER INFORMATION: Xaa can be Thr or Ile
<220> FEATURE:
<221> NAME/KEY: VARIANT
<222> LOCATION: (127)..(127)
<223> OTHER INFORMATION: Xaa can be Pro, Thr or Leu
<220> FEATURE:
<221> NAME/KEY: VARIANT
<222> LOCATION: (131)..(131)
<223> OTHER INFORMATION: Xaa can be Asn or Thr
<220> FEATURE:
<221> NAME/KEY: VARIANT
<222> LOCATION: (134)..(134)
<223> OTHER INFORMATION: Xaa can be Tyr or Phe
<220> FEATURE:
<221> NAME/KEY: VARIANT
<222> LOCATION: (140)..(140)
<223> OTHER INFORMATION: Xaa can be Thr or Ser
<220> FEATURE:
<221> NAME/KEY: VARIANT
<222> LOCATION: (143)..(143)
<223> OTHER INFORMATION: Xaa can be Thr or Ser
<220> FEATURE:
<221> NAME/KEY: VARIANT
<222> LOCATION: (158)..(158)
<223> OTHER INFORMATION: Xaa can be Phe or Leu
<220> FEATURE:
<221> NAME/KEY: VARIANT
<222> LOCATION: (159)..(159)
<223> OTHER INFORMATION: Xaa can be Gly or Ala
<220> FEATURE:
<221> NAME/KEY: VARIANT
<222> LOCATION: (160)..(160)
<223> OTHER INFORMATION: Xaa can be Arg or Lys
<220> FEATURE:
<221> NAME/KEY: VARIANT
<222> LOCATION: (161)..(161)
<223> OTHER INFORMATION: Xaa can be Phe or Tyr
<220> FEATURE:
<221> NAME/KEY: VARIANT
<222> LOCATION: (168)..(168)
<223> OTHER INFORMATION: Xaa can be Val or Ala
<220> FEATURE:
<221> NAME/KEY: VARIANT
<222> LOCATION: (178)..(178)

<223> OTHER INFORMATION: Xaa can be Gln or Pro
<220> FEATURE:
<221> NAME/KEY: VARIANT
<222> LOCATION: (183)..(183)
<223> OTHER INFORMATION: Xaa can be Cys or Phe
<220> FEATURE:
<221> NAME/KEY: VARIANT
<222> LOCATION: (184)..(184)
<223> OTHER INFORMATION: Xaa can be Ala  or Val
<220> FEATURE:
<221> NAME/KEY: VARIANT
<222> LOCATION: (193)..(193)
<223> OTHER INFORMATION: Xaa can be Leu or Ser
<220> FEATURE:
<221> NAME/KEY: VARIANT
<222> LOCATION: (194)..(194)
<223> OTHER INFORMATION: Xaa can be Ala  or Val
<220> FEATURE:
<221> NAME/KEY: VARIANT
<222> LOCATION: (198)..(198)
<223> OTHER INFORMATION: Xaa can be Ile or Met
<220> FEATURE:
<221> NAME/KEY: VARIANT
<222> LOCATION: (200)..(200)
<223> OTHER INFORMATION: Xaa can be Phe or Tyr
<220> FEATURE:
<221> NAME/KEY: VARIANT
<222> LOCATION: (204)..(204)
<223> OTHER INFORMATION: Xaa can be Asn or Ser
<220> FEATURE:
<221> NAME/KEY: VARIANT
<222> LOCATION: (206)..(206)
<223> OTHER INFORMATION: Xaa can be Cys or Tyr
<220> FEATURE:
<221> NAME/KEY: VARIANT
<222> LOCATION: (207)..(207)
<223> OTHER INFORMATION: Xaa can be Ser or Asn
<220> FEATURE:
<221> NAME/KEY: VARIANT
<222> LOCATION: (209)..(209)
<223> OTHER INFORMATION: Xaa can be Val  or Leu
<220> FEATURE:
<221> NAME/KEY: VARIANT
<222> LOCATION: (213)..(213)
<223> OTHER INFORMATION: Xaa can be Met, Leu or Ile
<220> FEATURE:
<221> NAME/KEY: VARIANT
<222> LOCATION: (220)..(220)
<223> OTHER INFORMATION: Xaa can be Cys or Phe
<220> FEATURE:
<221> NAME/KEY: VARIANT
<222> LOCATION: (221)..(221)
<223> OTHER INFORMATION: Xaa can be Tyr or Cys
<220> FEATURE:
<221> NAME/KEY: VARIANT
<222> LOCATION: (224)..(224)
<223> OTHER INFORMATION: Xaa can be Ala or Val
<220> FEATURE:
<221> NAME/KEY: VARIANT
<222> LOCATION: (225)..(225)
<223> OTHER INFORMATION: Xaa can be Ser or Tyr

<400> SEQUENCE: 434

```
Met Xaa Xaa Xaa Xaa Ser Gly Xaa Leu Gly Pro Leu Leu Val Leu Gln
1               5                   10                  15

Ala Xaa Xaa Phe Leu Leu Thr Xaa Ile Leu Thr Ile Pro Gln Ser Leu
            20                  25                  30

Asp Ser Trp Trp Thr Ser Leu Asn Phe Leu Gly Xaa Xaa Xaa Xaa Cys
        35                  40                  45

Xaa Gly Xaa Asn Ser Gln Ser Xaa Xaa Ser Xaa His Xaa Pro Xaa Xaa
    50                  55                  60

Cys Pro Pro Xaa Cys Pro Gly Tyr Arg Trp Met Cys Leu Arg Arg Phe
65                  70                  75                  80
```

-continued

```
Ile Ile Phe Leu Xaa Ile Leu Leu Leu Cys Leu Ile Phe Leu Leu Val
                85                  90                  95

Leu Leu Asp Tyr Gln Gly Met Leu Pro Val Cys Pro Leu Xaa Pro Gly
            100                 105                 110

Xaa Xaa Thr Thr Ser Thr Gly Pro Cys Xaa Thr Cys Thr Xaa Xaa Ala
        115                 120                 125

Gln Gly Xaa Ser Met Xaa Pro Ser Cys Cys Cys Xaa Lys Pro Xaa Asp
    130                 135                 140

Gly Asn Cys Thr Cys Ile Pro Ile Pro Ser Ser Trp Ala Xaa Xaa Xaa
145                 150                 155                 160

Xaa Leu Trp Glu Trp Ala Ser Xaa Arg Phe Ser Trp Leu Ser Leu Leu
                165                 170                 175

Val Xaa Phe Val Gln Trp Xaa Xaa Gly Leu Ser Pro Thr Val Trp Leu
            180                 185                 190

Xaa Xaa Ile Trp Met Xaa Trp Xaa Trp Gly Pro Xaa Leu Xaa Xaa Ile
        195                 200                 205

Xaa Ser Pro Phe Xaa Pro Leu Leu Pro Ile Phe Xaa Xaa Leu Trp Xaa
    210                 215                 220

Xaa Ile
225
```